US012714111B2

(12) United States Patent
Scheel

(10) Patent No.: US 12,714,111 B2
(45) Date of Patent: Aug. 25, 2026

(54) SEX-LINKED RNAi INSECTICIDE MATERIALS AND METHODS

(71) Applicant: Indiana University Research and Technology Corporation, Indianapolis, IN (US)

(72) Inventor: Molly Duman Scheel, Granger, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 1077 days.

(21) Appl. No.: 17/288,748

(22) PCT Filed: Oct. 26, 2019

(86) PCT No.: PCT/US2019/058232
§ 371 (c)(1),
(2) Date: Apr. 26, 2021

(87) PCT Pub. No.: WO2020/087053
PCT Pub. Date: Apr. 30, 2020

(65) Prior Publication Data

US 2022/0248690 A1 Aug. 11, 2022

Related U.S. Application Data

(60) Provisional application No. 62/751,052, filed on Oct. 26, 2018.

(51) Int. Cl.
*A01N 63/60* (2020.01)
*A01K 67/68* (2025.01)
*C12N 15/113* (2010.01)

(52) U.S. Cl.
CPC .............. *A01N 63/60* (2020.01); *A01K 67/68* (2025.01); *C12N 15/113* (2013.01); *C12N 2310/14* (2013.01); *C12N 2320/00* (2013.01)

(58) Field of Classification Search
CPC ... A01N 63/60; C12N 15/113; C12N 2310/14
See application file for complete search history.

(56) References Cited

U.S. PATENT DOCUMENTS

2017/0071208 A1* 3/2017 Paldi ...................... A01K 67/68
2018/0155739 A1 6/2018 Hu

FOREIGN PATENT DOCUMENTS

WO 2018/111996 6/2018

OTHER PUBLICATIONS

Salvemini, Marco, et al. "Genomic organization and splicing evolution of the doublesex gene, a *Drosophila* regulator of sexual differentiation, in the dengue and yellow fever mosquito *Aedes aegypti*." BMC evolutionary biology 11 (2011): 1-19. (Year: 2011).*

Airs, Paul M., and Lyric C. Bartholomay. "RNA interference for mosquito and mosquito-borne disease control." Insects 8.1 (2017): 4. (Year: 2017).*

GenBankDSX (GenBankDSX, Aedes aegypti female specific 1 protein (DSXF1) mRNA, complete cds, revision from Mar. 21, 2011 , retrieved Jul. 2, 2024) (Year: 2011).*

Mysore K, Sun L, Li P, et al. A Conserved Female-Specific Requirement for the GGT Gene in Mosquito Larvae Facilitates RNAi-Mediated Sex Separation in Multiple Species of Disease Vector Mosquitoes. Pathogens. 2022; 11(2):169. (Year: 2024).*

Genetics, https://learn.genetics.utah.edu/content/pigeons/sexlinkage/, retrieved Jun. 21, 2024 (Year: 2024).*

Whyard, Steve, et al. "Silencing the buzz: a new approach to population suppression of mosquitoes by feeding larvae double-stranded RNAs." Parasites & vectors 8 (2015): 1-11. (Year: 2015).*

Flavell, Laura. Deciphering the molecular mechanisms underlying the photoperiodic clock in the parasitic wasp, *Nasonia vitripennis*. Diss. University of Leicester, 2017. (Year: 2017).*

GenBankGGT1, Aedes aegypti gamma-glutamyltranspeptidase 1 (LOC23687751), transcript variant X1, mRNA, https://www.ncbi.nlm.nih.gov/nuccore/1218216909?sat=4&satkey=199882336, revision Jul. 20, 2017, retrieved Jul. 2, 2024. . (Year: 2017).*

Fakhr, Elham, F. Zare, and Ladan Teimoori-Toolabi. "Precise and efficient siRNA design: a key point in competent gene silencing." Cancer gene therapy 23.4 (2016): 73-82. (Year: 2016).*

International Search Report and Written Opinion issued by the International Searching Authority, dated Feb. 20, 2020, for International Patent Application No. PCT/US2019/058232; 8 pages.

Molly Duman Scheel, et al. "Developmental neurogenetics of sexual dimorphism in Aedes aegypti", Frontiers in Ecology and Evolution, Jun. 16, 2015, vol. 3, No. 61; 8 pages.

Keshava Mysore, et al., "SiRNA-Mediated Silencing of doublesex during Female Development of the Dengue Vector Mosquito *Aedes aegypti*", PLOS Neglected Tropical Diseases, Nov. 6, 2015, vol. 9; 21 pages.

Keshava Mysore, et al., "Identification of Aedes aegypti cis-regulatory elements that promote gene expression in olfactory receptor neurons of distantly related dipteran insects", Parasites & Vectors, Jul. 11, 2018, vol. 11; 11 pages.

Michael Tomchaney, et al. "Examination of the genetic basis for sexual dimorphism in the *Aedes aegypti* (dengue rector mosquito) pupal brain", Biology of Sex Differences, Oct. 21, 2014, vol. 5; 22 pages.

(Continued)

*Primary Examiner* — Ekaterina Poliakova-Georgantas
*Assistant Examiner* — John Charles Mckillop
(74) *Attorney, Agent, or Firm* — Faegre Drinker Biddle & Reath LLP

(57) ABSTRACT

The present disclosure provides insecticides that can specifically target mosquitoes based on their sex. These sex-specific insecticides prevent maturation or development of larvae into adult insects using interfering RNA (iRNA). The present disclosure further provides compositions comprising sex-linked iRNA and methods of controlling, reducing, or treating an insect infestation with the iRNA or compositions described herein. The compositions and methods described herein can be used to sort mosquitoes based on sex.

8 Claims, 5 Drawing Sheets

Specification includes a Sequence Listing.

(56) References Cited

OTHER PUBLICATIONS

Andrew Brantley Hall et al: "A male-determining factor in the mosquito *Aedes aegypti*" , SCIENCE, vol. 348, No. 6240, Jun. 12, 2015 (Jun. 12, 2015), pp. 1268-1270, XP055470626.
Keshava Mysore et al: "siRNA-Mediated Silencing of doublesex during Female Development of the Dengue Vector Mosquito *Aedes aegypti*" , PLOS Neglected Tropical Diseases, vol. 9, No. 11, Nov. 6, 2015 (Nov. 6, 2015), p. e0004213, XP055429737,.
Mysore Keshava et al: "A Conserved Female-Specific Requirement for the GGT Gene in Mosquito Larvae Facilitates RNAi-Mediated Sex Separation in Multiple Species of Disease Vector Mosquitoes", PATHOGENS, vol. 11, No. 2, Jan. 27, 2022 (Jan. 27, 2022), p. 169, XP55976638.
Mysore Keshava et al: "A functional requirement for sex-determination M/m locus region lncRNA genes in Aedes aegypti female larvae" , Scientific Reports, vol. 11, No. 1, May 20, 2021 (May 20, 2021), XP55975906.
Mysore Keshava et al: "Yeast interfering RNA larvicides targeting neural genes induce high rates of Anopheles larval mortality", Malaria Journal, vol. 16, No. 1, Nov. 13, 2017 (Nov. 13, 2017), XP55977463.
Steve Whyard et al: "Silencing the buzz: a new approach to population suppression of mosquitoes by feeding larvae double-stranded RNAs", Parasites & Vectors, Biomed Central Ltd, London UK, vol. 8, No. 1, Feb. 12, 2015 (Feb. 12, 2015), p. 96, XP021215606.

* cited by examiner

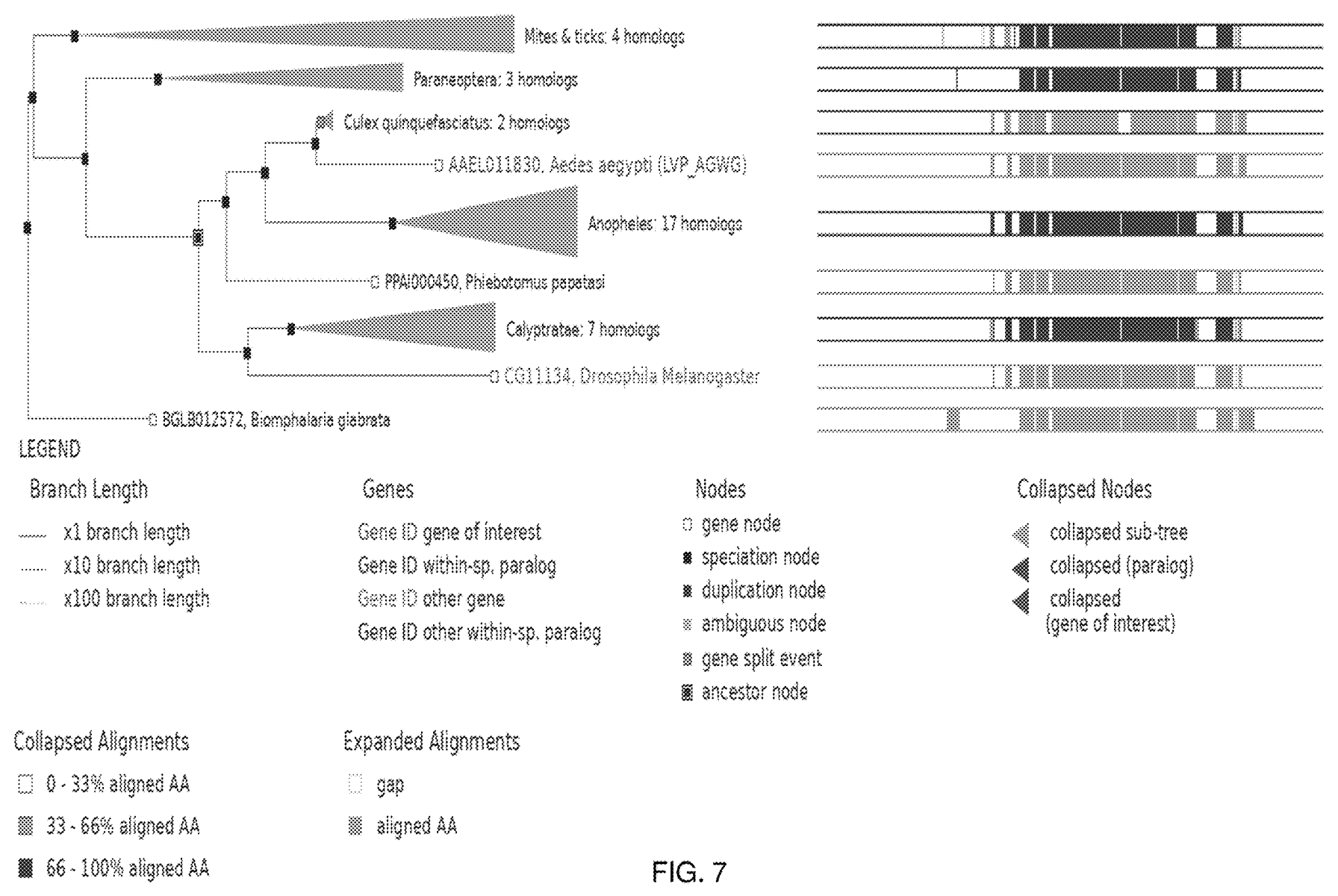

Mites & ticks: 4 homologs
Paraneoptera: 3 homologs
Culex quinquefasciatus: 2 homologs
AAEL011830, Aedes aegypti (LVP_AGWG)
Anopheles: 17 homologs
PPAI000450, Phlebotomus papatasi
Calyptratae: 7 homologs
CG11134, Drosophila Melanogaster
BGLB012572, Biomphalaria glabrata

LEGEND

Branch Length
x1 branch length
x10 branch length
x100 branch length

Genes
Gene ID gene of interest
Gene ID within-sp. paralog
Gene ID other gene
Gene ID other within-sp. paralog Nodes
gene node
speciation node
duplication node
ambiguous node
gene split event
ancestor node Collapsed Nodes
collapsed sub-tree
collapsed (paralog)
collapsed (gene of interest)

Collapsed Alignments
0 - 33% aligned AA
33 - 66% aligned AA
66 - 100% aligned AA Expanded Alignments
gap
aligned AA

FIG. 7

SEQUENCE LISTING

```
<160> NUMBER OF SEQ ID NOS: 203

<210> SEQ ID NO 1
<211> LENGTH: 25
<212> TYPE: RNA
<213> ORGANISM: Aedes aegypti

<400> SEQUENCE: 1

gaaguauucu uccagcuaau auaaa                                    25


<210> SEQ ID NO 2
<211> LENGTH: 25
<212> TYPE: RNA
<213> ORGANISM: Aedes aegypti

<400> SEQUENCE: 2

aucauauaca uguugaauua uuguu                                    25


<210> SEQ ID NO 3
<211> LENGTH: 25
<212> TYPE: RNA
<213> ORGANISM: Aedes aegypti

<400> SEQUENCE: 3

gguuuacuaa aaaucacuuu ccuug                                    25


<210> SEQ ID NO 4
<211> LENGTH: 25
<212> TYPE: RNA
<213> ORGANISM: Aedes aegypti

<400> SEQUENCE: 4

agaaucuucu uacaaucacu gccuc                                    25


<210> SEQ ID NO 5
<211> LENGTH: 25
<212> TYPE: RNA
<213> ORGANISM: Aedes aegypti

<400> SEQUENCE: 5

gacuaauguc uggaauuagu auaaa                                    25


<210> SEQ ID NO 6
<211> LENGTH: 25
```

<212> TYPE: RNA
<213> ORGANISM: Aedes aegypti

<400> SEQUENCE: 6
accaacuuau aacaaagaaa agguc 25

<210> SEQ ID NO 7
<211> LENGTH: 25
<212> TYPE: RNA
<213> ORGANISM: Aedes aegypti

<400> SEQUENCE: 7
gucacuaagc ucuauaauca aaaua 25

<210> SEQ ID NO 8
<211> LENGTH: 25
<212> TYPE: RNA
<213> ORGANISM: Aedes aegypti

<400> SEQUENCE: 8
ggaccaacuu uuacuucaga uaaga 25

<210> SEQ ID NO 9
<211> LENGTH: 25
<212> TYPE: DNA
<213> ORGANISM: Aedes aegypti
<220> FEATURE:
<223> OTHER INFORMATION: Description of Combined DNA/RNA Molecule: Aedes aegypti oligonucleotide

<400> SEQUENCE: 9
cauccaaccu ucaagcgaau cagtg 25

<210> SEQ ID NO 10
<211> LENGTH: 25
<212> TYPE: RNA
<213> ORGANISM: Aedes aegypti

<400> SEQUENCE: 10
auugagacuu accaacugau caguu 25

<210> SEQ ID NO 11
<211> LENGTH: 25
<212> TYPE: RNA
<213> ORGANISM: Aedes aegypti

<400> SEQUENCE: 11
caagugaaaa uaaacaucaa gauuu 25

<210> SEQ ID NO 12
<211> LENGTH: 25
<212> TYPE: RNA
<213> ORGANISM: Aedes aegypti

<400> SEQUENCE: 12
gauaaagcau ucauuccgcu acuua 25

<210> SEQ ID NO 13
<211> LENGTH: 25
<212> TYPE: RNA
<213> ORGANISM: Aedes aegypti

<400> SEQUENCE: 13
guuuuuauug uuugcaucaa caguu 25

<210> SEQ ID NO 14
<211> LENGTH: 25
<212> TYPE: RNA
<213> ORGANISM: Aedes aegypti

<400> SEQUENCE: 14
agcagaaaga uugaaauuau uacca 25

<210> SEQ ID NO 15
<211> LENGTH: 25
<212> TYPE: RNA
<213> ORGANISM: Aedes aegypti

<400> SEQUENCE: 15
agcguugaaa aaucuauaaa aaccu 25

<210> SEQ ID NO 16
<211> LENGTH: 25
<212> TYPE: RNA
<213> ORGANISM: Aedes aegypti

<400> SEQUENCE: 16
agcgauggaa gauuguaaaa aucga 25

<210> SEQ ID NO 17
<211> LENGTH: 25
<212> TYPE: RNA
<213> ORGANISM: Aedes aegypti

<400> SEQUENCE: 17
agucaggguu uauuucauug uucga 25

<210> SEQ ID NO 18
<211> LENGTH: 25
<212> TYPE: RNA
<213> ORGANISM: Aedes aegypti

<400> SEQUENCE: 18
cauguugaau uauuguuuug uuaaa 25

<210> SEQ ID NO 19
<211> LENGTH: 25
<212> TYPE: RNA
<213> ORGANISM: Aedes aegypti

<400> SEQUENCE: 19
uggcaaauua uccaagaaca ucuac 25

<210> SEQ ID NO 20
<211> LENGTH: 25
<212> TYPE: RNA
<213> ORGANISM: Aedes aegypti

<400> SEQUENCE: 20
aaauuaucca agaacaucua caucu 25

<210> SEQ ID NO 21
<211> LENGTH: 25
<212> TYPE: RNA
<213> ORGANISM: Aedes aegypti

<400> SEQUENCE: 21
aaacgagaau uuguggaaau aguug 25

<210> SEQ ID NO 22
<211> LENGTH: 25
<212> TYPE: RNA
<213> ORGANISM: Aedes aegypti

<400> SEQUENCE: 22
aaacgagaau uuguggaaau aguug 25

<210> SEQ ID NO 23
<211> LENGTH: 25
<212> TYPE: RNA
<213> ORGANISM: Aedes aegypti

<400> SEQUENCE: 23
ggucucuucu aucaagcaua agguc 25

<210> SEQ ID NO 24
<211> LENGTH: 25
<212> TYPE: RNA
<213> ORGANISM: Aedes aegypti

<400> SEQUENCE: 24
cuaucaagca uaaggucucu acagu 25

<210> SEQ ID NO 25
<211> LENGTH: 25
<212> TYPE: RNA
<213> ORGANISM: Aedes aegypti

<400> SEQUENCE: 25
aaagugcauc augugauaaa aucga 25

<210> SEQ ID NO 26
<211> LENGTH: 25
<212> TYPE: RNA
<213> ORGANISM: Aedes aegypti

<400> SEQUENCE: 26
auuaugaaca acauguuuaa auaaa 25

<210> SEQ ID NO 27
<211> LENGTH: 25
<212> TYPE: RNA
<213> ORGANISM: Aedes aegypti

<400> SEQUENCE: 27
ugcaaagaaa cguuacuaua ucuug 25

<210> SEQ ID NO 28
<211> LENGTH: 25
<212> TYPE: RNA
<213> ORGANISM: Aedes aegypti

<400> SEQUENCE: 28
gaagcauuca aacaugcuua cggca 25

<210> SEQ ID NO 29
<211> LENGTH: 25
<212> TYPE: RNA
<213> ORGANISM: Aedes aegypti

<400> SEQUENCE: 29
cggaggucau uucuucauca aagaa 25

<210> SEQ ID NO 30
<211> LENGTH: 25
<212> TYPE: RNA
<213> ORGANISM: Aedes aegypti

<400> SEQUENCE: 30
caugaaucau uugccaaaua ccucu 25

<210> SEQ ID NO 31
<211> LENGTH: 25
<212> TYPE: RNA
<213> ORGANISM: Aedes aegypti

<400> SEQUENCE: 31
gaauaaauug uuuuaggauc aagaa 25

<210> SEQ ID NO 32
<211> LENGTH: 25
<212> TYPE: RNA
<213> ORGANISM: Aedes aegypti

<400> SEQUENCE: 32
cagcaguacu gaauaaauug uuuua 25

<210> SEQ ID NO 33
<211> LENGTH: 25
<212> TYPE: RNA
<213> ORGANISM: Aedes aegypti

<400> SEQUENCE: 33
gaccuggaac augggaauau cgaua 25

<210> SEQ ID NO 34
<211> LENGTH: 25
<212> TYPE: RNA
<213> ORGANISM: Aedes aegypti

<400> SEQUENCE: 34
ggcuaugcaa accaauucaa aauca 25

<210> SEQ ID NO 35
<211> LENGTH: 25
<212> TYPE: RNA
<213> ORGANISM: Aedes aegypti

<400> SEQUENCE: 35
guggcauuaa ugcagcaaau aauca 25

<210> SEQ ID NO 36
<211> LENGTH: 25
<212> TYPE: RNA
<213> ORGANISM: Aedes aegypti

<400> SEQUENCE: 36
cugaagcguu uccaacgaaa caagu 25

<210> SEQ ID NO 37
<211> LENGTH: 25
<212> TYPE: RNA
<213> ORGANISM: Aedes aegypti

<400> SEQUENCE: 37
caguuuauuc auaaguaauc aucua 25

<210> SEQ ID NO 38
<211> LENGTH: 25
<212> TYPE: RNA
<213> ORGANISM: Aedes aegypti

<400> SEQUENCE: 38
ggacaguuuc cuacuaucaa aaccg 25

<210> SEQ ID NO 39
<211> LENGTH: 25
<212> TYPE: RNA
<213> ORGANISM: Aedes aegypti

<400> SEQUENCE: 39
guaaacauga gaauugaaau ucaua 25

<210> SEQ ID NO 40
<211> LENGTH: 25
<212> TYPE: RNA
<213> ORGANISM: Aedes aegypti

<400> SEQUENCE: 40
aaccagaauc gguaaccuaa auugu 25

<210> SEQ ID NO 41
<211> LENGTH: 25
<212> TYPE: RNA
<213> ORGANISM: Aedes aegypti

<400> SEQUENCE: 41
gaacaugcua ugaaagaaua uccug 25

<210> SEQ ID NO 42
<211> LENGTH: 25
<212> TYPE: RNA
<213> ORGANISM: Aedes aegypti

<400> SEQUENCE: 42
aaaauaucga uggagaugau cugca 25

<210> SEQ ID NO 43
<211> LENGTH: 25
<212> TYPE: RNA
<213> ORGANISM: Aedes albopictus

<400> SEQUENCE: 43
gcaucaagcu ugaugaugaa auuua 25

<210> SEQ ID NO 44
<211> LENGTH: 25
<212> TYPE: RNA
<213> ORGANISM: Aedes albopictus

<400> SEQUENCE: 44
aaacuuggca gaaggcuaaa gcaau 25

<210> SEQ ID NO 45
<211> LENGTH: 25
<212> TYPE: RNA
<213> ORGANISM: Aedes albopictus

<400> SEQUENCE: 45
auaaagggaa uuuacgauca ugaau 25

<210> SEQ ID NO 46
<211> LENGTH: 25
<212> TYPE: RNA
<213> ORGANISM: Anopheles gambiae

<400> SEQUENCE: 46
agccacgugg augcaugaua aucga 25

<210> SEQ ID NO 47
<211> LENGTH: 25
<212> TYPE: RNA
<213> ORGANISM: Anopheles gambiae

<400> SEQUENCE: 47
cguggaugca ugauaaucga auagu 25

<210> SEQ ID NO 48
<211> LENGTH: 25
<212> TYPE: RNA
<213> ORGANISM: Culex quinquefasciatus

<400> SEQUENCE: 48
agcuuucuga agaagcccau cucga 25

<210> SEQ ID NO 49
<211> LENGTH: 25
<212> TYPE: RNA
<213> ORGANISM: Culex quinquefasciatus

<400> SEQUENCE: 49
caauccacag cguugagcuu ucuga 25

<210> SEQ ID NO 50
<211> LENGTH: 25
<212> TYPE: RNA
<213> ORGANISM: Culex quinquefasciatus

<400> SEQUENCE: 50
agaauaucga uggagaugau cugca 25

<210> SEQ ID NO 51
<211> LENGTH: 25
<212> TYPE: RNA
<213> ORGANISM: Culex quinquefasciatus

<400> SEQUENCE: 51
acgauuuguu cauucagaau aucga 25

<210> SEQ ID NO 52
<211> LENGTH: 25
<212> TYPE: RNA
<213> ORGANISM: Culex quinquefasciatus

<400> SEQUENCE: 52
aucuugagga uagaauggca aacgc 25

<210> SEQ ID NO 53
<211> LENGTH: 17
<212> TYPE: DNA

<213> ORGANISM: Artificial Sequence
<220> FEATURE:
<223> OTHER INFORMATION: Description of Artificial Sequence: Synthetic primer

<400> SEQUENCE: 53
gtaaaacgac ggccagt 17

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cacacaggaa acagctatga ccat 24

<210> SEQ ID NO 55
<211> LENGTH: 2706
<212> TYPE: DNA
<213> ORGANISM: Aedes aegypti

<400> SEQUENCE: 55
taattttacc atggattcag tagtttctac aataaaattc atttcagtgt ggatggatca 60
aggtcggtca cactacggat acggtgagga tacgttcctt ggggcccgct agatggaatg 120
aggcgatagt tggatgttcc ctaattggga taaaccccaa ctaaagagca agcgtatgtc 180
aatgtcttta tgtttaactg tccttataat tttgaataaa atgagtacag catgtattta 240
taatattgta cacactcagt tttcgtttct cagttcggta atttatttta cggttttcga 300
ctgtaaaatg taaagtttac cgacctatca gctcattttg ttgaaattta ctgttattca 360
gtacacattt tcaactttta ctgaatacag taattgcatt tactgagtgt ttcgtaaatg 420
tttgaattta ctgaaactca tcagtaaata gaaaaagtca gtaaaaataa ttactgagtt 480
atcggttcag gatatgcttt actgaacagt cctcaaaacg aaaggaaaac attatcgagc 540
gcatgcatag aaatgtcaaa aacaattcgg tgactttatc ataaatttca acggattctt 600
ggtatcgctt cttgaatgga aatcgttttt gattgtttat gctgtgcttg gcttactgat 660
ggtaggtaca ttgttagatt atttgactcc cgactatcag atattgcaga aaataagaat 720
cattttgtga ttagatttca ctcaatcgat caaatcgttg caaattaatt tcgtcggtgg 780
tgaaaagcag gagcggatct ttccgttacc agttatgttt ttcttgtaat tcctactcaa 840
attccatcgt gattcaacca gggatgagaa aagtactgga gaaaacattt accgcctcta 900
catttacatc ttcctacacg accatcaaaa tccaaagcaa accatgacgg ttcaaaacaa 960
aaaatgtcac ggctcttcaa aaaatgtaat cttcttcttc ctaacgtttt tcaaccccga 1020
attcgaaatg actcgagcac agtggtgaca cgatttttgc ggttttcggg gtcttgcatt 1080
tttgctcgat aaaggcagta tgaaattgaa cttgtttata tgtaacgtaa cggaatgatt 1140
gtggtctttc tgttagagct aatagatttc aattagttga aaacacaagc gaaatattag 1200
cgattgaatg atttaacact tttttcaatc attctgcttg gaatggctgc ccaaaaatgg 1260
tcatagtgga gagacaaaaa cagtcaagca gtgtgtgaac cgttggcagc gcaacgcctg 1320
atggtattga tgctgctgct gctttgtgtt ttggtggaat ggcagaatcg atgaactgtg 1380
gtgaattgtg gtcacagttc ccaagactgg attcaacaca tttctaattc cgaaataatc 1440
gagtgaacga atcttattaa gattctgcga ttgtcagtaa tcctattctg ctacgcaacc 1500
caaatttttg gtgccttttg ttgaatccta ccatgaggag ctggcatacg tatttgttgt 1560
tgaaaagatc cgtccagaaa gtgcttggac ggaagttctg gctgatgaaa tgcacaattg 1620
aataaatcta agaggcaaaa cgggattatt taggaatact gggtttcatt taataagctg 1680
agaaactcag caaattattg taaataaacc aatttcaccg aaaaagacag cgttgtatgt 1740
gcagcaaaaa ctactgacaa aatcagcatt ttttgacagc gcatgaatct atagctttac 1800
ggagttttcg gtagcaatat tttttactga gttaactctg ctgttcaaaa acccagtaaa 1860
ttttactgac ttcggtaatc aaatctaagt gtgtaactag tttgttcaat agtggttatc 1920
acgcccaata gtatgggtgc cctagtgtag atgtagttgt gaaccttaca cgctaacata 1980
aaagtaccca ttaaatgggt ttctagtacc catttttatg gtcagtatgg agttgtcaga 2040
aaaagagtac ttttcagtga cataaaaaag ggtactttaa cctcattatg aagtattctt 2100
ccagctaata taaatgggta catagtacac atgatgtagt ttgcaaggca atagcgccat 2160
tttcaatttc agttgttttt cagctcggtg ttaatgaaaa aaagtcaggg tttatttcat 2220
tgttcgacaa ataaataatt atggaggagc agattgcacg cactctttgc gacacgtaag 2280
taatatcagc atatacttct cagaaagtag atcttttaac aatcgttttt ctgattgtag 2340
atttttggat gactgcagct gagttcaatt ccaactgcag cgatttccta agtacctggg 2400
tcgtctacta aatgatcata tacatgttga attattgttt tgttaaatta tgaaataaat 2460
gtatgatgta ttttattaat tccgttattt atgctgttat tcattatatg gaactttcta 2520
aaccaaagct tttgtcataa cctcaatcca ctgcttcgct cataaaataa tggggtttta 2580
ttacccatgt tcatatcgga ggtcaagagt gataaatacc cattatttga agttcgaagc 2640
gaatactctt taatgagtaa gtcgagttta ctctttaaat gagttaaacc acttttcttg 2700
aaaatg 2706

<210> SEQ ID NO 56
<211> LENGTH: 1237
<212> TYPE: DNA
<213> ORGANISM: Aedes aegypti

<400> SEQUENCE: 56
tttggtggaa tggcagaatc gatgaactgt ggtgaattgt ggtcacagtt cccaagactg 60
gattcaacac atttctaatt ccgaaataat cgagtgaacg aatcttatta agattctgcg 120
attgtcagta atcctattct gctacgcaac ccaaattttt ggtgcctttt gttgaatcct 180
accatgagga gctggcatac gtatttgttg ttgaaaagat ccgtccagaa agtgcttgga 240
cggaagttct ggctgatgaa atgcacaatt gaataaatct aagaggcaaa acgggattat 300
ttaggaatac tgggtttcat ttaataagct gagaaactca gcaaattatt gtaaataaac 360
caatttcacc gaaaaagaca gcgttgtatg tgcagcaaaa actactgaca aaatcagcat 420
tttttgacag cgcatgaatc tatagcttta cggagttttc ggtagcaata ttttttactg 480
agttaactct gctgttcaaa aacccagtaa attttactga cttcggtaat caaatctaag 540
tgtgtaacta gtttgttcaa tagtggttat cacgcccaat agtatgggtg ccctagtgta 600
gatgtagttg tgaaccttac acgctaacat aaaagtaccc attaaatggg tttctagtac 660
ccatttttat ggtcagtatg gagttgtcag aaaaagagta cttttcagtg acataaaaaa 720
gggtacttta acctcattat gaagtattct tccagctaat ataaatggtt gtttttcagc 780
tcggtgttaa tgaaaaaaag tcagggttta tttcattgtt cgacaaataa ataattatgg 840

```
aggagcagat tgcacgcact ctttgcgaca catttttgga tgactgcagc tgagttcaat     900

tccaactgca gcgatttcct aagtacctgg gtcgtctact aaatgatcat atacatgttg     960

aattattgtt ttgttaaatt atgaaataaa tgtatgatgt attttattaa ttccgttatt    1020

tatgctgtta ttcattatat ggaactttct aaaccaaagc ttttgtcata acctcaatcc    1080

actgcttcgc tcataaaata atggggtttt attacccatg ttcatatcgg aggtcaagag    1140

tgataaatac ccattatttg aagttcgaag cgaatactct ttaatgagta agtcgagttt    1200

actctttaaa tgagttaaac cacttttctt gaaaatg                             1237
```

<210> SEQ ID NO 57
<211> LENGTH: 635
<212> TYPE: DNA
<213> ORGANISM: Aedes aegypti

<400> SEQUENCE: 57

```
taattttacc atggattcag tagtttctac aataaaattc atttcagtgt ggatggatca      60

aggtcggtca cactacggat acggtgagga tacgttcctt ggggcccgct agatggaatg     120

aggcgatagt tggatgttcc ctaattggga taaaccccaa ctaaagagca agcttgtttt     180

tcagctcggt gttaatgaaa aaaagtcagg gtttatttca ttgttcgaca aataaataat     240

tatggaggag cagattgcac gcactctttg cgacacattt ttggatgact gcagctgagt     300

tcaattccaa ctgcagcgat ttcctaagta cctgggtcgt ctactaaatg atcatataca     360

tgttgaatta ttgttttgtt aaattatgaa ataaatgtat gatgtatttt attaattccg     420

ttatttatgc tgttattcat tatatggaac tttctaaacc aaagcttttg tcataacctc     480

aatccactgc ttcgctcata aaataatggg gttttattac ccatgttcat atcggaggtc     540

aagagtgata aatacccatt atttgaagtt cgaagcgaat actctttaat gagtaagtcg     600

agtttactct ttaaatgagt taaaccactt ttctt                                635
```

<210> SEQ ID NO 58
<211> LENGTH: 625
<212> TYPE: DNA
<213> ORGANISM: Aedes aegypti

<400> SEQUENCE: 58

```
taattttacc atggattcag tagtttctac aataaaattc atttcagtgt ggatggatca      60

aggtcggtca cactacggat acggtgagga tacgttcctt ggggcccgct agatggaatg     120

aggcgatagt tggatgttcc ctaattggga taaaccccaa ctaaagagca agcctcggtg     180

ttaatgaaaa aaagtcaggg tttatttcat tgttcgacaa ataaataatt atggaggagc     240

agattgcacg cactctttgc gacacatttt tggatgactg cagctgagtt caattccaac     300

tgcagcgatt tcctaagtac ctgggtcgtc tactaaatga tcatatacat gttgaattat     360

tgttttgtta aattatgaaa taaatgtatg atgtatttta ttaattccgt tatttatgct     420

gttattcatt atatggaact ttctaaacca aagcttttgt cataacctca atccactgct     480

tcgctcataa aataatgggg ttttattacc catgttcata tcggaggtca agagtgataa     540

atacccatta tttgaagttc gaagcgaata ctctttaatg agtaagtcga gtttactctt     600

taaatgagtt aaaccacttt tcttg                                           625
```

<210> SEQ ID NO 59
<211> LENGTH: 2481
<212> TYPE: DNA
<213> ORGANISM: Aedes aegypti

<400> SEQUENCE: 59

```
taattttacc atggattcag tagtttctac aataaaattc atttcagtgt ggatggatca     60
aggtcggtca cactacggat acggtgagga tacgttcctt ggggcccgct agatggaatg    120
aggcgatagt tggatgttcc ctaattggga taaaccccaa ctaaagagca agcgtatgtc    180
aatgtcttta tgtttaactg tccttataat tttgaataaa atgagtacag catgtattta    240
taatattgta cacactcagt tttcgtttct cagttcggta atttatttta cggttttcga    300
ctgtaaaatg taaagtttac cgacctatca gctcattttg ttgaaattta ctgttattca    360
gtacacattt tcaactttta ctgaatacag taattgcatt tactgagtgt ttcgtaaatg    420
tttgaattta ctgaaactca tcagtaaata gaaaaagtca gtaaaaataa ttactgagtt    480
atcggttcag gatatgcttt tactgaacag tcctcaaaac gaaaggaaaa cattatcgag    540
cgcatgcata gaaatgtcaa aaacaattcg gtgactttat cataaatttc aacggattct    600
tggtatcgct tcttgaatgg aaatcgtttt tgattgttta tgctgtgctt ggcttactga    660
tggtaggtac attgttagat tatttgactc ccgactatca gatattgcag aaaataagaa    720
tcattttgtg attagatttc actcaatcga tcaaatcgtt gcaaattaat ttcgtcggtg    780
gtgaaaagca ggagcggatc tttccgttac cagttatgtt ttcttgtaat tcctactcaa    840
attccatcgt gattcaacca gggatgagaa aagtactgga gaaaacattt accgcctcta    900
catttacatc ttcctacacg accatcaaaa tccaaagcaa accatgacgg ttcaaaacaa    960
aaaatgtcac ggctcttcaa aaaatgtaat cttcttcttc ctaacgtttt tcaaccccga   1020
attcgaaatg actcgagcac agtggtgaca cgatttttgc ggttttcggg gtcttgcatt   1080
tttgctcgat aaaggcagta tgaaattgaa cttgtttata tgtaacgtaa cggaatgatt   1140
gtggtctttc tgttagagct aatagatttc aattagttga aaacacaaac gaaatattag   1200
cgattgaatg atttaacact tttttcaatc attctgcttg gaatggctgc ccgaaaatgg   1260
tcatagtgga gagacaaaaa cagtcaagca gtgtgtgaac cgttggcagc gcaacgcctg   1320
atggtattga tgctgctgct gctttgtgtt ttggtggaat ggcagaatcg atgaactgtg   1380
gtgaattgtg gtcacagttc ccaagactgg attcaacaca tttctaattc cgaaataatc   1440
gagtgaacga atcttattaa gattctgcga ttgtcagtaa tcctattctg ctacgcaacc   1500
caaattttg gtgccttttg ttgaatccta ccatgaggag ctggcatacg tatttgttgt    1560
tgaaaagatc cgtccagaaa gtgcttggac ggaagttctg gctgatgaaa tgcacaattg   1620
aataaatcta agaggcaaaa cggatattt taggaatact gggtttcatt taataagctg    1680
agaaactcag caaattattg taaataaacc aatttcaccg aaaaagacag cgttgtatgt   1740
gcagcaaaaa ctactgacaa aatcagcatt tttgacagcg catgaatcta tagctttacg   1800
gagttttcgg tagcaatatt ttttactgag ttaactctgc tgttcaaaaa cccagtaaat   1860
tttactgact tcggtaatca aatctaagtg tgtaactagt ttgttcaata gtggttatca   1920
cgcccaatag tatgggtgcc ctagtgtaga tgtagttgtg aaccttacac gctaacataa   1980
aagtacccat taaatgggtt tctagtaccc atttttatgg tcagtatgga gttgtcagaa   2040
aaagagtact tttcagtgac ataaaaaagg gtactttaac ctcattatga agtattcttc   2100
cagctaatat aaatgggtac atagtacaca tgatgtagtt tgcaaggcaa tagcgccatt   2160
ttcaatttca gttgtttttc agctcggtgt taatgaaaaa aagtcagggt ttatttcatt   2220
gttcgacaaa taaataatta tggaggagca gattgcacgc actctttgcg acacgtaagt   2280
```

```
aatatcagca tatacttctc agaaagtaga tcttttaaca atcgtttttc tgattgtaga   2340

tttttggatg actgcagctg agttcaatgc caactgcagc gatttcctaa gtacctgggt   2400

cgtctactaa atgatcatat acatgttgaa ttattgtttt gttaaattat gaaataaatg   2460

tatgatgtat tttattaatt c                                             2481
```

<210> SEQ ID NO 60
<211> LENGTH: 577
<212> TYPE: DNA
<213> ORGANISM: Aedes aegypti

<400> SEQUENCE: 60

```
aatctatagc tttacggagt tttcggtagc aatatttttt actgagttaa ctctgctgtt     60

caaaaaccca gtaaatttta ctgacttcgg taatcaaatc taagtgtgta actagtttgt    120

tcaatagtgg ttatcacgcc caatagtatg ggtgccctag tgtagatgta gttgtgaacc    180

ttacacgcta acataaaagt acccattaaa tgggtttcta gtacccattt ttatggtcag    240

tatggagttg tcagaaaaag agtacttttc agtgacataa aaaagggtac tttaacctca    300

ttatgaagta ttcttccagc taatataaat ggttgttttt cagctcggtg ttaatgaaaa    360

aaagtcaggg tttatttcat tgttcgacaa ataaataatt atggaggagc agattgcacg    420

cactctttgc gacacatttt tggatgactg cagctgagtt caatgccaac tgcagcgatt    480

tcctaagtac ctgggtcgtc tactaaatga tcatatacat gttgaattat tgttttgtta    540

aattatgaaa taaatgtatg atgtatttta ttaattc                             577
```

<210> SEQ ID NO 61
<211> LENGTH: 418
<212> TYPE: DNA
<213> ORGANISM: Aedes aegypti

<400> SEQUENCE: 61

```
taattttacc atggattcag tagtttctac aataaaattc atttcagtgt ggatggatca     60

aggtcggtca cactacggat acggtgagga tacgttcctt ggggcccgct agatggaatg    120

aggcgatagt tggatgttcc ctaattggga taaaccccaa ctaaagagca agcttgtttt    180

tcagctcggt gttaatgaaa aaaagtcagg gtttatttca ttgttcgaca aataaataat    240

tatggaggag cagattgcac gcactctttg cgacacattt ttggatgact gcagctgagt    300

tcaatgccaa ctgcagcgat ttcctaagta cctgggtcgt ctactaaatg atcatataca    360

tgttgaatta ttgttttgtt aaattatgaa ataaatgtat gatgtatttt attaattc      418
```

<210> SEQ ID NO 62
<211> LENGTH: 407
<212> TYPE: DNA
<213> ORGANISM: Aedes aegypti

<400> SEQUENCE: 62

```
taattttacc atggattcag tagtttctac aataaaattc atttcagtgt ggatggatca     60

aggtcggtca cactacggat acggtgagga tacgttcctt ggggcccgct agatggaatg    120

aggcgatagt tggatgttcc ctaattggga taaaccccaa ctaaagagca agcctcggtg    180

ttaatgaaaa aaagtcaggg tttatttcat tgttcgacaa ataaataatt atggaggagc    240

agattgcacg cactctttgc gacacatttt tggatgactg cagctgagtt caatgccaac    300

tgcagcgatt tcctaagtac ctgggtcgtc tactaaatga tcatatacat gttgaattat    360

tgttttgtta aattatgaaa taaatgtatg atgtatttta ttaattc                  407
```

<210> SEQ ID NO 63
<211> LENGTH: 514
<212> TYPE: DNA
<213> ORGANISM: Aedes aegypti

<400> SEQUENCE: 63

```
taacataaaa gtacccatta aatgggtttc tagtacccat ttttatggtc agtatggagt     60

tgtcagaaaa agagtacttt tcagtgacat aaaaaagggt actttaacct cattatgaag    120

tattcttcca gctaatataa atgggtacat agtacacatg atgtagtttg caaggcaata    180

gcgccatttt caatttcagt tgtttttcag ctcggtgtta atgaaaaaaa gtcagggttt    240

atttcattgt tcgacaaata aataattatg gaggagcaga ttgcacacac tctttgcgac    300

acgtaagtaa tatcagcata tacttctcag aaagtagatc ttttaacaat cgtttttctg    360

attgtagatt tttggatgac tgcagctgag ttcaatgcca actgcagcga tttccgtagt    420

acctgggtcg tctactaaat gatcatatac atgttgaatt attgttttct taaattatga    480

aataaatgta cgatgtattt tattaattcc gtta                                514
```

<210> SEQ ID NO 64
<211> LENGTH: 449
<212> TYPE: DNA
<213> ORGANISM: Aedes aegypti

<400> SEQUENCE: 64

```
taacataaaa gtacccatta aatgggtttc tagtacccat ttttatggtc agtatggagt     60

tgtcagaaaa agagtacttt tcagtgacat aaaaaagggt actttaacct cattatgaag    120

tattcttcca gctaatataa atgggtacat agtacacatg atgtagtttg caaggcaata    180

gcgccatttt caatttcagt tgtttttcag ctcggtgtta atgaaaaaaa gtcagggttt    240

atttcattgt tcgacaaata aataattatg gaggagcaga ttgcacacac tctttgcgac    300

acatttttgg atgactgcag ctgagttcaa tgccaactgc agcgatttcc gtagtacctg    360

ggtcgtctac taaatgatca tatacatgtt gaattattgt tttcttaaat tatgaaataa    420

atgtacgatg tattttatta attccgtta                                      449
```

<210> SEQ ID NO 65
<211> LENGTH: 524
<212> TYPE: DNA
<213> ORGANISM: Aedes aegypti

<400> SEQUENCE: 65

```
tgggtacacg ctaacataaa agtacccatt aaatgggttt ctagtaccca tttttatggt     60

cagtatggag ttgtcagaaa aagagtactt ttcagtgaca taaaaaaggg tactttaacc    120

tcattatgaa gtattcttcc agctaatata aatgggtaca tagtacacat gatgtagttt    180

gcaaggcaat agcgccattt tcaatttcag ttgtttttcc gctcggtgtt aatgaaaaaa    240

gtcagggttt atttcattgt tcgacaaata aataattatg gaggagcaga ttgcacgcac    300

tctttgcgac acgtaagtaa tatcagcata tacttctcag aaagtagatc ttttaacaat    360

cgtttttctg attgtagatt tttggatgac tgcagctgag ttcaatgcca actgcagcga    420

tttccgtagt acctgggtcg tctactaaat gatcatatac atgttgaatt attgttttgt    480

taaattatga aataaatgta cgatgtattt tattaattcc gtta                    524
```

<210> SEQ ID NO 66

<211> LENGTH: 459
<212> TYPE: DNA
<213> ORGANISM: Aedes aegypti

<400> SEQUENCE: 66

```
tgggtacacg ctaacataaa agtacccatt aaatgggttt ctagtaccca tttttatggt     60

cagtatggag ttgtcagaaa aagagtactt ttcagtgaca taaaaaaggg tactttaacc    120

tcattatgaa gtattcttcc agctaatata aatgggtaca tagtacacat gatgtagttt    180

gcaaggcaat agcgccattt tcaatttcag ttgtttttcc gctcggtgtt aatgaaaaaa    240

gtcagggttt atttcattgt tcgacaaata aataattatg gaggagcaga ttgcacgcac    300

tctttgcgac acatttttgg atgactgcag ctgagttcaa tgccaactgc agcgatttcc    360

gtagtacctg ggtcgtctac taaatgatca tatacatgtt gaattattgt tttgttaaat    420

tatgaaataa atgtacgatg tattttatta attccgtta                           459
```

<210> SEQ ID NO 67
<211> LENGTH: 562
<212> TYPE: DNA
<213> ORGANISM: Aedes aegypti

<400> SEQUENCE: 67

```
agaaaaataa aacatcggca ataatcggcg tgacgatagc ctgcacgcta acataaaagt     60

acccattaaa tgggtttcta gtacccattt ttatggtcag tatggagttg tcagaaaaag    120

agtacttttc agtgacataa aaaagggtac tttaacctca ttatgaagta ttcttccagc    180

taatataaat gggtacatag tacacatgat gtagtttgca aggcaatagc gccattttca    240

atttcagttg tttttcagct cggtgttaat gaaaaaaagt cagggtttat ttcattgttc    300

gacaaataaa taattatgga ggagcagatt gcacacactc tttgcgacac gtaagtaata    360

tcagcatata cttctcagaa agtagatctt ttaacaatcg tttttctgat tgtagatttt    420

tggatgactg cagctgagtt caatgccaac tgcagcgatt tccgtagtac ctgggtcgtc    480

tactaaatga tcatatacat gttgaattat tgttttctta aattatgaaa taaatgtacg    540

atgtatttta ttaattccgt ta                                             562
```

<210> SEQ ID NO 68
<211> LENGTH: 497
<212> TYPE: DNA
<213> ORGANISM: Aedes aegypti

<400> SEQUENCE: 68

```
agaaaaataa aacatcggca ataatcggcg tgacgatagc ctgcacgcta acataaaagt     60

acccattaaa tgggtttcta gtacccattt ttatggtcag tatggagttg tcagaaaaag    120

agtacttttc agtgacataa aaaagggtac tttaacctca ttatgaagta ttcttccagc    180

taatataaat gggtacatag tacacatgat gtagtttgca aggcaatagc gccattttca    240

atttcagttg tttttcagct cggtgttaat gaaaaaaagt cagggtttat ttcattgttc    300

gacaaataaa taattatgga ggagcagatt gcacacactc tttgcgacac atttttggat    360

gactgcagct gagttcaatg ccaactgcag cgatttccgt agtacctggg tcgtctacta    420

aatgatcata tacatgttga attattgttt tcttaaatta tgaaataaat gtacgatgta    480

ttttattaat tccgtta                                                   497
```

<210> SEQ ID NO 69
<211> LENGTH: 542

<212> TYPE: DNA
<213> ORGANISM: Aedes aegypti

<400> SEQUENCE: 69

```
atgagtgtgt tcacttttcc atacacgcta acataaaagt acccattaaa tgggtttcta     60
gtacccattt ttatggtcag tatggagttg tcagaaaaag agtacttttc agtgacataa    120
aaaagggtac tttaacctca ttatgaagta ttcttccagc taatataaat gggtacatag    180
tacacatgat gtagtttgca aggcaatagc gccattttca atttcagttg tttttcagct    240
cggtgttaat gaaaaaaagt cagggtttat ttcattgttc gacaaataaa taattatgga    300
ggagcagatt gcacacactc tttgcgacac gtaagtaata tcagcatata cttctcagaa    360
agtagatctt ttaacaatcg tttttctgat tgtagatttt tggatgactg cagctgagtt    420
caatgccaac tgcagcgatt tcctaagtac ctgggtcgtc tactaaatga tcatatacat    480
gttgaattat tgttttgtta aattatgaaa taaatgtacg atgtatttta ttaattccgt    540
ta                                                                   542
```

<210> SEQ ID NO 70
<211> LENGTH: 477
<212> TYPE: DNA
<213> ORGANISM: Aedes aegypti

<400> SEQUENCE: 70

```
atgagtgtgt tcacttttcc atacacgcta acataaaagt acccattaaa tgggtttcta     60
gtacccattt ttatggtcag tatggagttg tcagaaaaag agtacttttc agtgacataa    120
aaaagggtac tttaacctca ttatgaagta ttcttccagc taatataaat gggtacatag    180
tacacatgat gtagtttgca aggcaatagc gccattttca atttcagttg tttttcagct    240
cggtgttaat gaaaaaaagt cagggtttat ttcattgttc gacaaataaa taattatgga    300
ggagcagatt gcacacactc tttgcgacac atttttggat gactgcagct gagttcaatg    360
ccaactgcag cgatttccta agtacctggg tcgtctacta aatgatcata tacatgttga    420
attattgttt tgttaaatta tgaaataaat gtacgatgta ttttattaat tccgtta       477
```

<210> SEQ ID NO 71
<211> LENGTH: 619
<212> TYPE: DNA
<213> ORGANISM: Aedes aegypti

<400> SEQUENCE: 71

```
atgtcaaaac acactacctc cactattgga gctacctcca ctaagggagc aaatggcaaa     60
ttatccaaga acatctacat ctggctttag aaattctgta cacgctaaca taaaagtacc    120
cattaaatgg gtttctagta cccatttta tggtcagtat ggagttgtca gaaaaagagt    180
acttttcagt gacataaaaa agggtacttt aacctcatta tgaagtattc ttccagctaa    240
tataaatggg tacatagtac acatgatgta gtttgcaagg caatagcgcc attttcaatt    300
tcagttgttt ttcagctcgg tgttaatgaa aaaaagtcag ggtttatttc attgttcgac    360
aaataaataa ttatggatga gcagattgca cgcactcttt gcgacacgta agtaatatca    420
gcatatactt ctcagaaagt agatctttta acaatcgttt ttctgattgt agatttttgg    480
atgactgcag ctgagttcaa tgccaactgc agcgatttcc gtagtacctg ggtcgtctac    540
taaatgatga tatacatgtt gaattattgt tttgttaaat tatgaaataa atgtacgatg    600
tattttatta attccgtta                                                 619
```

<210> SEQ ID NO 72
<211> LENGTH: 554
<212> TYPE: DNA
<213> ORGANISM: Aedes aegypti

<400> SEQUENCE: 72
atgtcaaaac acactacctc cactattgga gctacctcca ctaagggagc aaatggcaaa 60
ttatccaaga acatctacat ctggctttag aaattctgta cacgctaaca taaaagtacc 120
cattaaatgg gtttctagta cccattttta tggtcagtat ggagttgtca gaaaaagagt 180
acttttcagt gacataaaaa agggtacttt aacctcatta tgaagtattc ttccagctaa 240
tataaatggg tacatagtac acatgatgta gtttgcaagg caatagcgcc attttcaatt 300
tcagttgttt ttcagctcgg tgttaatgaa aaaaagtcag ggtttatttc attgttcgac 360
aaataaataa ttatggatga gcagattgca cgcactcttt gcgacacatt tttggatgac 420
tgcagctgag ttcaatgcca actgcagcga tttccgtagt acctgggtcg tctactaaat 480
gatgatatac atgttgaatt attgttttgt taaattatga aataaatgta cgatgtattt 540
tattaattcc gtta 554

<210> SEQ ID NO 73
<211> LENGTH: 482
<212> TYPE: DNA
<213> ORGANISM: Aedes aegypti

<400> SEQUENCE: 73
atgaaatgag tttcttgtac ccatttttat ggccagtatg gaattgtcag aaaaagggta 60
cttttctgtg acataaaaaa tgggtacttt aacctcattg tgaagtatcc ttccagctaa 120
tataaatggg taaatagtgc acatgatagt ttgcaaatca acatcgccat tttcaattt 180 ctgtttattt ttaccgctcg gtgttagtga aaagttagtg gttttatcaa ttgtacgata 240
tattcttatg gacgaaaaga ttgttcatac tattttcgac acgtaagtag aatctgcggt 300
tactttcccg taaattgatc tattaataac cggttttctg gtagtagatt tgtggatgac 360
cgcatcagcg tagttcattg ccgactgcag cgatttcgtg agtgcctggg ttgtctgcta 420
gatgatcgca tacgtgttgg aattcatttt ttaactttga aataaatgtg cgttgtattt 480
ta 482

<210> SEQ ID NO 74
<211> LENGTH: 417
<212> TYPE: DNA
<213> ORGANISM: Aedes aegypti

<400> SEQUENCE: 74
atgaaatgag tttcttgtac ccatttttat ggccagtatg gaattgtcag aaaaagggta 60
cttttctgtg acataaaaaa tgggtacttt aacctcattg tgaagtatcc ttccagctaa 120
tataaatggg taaatagtgc acatgatagt ttgcaaatca acatcgccat tttcaattt 180 ctgtttattt ttaccgctcg gtgttagtga aaagttagtg gttttatcaa ttgtacgata 240
tattcttatg gacgaaaaga ttgttcatac tattttcgac acatttgtgg atgaccgcat 300
cagcgtagtt cattgccgac tgcagcgatt tcgtgagtgc ctgggttgtc tgctagatga 360
tcgcatacgt gttggaattc attttttaac tttgaaataa atgtgcgttg tatttta 417

<210> SEQ ID NO 75
<211> LENGTH: 928

<212> TYPE: DNA
<213> ORGANISM: Aedes aegypti

<400> SEQUENCE: 75
ttgttctggt gttgagtgat tgtaagtgtt cgtagttcag tgtgtagtgt ttttgagatt 60
ttgtttaaat ttaaaacgag aatttgtgga aatagttgca ggtagtgttt gtaattgtcg 120
tgcagttttc tccgtcaaca aaccccatgt tagtccgtag tatagtagcc taccatagaa 180
tgtcaccatc atccatccaa catacgatgc ttccatcacc caccaccaga gggataggca 240
gagtctattg gtaaccaaaa acggataatg aaacgaatta tcaagatgga cggtctaacg 300
ggcacgatga tttctctgag tcgacacgaa tggtctgggt cactgaccag gacttagaaa 360
acagtgaccc aggtttacta aaaatcactt tccttgtaac cctcaaccaa atacggtcgt 420
aaactggaag cgtaagctag tgatagttaa ttagaacacg aaaagacgca gaggagttga 480
gtgaagtgga ataggacagc aggtaatcag gttcttcctc caaggccgct ctcaacaaac 540
ctaacacctt attatggatt cgtagaaccc cgctgttttg gacagaactt cggttctggc 600
ggttcatcaa ccaacccccc ccccccctta cgttgtgggc agttccggcg aagacgccgt 660
tgaccgagtc cgtcaccata ctcggaggct cggggaatgg acgaggtcca gaaatgacgt 720
catcgtcatc ccaaaatgga aggagtagga gagaagccga ccatcatcgt agacacagca 780
atggagaagg tcgtggtgat ggatggtgga agaagagggg ccccgaagaa gttagaagaa 840
aaggacaggt tagagtagat taagaaagtg ggaaagctgt gaaagtaaag gccggaaaag 900
tccggaataa atgtagtttg tgtcgaaa 928

<210> SEQ ID NO 76
<211> LENGTH: 865
<212> TYPE: DNA
<213> ORGANISM: Aedes aegypti

<400> SEQUENCE: 76
ttgttctggt gttgagtgat tgtaagtgtt cgtagttcag tgtgtagtgt ttttgagatt 60
ttgtttaaat ttaaaacgag aatttgtgga aatagttgca ggtagtgttt gtaattgtcg 120
tgcagttttc tccgtcaaca aaccccatgt tagtccgtag tatagtagcc taccatagaa 180
tgtcaccatc atccatccaa catacgatgc ttccatcacc caccaccaga gggataggca 240
gagtctattg gtaaccaaaa acggataatg aaacgaatta tcaagatgga cggtctaacg 300
ggcacgatga tttctctgag tcgacacgaa tggtctgggt cactgaccag gacttagaaa 360
acagtgaccc aggtttacta aaaatcactt tccttgtaac cctcaaccaa atacggtcgt 420
aaactggaag cgtaagctag tgatagttaa ttagaacacg aaaagacgca gaggagttga 480
gtgaagtgga ataggacagc agaaccccgc tgttttggac agaacttcgg ttctggcggt 540
tcatcaacca accccccccc cccttacgt tgtgggcagt tccggcgaag acgccgttga 600
ccgagtccgt caccatactc ggaggctcgg ggaatggacg aggtccagaa atgacgtcat 660
cgtcatccca aaatggaagg agtaggagag aagccgacca tcatcgtaga cacagcaatg 720
gagaaggtcg tggtgatgga tggtggaaga agaggggccc cgaagaagtt agaagaaaag 780
gacaggttag agtagattaa gaaagtggga aagctgtgaa agtaaaggcc ggaaaagtcc 840
ggaataaatg tagtttgtgt cgaaa 865

<210> SEQ ID NO 77
<211> LENGTH: 787
<212> TYPE: DNA

<213> ORGANISM: Aedes aegypti

<400> SEQUENCE: 77

```
aaccccatgt tagtccgtag tatagtagcc taccatagaa tgtcaccatc atccatccaa      60
catacgatgc ttccatcacc caccaccaga gggataggca gagtctattg gtaaccaaaa     120
acggataatg aaacgaatta tcaagatgga cggtctaacg ggcacgatga tttcacggag     180
tcgacacgaa tggtctgggt cactgaccag gacttaaagg acagtgaccc aggtttacta     240
aaaatcactt ttcttgtaat cctcaaccaa atacggtcgt aaactggaag cgtaagctag     300
tgatagttaa ttagaacacg aaaagacgca gaggagttga gtgaagtgga ataggacagc     360
aggtaatcag gttcttcctc caaggccgct ctcaacaaac ctaacacctt attatggatt     420
cgtagaaccc cgctgttttg gacagaactt cggttctggc ggttcagcaa ccgacccccc     480
cccctttac gttgtgggca gttccggcga aaacgccgtt gaccgagtcc gtcaccatac     540
tcggaggctc ggggaatgga cgaggtccag aaatgccgtc atcgtcatcc caaaatggaa     600
ggagtaggag agaagccgac catcatcgta gacacagcaa tggagaaggt cgtggtgatg     660
gatggtggaa gaagaggggc cccgaagaag ttagaagaaa aggacaggtt agagtagatt     720
aagaaagtgg gaaagctgtg aaagtaaagg ccggaaaagt ccggaataaa tgtagtttgt     780
gtcgaaa                                                               787
```

<210> SEQ ID NO 78
<211> LENGTH: 724
<212> TYPE: DNA
<213> ORGANISM: Aedes aegypti

<400> SEQUENCE: 78

```
aaccccatgt tagtccgtag tatagtagcc taccatagaa tgtcaccatc atccatccaa      60
catacgatgc ttccatcacc caccaccaga gggataggca gagtctattg gtaaccaaaa     120
acggataatg aaacgaatta tcaagatgga cggtctaacg ggcacgatga tttcacggag     180
tcgacacgaa tggtctgggt cactgaccag gacttaaagg acagtgaccc aggtttacta     240
aaaatcactt ttcttgtaat cctcaaccaa atacggtcgt aaactggaag cgtaagctag     300
tgatagttaa ttagaacacg aaaagacgca gaggagttga gtgaagtgga ataggacagc     360
agaaccccgc tgttttggac agaacttcgg ttctggcggt tcagcaaccg accccccccc     420
cctttacgtt gtgggcagtt ccggcgaaaa cgccgttgac cgagtccgtc accatactcg     480
gaggctcggg gaatggacga ggtccagaaa tgccgtcatc gtcatcccaa aatggaagga     540
gtaggagaga agccgaccat catcgtagac acagcaatgg agaaggtcgt ggtgatggat     600
ggtggaagaa gaggggcccc gaagaagtta gaagaaaagg acaggttaga gtagattaag     660
aaagtgggaa agctgtgaaa gtaaaggccg gaaaagtccg gaataaatgt agtttgtgtc     720
gaaa                                                                  724
```

<210> SEQ ID NO 79
<211> LENGTH: 2116
<212> TYPE: DNA
<213> ORGANISM: Aedes aegypti

<400> SEQUENCE: 79

```
cgtaaataac actgcaccgc tcaaacgtca gatagtgaac tcgtgcatcg gtccattgtg      60
gtgatttcga aatgtcaaac tattgattgt tgtgaaatgg atgcaattga gatggtgatg     120
atcatgtggt aagtgcgatg aaattttatc tgagaatcgt ttctttgccg gccagtgaaa     180
```

```
tatccccgta gattgacggc caaaatcaac ccggaaaatt ttcactagag aagaataaat    240
tctcaaatcg aagtccatca catttaagta attaattata actttgaaaa ttgaggttat    300
gttttatgct tctcaaaaaa atttgatgat aattagattt tatttttatt attgctagtc    360
tttggaataa tttcgtgggt tcatttgaat tcagttttga aaacttttct ccttaatatt    420
cctaacaatt tctatcctac aataaattaa attgataaaa attacataat aaaaatcata    480
acaattcaac taaatttaca acacatgcac aaaaactaaa ataaagaaat ggccatcatg    540
caaaataatt acaaaattta caagagaaaa atctcatatt ttttttggtt gaattaacga    600
gtttttggtt taagaagtcc tcctagacaa agctattaac aggaaacact tcacaaccaa    660
aactcccaca acacaaatat acacgcaatc aatgcttttt cttttaggta ctacgaccat    720
tcatctctag tggcttcatt cagctttaac actgcccctg attaaacgac tgattacaat    780
caggacagct gccgataatg aaggctagta gacgtccttc tgtctcacta ccacaatggg    840
tactcagtga gtagatcttc atgaacatgg gcccaattaa cacaaattaa aacttcctaa    900
gaatcttctt acaatcactg cctccgcagc attgagaaaa gacgtcgaag aggtcaagca    960
tccgaagagc atcgcgtacg aagactgaat gaaatagtgg ctctagaaga actattaaca   1020
gaggtaacta tccatatcag ttgtactacc cattcgctac acacttgcct attaacgtct   1080
ttctcacttt caggaactct gtccgtgctg agacgaactt ccctggattc gagttatgta   1140
acacccacat gatttcactt tcggtgagta aactcagcaa ctctcattgc tcctacaact   1200
acaagaaacc cacaatccgg cttcctctca gacacctcta gtgttctacc ggaatccctg   1260
aaaaagaaga acttttaact tttcagttca tctccaagta gtcagctatc agtgtatgtg   1320
agagacctag tggtcttgta gctactctta ctgcttcttc agcatacctg ctctcatttt   1380
actctcaaca gagtctgaaa atcatttggc cttagtaccc gaattcaaat tcgcagtact   1440
aggactgata ccaaacaaaa aaacacagcc aaatcagatt gaggcaaatc tttgaccggg   1500
agaacaacat tgtagaaaac tctaggaatt cttacctaaa agaattagat tttctaaatg   1560
gttcattgat aaaaaaaaaa cagtctccaa cacgcaaaca gtcgtttgtg tgtggaaact   1620
caactcttct caaacatcaa actctcattt ctagtgatgc tctactacta tctacttatt   1680
ctctttctct ctcatggact gtaagggatc gttcaaatat tacgtaacgc actaggggga   1740
gggagggggt ccagcggagt gttacggttc atacaaaaat ttcaaatttt ccatacaaaa   1800
cctgttacgt gggggaggga gggggtctag aagtgactaa ttttgcgtta cgtaatattt   1860
gaatcgtccc taatatgcaa tttgtcggaa tccttaatga gttttattta tgaaacattt   1920
cagttaacta ataattcatt tttgtattat ttcaggtgtt tcaactccac agtgacgaaa   1980
atgctcatca tatcaatcac cacttctgaa tgggtgttgt cgcgcaacgt agtttgcaat   2040
gaaatttaaa attaaaaaga actatttatg agctaagagt atcacaaatt tgaaaaccta   2100
gttaattgaa aatgcc                                                   2116
```

```
<210> SEQ ID NO 80
<211> LENGTH: 1252
<212> TYPE: DNA
<213> ORGANISM: Aedes aegypti

<400> SEQUENCE: 80

taaataacac tgcaccgctc aaacgtcaga tagtgaactc gtgcatcggt ccattgtggt     60
gatttcgaaa tgtcaaacta ttgattgttg tgaaatggat gcaattgaga tggtgatgat    120
```

```
catgtggtaa gtgcgatgaa attttatctg agaatcgttt ctttgccggc cagtgaaata    180
tccccgtaga ttgacggcca aaatcaaccc ggaaaatttt cactagagaa gaataaattc    240
tcaaatcgaa gtccatcaca tttaagtaat taattataac tttgaaaatt gaggttatgt    300
tttatgcttc tcaaaaaaat ttgatgataa ttagatttta tttttattat tgctagtctt    360
tggaataatt tcgtgggttc atttgaattc agttttgaaa acttttctcc ttaatattcc    420
taacaatttc tatcctacaa taaattaaat tgataaaaat tacataataa aaatcataac    480
aattcaacta aatttacaac acatgcacaa aaactaaaat aaagaaatgg ccatcatgca    540
aaataattac aaaatttaca agagaaaaat ctcatatttt ttttggttga attaacgagt    600
ttttggttta agaagtcctc ctagacaaag ctattaacag gaaacacttc acaaccaaaa    660
ctcccacaac acaaatatac acgcaatcaa tgctttttct tttaggtact acgaccattc    720
atctctagtg gcttcattca gctttaacac tgcccctgat taaacgactg attacaatca    780
ggacagctgc cgataatgaa ggctagtaga cgtccttctg tctcactacc acaatgggta    840
ctcagtgagt agatcttcat gaacatgggc ccaattaaca caaattaaaa cttcctaaga    900
atcttcttac aatcactgcc tccgcagcat tgagaaaaga cgtcgaagag gtcaagcatc    960
cgaagagcat cgcgtacgaa gactgaatga aatagtggct ctagaagaac tattaacaga   1020
ggaactctgt ccgtgctgag acgaacttcc ctggattcga gttatgtaac acccacatga   1080
tttcactttc ggtgtttcaa ctccacagtg acgaaaatgc tcatcatatc aatcaccact   1140
tctgaatggg tgttgtcgcg caacgtagtt tgcaatgaaa tttaaaatta aaaagaacta   1200
tttatgagct aagagtatca caaatttgaa aacctagtta attgaaaatg cc           1252
```

<210> SEQ ID NO 81
<211> LENGTH: 675
<212> TYPE: DNA
<213> ORGANISM: Aedes aegypti

<400> SEQUENCE: 81

```
cgtaaataac actgcaccgc tcaaacgtca gatagtgaac tcgtgcatcg gtccattgtg     60
gtgatttcga aatgtcaaac tattgattgt tgtgaaatgg atgcaattga gatggtgatg    120
atcatgtggt actacgacca ttcatctcta gtggcttcat tcagctttaa cactgcccct    180
gattaaacga ctgattacaa tcaggacagc tgccgataat gaaggctagt agacgtcctt    240
ctgtctcact accacaatgg gtactcagtg agtagatctt catgaacatg ggcccaatta    300
acacaaatta aaacttccta agaatcttct tacaatcact gcctccgcag cattgagaaa    360
agacgtcgaa gaggtcaagc atccgaagag catcgcgtac gaagactgaa tgaaatagtg    420
gctctagaag aactattaac agaggaactc tgtccgtgct gagacgaact tccctggatt    480
cgagttatgt aacacccaca tgatttcact ttcggtgttt caactccaca gtgacgaaaa    540
tgctcatcat atcaatcacc acttctgaat gggtgttgtc gcgcaacgta gtttgcaatg    600
aaatttaaaa ttaaaaagaa ctatttatga gctaagagta tcacaaattt gaaaacctag    660
ttaattgaaa atgcc                                                     675
```

<210> SEQ ID NO 82
<211> LENGTH: 1232
<212> TYPE: DNA
<213> ORGANISM: Aedes aegypti

<400> SEQUENCE: 82

```
attgtggtga tttcgaaatg tcaaactatt gattgttgtg aaatggatgc aactgagatg     60
```

```
gtgatgatca tgaggtaagt gcgatgaaat tttatctgag aattgttact ttgccggcca    120
gtgaaatatc cccgtagatt gacggccaaa atcaacccgg aaaatggatt ttcactagag    180
aggtataaat tctcaaattg aagtccatca catttcagta attaattata acattgaaga    240
gtgaggttat gttctatgcc tctcaaacaa attttatgat agaatttctt taattattgc    300
tagtctttgg tataattttg tgggttcatt tgaattcagt tttgaaaaat tttctcctta    360
atattcctac caatttctat cctacaataa attaaattga taaaaattac ataataaaac    420
tcataacaat tcaactaaat ttacaacaca tgcacaaaaa ctaaaataaa gaaatggcca    480
tcatgcaaaa tatttacaaa atttacaaga gaaaaatctc atttttggtt taattaacga    540
gtatttggtt taggaagtcc tcctagacaa agctattaac aggaaacact tcacaaccaa    600
aactctcaca acacaaattt acacgcaatc aatgcttctt cttttaggta ctacgaccat    660
tcatctttaa tggcttcatt cagctttaac actgcacctg ataaaacgat tgtttacaat    720
caggacagtt gccgataatg aaggctagta gacgtccttc tgtctcatca ccacaatggg    780
tactcagaat cttcttacaa tcactgcctc cgcagcattg agacaagacg tcgaagaggt    840
caagcatccg aagagcatcg cgtacgaaga ctggatggaa tagtggctct agaagaacta    900
ttaacagagg aactctgtcc gtgctgagac gaacttctct ggattcgagt tatgcaacac    960
tcacatgatc tcactttcgg tgtttcaact ccactgtgac gaaaatgctc atcatatcaa   1020
tcaccacttc tgaatgggtg ttgtcgcgca acgtaatttg caatgaaatt tgaaattaaa   1080
aagaactaat tacgagctaa gagtatcaca gtgcataatt tgataaccta gtaagttgaa   1140
aatgcctaaa aaattcgaaa atctagaaaa tttgaaaatt ctaattatac agataatcac   1200
acataactca ttgtaaataa aatctatggt tc                                 1232
```

```
<210> SEQ ID NO 83
<211> LENGTH: 1974
<212> TYPE: DNA
<213> ORGANISM: Aedes aegypti

<400> SEQUENCE: 83

attgtggtga tttcgaaatg tcaaactatt gattgttgtg aaatggatgc aactgagatg     60
gtgatgatca tgaggtaagt gcgatgaaat tttatctgag aattgttact ttgccggcca    120
gtgaaatatc cccgtagatt gacggccaaa atcaacccgg aaaatggatt ttcactagag    180
aggtataaat tctcaaattg aagtccatca catttcagta attaattata acattgaaga    240
gtgaggttat gttctatgcc tctcaaacaa attttatgat agaatttctt taattattgc    300
tagtctttgg tataattttg tgggttcatt tgaattcagt tttgaaaaat tttctcctta    360
atattcctac caatttctat cctacaataa attaaattga taaaaattac ataataaaac    420
tcataacaat tcaactaaat ttacaacaca tgcacaaaaa ctaaaataaa gaaatggcca    480
tcatgcaaaa tatttacaaa atttacaaga gaaaaatctc atttttggtt taattaacga    540
gtatttggtt taggaagtcc tcctagacaa agctattaac aggaaacact tcacaaccaa    600
aactctcaca acacaaattt acacgcaatc aatgcttctt cttttaggta ctacgaccat    660
tcatctttaa tggcttcatt cagctttaac actgcacctg ataaaacgat tgtttacaat    720
caggacagtt gccgataatg aaggctagta gacgtccttc tgtctcatca ccacaatggg    780
tactcagtga gtagatcttc atgaacatgg gcccaattaa tacacattaa aacttcctag    840
gaatcttctt acaatcactg cctccgcagc attgagacaa gacgtcgaag aggtcaagca    900
```

```
tccgaagagc atcgcgtacg aagactggat ggaatagtgg ctctagaaga actattaaca    960
gaggtaacta tccataccag ttgcactacc cattcgcttc acacttgcct atttacgtct   1020
ttcttatttt caggaactct gtccgtgctg agacgaactt ctctggattc gagttatgca   1080
acactcacat gatctcactt tcggtgagta aacttagcaa ctctcattgc tcctataact   1140
acaagaaacc cacaatccgg cttcctctca gacacctcta gtgttctacc ggaatccctg   1200
aaaaagaaga acttttaact tttcagttca tctccaagta gtcagctatc agtgtatgtg   1260
agagacctag tggtcttgta gctactctta ctgcttcttc agcatacctg ctctcatttt   1320
actctcaaca gagtctgaaa atcatttggc cttagtaccc gaattcaaat tcgcagtact   1380
aggactgata ccaaacaaaa aaacacagcc aaatcagatt gaggcaaatc tttgaccggg   1440
agaacaacat tgtagaaaac tctaggaatt cttacctaaa agaattagat tttctaaatg   1500
gttcattgat aaaaacctgt ctccaacacg caaacattcg tttgtgtgtg gaaacccaac   1560
tcttctcaaa catcaaactc tcacttctag tgatgctcta ctaatatcta cttattctct   1620
tctctctcaa ggactgcaat atgcaatttg tcggaatcct caatgagttt catttatgaa   1680
acatttcagt taactaataa ttcacttttg tttcatttca ggtgtttcaa ctccactgtg   1740
acgaaaatgc tcatcatatc aatcaccact tctgaatggg tgttgtcgcg caacgtaatt   1800
tgcaatgaaa tttgaaatta aaaagaacta attacgagct aagagtatca cagtgcataa   1860
tttgataacc tagtaagttg aaaatgccta aaaaattcga aaatctagaa aatttgaaaa   1920
ttctaattat acagataatc acacataact cattgtaaat aaaatctatg gttc         1974
```

<210> SEQ ID NO 84
<211> LENGTH: 1225
<212> TYPE: DNA
<213> ORGANISM: Aedes aegypti

<400> SEQUENCE: 84

```
attgtggtga tttcgaaatg tcaaactatt gattgttgtg aaatggatgc aactgagatg     60
gtgatgatca tgaggtaagt gcgatgaaat tttatctgag aattgttact ttgccggcca    120
gtgaaatatc cccgtagatt gacggccaaa atcaacccgg aaaatggatt ttcactagag    180
aggtataaat tctcaaattg aagtccatca catttcagta attaattata acattgaaga    240
gtgaggttat gttctatgcc tctcaaacaa attttatgat agaatttctt taattattgc    300
tagtctttgg tataattttg tgggttcatt tgaattcagt tttgaaaaat tttctcctta    360
atattcctac caatttctat cctacaataa attaaattga taaaaattac ataataaaac    420
tcataacaat tcaactaaat ttacaacaca tgcacaaaaa ctaaaataaa gaaatggcca    480
tcatgcaaaa tatttacaaa atttacaaga gaaaaatctc atttttggtt taattaacga    540
gtatttggtt taggaagtcc tcctagacaa agctattaac aggaaacact tcacaaccaa    600
aactctcaca acacaaattt acacgcaatc aatgcttctt cttttaggta ctacgaccat    660
tcatctttaa tggcttcatt cagctttaac actgcacctg ataaaacgat tgtttacaat    720
caggacagtt gccgataatg aaggctagta gacgtccttc tgtctcatca ccacaatggg    780
aatcttctta caatcactgc ctccgcagca ttgagacaag acgtcgaaga ggtcaagcat    840
ccgaagagca tcgcgtacga agactggatg gaatagtggc tctagaagaa ctattaacag    900
aggaactctg tccgtgctga gacgaacttc tctggattcg agttatgcaa cactcacatg    960
atctcacttt cggtgtttca actccactgt gacgaaaatg ctcatcatat caatcaccac   1020
ttctgaatgg gtgttgtcgc gcaacgtaat ttgcaatgaa atttgaaatt aaaaagaact   1080
```

aattacgagc taagagtatc acagtgcata atttgataac ctagtaagtt gaaaatgcct 1140
aaaaaattcg aaaatctaga aaatttgaaa attctaatta tacagataat cacacataac 1200
tcattgtaaa taaaatctat ggttc 1225

<210> SEQ ID NO 85
<211> LENGTH: 620
<212> TYPE: DNA
<213> ORGANISM: Aedes aegypti

<400> SEQUENCE: 85
gaaatggatg caactgagat ggtgatgatc atgaggtact acgaccattc atctttaatg 60
gcttcattca gctttaacac tgcacctgat aaaacgattg tttacaatca ggacagttgc 120
cgataatgaa ggctagtaga cgtccttctg tctcatcacc acaatgggta ctcagaatct 180
tcttacaatc actgcctccg cagcattgag acaagacgtc gaagaggtca agcatccgaa 240
gagcatcgcg tacgaagact ggatggaata gtggctctag aagaactatt aacagaggaa 300
ctctgtccgt gctgagacga acttctctgg attcgagtta tgcaacactc acatgatctc 360
actttcggtg tttcaactcc actgtgacga aaatgctcat catatcaatc accacttctg 420
aatgggtgtt gtcgcgcaac gtaatttgca atgaaatttg aaattaaaaa gaactaatta 480
cgagctaaga gtatcacagt gcataatttg ataacctagt aagttgaaaa tgcctaaaaa 540
attcgaaaat ctagaaaatt tgaaaattct aattatacag ataatcacac ataactcatt 600
gtaaataaaa tctatggttc 620

<210> SEQ ID NO 86
<211> LENGTH: 613
<212> TYPE: DNA
<213> ORGANISM: Aedes aegypti

<400> SEQUENCE: 86
gaaatggatg caactgagat ggtgatgatc atgaggtact acgaccattc atctttaatg 60
gcttcattca gctttaacac tgcacctgat aaaacgattg tttacaatca ggacagttgc 120
cgataatgaa ggctagtaga cgtccttctg tctcatcacc acaatgggaa tcttcttaca 180
atcactgcct ccgcagcatt gagacaagac gtcgaagagg tcaagcatcc gaagagcatc 240
gcgtacgaag actggatgga atagtggctc tagaagaact attaacagag gaactctgtc 300
cgtgctgaga cgaacttctc tggattcgag ttatgcaaca ctcacatgat ctcactttcg 360
gtgtttcaac tccactgtga cgaaaatgct catcatatca atcaccactt ctgaatgggt 420
gttgtcgcgc aacgtaattt gcaatgaaat ttgaaattaa aaagaactaa ttacgagcta 480
agagtatcac agtgcataat ttgataacct agtaagttga aaatgcctaa aaaattcgaa 540
aatctagaaa atttgaaaat tctaattata cagataatca cacataactc attgtaaata 600
aaatctatgg ttc 613

<210> SEQ ID NO 87
<211> LENGTH: 1247
<212> TYPE: DNA
<213> ORGANISM: Aedes aegypti

<400> SEQUENCE: 87
acggccattc atctctagtg ggcttcattc agctttaaca ctgcacctga ttaaacgact 60
gattacaatc aggacagctg ccgataatga aggctagtag acgtccttct gtctcactac 120

```
ccacaatggg gtactcagtg agtagatctt catgaacatg ggcccaatta acacaaatta    180
aaacttccta gaatcttctt acaatcactg cctccgcagc attgagaaaa gacgtcgaag    240
aggtcaagca tccgaagagc atcgcgtacg aagactgaat gaaatagtgg ctctagaaga    300
actattaaca gaggtaacta tccatatcag ttgtactacc cattcgctac acacttgcct    360
atttacgtcc ttctcacttt caggaactct gtccgtgctg agacgaactt ccctggattc    420
gagttatgta acacccacat gatttcactt tcggtgagta aactcagcaa ctctcattcc    480
tcctacaact acaagaaacc cacaatccgg cttcctctca gacacctcta gtgttctacc    540
ggaatccctg aaaaagaaga acttttaact tttcagttca tctccaagta gtcagctatc    600
agtgtatgtg agagacctag tggtctgtag ctactcttac tgcttcttca gcatacctgc    660
tctcatttta ctctcaacag atctgaaaat catttggcct tagtacccga attcaaattc    720
gcagttacta ggactgatac caaaacaaaa aaacacagcc aaatcattga ggcaatatct    780
ttgaccggtg aggaacaaca ttgtagaaaa ctctaggaat tcttacctaa aagaattaga    840
ttttctaaat gggatcattg ataaaaacct gtctccaaca cgcaaacagt cgttgtgtgt    900
ggaaacccaa ctcttctcaa acatcaaact ctcacttcta gtgatgctct actactatct    960
acttattctc ttctttctca tggactgcaa tatgcaattt gtcggaatcc tcaatgagtt   1020
tcattttatg aagcatttca gttaactaat aattcacttt tgtttcattt caggtgtttc   1080
aactccactg tgacgaaaat gcgcatcata tcaatcacca cttctgaatg ggtgttgtca   1140
cgcaacgtaa tttgccaatg aaatttgaaa ttaaaaagaa ctaattacga gctaaaagta   1200
tcacagtgca aaatttgata acctagtaaa ttgaaaatgc ctaaaaa                 1247
```

```
<210> SEQ ID NO 88
<211> LENGTH: 496
<212> TYPE: DNA
<213> ORGANISM: Aedes aegypti

<400> SEQUENCE: 88

acggccattc atctctagtg ggcttcattc agctttaaca ctgcacctga ttaaacgact     60
gattacaatc aggacagctg ccgataatga aggctagtag acgtccttct gtctcactac    120
ccacaatggg aatcttctta caatcactgc ctccgcagca ttgagaaaag acgtcgaaga    180
ggtcaagcat ccgaagagca tcgcgtacga agactgaatg aaatagtggc tctagaagaa    240
ctattaacag aggaactctg tccgtgctga gacgaacttc cctggattcg agttatgtaa    300
cacccacatg atttcacttt cggtgtttca actccactgt gacgaaaatg cgcatcatat    360
caatcaccac ttctgaatgg gtgttgtcac gcaacgtaat ttgccaatga aatttgaaat    420
taaaaagaac taattacgag ctaaaagtat cacagtgcaa aatttgataa cctagtaaat    480
tgaaaatgcc taaaaa                                                    496
```

```
<210> SEQ ID NO 89
<211> LENGTH: 383
<212> TYPE: DNA
<213> ORGANISM: Aedes aegypti

<400> SEQUENCE: 89

gtcgtattcg gatcgcttat tgtggacagt tgtggacaaa tggacaagtt tttacatttt     60
cgggtaagtt taaaatcgaa aaacttcatt aatttcgtcg ttagctaaag aaatgccgtg    120
atctttgcag gtttgttgaa aaacgcagtt gcggactgga gccatggcag atttctacgg    180
ccaaaagcgg acgcatagaa aactgtattc cggtcaatgc gaggactaat gtctggaatt    240
```

agtataaact gcagattttt cagccttgga gaaaatttat agttaataag atgatgaaac 300
attgtagcat tgtaggttaa gtgcattacg ttattatttt aaattttata taagctataa 360
taaagtgttt tattgctcat tga 383

<210> SEQ ID NO 90
<211> LENGTH: 316
<212> TYPE: DNA
<213> ORGANISM: Aedes aegypti

<400> SEQUENCE: 90
gtcgtattcg gatcgcttat tgtggacagt tgtggacaaa tggacaagtt tttacatttt 60
cgggtttgtt gaaaaacgca gttgcggact ggagccatgg cagatttcta cggccaaaag 120
cggacgcata gaaaactgta ttccggtcaa tgcgaggact aatgtctgga attagtataa 180
actgcagatt tttcagcctt ggagaaaatt tatagttaat aagatgatga aacattgtag 240
cattgtaggt taagtgcatt acgttattat tttaaatttt atataagcta taataaagtg 300
ttttattgct cattga 316

<210> SEQ ID NO 91
<211> LENGTH: 383
<212> TYPE: DNA
<213> ORGANISM: Aedes aegypti

<400> SEQUENCE: 91
gtcgtattcg gatcgcttat tgtggacagt tgtggacaaa tggacaagtt tttacatttt 60
cgggtaagtt taaaatcgaa aaacttcatt aatttcgtcg ttagctaaag aaatgccgtg 120
atctttgcag gtttgttgaa aaacgcagtt gcggactgga gccatggcag atttctacgg 180
ccaaaagcgg acgcatagaa aactgtattc cggtcaatgc gaggactaat gtctggaatt 240
agtataaact gcagattttt cagccttgga gaaaatttat agttaataag atgatgaaac 300
attgtagcat tgtaggttaa gtgcattacg ttattatttt aaattttata taagctataa 360
taaagtgttt tattgctcat tga 383

<210> SEQ ID NO 92
<211> LENGTH: 316
<212> TYPE: DNA
<213> ORGANISM: Aedes aegypti

<400> SEQUENCE: 92
gtcgtattcg gatcgcttat tgtggacagt tgtggacaaa tggacaagtt tttacatttt 60
cgggtttgtt gaaaaacgca gttgcggact ggagccatgg cagatttcta cggccaaaag 120
cggacgcata gaaaactgta ttccggtcaa tgcgaggact aatgtctgga attagtataa 180
actgcagatt tttcagcctt ggagaaaatt tatagttaat aagatgatga aacattgtag 240
cattgtaggt taagtgcatt acgttattat tttaaatttt atataagcta taataaagtg 300
ttttattgct cattga 316

<210> SEQ ID NO 93
<211> LENGTH: 383
<212> TYPE: DNA
<213> ORGANISM: Aedes aegypti

<400> SEQUENCE: 93
gtcgtattcg gatcgcttat tgtggacagt tgtggacaaa tggacaagtt tttacatttt 60

```
cgggtaagtt taaaatcgaa aaacttcatt aatttcgtcg ttagctaaag aaatgccgtg    120

atctttgcag gtttgttgaa aaacgcagtt gcggactgga gccatggcag atttctacgg    180

ccaaaagcgg acgcatagaa aactgtattc cggtcaatgc gaggactaat gtctggaatt    240

agtataaact gcagattttt cagccttgga gaaaatttat agttaataag atgatgaaac    300

attgtagcat tgtaggttaa gtgcattacg ttattatttt aaattttata taagctataa    360

taaagtgttt tattgctcat tga                                            383
```

```
<210> SEQ ID NO 94
<211> LENGTH: 316
<212> TYPE: DNA
<213> ORGANISM: Aedes aegypti

<400> SEQUENCE: 94

gtcgtattcg gatcgcttat tgtggacagt tgtggacaaa tggacaagtt tttacatttt     60

cgggtttgtt gaaaaacgca gttgcggact ggagccatgg cagatttcta cggccaaaag    120

cggacgcata gaaaactgta ttccggtcaa tgcgaggact aatgtctgga attagtataa    180

actgcagatt tttcagcctt ggagaaaatt tatagttaat aagatgatga aacattgtag    240

cattgtaggt taagtgcatt acgttattat tttaaatttt atataagcta taataaagtg    300

ttttattgct cattga                                                    316
```

```
<210> SEQ ID NO 95
<211> LENGTH: 3205
<212> TYPE: DNA
<213> ORGANISM: Aedes aegypti

<400> SEQUENCE: 95

taaagtgtcc tagctaaaaa aaagtaaggt tacaaattat agtaaccatg tggtgtatat     60

aatagtttgt gctttttttt ctagtttgcc ctaaattacg attagtatcg aatgttagta    120

gttcaaatta gtggtataaa agtgttagta cggttagtaa tgtttactta cttacttatt    180

tggctttaca tcaattatct tgataaagcc tcgccaacaa tatttcgcca attccctcgg    240

ttcatggccg cttctctcca tcctcgactg tgacccacgc tctccaggtc ctggtgtacc    300

tggtcaatcc acctagctcg ctgcgcccca cgccttcttg ttccgaccgg attcgtggcg    360

aacaccatct ttacagggtt gttgtccggc attcttgcaa catgccctgc ccagcgtatc    420

cttccagctt tagctacctt cacgatactg ggttcgccgt agagttgagc gagctcgtgg    480

ttcatccttc gccgccacac gccgttctcc tgcacgccgc cgaagatcgt ccttagcact    540

cggcgttcga aaaccccaag agcttgcaag tcctcctcga gcatagtcca cgcctcatgc    600

ccatagagga ctaccggtct tatgagcgtt ttgtacatcg tgcatttggt gcgggggtga    660

atctttcttg accgcagttt cttctggagc ccatagtagg cacgacttcc gctgatgatg    720

tgccttcgta tttcccgact aacattgtta tcagccgtca acaaagatcc gaggtagacg    780

aactcgtcca ccacctcgaa ggtatccccg tctattgtaa cactgcttcc taggcgggcc    840

ctgtcgcgct cagttccgcc aaccagcatg tactttgttt tcgacgcatt caccattagc    900

ccgactcttg ttgcttcgcg tttcaggcgg gtgaacaaat ctgccaccgt ttcaaatttt    960

ctcccaataa tatccatgtc gtccgcgaag caaacaaatt gtccggatct cgtgaaaatc   1020

gtgcctcgac tgttaagtcc ggctctccgc atgacacctt caagcgcaat attgaacaac   1080

aggcacgaaa gtccgtcgcc ctgtcgtagt ccccgccgag actcgaacga actggagtgt   1140

tcgcccgaga tcttcacgca gttttgcaca ccgtccatcg ttgctctgat caatcttgtg   1200
```

```
agcttcccgg gaaagctgtt ctcgtccatg attttccata gctctaggcg gtcgatacta   1260

tcgtatgccg ccttgaaatc gatgaacaaa tggtgcgtag ggacctggta ctcacggcat   1320

ttctggagga tttgccgcac gaaaaagatc tggtccgttg tcgagcggcc gtcgatgaaa   1380

cctgcttgat aacttcccac gaactcgttt gctacaggtg atagacgacg gaagagaatc   1440

tgggatagca ctttataggc ggcgtttagg atggtgattg cacgataatt ttcacactcc   1500

agtttgtcgc ccttttgta gatagggcat ataacgcctt gcttccactc ctccggtagc   1560

tgttccgttt cccagattct gactatcagc cgatgcagac aagcggccaa cctgtccggg   1620

cccatcttga tgagttcggc tccgatacca tccttgccag cggctttgtt gttcttgagc   1680

tgttgaatgg catccttaac ttcccccatc gtgggagctg gttgatttcc gctgtccgct   1740

gtgctgacgt agccatcgct ttcgctgtcc tgaccttctg tgcctgtgtt ctctgcgcca   1800

ttcaggtgtt catcgtagtg ctgcttccac ctttcgatca cctcgcgtcc gtccgtcaag   1860

atgctcccat ccttatcccg gcacatctca gctcgcggca cgaagccttt gcgggatgtg   1920

ttgagcttct gatagaactt ccgcgtttct tgagaacggt acagcaactc catctcttgg   1980

cattccacct cttccaggcg gcgcttttg tcccggaata ggcgggtttg ctgtttccgc   2040

ttcagtctgt atcgttccac gttttgccgc gtaccatgct gcagcattgc agcccgcgct   2100

gcattcttct cctctaaaac ctccaggcac tcctcgtcga accaatcgtt tcttgagctc   2160

cgttccacat atccgacaac gctttcggca gcgtcgttaa tggctgcttt gactgtcctc   2220

cagcagtcct caagaggggc cctatcgagc tcgccctcat ccggcaacgc tgcctcaaga   2280

tgctgcgcgt acgcattggc gacatccggt tgtttcagcc gctcgagatt gtaccggggc   2340

gggcgtcggt accgtacata gtaatgttta aaatacgatt aatttgttag ttcctaatta   2400

aaaatatgtt aaaacagttg tgaacaagca gttaaacacg aaaacgaaca tctataacaa   2460

ttaccaactt ataacaaaga aaaggtaaag catctattgt aaaaattgta attgattgta   2520

acatttgtgt aaaatggtgg taaattgtga gagacgtatt ggtactaatc catatgggtt   2580

aggtccgaaa tcgggccttt tcttttgcg tttcctcgcg tggtttatcc cggaggaact   2640

tctttcatcc gcagtgaagc caaaggacca gtttggagtg taggaaagtt ggttggtgtg   2700

ccgataacca gcttagttcc gcccgccatc ttggagcgtc cgttccaaca atagcatcga   2760

cgccattttg aaatttcggc cattgcaaca tctttacggc ttccttcccg ctttcaacgt   2820

tcggtcagtc ggattaagac caatcccgac aaggaacccg aacgaaagaa gcccagctgg   2880

tgggccacag tccgtccagc aaccctacat tgccacaatc cgtccaacaa ccctacattt   2940

ccacaccggc aagaaacaga ttcgaaagaa gcccagctgg tgggccctag tccattcagc   3000

aatcacggaa tccagtcgat gaaggccatg ctggtgggcc atagtccgtt cagcagccat   3060

ctctgggaaa tagcttaacg ccctcggtcg aggaccgaat accgaccctc tttcgcccgt   3120

tttctcgcca acaacccgcc caattcgccg acatccagcc aagctagcca ctgttcatca   3180

ccatcaagcc tcgccaacaa cccac                                        3205
```

<210> SEQ ID NO 96
<211> LENGTH: 842
<212> TYPE: DNA
<213> ORGANISM: Aedes aegypti

<400> SEQUENCE: 96

```
taaagtgtcc tagctaaaaa aaagtaaggt tacaaattat agtaaccatg tggtgtatat     60
```

```
aatagtttgt gctttttttt ctagtttgcc ctaaattacg attagtatcg aatgttagta    120

gttcaaatta gtggtataaa agtgttagta cgttgtgaac aagcagttaa acacgaaaac    180

gaacatctat aacaattacc aacttataac aaagaaaagg tccgaaatcg ggccttttct    240

ttttgcgttt cctcgcgtgg tttatcccgg aggaacttct ttcatccgca gtgaagccaa    300

aggaccagtt tggagtgtag gaaagttggt tggtgtgccg ataaccagct tagttccgcc    360

cgccatcttg gagcgtccgt tccaacaata gcatcgacgc cattttgaaa tttcggccat    420

tgcaacatct ttacggcttc cttcccgctt tcaacgttcg gtcagtcgga ttaagaccaa    480

tcccgacaag gaacccgaac gaaagaagcc cagctggtgg gccacagtcc gtccagcaac    540

cctacattgc cacaatccgt ccaacaaccc tacatttcca caccggcaag aaacagattc    600

gaaagaagcc cagctggtgg gccctagtcc attcagcaat cacggaatcc agtcgatgaa    660

ggccatgctg gtgggccata gtccgttcag cagccatctc tgggaaatag cttaacgccc    720

tcggtcgagg accgaatacc gaccctcttt cgcccgtttt ctcgccaaca acccgcccaa    780

ttcgccgaca tccagccaag ctagccactg ttcatcacca tcaagcctcg ccaacaaccc    840

ac                                                                   842
```

<210> SEQ ID NO 97
<211> LENGTH: 631
<212> TYPE: DNA
<213> ORGANISM: Aedes aegypti

<400> SEQUENCE: 97

```
gctaaaaaag taaggttaca aattatagta accatgtggt gtatataatg gtttgtgctt     60

ttttttccta gtttgcccta aattacgatt agtatcgaat gttaatagtc caaattagtg    120

gtataaaagt gttagtacgg ttagtaattt tttaaatacg attaatttgt tagttcctaa    180

ttaaaattat gttaaaacag ttgtgaacaa gcagttagac acgaaaacga acatctataa    240

caattaccaa cttataacaa agaaaaggta aagcatctat tgtaaaaatt gtaattgatt    300

gtaaaattgt gtaaaatggt ggtaaattgt gagagacgta ttggtactaa tccatatggg    360

ttaggtccga aatcgggcct tttctttttg cgtttcctcg cgtggtttat cccggaggaa    420

cttctttcat ccgcagtgaa gccaaaggac cagtttggag tgtaggaaag ttggttggtg    480

tgccgataac cagcttagtt ccgcccgcca tcttggagcg tccgttccaa caatagcatc    540

gacgccattt tgaaatttcg gccattgcaa catctctacg gcttccttcc cgctttcaac    600

gttcggtcag tcggattaag accaatcccg a                                   631
```

<210> SEQ ID NO 98
<211> LENGTH: 473
<212> TYPE: DNA
<213> ORGANISM: Aedes aegypti

<400> SEQUENCE: 98

```
gctaaaaaag taaggttaca aattatagta accatgtggt gtatataatg gtttgtgctt     60

ttttttccta gtttgcccta aattacgatt agtatcgaat gttaatagtc caaattagtg    120

gtataaaagt gttagtacgt tgtgaacaag cagttagaca cgaaaacgaa catctataac    180

aattaccaac ttataacaaa gaaaaggtcc gaaatcgggc cttttctttt tgcgtttcct    240

cgcgtggttt atcccggagg aacttctttc atccgcagtg aagccaaagg accagtttgg    300

agtgtaggaa agttggttgg tgtgccgata accagcttag ttccgcccgc catcttggag    360

cgtccgttcc aacaatagca tcgacgccat tttgaaattt cggccattgc aacatctcta    420
```

cggcttcctt cccgctttca acgttcggtc agtcggatta agaccaatcc cga 473

<210> SEQ ID NO 99
<211> LENGTH: 440
<212> TYPE: DNA
<213> ORGANISM: Aedes aegypti

<400> SEQUENCE: 99
tcgaatgtta atagtccaaa ttagtggtat aaaagtgtta gtacggttag taattttta 60 aatacgatta atttgttagt tcctaattaa aattatgtta aaacagttgt gaacaagcag 120
ttagacacga aaacgaacat ctataacaat taccaactta taacaaagaa aaggtccgaa 180
atcgggcctt ttctttttgc gtttcctcgc gtggtttatc ccggaggaac ttctttcatc 240
cgcagtgaag ccaaaggacc agtttggagt gtaggaaagt tggttggtgt gccgataacc 300
agcttagttc cgcccgccat cttggagcgt ccgttccaac aatagcatcg acgccatttt 360
gaaatttcgg ccattgcaac atctctacgg cttccttccc gctttcaacg ttcggtcagt 420
cggattaaga ccaatcccga 440

<210> SEQ ID NO 100
<211> LENGTH: 1450
<212> TYPE: DNA
<213> ORGANISM: Aedes aegypti

<400> SEQUENCE: 100
agcttgttgg cgctgccaca atttccccag gtctgtccga acctgccagt aagcccctat 60
atccaattcc aactctccca aaaacatatg gacagcctta ctggcacggt aaacctagct 120
gtccatgctt aaaaagatcc gacaacgtca tttcctcaat tagcatatgt aacaatcttt 180
ctaactggta ttttctgaca gtggtttgag taagtccgac aaccgttacg agttgtgtcg 240
gcccaattgc taccctgcgc agaatggttg acaatccgac gaagtgtcaa acttcggcac 300
ttcgtcatcg ttcttattgg atcgagtggt ggtaatataa gacgaatcaa ggggattcgt 360
ccttctttgc cgtttgactt ttgaagaaaa tagtagtgcg cgcccgtaaa gtgtcctagc 420
taaaaaaagt aaggttacaa attatagtaa ccatgtggtg tatataatag tttgtgcttt 480
tttttctagt ttgccctaaa ttacgattag tatcgaatgt tagtagttca aattagtggt 540
ataaaagtgt tagtacggtt agtaatgttt aaaatacgat taatttgtta gttcctaatt 600
aaaaatatgt taaaacagtt gtgaacaagc agttaaacac gaaaacgaac atctataaca 660
attaccaact tataacaaag aaaaggtaaa gcatctattg taaaaattgt aattgattgt 720
aacatttgtg taaaatggtg gtaaattgtg agagacgtat tggtactaat ccatatgggt 780
taggtccgaa atcgggcctt ttctttttgc gtttcctcgc gtggtttatc ccggaggaac 840
ttctttcatc cgcagtgaag ccaaaggacc agtttggagt gtaggaaagt tggttggtgt 900
gccgataacc agcttagttc cgcccgccat cttggagcgt ccgttccaac aatagcatcg 960
acgccatttt gaaatttcgg ccattgcaac atctttacgg cttccttccc gctttcaacg 1020
ttcggtcagt cggattaaga ccaaacccga caaggaaccc gaacgaaaga agcccagctg 1080
gtgggccaca gtccgtccag caaccctaca ttgccacaat ccgtccaaca accctacatt 1140
tccacaccag caagaaacag attcgaaaga agcccagctg gtgggcccta gtccattcag 1200
caatcacgga atccagtcga tgaaggccat gctggtgggc catagtccgt tcagcagcca 1260
tctctgggaa atagcttaac gccctcggtc gaggaccgaa taccgaccct ctttcgcccg 1320

```
ttttctcgcc aacaacccgc ccaattcgcc gacatccagc caagctagcc actgttcatc   1380

accatcaagc ctcgccaaca acccaccaaa agcgcaagta ccatgtaacc gtctctccac   1440

cataccaata                                                          1450
```

<210> SEQ ID NO 101
<211> LENGTH: 1291
<212> TYPE: DNA
<213> ORGANISM: Aedes aegypti

<400> SEQUENCE: 101

```
agcttgttgg cgctgccaca atttccccag gtctgtccga acctgccagt aagcccctat     60

atccaattcc aactctccca aaaacatatg gacagcctta ctggcacggt aaacctagct    120

gtccatgctt aaaaagatcc gacaacgtca tttcctcaat tagcatatgt aacaatcttt    180

ctaactggta ttttctgaca gtggtttgag taagtccgac aaccgttacg agttgtgtcg    240

gcccaattgc taccctgcgc agaatggttg acaatccgac gaagtgtcaa acttcggcac    300

ttcgtcatcg ttcttattgg atcgagtggt ggtaatataa gacgaatcaa ggggattcgt    360

ccttctttgc cgtttgactt ttgaagaaaa tagtagtgcg cgcccgtaaa gtgtcctagc    420

taaaaaaagt aaggttacaa attatagtaa ccatgtggtg tatataatag tttgtgcttt    480

tttttctagt ttgccctaaa ttacgattag tatcgaatgt tagtagttca aattagtggt    540

ataaaagtgt tagtacgttg tgaacaagca gttaaacacg aaaacgaaca tctataacaa    600

ttaccaactt ataacaaaga aaaggtccga aatcgggcct tttctttttg cgtttcctcg    660

cgtggtttat cccggaggaa cttctttcat ccgcagtgaa gccaaaggac cagtttggag    720

tgtaggaaag ttggttggtg tgccgataac cagcttagtt ccgcccgcca tcttggagcg    780

tccgttccaa caatagcatc gacgccattt tgaaatttcg gccattgcaa catctttacg    840

gcttccttcc cgctttcaac gttcggtcag tcggattaag accaaacccg acaaggaacc    900

cgaacgaaag aagcccagct ggtgggccac agtccgtcca gcaaccctac attgccacaa    960

tccgtccaac aaccctacat ttccacacca gcaagaaaca gattcgaaag aagcccagct   1020

ggtgggccct agtccattca gcaatcacgg aatccagtcg atgaaggcca tgctggtggg   1080

ccatagtccg ttcagcagcc atctctggga aatagcttaa cgccctcggt cgaggaccga   1140

ataccgaccc tctttcgccc gttttctcgc caacaacccg cccaattcgc cgacatccag   1200

ccaagctagc cactgttcat caccatcaag cctcgccaac aacccaccaa aagcgcaagt   1260

accatgtaac cgtctctcca ccataccaat a                                  1291
```

<210> SEQ ID NO 102
<211> LENGTH: 1230
<212> TYPE: DNA
<213> ORGANISM: Aedes aegypti

<400> SEQUENCE: 102

```
agcttgttgg cgctgccaca atttccccag gtctgtccga acctgccagt aagcccctat     60

atccaattcc aactctccca aaaacatatg gacagcctta ctggcacggt aaacctagct    120

gtccatgctt aaaaagatcc gacaacgtca tttcctcaat tagcatatgt aacaatcttt    180

ctaactggta ttttctgaca gtggtttgag taagtccgac aaccgttacg agttgtgtcg    240

gcccaattgc taccctgcgc agaatggttg acaatccgac gaagtgtcaa acttcggcac    300

ttcgtcatcg ttcttattgg atcgagtggt ggtaatataa gacgaatcaa ggggattcgt    360

ccttctttgc cgtttgactt ttgaagaaaa tagtagtgcg cgcccgtaaa gtgtcctagc    420
```

taaaaaaatt tgccctaaat tacgattagt atcgaatgtt agtagttcaa attagtggta 480
taaaagtgtt agtacgttgt gaacaagcag ttaaacacga aaacgaacat ctataacaat 540
taccaactta taacaaagaa aaggtccgaa atcgggcctt ttctttttgc gtttcctcgc 600
gtggtttatc ccggaggaac ttctttcatc cgcagtgaag ccaaaggacc agtttggagt 660
gtaggaaagt tggttggtgt gccgataacc agcttagttc cgcccgccat cttggagcgt 720
ccgttccaac aatagcatcg acgccatttt gaaatttcgg ccattgcaac atctttacgg 780
cttccttccc gctttcaacg ttcggtcagt cggattaaga ccaaacccga caaggaaccc 840
gaacgaaaga agcccagctg gtgggccaca gtccgtccag caaccctaca ttgccacaat 900
ccgtccaaca accctacatt tccacaccag caagaaacag attcgaaaga agcccagctg 960
gtgggcccta gtccattcag caatcacgga atccagtcga tgaaggccat gctggtgggc 1020
catagtccgt tcagcagcca tctctgggaa atagcttaac gccctcggtc gaggaccgaa 1080
taccgaccct ctttcgcccg ttttctcgcc aacaacccgc ccaattcgcc gacatccagc 1140
caagctagcc actgttcatc accatcaagc ctcgccaaca acccaccaaa agcgcaagta 1200
ccatgtaacc gtctctccac cataccaata 1230

<210> SEQ ID NO 103
<211> LENGTH: 660
<212> TYPE: DNA
<213> ORGANISM: Aedes aegypti

<400> SEQUENCE: 103
aaatagtagt gcgcgccgta aagtgtccta gctaaaaaag taaggttaca aattatagta 60
accatgtggt gtatataatg gtttgtgctt ttttttctag tttgccctaa attacgatta 120
gtatcgaatg ttagtagtcc aaattagtgg tataaaagtg ttagtacggt tagtaatttt 180
ttaaatacga ttaatttgtt agttcctaat taaaattatg ttaaaacagt tgtgaacaag 240
cagttagaca cgaaaacgaa catctataac aattaccaac ttataacaaa gaaaaggtaa 300
agcatctatt gtaaaaattg taattgattg taaaattgtg taaaatggtg gtaaattgtg 360
agagacgtat tggtactaat ccatatgggt taggtccgaa atcgggcctt ttctttttgc 420
gtttcctcgc gtggtttatc ccggaggaac ttctttcatc cgcagtgaag ccaaaggacc 480
agtttggagt gtaggaaagt tggttggtgt gccgataacc agcttagttc cgcccgccat 540
cttggagcgt ccattccaac aatagcatcg acgccatttt gaaatttcgg ccattgcaac 600
atctctacgg cttccttccc gctttcaacg ttcggtcagt cggattaaga ccaatcccga 660

<210> SEQ ID NO 104
<211> LENGTH: 441
<212> TYPE: DNA
<213> ORGANISM: Aedes aegypti

<400> SEQUENCE: 104
aaatagtagt gcgcgccgta aagtgtccta gctaaaaaat ttgccctaaa ttacgattag 60
tatcgaatgt tagtagtcca aattagtggt ataaaagtgt tagtacgttg tgaacaagca 120
gttagacacg aaaacgaaca tctataacaa ttaccaactt ataacaaaga aaaggtccga 180
aatcgggcct tttctttttg cgtttcctcg cgtggtttat cccggaggaa cttctttcat 240
ccgcagtgaa gccaaaggac cagtttggag tgtaggaaag ttggttggtg tgccgataac 300
cagcttagtt ccgcccgcca tcttggagcg tccattccaa caatagcatc gacgccattt 360

```
tgaaatttcg gccattgcaa catctctacg gcttccttcc cgctttcaac gttcggtcag    420

tcggattaag accaatcccg a                                              441


<210> SEQ ID NO 105
<211> LENGTH: 1360
<212> TYPE: DNA
<213> ORGANISM: Aedes aegypti

<400> SEQUENCE: 105

catatggaca gccttactgg cacggtaaac ctagctgtcc atgcttaaaa agatccgaca     60

acgtcatttc ctcaattagc atatgtaaca atctttctaa ctggtatttt ctgacagtgg    120

tttgagtaag tccgacaacc gttacgagtt gtgtcggccc aattgctacc ctgcgcagaa    180

tggttgacaa tccgacgaag tgtcaaactt cggcacttcg tcatcgttct tattggatcg    240

agtggtggta atataagacg aatcaagggg attcgtcctt ctttgccgtt tgacttttga    300

agaaaatagt agtgcgcgcc gtaaagtgtc ctagctaaaa aagtaaggtt acaaattata    360

gtaaccatgt ggtgtatata atagtttgtg cttttttttct agtttgccct aaattacgat    420

tagtatcgaa tgttagtagt tcaaattagt ggtataaaag tgttagtacg gttagtaata    480

attaaaatac gattaatttg ttagttccta attaaaaata tgttaaaaca gttgtgaaca    540

agcagttaaa cacgaaaacg aacatctata acaattacca acttataaca aagaaaaggt    600

aaagcatcta ttgtaaaaat tgtaattgat tgtaaaattg tgtaaaatgg tggtaaattg    660

tgagagacgt attggtacta atccatatgg gttaggtccg aaatcgggcc ttttcttttt    720

gcgtttcctc gcgtggttta tcccggagga acttctttta tccgcagtga agccaaagga    780

ccagtttgga gtgtaggaaa gttggttggt gtgccgataa ccagcttagt tccgcccgcc    840

atcttggagc gtccgttcca acaatagcat cgacgccatt ttgaaatttc ggccattgca    900

acatctttac ggcttcctta ccgctttcaa cgttcggtca gtcggattaa gaccaatccc    960

gacaaggaac ccgaacgaaa gaagcccagc tggtgggcca cagtccgtcc agcaacccta   1020

cattgccaca atccgtccaa caaccctaca tttccacacc ggcaagaaac agattcgaaa   1080

gaagcccagc tggtgggccc tagtccattc agcaatcacg gaatccagtc gatgaaggcc   1140

atgctggtgg gtcatagtcc gttcagcagc catctcaggg aaatagctta acgccctcgg   1200

tcgaggaccg aataccgacc ctctttcgcc cgttttctcg ccaacaaccc gcccaattcg   1260

ccgacatcca gccaagttag ccaccgttca tcaccatcaa gcctcgccaa caacccacca   1320

aaagcgcaag taccatgtaa ccgtctctcc accataccaa                         1360


<210> SEQ ID NO 106
<211> LENGTH: 1142
<212> TYPE: DNA
<213> ORGANISM: Aedes aegypti

<400> SEQUENCE: 106

catatggaca gccttactgg cacggtaaac ctagctgtcc atgcttaaaa agatccgaca     60

acgtcatttc ctcaattagc atatgtaaca atctttctaa ctggtatttt ctgacagtgg    120

tttgagtaag tccgacaacc gttacgagtt gtgtcggccc aattgctacc ctgcgcagaa    180

tggttgacaa tccgacgaag tgtcaaactt cggcacttcg tcatcgttct tattggatcg    240

agtggtggta atataagacg aatcaagggg attcgtcctt ctttgccgtt tgacttttga    300

agaaaatagt agtgcgcgcc gtaaagtgtc ctagctaaaa aatttgccct aaattacgat    360

tagtatcgaa tgttagtagt tcaaattagt ggtataaaag tgttagtacg ttgtgaacaa    420
```

```
gcagttaaac acgaaaacga acatctataa caattaccaa cttataacaa agaaaaggtc    480

cgaaatcggg ccttttcttt ttgcgtttcc tcgcgtggtt tatcccggag gaacttcttt    540

tatccgcagt gaagccaaag gaccagtttg gagtgtagga aagttggttg gtgtgccgat    600

aaccagctta gttccgcccg ccatcttgga gcgtccgttc caacaatagc atcgacgcca    660

ttttgaaatt tcggccattg caacatcttt acggcttcct taccgctttc aacgttcggt    720

cagtcggatt aagaccaatc ccgacaagga acccgaacga aagaagccca gctggtgggc    780

cacagtccgt ccagcaaccc tacattgcca caatccgtcc aacaacccta catttccaca    840

ccggcaagaa acagattcga aagaagccca gctggtgggc cctagtccat tcagcaatca    900

cggaatccag tcgatgaagg ccatgctggt gggtcatagt ccgttcagca gccatctcag    960

ggaaatagct taacgccctc ggtcgaggac cgaataccga ccctctttcg cccgttttct   1020

cgccaacaac ccgcccaatt cgccgacatc cagccaagtt agccaccgtt catcaccatc   1080

aagcctcgcc aacaacccac caaaagcgca agtaccatgt aaccgtctct ccaccatacc   1140

aa                                                                  1142
```

<210> SEQ ID NO 107
<211> LENGTH: 660
<212> TYPE: DNA
<213> ORGANISM: Aedes aegypti

<400> SEQUENCE: 107

```
aaatagtagt gcgcgccgta aagtgtccta gctaaaaaag taaggttaca aattatagta     60

accatgtggt gtatataatg gtttgtgctt ttttttctag tttgccctaa attacgatta    120

gtatcgaatg ttagtagtcc aaattagtgg tataaaagtg ttagtacggt tagtaatttt    180

ttaaatacga ttaatttgtt agttcctaat taaaattatg ttaaaacagt tgtgaacaag    240

cagttagaca cgaaaacgaa catctataac aattaccaac ttataacaaa gaaaaggtaa    300

agcatctatt gtaaaaattg taattgattg taaaattgtg taaaatggtg gtaaattgtg    360

agagacgtat tggtactaat ccatatgggt taggtccgaa atcgggcctt ttcttttttgc    420

gtttcctcgc gtggtttatc ccggaggaac ttctttcatc cgcagtgaag ccaaaggacc    480

agtttggagt gtaggaaagt tggttggtgt gccgataacc agcttagttc cgcccgccat    540

cttggagcgt ccattccaac aatagcatcg acgccatttt gaaatttcgg ccattgcaac    600

atctctacgg cttccttccc gctttcaacg ttcggtcagt cggattaaga ccaatcccga    660
```

<210> SEQ ID NO 108
<211> LENGTH: 441
<212> TYPE: DNA
<213> ORGANISM: Aedes aegypti

<400> SEQUENCE: 108

```
aaatagtagt gcgcgccgta aagtgtccta gctaaaaaat ttgccctaaa ttacgattag     60

tatcgaatgt tagtagtcca aattagtggt ataaaagtgt tagtacgttg tgaacaagca    120

gttagacacg aaaacgaaca tctataacaa ttaccaactt ataacaaaga aaaggtccga    180

aatcgggcct tttctttttg cgtttcctcg cgtggtttat cccggaggaa cttctttcat    240

ccgcagtgaa gccaaaggac cagtttggag tgtaggaaag ttggttggtg tgccgataac    300

cagcttagtt ccgcccgcca tcttggagcg tccattccaa caatagcatc gacgccattt    360

tgaaatttcg gccattgcaa catctctacg gcttccttcc cgctttcaac gttcggtcag    420
```

tcggattaag accaatcccg a 441

<210> SEQ ID NO 109
<211> LENGTH: 418
<212> TYPE: DNA
<213> ORGANISM: Aedes aegypti

<400> SEQUENCE: 109
gttagacgcg aaaacgaaca tctataacaa ttaccaactt ataacaaaga aaaggtaaag 60
catctattgt aaaaattgta attgattgta aaattgtgta aaatggtggt aaattgtgag 120
agacgtattg gtactaatcc atatgggtta ggtccgaaat cgggcctttt ctttttgcgt 180
ttcctcgcgt ggtttatccc ggaggaactt ctttcatccg cagtgaagcc aaaggaccag 240
tttggagtgt aggaaagttg gttggtgtgc cgataaccag cttagttccg cccgccatct 300
tggagcgtcc gttccaacaa tagcatcgac gccattttga aatttcggcc attgcaacat 360
ctctacggct tccttcccgc tttcaacgtt cggtcagtcg gattaagacc aatcccga 418

<210> SEQ ID NO 110
<211> LENGTH: 321
<212> TYPE: DNA
<213> ORGANISM: Aedes aegypti

<400> SEQUENCE: 110
gttagacgcg aaaacgaaca tctataacaa ttaccaactt ataacaaaga aaaggtccga 60
aatcgggcct tttctttttg cgtttcctcg cgtggtttat cccggaggaa cttctttcat 120
ccgcagtgaa gccaaaggac cagtttggag tgtaggaaag ttggttggtg tgccgataac 180
cagcttagtt ccgcccgcca tcttggagcg tccgttccaa caatagcatc gacgccattt 240
tgaaatttcg gccattgcaa catctctacg gcttccttcc cgctttcaac gttcggtcag 300
tcggattaag accaatcccg a 321

<210> SEQ ID NO 111
<211> LENGTH: 662
<212> TYPE: DNA
<213> ORGANISM: Aedes aegypti

<400> SEQUENCE: 111
aaatagtagt gcgcgccgta aagtgtccta gctaaaaaaa gtaaggttac aaattatagt 60
aaccatgtgg tgtatataat agtttgtgct tttttttct agtttgccct aaattacgat 120
tagtatcgaa tgttagtagt ccaaattagt ggtataaaag tgttagtacg gttagtaatt 180
ttttaaatac gattaatttg ttagttccta attaaaatta tgttaaaaca gttgtgaaca 240
agcagttaga cacgaaaacg aacatctata acaattacca acttataaca aagaaaaggt 300
aaagcatcta ttgtaaaaat tgtaattgat tgtaaaattg tgtaaaatgg tggtaaattg 360
tgagagacgt attggtacta atccatatgg gttaggtccg aaatcgggcc ttttcttttt 420
gcgtttcctc gcgtggttta tcccggagga acttctttca tccgcagtga agccaaagga 480
ccagtttgga gtgtaggaaa gttggttggt gtgccgataa ccagcttagt tccgcccgcc 540
atcttggagc gtccgttcca acaatagcat cgacgccatt ttgaaatttc ggccattgca 600
acatctctac ggcttccttc ccgctttcaa cgttcggtca gtcggattaa gaccaatccc 660
ga 662

<210> SEQ ID NO 112
<211> LENGTH: 442

<212> TYPE: DNA
<213> ORGANISM: Aedes aegypti

<400> SEQUENCE: 112
aaatagtagt gcgcgccgta aagtgtccta gctaaaaaaa tttgccctaa attacgatta 60
gtatcgaatg ttagtagtcc aaattagtgg tataaaagtg ttagtacgtt gtgaacaagc 120
agttagacac gaaaacgaac atctataaca attaccaact tataacaaag aaaaggtccg 180
aaatcgggcc ttttcttttt gcgtttcctc gcgtggttta tcccggagga acttctttca 240
tccgcagtga agccaaagga ccagtttgga gtgtaggaaa gttggttggt gtgccgataa 300
ccagcttagt tccgcccgcc atcttggagc gtccgttcca acaatagcat cgacgccatt 360
ttgaaatttc ggccattgca acatctctac ggcttccttc ccgctttcaa cgttcggtca 420
gtcggattaa gaccaatccc ga 442

<210> SEQ ID NO 113
<211> LENGTH: 32767
<212> TYPE: DNA
<213> ORGANISM: Aedes aegypti

<400> SEQUENCE: 113
gctagtctac gtgtgttcaa atgtcactaa gctctataat caaaatagga aaaagaaaca 60
aaattattca gatttctttg aaacttttta tatattgtag actgaagtgt gtttaaatat 120
ttgattgact tcaaatctga ccaatatttt tggtgcttaa tcaacgatca gtggaatctg 180
tttttgtgga gtcatcttca gcaatcaggt ttgttatttt catttatcca cctgctgatt 240
ggccaaacat attgcttgta tccgtgtggg gcccagatgt ggttgttgcg ttcgtttttc 300
gaaacctccc gatggccgct aatgaaatga aaaaaaaaat agagttctgt tttcaatcat 360
ggtaaatatg aacttacagt ttaatgaata tccatgcgcc tgtaatcact gtcattttag 420
gcgatgtatc gcccctcttc ctgtttagaa actgatgtat aatcaaattt cattaaatta 480
cattttaact acaagacctt tggaaactga aaaccgatca gtgaattttc ccaacagttt 540
tttttctgtt cgttgtaccg cattgaacca cgttcgtccc acgtgttgaa atataattgt 600
acgcattcaa atcctaaatg tgtgacattg gcattacact gcagagcatg tggatactat 660
atgaaatggc agtacatttt attggaatct aatagttttt aaatgttgca catagatcaa 720
agtttgagac cctagtgtcg tgacgcaacc tggtttggac agtatcagcc gaattaagct 780
ggccaaattt tcttcactcc ttaaaagtgc gactaatcgc tctaaaattc tccaatagac 840
tgatttaatc atatcacggc agtggcaatg aaccctagac ggcaacgctt cggtaccgat 900
ccacgcactc gtgtttagct tcgtaagccg ctgtcctcag gacgcggagt aggcacacgc 960
tctccttcct tttcacactc tcgatggccg cttgcaatgc gttcctatgc gatcaaaagc 1020
cgaacgccct gctcacttcg tgtctgtctt tcagccgaag cattcgtctc cacccaaatt 1080
tcgggtcccg agcccaatca tatcccgaaa tctcatttga aacatccggc gctgcagagg 1140
aagactgcca taattatttc gcgcggcatc atttttattt tcatatttta tagcaggttt 1200
caaataggcg acgtacacgc taaacatttt taagtcatgt ctcatacttt tacctcatat 1260
ttctaatgaa atctatatct actacaatat tcccctcctc tactctctct gatatatata 1320
tatttttctg ttcgacaaag tatatatttt ttttttggtc tgtttttaat ttacgtgatg 1380
atccattgaa acttacataa aaacaagcat cagttcaagc ctgagtcatt tcaatgcata 1440
tttaaaaaat ggctgaattt aaaaagttga cattatctag taagttgaat tgacgcaaca 1500

```
ttgatttttt tctactcaag cctgagaaaa cgcattaact caaatttatc atattgagcc   1560
gaactatccc catttggtag atgcagattg ccctattcaa catcgtgagg aagagagata   1620
ataccgagtg atttgagatt gaaagaataa tcgatttact tataataact caataattaa   1680
gtaaaaaatc ttcttgtaag acaactttta gtgtactttt gcgtttcatc ttaaaaatca   1740
actgtaccaa aaaaagtaaa tgactccata gtgtggccag tttgatactg tttgactttt   1800
ctttttctta agcatactca gccagaagat gttcattgtt tcttcttaat ttccttatca   1860
aaccgaacac gtatttgttt ggaagtataa tcctaattga agctttaatt aaaaaaaata   1920
aagctgttac ccaaccagca ttaactctaa tcctaatcga atgaaaatcc aatccaattt   1980
taaaattaat ctgactccaa tccaaatcca atcacaaata aatcttattc aaatttaagc   2040
caaacacaat ccaaaatcaa tcctttaaat ccaaactcat caaaattcaa accgaatcca   2100
atctatatcg tatccttatc cgataaaaat ccgatccaat tttaattcaa atatgatcca   2160
atgctaattc aacaaaaatc cgatccgaat ccaatccaaa ttcaatttca acccaatgaa   2220
atttggatcc aaattaaatt ttaattcaat ccaaattgca ttcaaatcca atccaattta   2280
atctaaatca attaaaattc taaccgaatt ttattcacat caaatcctaa aacaatcaaa   2340
attcaaccaa ataaatatat tccaaatcca aattaaatct aaatctaatc catatccttt   2400
ctaaattcaa cacaaatcca agctaaataa aatcaaaacc aatccacctc taatccaaat   2460
ctagttcaat tcaaatcaaa ttccaatcaa aatcccatcg aaatccaatt taaattaaat   2520
tgaatcaaaa tgtaattcat atttttttat aaatttcagc cgaacctagt gcatactcag   2580
tctaaattta atgcagttca attcaaatcc gaacaaattc aaaccaattc aaatccaaat   2640
ctaactctaa tccaatctaa atccaaatgc aatccaaatc catactaacc taattttaag   2700
tgtgatccaa acctaatttg actccattcc aaataaatcc aaccctaatg aaaactaaat   2760
ccaaaataat ccaaatccaa tccaatccaa cccaatagaa tccaaaatga atacgatcta   2820
aatccaatac gtttccaata actatccgac ccaaaatcca attcaaatct aaccaaatcc   2880
taaaatccaa tttagcttga atccaaatca aatggaaaat aaatcagaat ccaattacaa   2940
ttccaatcca ataaaatccg atccaaatct aactataatc aaaattcaaa ccgaacccga   3000
tcaaaatcaa attcaataaa ttttgattcc aaatccaatc caacttagtc ctgggcccaa   3060
attcaattca aatccaaaac aaatcgcatt caaatcaaat tttatccaag tccaatgaaa   3120
ttctaaaatc taataagccg aatccgattt aatccaaatg caaatctaaa ctaaacctta   3180
tcctaatcca ttccaaaaac aattcaaatc taatccaaat atcttcaaaa tccaatcccc   3240
ctctaatcga aattacaatc caatttaaat acaaaacaaa ttcaatccat attcaatcga   3300
catcccaaac gaatccatcc aattccagtc atatcacaat ccaatccaaa tccaatcaaa   3360
caaaatccaa tacaaaacca atcaaattcc aattcaatct aatcctaatt ctttacaaag   3420
ccaatctgaa tccagtgtaa accaaatcca atcgaaatcg aatccatcca aattttaatt   3480
gaattcagtt tccattcaag tcctaataaa tttcacatcc tgaatccgtt ccaaattcta   3540
tctaaattta attccaatcc aaatctaatc caaattcgtt tctaatccaa ttagaaataa   3600
aattgaattc aaaggttttt ttttttatta atctaagcca aaccatttac atattcaata   3660
taaattcatt ccaaatctaa actaatccaa gtcccattga aatccaaatc aaactcaagt   3720
ccgatcttaa tacaaataca attcaaatcc atatcgactt cattccaaat cttattcaac   3780
tcccaatgct caattcaatc catagtataa tctaatctaa ttcaaatcca gtccaaactc   3840
tcttcaagtc ccatccattt tttttattaa attcaaataa agtcgaatct caattcgatc   3900
```

```
tatgtccaat ttaaataaaa tttaattcat tttacatcca agtcaaagcc aaatctagtg   3960
tttattcaat ctcaaacaaa tcggatccaa atgttatcct aattcaattc aaatacaatc   4020
caaacaaatt gaattccaat tgaaatccaa atccaactta aaaccatgac aactccaaat   4080
aaaaccaaat ccattccaac tttattccaa atctaattca actccaatcc aatacagatc   4140
caattcacat ccactccaat ccgaatacaa tctaatccat tccagatcaa ataaaccaaa   4200
tcccaagaaa atctaaagcc aatccatatg taatcaaaat ttatttcaaa ttcaatccaa   4260
attcaacata aacgaatgtt gctagcgcaa tttgccaaat actgttttc aagttatcaa   4320
aaaaacttca tctttcatct tcgacctcaa ttcaaccggt acatacactc atccacgaat   4380
tttacctcgg agtcctcgcg ctccatttag tgttctcgta gaacttttgc tatgaaattt   4440
tatatatctc atctcggaga cctctcgctc cggcattatc gaaccatttt cccttgtttt   4500
ttttaccgcg gagacctctc gctccatatt tgcttctagg agacctctcg ctccagtatc   4560
tttatttcat tttttttct cattttagac aatttcggaa acttttccct tgttgcaata   4620
attgaataaa tttcacatcc atttttaata tcactttctt tgtatcgtaa atgtctgcca   4680
ccaaaaactc aaaataaaaa tgacccacac caaatttcga tccacgtggc ttgaccacca   4740
ttttgttagg aattgcattc cgcttgcgtt attcctgaac gtattttttc accttataac   4800
cagcttatat caccaattaa atacttacgg gagcgtgaac tacgccattg tcgtgacgca   4860
acctggtttg gacggtatca gccgaattaa gctggccaaa ttttcttcac tccttaaaag   4920
tgcgactaat cgctctaaaa ttctccagta gactgattta atcatatcac ggcagtggca   4980
atgaacccta gacggcaacg cttcggtacc gatccacgca ctcgtgttta gcttcgtaag   5040
ccgctgtcct caggacgcgg agtaggcaca cgctcttctt ccttttcaca ctctcgatgg   5100
ccgcttgcaa tgcgttccta tgcgatcaaa agccgaacgc cctgctcact tcgtgtctgt   5160
ctttgagccc aagcattcgt ctccacccaa atttcgggtc ccgagcccaa tcatatcccg   5220
aaatctcatt tgaaacatcc ggcgctgcag aggaagactg ccataattat ttcgcgcggc   5280
atcattttta ttttcatatt ttatagcagg tttcaaatag gcgacgtaca cgctaaacat   5340
ttttaagtca tgtctcatat ttttacctca tatttctaat gaaatctata tctactacac   5400
ctagaagccg ttttatctga tttttgcaca taaaatataa tggagattta atctcagtgc   5460
cggacaatta tgggttggta tgggccatct ttcaccgaaa agattgttgc cacatactca   5520
acaaccctga atgaatcaaa ttcattcacc tgaaaagaga aggacatacg aagataagtc   5580
ttcggtatgt ttcattatcg tacgtactat gattgattta gagattcatg tgatcaatag   5640
agtttcttca gcaaaaccat tactttatcg agtgttgaaa actacgccat agaaagccaa   5700
aaaagcgttg ttggtaaagt tgatggctct gaacgatccg gaataccaac gcagtgccat   5760
gtcaaatgct ggcactcccg accgcccccg aaatggaacc gatgagtttc aatctttcta   5820
ctttgcgcta gtatcggaat tagcaacgga atggtccaaa cagataccgc ataacgcaac   5880
tacactcatc agacacagtt tgctgggtgt gccaaatgct gcagcttcca tttgtctgct   5940
tcgtcaatcg gccagggtac gagaagcatc tgcgatgtgg tagcctgtgg gaactacgtc   6000
caagttctgg aacaattaga aagtcgaaca gttgatcgct aattatcaaa ttgagaaagt   6060
tcgacgtaaa ctaccttatg gcaagtgaag gaaaaaaaac gcagattaca gtaatgaaat   6120
tgatcactct tccgtctatg gtcgattgtt gaaaccctga aaagttttat cagaatcagt   6180
agccgcattc ccatgacttt gtcaggtatc tttggtactt accctgcatt tttatgattt   6240
```

-continued

```
gctttttata aaacctgcta atttacaatg agtactagtc tgaaactaaa acttgttgat   6300
attttttaca tattttttc gacgttactt gacaataata agtagttgta ggtactatgc    6360
gctttgtcat acatccatgg ttcagccgtg tagttccggc gtatagaata gaactacgga   6420
cgacctgttc cggtggtaag agtccaccaa acggggtaac cccaattcaa ggtgtgatgc   6480
gaaaaaccgt gctgaggaat gaatggtcga aggggtgaaa aagatgttcg gccgttaacg   6540
gagcctgtgg ggcacctggg cacccctcac agtattttgt cccttaccgc gttaatgcag   6600
ggctctggcg tggtggacct cttttcccgt gctactcgtg ggatccaatc atgaatacaa   6660
acttaaacca aaatcaaaat aatagtagta gtgcaggtag tagcagtagt agggaagcga   6720
acccccttcgc aagaagtggg ttagctaggt ctccgttgag gagagcggaa gcaggaggag  6780
gcagcagtgc acgtagtgcc agtgctggaa accatatttc atccccggct aacgcatcgg   6840
gtgaggttat ggatggagcg tggttgatga gggccatcaa taaaagtaga gatgggctct   6900
ctgcgatgga agtggttgca cagcagctcg actccataat tgactttgcg tcctcgaagt   6960
ccaacatcag caaggacctc aagcaggccc tgttcagact tcgtaagtcg atgttcgcgg   7020
ccaagcagaa ccatgctgaa cccatggcga ctgtggctgc ggcagaaccc gtggaattga   7080
aggtgccgaa gtctacccag acggagccct tcgtcttcgc gggtagcccc aaaagtgcgg   7140
aagcgaatgc ttacaacaag caatcgcaga agcgcgcgag gcagccgtca ggggaggagc   7200
tacccggcgg cgctcgcaag gccaggcgga tattaacccc gaaaaccggc agaagtgccg   7260
gaaaatcgga ccccagccag gcgtcccgga aagccgagaa gggtgggccc gaaaaggctg   7320
gcccctcacg gagtgatggg aacagggggt tgcgaccttt gagaggtcct caatcaccac   7380
aggttagggc ggatcagggg ggggacgccc cctggacaac cgtagtgaga aagaagaaga   7440
aggagaagca ggaagttcag gagcgcaggg ataccaggcc taagagaagt aggagggtag   7500
gtgccaagcg cgaaaagggt gatgcgatca tcatcaagac ggaagagtcc aagtactcgg   7560
aagtcctgaa ggcgatgcgc agtgacgcga agctcgcaga tcttggagcc gacgtacgca   7620
gtgtcagacg cactcgtaca ggtgaaatga ttctcgagct taagcgtgac aaggagcgca   7680
agggcgccgc ctacaaaagt ttggcggaag aggtccttgg cgagggtgtc gaagtgaggg   7740
ctctgacgca gtcagtgact ctgaaggtga tgaaccttga cgagatcacc aacgcagaag   7800
agctcgtcac agcactgcgg caacagtgcg agattcaggt gaccaccgct gccgttcagc   7860
tacggaaagg tccggcaggt actcaggtgg ccttagtaca cctacctgtg gcggacgcaa   7920
ataagtccgc taaggtaggc aagatcaagg ttggttggtc agtatgctca ctgaacatac   7980
atgagcaacc ggtgatctgc tttaggtgta gggaaccagg acacaagtcc tggggctgta   8040
aaggccctga taggaccaag ttgtgtaggc gttgtggtga ggaaggtcat aaggcactag   8100
gctgcaagaa ccctcccaag tgcttgattt gttccggcaa gtccgtgaac aacaatcatc   8160
caacgggagg ctcaaggtgc ccgaccttca aactagccat taacgaaaag tcacagtgca   8220
ggtaacgcag ctgaacctga accactgtga cgcagctcag caactgctgt atcaggcagt   8280
tgctgagtgg gggacggaca tcgccatcat atcggaccca taccgagtac ccgccggcaa   8340
cggcaactgg gtagtggatg gatccggaaa aatggcggcg atatggacga cgggtaaata   8400
ccccgtccag gagttggtgt ctactaccta cgagggcttc gtgatcgcca aggtgaacgg   8460
ggtcctcttt tgtagctgct atgcgcctcc gagttggtcg accgagcggt tcacgcagat   8520
gctggactgc atgacgaccg tgttgacagg gcgaaggcca gtagtaatag cgggtgactt   8580
caatgcctgg gccgtggaat ggggaagccg tatcacgaac cagcgaggtc aaatcctgct   8640
```

```
agaggcactg gccgtgctag atgtcgatct ggctaatgtt ggtaccaaaa gtaccttcag   8700
ccgaaacgga gcggagtcga ttatcgacgt tactttttgt agtcctggcc taacgagtag   8760
ttcgaactgg agggtagaca atgcctacac tcacagcgac cacctggcgg ttcgctacag   8820
tatcgactac aacaacagca ggcagcgcgt agaggaagcg gctaggtcac ggccaagccc   8880
tcgtaggtgg aagacatcgt acttcaatga cgaagtactt agggaggcgc tccgtcgtga   8940
gcgtaaccta ctcggcctaa gcggggacga actggtagcg gtgctttcgc gtgcgtgcga   9000
tgcgaccatg cctaggaaag tccaccctag aaatgggaga ccaccgacgt actggtggac   9060
tcaagcaatt gcgaacctgc gccgtgcctg cctacgggcc aggaggcgga tgcagcgagc   9120
acgtaccgag caggagcgtg aagaacgacg ggcggtgttc accgctgcca aagtcgcgct   9180
gaagtccgag ataagggcaa gcaaaaaggc ctgcttcgag ggactctgtc agagtgccaa   9240
cgcgaacccg tggggtgatg cctacaggat cgtaatggcg aagacaagag gtgcaattgc   9300
tcctacggag caatctccac agatgctgga ggggatcatc gaggggctct tcccgcgtca   9360
caaccctagc ccatggcctc cttttgtagg acagccgggg attggggctg gcgatgagga   9420
tagagtaact gatgaggaac ttgtagggat tgcaaaatcc ctaagcatgg ggaaggcacc   9480
aggtccggac ggagttccaa acctggccct caaagtcgca atcttggagg ctcccggtat   9540
gttcagatct gctatgcaga tatgcctgga cgagggagta tttccagatg cgtggaagag   9600
gcagagcctg gtactattgc caaaggcggg gaaaccaccc ggtgacccgt cggcgtatag   9660
accaatatgc ttgattgaca cggtggggaa agtgctcgag aagatcatcc tcaacagact   9720
gtcgaggtac accgagggtg taaatggtct ctcaggcaac cagttcggct tccggaaagg   9780
gaggtccact gtagacgcta ttctgacggt taagaaaacc gctgagatag cactccagcg   9840
taagaggagg ggtattcgct actgcgcagt agtgactctg gatgtaagga acgcatttaa   9900
tagtgccagt tgggcggcta ttgccgatgc gctcctgcgt ctggggatac ccgagtacct   9960
gtacaagatt ctcggaagtt acttccagaa tcgggtatta gtctatgaca cagaggtggg  10020
tcggaagtgc tttcacataa cctcaggagt cccgcaaggt tccatcctgg gtccggtgtt  10080
atggaatgtc atgtacgacg aggtgttgag actaaaattc ccggcgggtg tggtcatcgt  10140
tggctttgcc gacgatatta cgctggaggt ctacggtgaa tcgatcgaag aagtggaact  10200
gactgcagcc cactcgatcg caattgtgga ggagtggatg agctccagga aactggaatt  10260
ggctcaccat aaaactgagg ctgttgttgt caacaaccga aagtcggtgc agcaagcggt  10320
gatcagtgta ggcgactgca caatcacttc gaagcgctcc gtcaaacact tgggggtgat  10380
gatcgacgat aagcttacct tcggtagcca tgtcgattat gcctgcaaga gagcctccac  10440
agctattgtg gcactgtccc ggatgatgtc caatagctct gcggtgtacg ccagcaagcg  10500
taagcttctg gccagtgtcg cctcgtccat actgaggtat ggtggcccgg cttggggcac  10560
ggctttgagt accgatagct accgtagcaa gctagagagt acttataggc taatgtgcct  10620
gagggttgcg agcgcgtacc gtaccgtgtc acacgatgca ctttgtgtca tcaccggtat  10680
gatgcctatt ggtatcctta tcatggaaga catagagtgc ttcgaaatgc gcggcacaag  10740
aggcatacgc aggactgcca gactggcctc catggtcaaa tggcagcgtg cgtgggacag  10800
ttccaccaag ggagtgtgga ctcacaggtt gattccgagg ttagatatct gggtcaatag  10860
gcgccatggg gaactaacat tccacctaac acaggtcctt tcgggtcatg gatgctttag  10920
acaatatcta caccggttcg gtcatgcggg ttctcccgaa tgtccagttt gtgcaggttt  10980
```

-continued

```
agaggaaacg gcggaacacg ttttgttcgt gtgcccgcgt ttccgcacaa tgcgtgaccg  11040
catgtttgcc acatgcggtc gggacacgac tccggacaat ttggtccaga ggatgtgtgc  11100
agacgagttt ggctggaatg ccgtttcatc ggctatcacc cacatcgtct cggaactcca  11160
aaggaggtgg cgtgtggact cgaggagtga ctagtgcaga cgctaatcaa caggtggtcc  11220
aagggttcgc agtcggctac gtaggtcata ccggtgccct acggccgaaa tcgaccctta  11280
cagcgattaa gtggccgcgg ggagaacatc ctggtagcgc tgctgtcgtg gcgccggcct  11340
actgggtgga tacgagcctc tggttgttcg gggcaggtgg aggccccttc gtcagcaatc  11400
ccagctcgtg ctagctgata gggcctgagc cttcagtagg tcaaattgcg aagcccgcag  11460
tatcagttct tgatacttgc ggtgcagctg ggcgcgggct tagtggtcga ccctgcccgc  11520
cttcagcgga caacaggagg tgaggaccac ccgggaagct ggcaatgcgc cagcatgcta  11580
ccttggtgga cccccataag cgtgtcatcg atgttcgttg ctgcatggct acgcagctaa  11640
cctggaggat gcgatgtgca atagcccctc tccgaagcaa tgccttcttg gtggtcccgg  11700
agagacgaag ggtttggcgg caatggaaat ggtttagtgg gtcgggggtg tagtcctgtt  11760
tactgcttgt acgtagtaaa tggtccccaa ccccacactc ccggacctcg gtccggagtc  11820
tgttgagcag attatccccc cattgcttag aaggaaaaaa aaaaaaaaaa aaaaagaggc  11880
atacgcagga ctgccagact ggcctccatg gtcaaatggc agcgtgcgtg ggacagttcc  11940
accaagggag tgtggactca caggttgatt ccgaggttag atatctgggt caataggcgc  12000
catggggaac taacattcca cctgacacag gtcctttcaa gccatggttg ctttagacag  12060
tatctacacc gtttcggtca tgcgggttct cccgaatgtc cagtttgtgc aggtttagag  12120
gaaacggcgg aacacgtttt gttcgtgtgc ccgcgtttcc gcacaatgcg tgaccgcatg  12180
ttagccacat gcggttggga cacgactccg gacaatttgg tccagaggat gtgtgaagac  12240
gagtttggct ggaatgccgt ttcatcggct atcacccaca tcgtctcgga actgcaaagg  12300
aggtggcgag tggactcgag gagtggctag tgcagacgct aaacaacagg tggtccaagg  12360
gttcgcagtc ggctacgtag gtcataccgg tgccctacgg tcgaaatcga cccttacagc  12420
gattaagtgg ccgcggggag aacatcctgg tagcgctgct gtcgtagcgc cggcctactg  12480
ggttagtacg agcctctggt tgttcggggc aggtggaggc cccttcgtca gcaatcccag  12540
ctggtgctag cagatagggc ctgagccttc agtaggtcaa attgcgaagc ccgcagtatc  12600
agttcttgat acctgcggtg cagctgggcg cgggcgtagt ggtcgaccct gcccgctttc  12660
agcggacaac gggaggtgag gaccacctgg gaagctggca aagcgccagc atgctacctt  12720
ggtggacccc cctaagcgtg tcatcgatgt tcgttgctgc atggctacgc agctaacctg  12780
gaggatgcga tgtgcaatag cccctctccg aagcaatgcc ttcttggtgg tcccggagag  12840
acgaagggtt tggcggcaat ggaaatggtt tagtgggtcg gggtgtagt cctgtttact  12900
gcttgcatgt agtaaatggt cactaacccc acacggcgtc tgttgagcag attatccccc  12960
cattgcttag aagaaaaaaa aaaaaaaaaa aaatacatct atggttataa gaactaaaac  13020
gtagtgaaag cgacaaaata catgcttact tctactataa attggcatgg tagaattaag  13080
caaacagtaa tggtttgcaa taccacacat tttttatcag tgtacttacc aatacatgca  13140
tttccaaaaa cggccacttt ctcaattttt gcacttttta tgtttattca cgactgcaca  13200
gcataaagtg aacataaata aacaatagat aagctgtgac agtccacttt gacagattca  13260
tgacgttttg caaactgtca acgaatgaca gtttgcccgc cggcgataaa tcccgccaag  13320
gggttcggcc gtgcggaatg tgatctaaag tgttgtaaat aatttgtaaa tagggttgta  13380
```

```
aaattgtttt tgatgcgcat cactgtaaat agttaattca tgttgtcaac ccataatacg  13440
ggatatttta taagatttaa aatttgtttt gtacatattt agcatgtttt aatttatttc  13500
attttctaat ttttaatctg tagaattgtg cacgtacgta aagaatattt tagcatgttt  13560
cattatttat ctttttaatt tgtagtaaag tttaattatg atttcgcgcg tttgtaattt  13620
taaaagattt tattttattt cgtattgtat ttgataattt atttgttcga catccacgaa  13680
ccgatggcgg ccgaagatga cttgagagag tgaattgggt gctaaaattt ttaatgaaat  13740
cttgttttta tttaataaca cgaaaaaaca tgttactgta actactttag caatttttcc  13800
cgctcaaata tgtcatgttt aaactttaat ttaaacttta atttaaaaat ttggtccata  13860
aatgaacctt gacacttttg atcatgtttg acgttcgctt agtcgacaaa aacaccacag  13920
gggttttagt tcgaccactg gggttgttcc tatctgacat ttcgtaaggg acacggaaaa  13980
caaaatacac acaaaatttg agtttaagcc aaagtatgtg acaaaatcta aataaatgtt  14040
ttttgggctt aaaccaacgg aaaacattag aaaattgagt aaacatgtgt tcttggccta  14100
aacttaagcg tttggcacag ccctgttcca atggctttag gaccctattg aaaaaaaaaa  14160
atgcaaaatc tcttcgtgct ttcgcatttt ttcatcgggg tggtggatag tgtaaccgtt  14220
tggttacaaa ttgttggttt ttgttttata tttgtttgtt cgtttcggaa ccttcacgtt  14280
tctcgtgtga taacagcaga aaatatcaca gaagcgttag ggtttgtgcc gctgttaata  14340
aacaggctac caattattca tcatggtagt cctggtgaaa tgtcaataag acggaatgtg  14400
ggaaaatcga gaaagaacgg ccattgctaa taaccggcct ctttctaatc aggcgtccgt  14460
gtgctgaaga cgtgattttt atagtgcaaa agtcagtggt tcaataccga taccccccc  14520
cccccttgccc ttagcaggag ctaagggaag aaaccgagct caggtaacaa aataccctgc  14580
accgctacga gcaaatagtt tataatttgt cttcgtccaa taggacctct tgttcttgtt  14640
cttgttttca tttcggatct tcggatccat cgtccagcac acggttcggc tcgggcacgg  14700
taaatggctg ggcatggcgt accattggta cctcgcgtac ctgcaggaat aaaatagacc  14760
cctttgtgcg gtccttagcc tcttgcccag caactcctat ccctacctcc tcgtggtact  14820
ggccggggta cgagtaacct tggggaagat cgggtaacca acccccggtg ggaactttgg  14880
tcgtatgctg acagggaagg gggggtttgc ttttgcaaac ctggagcgtc tgtactccac  14940
gttaggagcg gctcacaaca gcgtctgttc cccatgtcag ggcggctga tcatcgtccg  15000
agtgccagag aaggactcta agctaaactg cgcactatgg ccctccgaac atttaggggg  15060
aatggtcctc cggaaatcta gggggttggt gtcaggccct gcaagccaac cgtaaaaaca  15120
catcagcaca ggaacgtcaa cgagagaata cggaccggaa caatcggcaa agaccacagc  15180
gacgaaaatg gactagcgat tggaaactcg gtacgtggaa ctgcaaatct ctcaacttca  15240
ttggaagtac tcgcatactc tccgatgtac tgaagacccg cggtttcgac atcgtagcgc  15300
tgcaggaggt gtgctgggca ggagcattgg tgcgaacgtt tagaggtaat cataccatct  15360
accagagctg cggcaacaca cgcgagctgg gaacagcttt catagtgatg ggtgatatgc  15420
aaaggcgcgt gatcgggtgg tggccgatca atgaacgaat gtgcaagtta agaatcaaag  15480
gccgattctt taacttcagc ataatcaacg tgcatagccc acactccgga agcactgatg  15540
atgacaagga cgcattttac gcgcagctcg aacgcgagta cgaccgctgc ccaagccacg  15600
acgtcaagat catcatagga gacttaaacg ctcaggttgg ccaggaggag gagtttagac  15660
cgacgattgg aaagttcagc gcccaccggc tgacgaacga gaacggccta cgactgatag  15720
```

-continued

```
atttgccgc ctccaagaac atggccattc gtagcaccta tttccagcac agcctcccgt 15780
atcggtacac ctggagatca cctcagcaga cagaatcgca aatcgaccac gttttgatcg 15840
atggacggca cttctccgac ataaccgacg tcagaaccta tcgtggcgcc aacattgact 15900
ccgaccacta cctggtgatg gtgaaactgc gcccaaaact atccgtcatc aacaatgtac 15960
ggtaccgacg cccgccccgg tacaatctcg agcggctgaa acaaccggat gtcgccaatg 16020
cgtacgcgca gcatcttgag gcagcgttgc cggatgaggg cgagctcgat agggcccctc 16080
ttgaggactg ctggaggaca gtcaaagcag ccattaacga cgctgccgaa agcgttgtcg 16140
gatatgtgga acggagttca agaaacgatt ggttcgacga ggagtgccag gaggttttag 16200
aggagaagaa tgcagcgcgg gctgcaatgc tgcagcatgg tacgcggcaa aacgtggaac 16260
gatacagact gaagcggaaa cagcaaaccc gcctattccg ggacaaaaag cgccgcctgg 16320
aagaggtgga atgccaagag atggagttgc tgtaccgttc tcaagaaacg cggaagttct 16380
atcagaagct caacacatcc cgcaaaggct tcgtgccgcg agctgagatg tgccgggata 16440
aggatgggag catcttgacg gacggacgcg aggtgaacga aaggtggaag cagcactacg 16500
atgaacacct gaatggcgca gagaacacag gcacagaagg tcaggacagc gaaggcgatg 16560
gctacgtcag cacagcggac agcggaaatc aaccagctcc cacgatgggg gaagttaagg 16620
atgccattca acagctcaag aacaacaaag ccgctggcaa ggatggtatc ggagccgaac 16680
tcatcaagat gggcccggac aggttagccg cttgtctgca tcggctgata gtcagaatct 16740
gggaaacgga acagctaccg gaggagtgga agcaaggcgt tatatgccct atctacaaaa 16800
agggcgacaa actggagtgt gaaaattatc gtgcaatcac catcctaaac gccgcctata 16860
aagtgctatc ccagattctc ttccgtcgtc tatcacctat agcaaacgag ttcgtgggaa 16920
gttatcaagc aggtttcatc gacggccgct cgacaacgga ccaaatcttt tccgtgcggc 16980
aaatcctcca gaaatgccgt gagtaccagg tccctacgca ccatttgttc atcgatttca 17040
aggcggcata cgatagtatc gaccgcatag agctatggaa aatcatggac gagaacagct 17100
ttcccgggaa gctcacaaga ttgatcagag caacgatgga cggtgtgcaa aactgcgtga 17160
agatctcggg cgaacactcc agttcgttcg agtctcggcg gggactacga cagggcgacg 17220
gactttcgtg cctgttgttc aatattgcgc ttgaaggtgt catgcggaga gccggactta 17280
acagtcgagg cacgattttc acgagatccg gacaatttgt ttgcttcgcg gacgacatgg 17340
atattattgg gagaaaattt gaaacggtgg cagatttgtt cacccgcctg aaacgcgaag 17400
caacaagagt cgggctaatg gtgaatgcgt cgaaaacaaa gtacatgctg gttggcggaa 17460
ccgagcgcga cagggcccgc ttaggaagca gtgttacgat agacggggat accttcgagg 17520
tggtggacga gttcgtctac ctcggatcct tgttgacggc tgacaacaat gttagtcggg 17580
aaatacgaag gcgcatcatc agcggaagtc gtgcctacta tgggctccag aagaaactgc 17640
ggtcaagaaa gattcacccc cgcaccaaat gcacgatgta caaaacgctc ataagaccgg 17700
tagtcctcta tgggcatgag gcgtggacta tgctcgagga ggacttgcaa gctcttgggg 17760
ttttcgaacg ccgagtgcta aggacgatct tcggcggcgt gcaggagaac ggcgtgtggc 17820
ggcgaaggat gaaccacgag ctcgctcaac tctacggcga acccagtatc gtgaaggtag 17880
ctaaagctgg aaggatgcgc tgggcagggc atgttgcaag aatgccggac aacaaccctg 17940
taaagatggt gttcgccacg aatccggtcg gaacaagaag gcgtggggcg cagcgagcta 18000
ggtggattga ccaggtacac caggacctgg agagcgtggg tcacagtcga ggatggagag 18060
aagcggccat gaaccgaggg aattggcgaa atattgttgg cgaggcttta tcaagataat 18120
```

```
tgatgtaaag ccaaataagt aagtaagtaa cggttcggct cgcgaagcca ttaggctccc  18180
gggcctaaat gttaaggacc ttgtcctcta gtaggaccaa ttggcccgtc aacggagttc  18240
agtacaagcc cgtacatccg cccgcttcgc cattccgtcg agagttccgg ccgcacagca  18300
ggattggtgt cgctgtgtcg gccattcgtc tatcccacaa caaacggcag cggtatgtac  18360
cggtatgaaa cattagaata ggacacactt aacaaattta acactgaaat tgaaaacaca  18420
gaacaacacg cacacgacac aattagaatt ttataataaa tgcatcagaa acgttaaagt  18480
tccctggagt tagtttttg tacgcgaaag cccttgatta cccagtagct agccgaccct  18540
gggattgccg gagagtctct tgtgtcctga gttggcctgg cactgtagca tttatccgtt  18600
agtttcagtt tactgttatt cagtacacat tttcaaattt tactgaatac agtaattgaa  18660
attgttgagt gtatcgtaaa tattcgaatt tactggaact caccagtaaa aagaaaaagt  18720
cagtaaaact aataactgaa ctatcggttc aagatatgct tttactgaac aatcctcaaa  18780
acgaaataaa aacattttcg agcacacgca ttgaaatgtc agaaacaatt tatcacaaat  18840
ttcaacggat tctgggtgtc gcttcttgaa tggcgttttt aattatttat gctgtgcttg  18900
gcttactcat ggcaggtaca ttaatcaaat tgtaagatta ttttactccc gactatcgga  18960
tattgcaaaa aaaggagaat cgttctgcga tcgaacaaat gattagattc cgctcaattg  19020
atcaaatcgt tgcaaattaa cttcgtggga gggcaaaacc aggaacaaat cttttcgtta  19080
cgaattgtta tattttcctg taattccttc tcgaatcaaa ttgaaatcaa attcaatcgc  19140
aattcaacgc attcctagaa ataatcgaat gaaaaaatct cgacaatatt ccgcgataat  19200
cagtgatcct gttcttttac gcaaaccaaa tttgttgtgc cttctgtaaa atcctaccat  19260
gaggagctgg tctacgtatt tgtagttgga aagatccgac aggagaaggc ttggacggaa  19320
attctgttga ctgcaatgaa ttgcacgaat taataaatcc aagaggcaaa acagaattat  19380
ttaggaatgc tgggtctcat tttataagct gaggaattca gtaaattatt gtaaactagt  19440
atgtcccggc aaacttcgtc ttgccatcaa gtaggctgtt gaaaaccgct acgaatcgtc  19500
ccatacaaaa tgacagttcc gttcactctc gtttttccga cattcccggt gaatatcatg  19560
gaacttttat acacacaaac acgtcggaac ccttgacgaa cgaaatggag aaagaatcat  19620
ccaaatccgc tgacccgttc gtaagccatt tcgtgacata caaacaccat tccattttta  19680
tttatataga taaaccaatt taccgaaaaa cacagcattg ttcttcttct tctttctggc  19740
gttacgtccc tactaggaca gagcctgctt ctcagcttag tgttcttatg agcacttcca  19800
cagttattaa ctgagagctt actatgccaa tgaccatttt ttgcatgtgt atatcgtgtg  19860
gcaggtacga agatactcta tgccctggga agtcgagaaa atttccaacc cgaaaagatc  19920
ctcgaccggt gggattcgaa cccacaaccc tcagcttggt cttgctgaat agctgcgcgt  19980
ttaccgctac ggctatctgg gccccacagc attgtatgta cagtaaaaac tactgacaaa  20040
atcagcattt tttgacagcg catgaatcta tagctttacg gagttttcgg tagcaataaa  20100
ttttactgag ttaattctgc tgttcaaaaa cccagtaaaa ttttaccgac ttcggtaatc  20160
aaatctaagt gtgtatgagt ttttcacatt agagacagct atgtgaatcg taaggcggct  20220
taatgaaatt gatatacgtt aattaagtat cactaacctc gcaattatgg ttttcatcaa  20280
gctaatatga aattcataat agccttatga tgtaggattt cattaatgga atgactaatg  20340
aaagcaatgg agatcataag gcgcgcaatg aaatttgtaa actttcatta tgttcaccta  20400
ttttttgat tatgattatc attccaaagg tatgaaatcc atattagcct tctgaaatcg  20460
```

-continued

```
gattttatgg aatttttaat gcttcataag gcaaaattta tggaattcgt tgattaattt  20520
cgttagattc cgcaatcaat taacgacagg gacactagcg tactgagaag aattcaaaac  20580
aaccaaagtt ttacagtaaa tctagtaata cacttcattt attttaacag taatccaaca  20640
taacgtgtac ttttctccaa tctctagaca acaataacaa atccacacgc tcttctgttt  20700
gtcattctaa gggccggaca ctgcagtctt ttatcatcct accaagtgag gggtcggaca  20760
ctactaattg tccaacactc ctccttagtg tcgacacctc taacacctct ctgcaatgga  20820
actcctcctg aattgggtcc taaaatgttt aatgaattct tgtttttact ttacaatacg  20880
aaagagcatg ttcttgccac tactttagca atttttccag ctcaaataac gactataaca  20940
tatttaaact ttaattttaa aaatggtttc aaatatgaat cttgacagtt ttgatcatgt  21000
ttgacgttca ctttctctac aaaaatgcca cagggctttt agttttaaca ctggggttgt  21060
tcctatctga catttcggaa gggacacgaa aatcaaaata tacccaaaaa tttgagttta  21120
agccaagggg tgtgacaaaa tttcaaaaac cgttaaaaat gtttttgggg attaaaccaa  21180
tgaaaaccat ttaaaaattg agtaaacatg catttctggc ctaaacttaa gcgtttggta  21240
ctaaaattag gacagggttt taggacccta ttcaagcgat ttcgccattc atggctgctt  21300
tacgtagaag acttctcctc gtctttcacc caccagtact acgtcagttc cgttcatgat  21360
tttacaccca tcggaaacaa aactaactgt atagccttca tctatcattc ggctcaccga  21420
tagaacattc agcttcagct ctggtacgta cagtacatcc ttcagcttga catccattcg  21480
ttcgtgcctc atgtttaatc cggtaaatct tgctgttcct ctcatggtta ccggaacgtt  21540
tcgaccatcc gccaaattcg tcagctctct ccaggctaac ggtttttcca aaatttcgag  21600
atttcctgtc atgtgcttcg aacaaccgct gtccattatc catccatgtg attcgttgcc  21660
gtttttgacc atcgtggtaa aacaaacttg atttccacca gaacctccgc ttccgtaacg  21720
accactatca aattggccac ccctgcttat gccacgagca ccaccatctc gatcatcata  21780
acctctttct cgccgttgtc tgtcgctgtg aactcgttgg gcatccgata gcttcggaca  21840
atcccgacgg taatgtcctt cttcccggca gtaatagcat actcctccag ccgtcgtcgc  21900
accatttctt atatccgagc gtcgcattgt cgctcgaagt gccttttctt cattctcttc  21960
ttgattttca catcgacgtc gccactcatc caaaagtttt cccttcacat agtccaactt  22020
taattcgtcc tctgatcggc cttccaacgc ggtaatcaac ggattgtaca ttgtatgtac  22080
agtaaaaact actgacaaaa tcagcatttt ttgacagcgc atgaatctat agctttacgg  22140
agttttcggt agcaataaat ttactgagt taactctgct gttcaaaaac ccagtaaaat  22200
tttaccgact tcggtaatca aatcatggtt accggaacgt ttcgaccatc cgccaaattc  22260
gtcagctctc tccaggctaa cggtttttcc aaaatttcga gatttcctgt caagtgcttc  22320
gaacaaccgc tgtccattat ccatccatgt gattcgttgc cgtttttgac catcgtggta  22380
aaacaaactt gatttccacc agaacctccg cttccgtgac gaccactatc aaattggcca  22440
cccctgctta tgccacgagc accaccatct cgatcatcat aacctctttc tcgccgttgt  22500
ctgtcgctgt gaactcgttg ggcatccgat agcttcggac aatcccgacg gtaatgtcct  22560
tcttcccggc agtaatagca tactcctcca gccgtcgtcg caccatttct tatatccgag  22620
cgtcgcattg tcgctcgaag tgccttttct tcattctctt cttgattttc acatcgacgt  22680
cgccactcat ccaaaagttt tcccttcaca tagtccaact ttaattcgtc ctctgatcgg  22740
ccttccaacg cggtaatcaa cggattgtac attgtatgta cagtaaaaac tactgacaaa  22800
atcagcattt tttgacagcg catgaatcta tagctttacg gagttttcgg tagcaataaa  22860
```

```
ttttactgag ttaactctgc tgttcaaaaa cccagtaaaa ttttaccgac ttcggtaatc  22920
aaatctaagt gtgtatgagt ttttcacatt agagacagct atgtgaatcg taaggcggct  22980
taatgaaatt gatatacgtt aattaagtat cactaacttc gcaattatgg ttttcatcaa  23040
gctaatatga aattcataat agccttatga tgtatgattt cattaatgga atgactaatg  23100
aaagcaatgg agatcataag gcgcgcaatg aaatttgtaa actttcatta tgttcaccta  23160
tttttttgat tatgattatc attccaaagg tatgaaatcc atattagcct tctgaaatcg  23220
gattttatgg aattttcaat gcttcataag gcaaaattta tggaattcgt tgattaattt  23280
tgttagattc cgcaatcaat taacgacagg gacactagcg tactgagaag aattcaaaac  23340
aaccaaagtt ttacagtaaa tctagtaata cacttcattt attttaacag taatccaaca  23400
taacttgtac ttttctccaa tctctagaca acaataacaa atccacacgc tcctctgttt  23460
gaaattctaa gggccggaca ctgcagtctt taatcatcct accaagtgag ggtcggaca  23520
ctactaattg tccaacactc ctccttagtg tcgacacctc taacacctct ctagaatgga  23580
actcctcctg aattcaagcg atttcgccat tcatggctgc tttacgtaga agacttctcc  23640
tcgtctttca cccaccagta ctacgtcagt tccgttcatg attttacacc catcggaaac  23700
aaaactaact gtatagcctt catctatcat tcggctcacc gatagaacat tcagcttcag  23760
ctctggtacg tacagtacat cagcttgaca tccattcgtt cgtgcctcat gtttaatccg  23820
gtaaatcttg ctgttcctct catggttacc ggaacgtttc gaccatccgc caaattcgtc  23880
agctctctcc aggctaacgg tttttccaaa atttcgagat ttcctgtcat gtgcttcgaa  23940
caaccgctgt ctattatcca tccatgtgat tcgttgccgt tttgaccat cgtggtaaaa  24000
caaacttgat ttccaccaga acctccgctt ccgtaacgac cactatcaaa ttggccaccc  24060
ctgcttatgc cacgagcacc accatctcga tcatcataac ctctttctcg ccgttgtctg  24120
tcgctgtgaa ctcgttgggc atccgatagc ttcggacaat cccgacggta atgtccttct  24180
tcccggcagt aatagcatac tcctccagcc gtcgtcgcac catttcttat atccgagcgt  24240
cgcattgtcg ctcgaagtgc cttttcttca ttctcttctt gattttcaca tcgacgtcgc  24300
cactcatcca aaagttttcc cttcacatag tccaacttta attcgtcctc tgatcggcct  24360
tccaacgcgg taatcaacgg attgtacgtt tcgggtaaac tcgacaataa tattgccaca  24420
atccagtgct ccccaagctt ctctcccatg ccgagcagct tatgcactaa ttccgaaagc  24480
tccaccaaat gcttagacat atcaccacct tcagacaaac gcatggagca cagcttccgc  24540
aacacatgta aggtaccgtg ggtaagtgg atacaaaaaa atcaatagtc aacttcattg  24600
ttatgtatag ctaacgttaa taatgtaatt caaacttttt tctgtgcatg acaaatgagg  24660
gactattata cttcaaatcg tcaattattt tgattttttc tgatttttat ctattgagca  24720
tgagggactt gaaaatttgc gccaaatgat ccacttgccc caccatggtg ggtaagtgg  24780
atcacctata aaaaaaactc tattctcaaa ataaatgtga tgtaatcatg tatagtatga  24840
ataatattac tgtcattctt gttatacgtg ctatgttata tattttgata gatttgaaat  24900
aaaaaaaaaa tcttcatttt atcaaaatat tatgaaaaat atttctcgaa aacttattca  24960
tacagactca agtgaaaaaa gtatacaaac ttactttatc gatcctacgt gttaagcagg  25020
cggaattcta cacgtaccgc tctgtaccaa ctcaactttt cacttttaga acgtttaatt  25080
tccggattta caaaacgacg aaagtaacat tttcaacttt cgcaacctaa ccactacttt  25140
cgccgccccg ctgtatggag agacaaagtg acttaaccac gaatcaaaac aaaacactac  25200
```

```
ttgagccgat tttacactgg tagaaaaacg tcgaaagtaa ctgaatgaaa cggcttatca  25260
ttttcttata attattttg tgggaaataa tagaaactac ctagtatttg aacgtgagct  25320
gagtgtatgc aaaatttgag cgaagtacac ggcaaaaaaa tgttaaaaag gtgattcatt  25380
ttaaaacagt tttagaagat agattgtgat ttttcctaat taattttctc aaaaccgtat  25440
aaaagttact tacgtcgatt tgaaaaagta atcgagattt gtacattagt ttacacttat  25500
tcgaacaaaa acaaacagag taactagaat attttggaga aaattcatcc atttcataca  25560
cctgagttgt acaaaagaat tgaagattat tcctaacgat gttttcgaaa gacactctta  25620
gtttaaaata ttaattacat ttactttttt ttaacatact gaaatctttt tattctgttt  25680
atggaaatat ttgtatcatc agcctagaac aatcgaaatg gtcaaaaaac gtacgataat  25740
atgctttcag gtggagaatt tgtataattt gctcttttgc atttcagctt agaaaaacca  25800
agaaaaattt tgtttaaatt tttcaatttt cattgttttt ttgtactaga aagattgtac  25860
aacactttta ggtggaataa ttgaaatttt ctcaggtcaa tttggcaaat tcaagctagg  25920
aatgaaaaat ataaaaggaa aacaaaactt gatgatacta aagcttattc aaacccgcgt  25980
aagtagtctg ccaatagtga taacaatagt tgatccactt accccatccc attaaaaagt  26040
gcgggtaagt gtaccatgac caatatgtct gtatttattt acaaaaatta cattctttca  26100
ttgtgattca tacaattaga attgaaatgt ttaccatgtg ttgaaaaaaa taatagtatt  26160
cgattttggg cagagataca atggattttt atcgacagaa aacaacttta aaatgaattg  26220
atttttgcag tcaacaagtt tgcttgtgtt agtgcacgtg tagtatcagt tttgcagtag  26280
tatcagtgtg tacgtgagaa tataacctaa aatgaagcaa aggtgtgaaa acattcggaa  26340
tattaaagta tttattctta ttacggacga atgatccact taccccactg ctacacttcc  26400
cccacggtac cttatcttgt tgcaaagcga tccccgttcg tgataccctt ttaactttga  26460
ccacatttca ttcgccgtct ctgctccgat gacatgagat aactgtccgt cttcgagtgc  26520
caacccaatc gtcgctctag cagaagcatc cttcgtaatc caattcgcat cagctccttc  26580
tggtttgggt tcattcacca ccgcccacaa tccatccttt accagcaata gctccatacg  26640
gaacttccag ctggcccagt tgaaactatt caaccgctcc atgacaactt tcgtttcact  26700
cattctcaaa atacgaacac ttcactacag tcgaatttcg ttcgttgcac tacgtttaat  26760
tgcacttcgt tttaattggg ctctcgttaa gtgggctata gcccacctaa aacgaaggca  26820
agcgtcactt tctgacataa accgcaattt gtcaatgttg gtagcccgga atttctattg  26880
taatcggtgt tttttacagc tcaaaactta gcccgattag tgaaagtctt tcactaatcg  26940
ggccactgtt ttagtgcaac gaacgaaagt tgactgtact tctcaatttc aattaaaata  27000
tcctatgatt tattcagcgc ttaccaattt aaaaaaagtc ctacgatttg gctcccaaca  27060
gccgcacaag cgctaaatat aataacacag tccaagcact ataaattttc gatttctcga  27120
cgcttacaca acgcaagttg aacttccgga tcaaagttga tttccgtatc cacaaatctt  27180
tctgaacttc ttctctatcc tgggaccata acctgttaga tgccgcaatc aattaacgac  27240
agggacacta gcgtactgag aagaattcaa aacaaccaaa gttttacagt aaatctagta  27300
atacacttca tttattttaa cagtaatcca acataacttg tacttttctc caatctctag  27360
acaacaataa caaatccaca cgctcttctg tttgtcattc taagggccgg acactgcagt  27420
cttttatcat cctaccaagt gaggggtcgg acactactaa ttgtccaaca aatttgcctg  27480
agtgtgagtc tagatgtttt tttattagca gaatagacca tttccgtgtt ttttttttta  27540
ttggcttata tgctttctgt caatttactg tacaaacttt cctaaggaac cggtattttt  27600
```

```
tgaagcctct acctattgga aaacaatgaa aaactggcgg cacgttagtt caccccttgg  27660

tcccgtacaa cttatttctc tccgattttt atacgacccc tttttcccct atgatttttt  27720

ctccacatcg tggtgaatat tgatcagctg gtttggaggg ttcggatcaa tcatgacaga  27780

tagaagtgct catggggacg tcacggaaaa ttctccacct ctgttcctct tccaccaacc  27840

tcaatggatt gtcctgttct tgacgttcgt gctggaattg tttatatttg ttgatatgga  27900

gttgacattc actgcgggaa atgttggtat attttatatg gagtttcgag ttaatgtcag  27960

gcgtgcaacg atctaccttt atttatgttt tcatcaattt tcattgctgt tttatttgct  28020

caaactgtga tttttgtcat aatctgatca caagcagcag ctttaccaag aagaaatact  28080

tcactggatc tggatttgga tttcacgacg gaacatttca caaccaccat ctccttcgcc  28140

tggggctgct gtgatgctcc ttgtatataa aaagagtcct gctcgcttcc ggttttctgg  28200

tcgatcaggg attggtgatg aggatttcag cgcgtagcag catactgttt ttgaagcttt  28260

tttttatccc tactggaaac ccggaagagg ttctcgattg gcactccatg ggtatcaagt  28320

gaccagaaca aaatgtcgcg tggagaaatc ctcacccctt ccacaatttt gccgccggcg  28380

gaggggagca gaaccctttt tgtgaactat cgtggagcac cgcagcggct gcggatgggg  28440

agatgaaaag gaaatttgtt gtggtcatga agaattccgt ggtggcggag gaccttcaga  28500

ttggtcgaac tgcgaaaatg acattttttta aggggaccta tgagacgagt atattaaacg  28560

gggaagtgct catggttcca gcaaatgaac ggggaagcgg gctttactgt tccggtgacc  28620

gtttgaccag agaatttgtt tattatagag aagcgcgaat tctgaaacca gaggttccaa  28680

tcgaaccgtc aaacgtggtt ccaatcgagc aaattcaata agactcaaag agatgttacg  28740

caaaagagac gatggatgtg tgttagtgaa aagcgataca aaagagacgt cattgataag  28800

cttggtttct tatggcgact aacaggatga cacgcacact aaagttttgt tggaatgact  28860

tcaattgttg atagtcattg caaatattgt ttataaacaa agtcaaaatc ctctccgcgt  28920

ttctctagta taaacaaatt ctctgcgttt gaccacataa ttgcttctga gctaacggca  28980

gatttctccg caatgttctg gatttattca ggtgtcgaag ataatggatg cgtgtcacta  29040

tttatttctt ttattcattc gctgagttta tgcagagaaa atagtgacgt cactatttgc  29100

ttagcataag catagcggaa gaataacaga gaaaactagt gacacgcatc caatgagaat  29160

atatactaag gtgtggaaga agaagctttg gctatgtatt agtaaagaga aaaaacgtaa  29220

acaaaaatag ctacgtcact aatttacacg gcttcttatg ggagctcgct cgcttgtagt  29280

tgtaaaacat tttgcaccgt acacggatgt cacgcacact aaatatcgtc ttcctcacct  29340

cggtatatat tctcattgac acgcatccat gatcttcgtc acctgagttg atccagaaca  29400

tgggtttttc cgctttttcc ttttcttccg agtgtccgat ttatgtctac aaacactcaa  29460

cacaggggtt ggattgaaat ttgtgggaaa atctccactt tgtataccca cagggttgaa  29520

acaactgtgc cgcacgacag tttccacatc aaaaagtggt gaatatccaa gttttcaaaa  29580

aattataata aaatattgca attttcacga atgattagac tttcatgacg aaattgagaa  29640

gctgccaata atgtactcat ggtacatttt caaacaccat cgaccgttca tccttgattt  29700

tagtcactac cagctggttt tgacacgaaa acacgatcag ctggaacatg agaacaatga  29760

cgatgactgt aaacatcgga ggaccagctg gtgttgttgt gtacacaaga ccagctggtg  29820

aatctagaac aaagaaaaaa tggtaaacat cgagccggcc ggagaaaact gtcatgaaca  29880

tcaggataat tgcatagggg gcggtgatcg taaaggggca gcgaaatcga tggcgaaatc  29940
```

```
tgagaaagac gaaatttaga tcactaaagt ctaagtggtg aaaaaaatcg caataaggag  30000
ttcatataaa ttagttctaa atgcgtcaat aatcattaaa aattatcgac tttcgaagaa  30060
aaatataaaa ataggggggta agatctgacg gaaatggtct attgtttaag aaaccgcgaa  30120
taattctcta attatttatt cacagtttgg tcacagcaca ggaaatcgca tgaaaattaa  30180
tctagtatag attatgaatt ttctaggaac ccggagcaat gccaggaagt tcgtccagcc  30240
gtcaagtctg tggttcctgg aaacatcagt tgctgataaa taaaactgca catgaacata  30300
tttttgtaag atcatgaaca taaatgtaat aaatggaaga tgtcggtttt aaaaactatt  30360
attttttta ataatctatc gtatattgta cagtcaactt tcgttcgttg cactaaaccc  30420
gtggcccgat tagtgaaaga ctttcgctaa tcgggctaag ttttgagctg tcaaaacacc  30480
gattacaata gaaattcagg gctaccaaca ttgacaaatt gcggtttgtc agaaagtgac  30540
acttgccttc gttttaggtg ggctatagcc cacttaacga gagcccaatt aaaacgaagt  30600
gcaattaaac gtagtgcaat taaacgtagt gcaacgaacg aaattcgact gtatatttct  30660
ttcactactg gactgcaaag tacggcctca tacgtgcgaa agtgtgaata aaagtgcggg  30720
attgcattga atcctgtagg tgtattcaga gcacttattc tttgatttac gaagaataag  30780
tcccccgaag acacctaccc gatttgatgc cattgcgcac ttttattagc gtttccgcac  30840
gtgtaaaaac ttctgcgata gtccagtggt gaaagaaatg cgcaatatta tagacagaat  30900
taaaccggag caaataataa aacaataccc atttatgagt aaaactcatt acccatttta  30960
aggcccatgg cacgggacga cttctagcgt agtcaacatc tccatgtgtt tacccatttt  31020
tgggtaaatt gaattgagag tgcaatcagg atgcgaagtt ttgtttaatg tttatgatcc  31080
gtaatcgagc aagtgtcgca ataaactgat aactgattgc ttgcttagag gcttgcagga  31140
tgcctttcaa tgttttctct ccatccaaaa ccatcgaaat gttgaatgtg cttcaacttt  31200
ttggcacatt attagctgat taaacaatat caaaaattga taatcaaacc atagcaacta  31260
attaaacaaa acaatggtct ttattttcac aattcttaca ctgtaagatc aaagtaccct  31320
ttaaagggta aaaaagtacc ctctttgaaa gaaactagtt taactcataa aaagagtaaa  31380
gggcctttac tcattaaaga gtaaacggct tgtacgtcag attaacgagt gaattttacc  31440
cattatccaa aaacattttt tctaagaaac agagtaaaat ttactctttt tgaaatatat  31500
aaaatgcaaa tcgattttaa tgtttcattt ctaagataaa taatcaatag aaaactatga  31560
ccataaaaac attttattga aaaatataat aacacatagt ttagtccgat gcgggagcat  31620
tatttattaa aggctgactt gctggcctag tactgctgct accggaggtt atgtgcagcg  31680
ggacaagcat acgagacttg gcatcagaag tctcgggcaa acatcctgtg aaatttgatt  31740
gttttcatag taagaacacg ataggaaaat aatttgaatg cacatacctt gaaattactg  31800
gctattctgg tttttattaa attgttacgg gtttgtgtac ataaactatt atatattgtg  31860
cagggtctaa ggaagaagtt aaatcttttt ttaaattgca aggaaacttt cacccattaa  31920
agagtaaatg gccggaatat ataaaagggt actaaacacc cattattcga aaaaaaaatt  31980
taccctttat tttgacgttt tcatatatca aaaaataatg ggtatttttt ccacattaaa  32040
gggtaatgac gagtttacag tgtacaactg acagtgggcg atattcactt atcgcccggg  32100
acatcctggc tacgaagaac acagtgtatc gatatatggt tgtcaggggc ctgtgctaaa  32160
cgcataaatg agtaaatgct actttgccca taaaatgagt gtgtgtactt ttagacgatt  32220
atgggtaaac tttacccata tttgggtaga ctgatcttag cgtgtacgct cgtcatagtg  32280
gttatcacgc ccaatggtat gggtgcccta gtgtagatgt agttgtgaac cttatacgct  32340
```

```
aagatcacac ggagaaaatg caaaatacta attagattgc tatttattat ttgtgtttca  32400

tttaaggtgt ttattatata caaattatat taattatgca tttccaatat atttttttata  32460

ctagacgatg catatttgga aattattttt tgtcatgcat ttgtgttgct tgttgctaca  32520

cttgggactt cgattttttt ttgtttcagt ttcggtatac caagatggcc ggaggaacaa  32580

ttttcctgtg tggttgtgaa tattaagttt ttctccttga tcgggcagtt ggaagtaaat  32640

taaaatagcc gtgattgaag taattcagtc ctgcggtagt gaccaaaacg tattagaaac  32700

gccggaaaca tttttcgccg tccggaatgg cgatttattg accgacccta aaagtaagat  32760

tcctcca                                                            32767
```

<210> SEQ ID NO 114
<211> LENGTH: 697
<212> TYPE: DNA
<213> ORGANISM: Aedes aegypti

<400> SEQUENCE: 114

```
gctagtctac gtgtgttcaa atgtcactaa gctctataat caaaatagga aaaagaaaca     60

aaattattca gatttctttg aaactttttta tatattgtag actgaagtgt gtttaaatat    120

ttgattgact tcaaatctga ccaatatttt tggtgcttaa tcaacgatca gtggaatctg    180

tttttgtgga gtcatcttca gcaatcagtt tcggtatacc aagatggccg gaggaacaat    240

tttcctgtgt ggttgtgaat attaagtttt tctccttgat cgggcagttg gaagtaaatt    300

aaaatagccg tgattgaagt aattcagtcc tgcggtagtg accaaaacgt attagaaacg    360

ccggaaacat ttttcgccgt ccggaatggc gatttattga ccgaccctaa aagtaagatt    420

cctccaggag gacgatgaga tttaaagcga tgaaaaggcc gacgtatgga tagtttccac    480

ccagcatccg gcaaaattcc catgaggcag gggatcttaa aatggacacc aaacaagatg    540

aaccatacgc tagaacaaag gagtccggga acacgatggg aagatgagta tgagagtgta    600

catttcaaat tagtattatc caaagtgaat aacatgttat tttaatgacg aacatgatga    660

taaaataaat aaatgggata tagtttgttt tattcta                             697
```

<210> SEQ ID NO 115
<211> LENGTH: 625
<212> TYPE: DNA
<213> ORGANISM: Aedes aegypti

<400> SEQUENCE: 115

```
cgtcatagtg gttatcacgc ccaatggtat gggtgcccta gtgtagatgt agttgtgaac     60

cttatacgct aagatcacac ggagaaaatg caaaatacta attagattgc tatttattat    120

ttgtgtttca tttaagtttc ggtataccaa gatggccgga ggaacaattt tcctgtgtgg    180

ttgtgaatat taagtttttc tccttgatcg ggcagttgga agtaaattaa aatagccgtg    240

attgaagtaa ttcagtcctg cggtagtgac caaaacgtat tagaaacgcc ggaaacattt    300

ttcgccgtcc ggaatggcga tttattgacc gaccctaaaa gtaagattcc tccaggagga    360

cgatgagatt taaagcgatg aaaaggccga cgtatggata gtttccaccc agcatccggc    420

aaaattccca tgaggcaggg gatcttaaaa tggacaccaa acaagatgaa ccatacgcta    480

gaacaaagga gtccgggaac acgatgggaa gatgagtatg agagtgtaca tttcaaatta    540

gtattatcca aagtgaataa catgttattt taatgacgaa catgatgata aaataaataa    600

atgggatata gtttgtttta ttcta                                          625
```

<210> SEQ ID NO 116
<211> LENGTH: 32767
<212> TYPE: DNA
<213> ORGANISM: Aedes aegypti

<400> SEQUENCE: 116
agtgtgcagt gctcaaatgt cactaaggta tatatttttt cttttcatgt tttctccagt 60
ttacgctttt cattcttaag tgatggcttt attacgatca tcttttcagg attattctga 120
ggtatgtaat gttttgcatg gcacaagagt tatataacgc taaatatggt aattctcaac 180
catcattcaa ccaaacaaat tttgaataac ctgaaccgaa tccatattat gcacactagt 240
ggtggtaagc accaacgtag ttagtaccag attttatccg gattttcaaa aatccaagat 300
taaatttagt aggtactccg ttcgataagc accaaaatcg gtattaaagc gaagtatgca 360
cttcgacaaa aaagtaatcg cctatctcga tgcgtggaaa atttcttgca acactgatat 420
taaaactcca ttataattta tgtgcgaaaa ccatatagaa gcaggttttc tgcctccaac 480
aatcttttat gtgccacttt taaattttat ttgtggacaa taaatttcaa agtctatgca 540
tgtatatacc actagcattg caatgcatta taaaggttac attagtacaa cctatttaag 600
ctgccaatat ttttgaagag cacaaacttg tataccaacg gttgcaaaaa tgtatcgcca 660
tcttatttct tcgctgctac tgtacgagtt ttcccaaagt attatcatta acagtaatac 720
acatcgcatt tcagccaaat atgtggatgt tcagtgtatt atatctggga tagcaagaat 780
aagttgtaag tattataaaa tggttgaaac attacagatt aataagctat tttttatgtt 840
acagctgtcc aaaaaaaatg caatcgcgtc ggaatcaaat tctaagacga tgaactccaa 900
tgaacatgta tcccgctcat gcaatgacta ttggttaaat catgcgatgc gctggacgca 960
atcgaagaac acagtcgtcc catattctcc agcagcactc gtagactccc acgctcttgt 1020
tggtatcatc cccgtagctg ctaacatcaa cacgaccaga taatttacta tttcgtggat 1080
ttctaactgg atcccgttag aatatgtatc aacttttatt ctccttaata aatgtgcatt 1140
actgtatgcg tatttgattt tcatcatcat ttttttacaa aaagaaaaat cgtaaatttt 1200
ttcgactaat tcatttattt actactcgcg atcacagata aaatatatta gcgtgaccgt 1260
ttgaaataag ttgcacctgc atttgcttta tgtgtgcact gcatttaaga atgagcgtga 1320
caaaactttt gtttttttatg tgcgtgacta attaattgca aatgccaagc ttgattgcaa 1380
aaatctatgg gtgctgcaca taaattccaa ttggagattg agttcagtga agaaatgctc 1440
aagaaaagca tttttctttt gatcgcagta cgcagttgaa aagaaatgtc aattcaaatg 1500
aagctcactg ttagggttga tttagcaaga catgtcctga ttttgagctt cttttgatgt 1560
gtcctgattt atttttcata tttcaagttt tgtcctgctt tcttcatagc tatttttgca 1620
tagctttggt aatatttcag agattgaaat ttttatattt taacctagat gtgcgtggaa 1680
tgtgtcagta gtcggatggt gccgaaaccg taaattaccc taaagcgaag tattgacttc 1740
gcagcaccaa tctggagttc gccggttgga cttccgaagc gaagttttga acgaactaac 1800
tgtcattgct ctgccggctc ggcttttatc tcgactgttt tagaaaactg tccaacatca 1860
cgtcgacgga agaagtttca ccacaacgga ggatttgtca gttcgagcgc gccaaaatcc 1920
ttccgattaa aaatgtgttg gcggtgctta aggtgcaact gtttgctatc cataaatgat 1980
gatcgatttt gtagtttggg aatgtgatat cggttctacc ggacatagat gaactgaaag 2040
tgtatcaaca tgcctgttgt tagcaagcat atgatccgga tagatcaccg aatgatcgat 2100
atgatataca ccagaaatat tttcttttca acgatagttt gaacatagat tgttcatgga 2160

```
tgccacgatg agtctatcgt gtgttacctt aagttcgttg ataaagaaga ggaaaatgag   2220
cgaagttctt tttctgaatt ttatcgggat gcacaatatg cacttcgaca gaaaagtaat   2280
cgcctatctc gatgcgtgga aaatttcttg caagaaatgc tcaagaaaag cattttcttt   2340
taacgcagta cgcagttgaa aagaaatctg cttacttttt taaaaagggc ggaactaaca   2400
aatataaaca aattaagttt tgcacagtaa aacattcaga tcactacgta gtatcaaaaa   2460
aatccatgga atgttagttt tatttgattt aacctgggag ggagaaacca atacgaaatt   2520
tatgtacgtc aaggtgagcc gagattctgc tgtcacgaac tgtcactgtg agcccagatc   2580
taaaacaatg gacaaacatg ataaaagcgc gtaattgatt aaaactaatt ttttgcattt   2640
tatcaaatgt gacaagaaat cgattgaaaa gctattcatg cttattcaaa agtaatgtca   2700
caatagcacc ttttatcctg attgaatata aagtgttcaa atacgcatta ttttactttt   2760
tccaataaaa acgaaaatta aatacacaga aaactttggc cctttttcca tgtttgtcca   2820
gaacgatcga aggaacacaa caaaagaaaa ctagcgattt tcatcaagtc tgccttgatt   2880
gtcgttggca agctggagtt ttcttgcaat tcaaaataac tttgtgtcat atttcgtgtg   2940
taatatcggt gcctccctcc caggatttaa ctatgaataa atcagtaaaa acaaaagggc   3000
ctaattagat tttgagaaat ttactccaaa agtgctattt cgcccatttc cccatttcat   3060
taatgatggc aaaagggcca ttctacaatt ttgattttat aacgggcact tgacatttta   3120
aagcatattt gaacgaaatg actgttgatt aattattatc ataaatcagt ttatgataac   3180
catgattcat acaatcaatt acaatgcaca ttaaattccc aaacctggga tttcgatatt   3240
aaaagcagag tattatgttg gaccgatgtg gtgtcctacc gctgcgtcac tacacgtata   3300
ttttctgcag aatatttaaa tacagtaaaa gcacagacaa acagacgtaa cacttagaac   3360
caatctcaat caaaatcata gccacgagga catgtacgcc aaatgctaaa atatgtgtat   3420
ttggccgacg ggccaacaga tggcggtagt gtataaacgt caaacacgaa caaaaacgat   3480
gcgagcgctg cgggtggcag attggccact taccatattt ttgaatcgac cgtttaaaag   3540
gtggtcgatg gacaatgatg agagtgtgac gtctggttgc ctgtggtaaa atgtaaaagc   3600
atcacattga tcattgggga tcgttgcaat gtaagaaaaa caataataat gctcaacaca   3660
ctatgttcgt tatgctcatg aatccaaaac taacggatcg aaagatgtcc attcgctctg   3720
acctccagac gacggcaaca tccctggcaa catgcattaa tttatccttc tgctgagcag   3780
tgctgcaaaa cttcgcatca cgaagcagct cacgagtgta ttgtaatttt tacgaatgat   3840
tagactttca tgacgaaatt gagaagctgc caataatgta ctgatggtac attttcaaac   3900
accatttacc tttcatcctt gatttttgac actaccagct ggtttcgacc agagaatttg   3960
tttattatag agaagcgcga attctgaaac caaaggctcc aatcgaaccg tcaaacgtgg   4020
ttccaatcga gcaaattcaa tgagactcat ggtggtaagc accatgatcg ctaatactag   4080
atttaatttg gattttcgaa aatcccggat taaatttagt accccattcg gtaagcacca   4140
aaaccggtat taaacaaaaa gaacgtagcc acacgtaaat gtatgcgtat gagaaagagc   4200
aggcaaaatg aagataggaa aatgacattc atatcggtgt tttgttttgt ttccacggtt   4260
cgctgatagt ttttatggaa aatcccagaa tttccagctt cgtctgcaga agctaccagt   4320
gttgtttttc gttgggaaaa tgtctcggag aatgcggtgg tggaaaaagc gtagcggata   4380
gttgtgatgc tgcactcgtt gatggaggaa ctagtgcata atgagtcagg ttgcaggatg   4440
ctgcactgga tggcgttgga aatcatcggc atcggatggt aatcgattga gcatgggatc   4500
```

```
ggaccaaaca ctgaaatccg gatacctcaa accgtttccg attattagga atcaatacaa   4560
tttccgctgg tagaatacgt agaggaattc tcctgattcc tcctgaaatt atacccggta   4620
ctcctccaga aattcttcag gattttcaca ggagctcttc agtaataaca caaaggcaaa   4680
agtttcacct aggatttctg cttaatttta ggaatttctc ctgaatcaaa ttaggtattc   4740
cttcaaaaat tgcaccacag atttttccag aaatgtaacc aaatgtccaa ggattcctgc   4800
ataattttca aaagaaatcc tacatgggac tccttttcga attctaccag ggtttttcca   4860
taaatcactc attattttcc ttcaggtatt tcataagtga ttcctggaag attttcgaaa   4920
gattcctaca taagttcaag cagagattac ttcaagagtt tttcgcagag atttctacaa   4980
aaattctgta aagatttctc tagaagctcg aaggatcctc caggaccttc taccgacatt   5040
cattctagga aaattcattc taagttctct cagaaattcc tccagagaat tcactcgaaa   5100
tttcttcaag gattcctaca gatattactc atgtaacagt ttcaaggatt cctccatcga   5160
atgctccttt aattactgaa gaatgtttcg taaaattcct ccagggattg atgtatgatt   5220
tctggaattc ctctaaaact tcgtcaaata atctttccag ggatgcttct agaaattcat   5280
ccgcgattct gttagaaact ctttctggga tttttgagt aattccagtt ttttttttg   5340
agtcatttaa gatttcttca gttatttctt ctggttgtct ttcaagattt catttatgta   5400
atctatcact tcaagatttt tatcggaaaa gttcgtattg aaagttccat caaaaagttc   5460
ctccgaaagt tcttttgggc agtttctacg gcagttcctt ctggtagtat atccatgaga   5520
ttcctccaaa agttctccca ggtacaaaaa aaatgaagta aattccggta cataccgaaa   5580
gaatttcccg aaggtacttc ctgaagcttc ctggatgaat taagcttcag gaagtgcctt   5640
cgggaaattc tttcggtatg ttccggaatt tacttcatat tttttatttt tttttgaat   5700
ttcctttgga actaccatcg gaatttcctt caaaatttc tttggattat ctttcggaat   5760
tgtctttgga aaggcctttg gaatttcctt cggaattttc tttcggattt cctttgaatt   5820
tttgaatttt ctcagaattt cttttggatt ttctttggaa tttccttgag aatttctttt   5880
gactttgaaa tttttctttg ggatttcttt cggaattttc ttttaattta cttcggaatt   5940
ccctgttttt tttcagaatt ttctttggac gtatctttaa aatttgcttt agaatttctt   6000
ttgggattta cttcggtatt tcctttggca tttccatcgt aatttccttc tgaatttgta   6060
tcggattttc ctttgaaatt tcattcagaa tttcttttc ctttggaatt tccataggaa   6120
tttgctttgg aacttccatc ggaatatctt ttggggtttc ctttggaatt ttctatgaaa   6180
cttttttgg aatttccttt gaattttact tctgcgtttc catcggaatt ccgtaggaat   6240
tttcattaga attaccttcg gaatttcctt ccgaattttc tctggaatta cctttgacat   6300
tttctttgga acatctttg gatttgactg cggcatttcc atcggaattt cttttggaac   6360
atctctagca ttttttttt ttgaaatttg ttcgaaattt gctttggcat ttccattgga   6420
attttattag gcaacttctt tcggaatttc ctttgtacac ccgattctgt ttttgcacgg   6480
ttttttttta cacggccgtg caaaaaaagt ttcgatacat ttttttccga caaaacctta   6540
tttttgcatg aaacgtcgaa aaatggcgtt acttttttg cacggttttt gaaattttta   6600
actgaaaact tttttgcac ggtgtgcaaa aacagaatcg ggtgtatttt cttttgccat   6660
tttcatcgga attttctcta gtattttctt tgaatttcct ttgaaatttc tcgttccttt   6720
ggaacatcct gcggaatttc gttagaaatt ttcttcgaaa tttcctttgg catttccatt   6780
gtaatttcct tcggcatttc tattgtaatt tccttcggat tttccttcgg catttccact   6840
gacatttctt tcgtgatttg gaacttccat tggaattccc gtgatttcct tcgaattttt   6900
```

```
gccttttcga tttgcctttg gaatttccat tggatatttt ttcggaattt ccttaggaat   6960
ttcatttgga attccattta gaatttctct atagaacatc cttcggaaag gatcgcagta   7020
ggcagcgcgc gcgaacgaat gtgtttaaaa ttgatctgtc acgcagtttt tgaaaaaaag   7080
tgtctagcgg aaataagtca gtttattctg cacgcattct gctggacagt gcttcgttaa   7140
agcccaagca gaaggtgaag atgcatcgaa gtcggacctc aaattttcag gagcgcggat   7200
ctggagagcc ggactgagag ctagatcggg tactcgctgg tagtgaccaa tcggacaaat   7260
tttctgcttg agccgctgtc tggttttcca aatttgtgtt cttgagggtt tgagttttgg   7320
gttcgtttca tcttcaccag aaaaatcgtt ttttttattg catcgtcgct aaagtttttt   7380
tttcttgttt tagtttgcac gcgttctctg agtttaggtt tccgcgttgc agagtgatat   7440
tttgcttttg tgaaatgagc atgctgatta aagtagctca cagctgatta atcaaggatg   7500
atcaatttgg tgagctcgct ccatgctttt gtttcaaatg tacaatatat tacgaaacgt   7560
atttttatca tgaaacagta gaaatgttac ttgttgtaaa ttaaatgatt taacaaaata   7620
tgaacagttc gccactatga gtgtctacat agactcttgt acattaacat ttaaaacctc   7680
ataccttcta ttcacctgat tttattatta taaaaatcac ctttgaatgg ttcgctgctt   7740
aaaatatcga cttacagtat gttcacgttg tctttagagt actgataggt attttttgaa   7800
ctgaggttgc ataaatcgca tcaattgcca aggtgaatcc tgaacttgca gctatgatcc   7860
ctccccactt acaaaactcc ttcccatgac aaccaaggag atgcagaggt gaggtcggtc   7920
ccaagtaaca atttgttgtc actctaacat tccttccctt cccttgattt tttaatgttt   7980
ggagttcttg aaagtttaca ttgaagatgg taatctactc ccaagctaca tctcttggtt   8040
ccttgtgcaa cttcgattat tctggtcatt cacgtagtag caactacgaa ttgcacggtt   8100
atcaatgctt atgtttagaa cttccttcgg aaagtttcta ggaagttttt tctagaaaat   8160
gttctagggt ttcatccagg agttccttcc agaatgctgg agaacggttg aaaaaattct   8220
ccgcaaaatt ctaggagaag ttcttagaga aatttttggg caaaatccct gtggaaatct   8280
tggaggagta tatactgatt gattcttggt ggatttttgg aggaattact gaagtattct   8340
gtagaaattc cttgaagcac ggcggaggga ttcctgaaag aaatttgaaa ggaatcccta   8400
gagtcattca tgaaacaatt tatggaagaa tcgtggaaga aatatctgga gaaaatttct   8460
ggaacttcca gacaaatttg tggaggacct tcaagtggaa tgcaatgtga ggatttcctg   8520
aatttttctt aaaaaaaaat ccagaaaaaa tattgaattc gaaggaagtt cctggattaa   8580
cttcctaaat gaactcttcg gaggaacttc cgaaaggaat ttcaatggaa attccgaaga   8640
aaattgcaaa cgaaatccga aataaaatct agtagaaatt ctagaggaaa tttaaaaaaa   8700
tcgaaggaaa atccaaagaa aatttggaat gaattccaaa cgatattccg aaaggaattt   8760
cgaaggaaat actaaaaaaa tgaatcaaaa gtgtcaagga taggaaccgg atccctatat   8820
tacaaaaaaa aaaccttgta gtttctggat taaacgagct ctaaatcttt gaaaagtatg   8880
tggaatactc ctcaatgaga tttgtgaata cacctggtcg atccagaaat aactcggcaa   8940
atttcaatga gatatttcag ggtttctact ggaagaatcg cttgtaaaca tttcttaatt   9000
gtttctgaaa aagtgtaaat aataattcgg gatttttatc aatcaaattt aatcaatcag   9060
atgtatctgc agcaaaccct ggaatgcaca tcttattgaa gaatcatttt attaaaatga   9120
tgatctttta tttgcatgtg acctgtttag tcagaatttg ttataattct cgaatcactg   9180
caaaatagct ttccattgaa aaaaatctag aacagctgaa tacattgggt aaggtgaaaa   9240
```

```
gatgggtaac ctaaagaaag gacctcccta ttttcccaca taataatcga gctaactttt   9300
ttctttctga aatctctcac acagtataag cacagactga cgaaatttcc atcgaccact   9360
catttaacga tcaattcaaa tacgcataat gtaacgaacc tcaaccagaa gcgcgcgttt   9420
ttcttcgtgt ttgacgcctt ctgcacggtc ttgttaccat gcccggattt aggggggggcc   9480
aagggggcaa atgccccggg ccttctgatt aagggggccc tccgagaaac caaaattaaa   9540
aacaacgtca ttttaaaata ccttctaata ttttctcttt agaaacttga acatataaca   9600
caaacgttta agtcaacttt ccaatacttg agttattttt tttcttcacc taatatctga   9660
ttcgcacagt atagtttagt caatgattgt aggattatca tattacatat gattacaaaa   9720
tacatgaatg ttaagccaaa attttctaaa ttcttctcta cttagttttt aaaaaacatg   9780
ggaatttaaa tgcgcttaac gtttttgcag gatcttaaaa aaatacggct aaacttgtaa   9840
agcattgctc aatttaaaga gtttattggg ttcctatcag aacttttaca tttaaacata   9900
tttgcaattc tatcagaaac ttgaagtgta agggaagttc ttacaaaaaa gccgaatttc   9960
atacaaaatg ttcaagttta gggaacttta tgacagcttc ttacaaaccg attgacctga  10020
aatttgaatt acatctaata aataacttga aatttgattt aagggaaatt aatcaaattc  10080
cattaaagag ttcggaaggt attaaaaaaa tatatttaaa aaaatgccaa aatttttaat  10140
tggagtatat tttaaatgtc aaattcgatg aaatgcaaaa ctttgtaaaa gattatactt  10200
atcgtaaatt gttagtcttc aaaatatcat agtatcaaaa tttgaacatg ttcgtcaaaa  10260
tgggagaatt ttaagaactt agaaacttag aatttgatga tttattcaca gatctaattt  10320
gaagctattt gcaacatgct atatgcaaca tcggtttgca agaagcagag atgcaggtct  10380
ccaaacttga ccatttttta tgaaaatcaa tcattgttga ttttttttgc cagtagagac  10440
aaactggaaa cttgtagaga atagaatcaa aatgagctct ggagcttttc tctccatacc  10500
aattatatag aagccaaaga acaagccaat cttctacgaa ttgttatatt tttcccattg  10560
gacggaaaaa taatcttaaa atactattga aaagtttgaa aacagttgaa ttttgcgatg  10620
tatatagcta acaatcgaaa atgtcacttg caccactatg catttgggcc tctcatatcg  10680
ttggaccgac catctcgttc aaaattcaaa ttcaaaacgt tggtttgtga aatcctaaaa  10740
cgtgctgaaa tttgtataaa agggccccat ttatgagatc tgacccgggc cccccgaagc  10800
ccaaatcagg cactgattgt tacacaaaac agtgtttcgt gcaacatgct caccagatga  10860
tgacggtgat aaatggccgg attttgaaga aaagtgttac gtcggtttgt ctatgctata  10920
agtcttatat ttgtgggctt cgtagccgtg cggttagcgg cgtcggtcgt ttaggcgtac  10980
tgtgctacga agtgtgggtt cgtaaattgt ctttttataa caaaatatat aaataaaata  11040
aaaaaatacc ttttgacgat cacatttcag aacgtgtttg tcagttatat attttggaac  11100
ccataggctt aggcgacatg gaccaactca tggtctgagc ctgaaaaaaa cagaggcaaa  11160
ggggccttca atcaaatatg caatacctac tatcagtaca acagtagctg ctcatgcccc  11220
tattaccgct cactaaggca gaaccggatg tttgtgtaaa atgcaatctt tttcgtactg  11280
atatcctcta gttacatcaa caactttcaa gtgaagtcgt ctgacattat atgcatttgt  11340
taaactaaat cactgtaata aaacacaaaa gaccctgtga aaggctatta tatcaatgtg  11400
ttccaataac cgcccagcaa aaaattttac aaaaaaaaat cagcgttgtt tttttataat  11460
ttgatttttt ttcatatttg cataacacta attctatttt cctttatttg gtttgggtca  11520
tcgtcgaatt ttatattttt cgattattgg taattttcgg tgatgataac acacactaga  11580
tttcgatttc acatgacgtt tcggcctact gacattcgac catcatcaga tttttatgcg  11640
```

```
aatcgatcga tcaccaccag tattgcaacc acacttatca tcaccgaaaa ttaccaataa  11700
tcgaaaaata tataattcta ttatcgtaac atatttctgt gctgtaggat gaagaatcac  11760
tattcaccac tgcttcatga acaatacata tttatacaag ttagcaaaga tatatataag  11820
tttgcaaagt tataatcact catgtcagtt agatattgta gtagtatcaa tcgtttgacc  11880
atcaacatat caggatgagg aacgaaattc gaaaatttta gtatgttcgt catgaaatct  11940
gtttcctcta aattttcatt gattgcctat actttgagct acattttgac ataaaaatag  12000
tgtgaacaga ctcaatagtt ctttttaata aatatttgaa cacataactt gttcttaatg  12060
agcggaatat aattcactga tggtaatcac aatattcttt tatactcacc taacctttac  12120
atagccattg actaaacaac gacaacaaat caacaaaaag atgatttatt ttgaaatccg  12180
tagctgttta ataaactgaa aataaactct aaaaaattac attacaacgt ttagctttca  12240
cattgcaaat gatgttacaa agtagtcttt cagcagaaaa tgaaacgtgt caataatatt  12300
acacaattgg ctttaaatat caaggtgacc taacaattgt acgttgattg tatgtaatgt  12360
attgattata taatattatg tttacaagta aaaaaaccta agaaacaata aaccctcctc  12420
ttagaatact tcctggaatt tctccggact tcctccagga attccttctg agattcgttc  12480
aagaattcta cctggatttt tttcaggaat ttctcctgag atatcgtcag gaatccctcc  12540
tgagattcct tcaagaatta tttcccggat tttttctgga atctcctgag aattctacag  12600
gaattcctcc tggaagccct cgaagaattc cttttgggat tggtccagga atttctccta  12660
cgattctttc cagaatttct cttggatttt ttccagaagt tcctctcaga atttctgcag  12720
gcatccctcc tgggatacct ccagaaattc ctcttgtgat ttctccctga aatccctcca  12780
gacattcctc ctgcaatccc tccaagaatt cctcctgcaa tcccatcaac aattcctcct  12840
agaattcttc cttcggactt cctcaaggaa ttcctacaag aattcttcct gagattcctt  12900
caagaattcc acctggtaat ttttcaggaa tttcttctga gattccttca aaaattgttc  12960
gacggatttt tccaggaata tctcctggat ttcggtaaaa aatcacgtaa aatttcgacg  13020
gagttacggt gttttatttt accgaactgt tcagctattg agattacggt aaaattcaca  13080
gattccggta aaatgggctt agtgtgtagc aattccacct aaaattccta cagattttta  13140
ctgggattcc tccaggaatt ccttcaaaca ttcttcctga gaaccctccg gatattttat  13200
attaaaattc ctcctgtgat tacttctggg attgctcctg gctttcctcc ataaattctt  13260
cctgtgattc cttcagagat tcccccagat tttttttttc ttgaattctt ccagaatttt  13320
ttcccattat tgctcctggg atttctcccg cgttattcca ggtgttttgt ttttggtttc  13380
tccaggaatt tttcatagga tttctccaga aattcgtcta ttagttcctc ccagagtttc  13440
tttcggagtt cttataggtg ctcctgcatg gattccatta ggagctcctg caatgattcc  13500
accatctttc ctttaggagt ttccctgaga ttcctcttga aatttatgct acattttctg  13560
ttaatatttc tacagcaatt tctccttaga tacctcctgg tattccttcg tggaatcgcc  13620
tgtaaaagtg tcgtgtgatt tctcgtggaa ttcctcttaa tccatacatc ctagaaatat  13680
tcccaggaat atttccgaaa aatcttttgg atattttact tggttttcta ccggttattt  13740
ttctgtgatt cgtcatttga tatcttcaaa aatatctcca aatactcgtg ccgggttttt  13800
ttcccgggat tttttaaaat atttgtccaa tttttcctta atggactttc cgaacaattg  13860
ttcacaaaat tgtcgaagaa atcaaagtta tttataaaaa atataaataa tctctcaggt  13920
tttatttatt cctctgttat attttccgaa atcttccaat agattcttct aagggttcca  13980
```

-continued

```
ttagaacctg tatcaagaag acctcttgta gatattggga gtcttgaaga atcctaacgg  14040
agattacttc agtagttcct cctatagttc cttcaaagat ttttctgttc agaaagtcaa  14100
agtattacta gaataataat gcgcttctta tatcccttct aataaaatcc taggggattt  14160
tagggaataa taacaaaagt tcagtaattg tcggttgact ttttcgaatt gctagacgaa  14220
ctcataaaag aaaaggttca gctggttgat ttaaggaaga acttcctaaa aacaacagta  14280
ggattacata cacactgaac gaatgcggta atttatttta tgtaggagtc tataaacaaa  14340
cactcaagaa agtcttgcca aaatcgttct aaaaaaatca caggggtaat ttctgagaaa  14400
atcatcaaaa gatttcatgg gggaatctgt aaaattccta aaaataaaaa atctttgaag  14460
gaatatggag tacttgtagg tttcatgtgg gaaaactcca ggcttttact gtaggagttg  14520
atgctcatga atccaagtgt aactccagga taatttgatg aaaaaaaatc tttgctgaaa  14580
aacttgaaaa aggtattttt gaggaaatac ggaatgatcc taaaagaatt cctgttaaaa  14640
attctggaag tatttatgaa aaacactgga aattcttctc tgacgaatgc ttcttcctga  14700
gacaaaactt atacaatgta ttcaatttga tacagcatga gtccatggaa gcatccattt  14760
cttgaatcaa tccgtgtaag agtttttagc aaaaactctg agggaatccc tgttggaact  14820
tctcgaggaa ttccttaaat aaatcatgaa atctcatgaa aattcttata gcaacccctg  14880
ggtttactca tccctgaagg tcaaatttat gaagaaagtt ttggattaaa ctgtacaaga  14940
ctacatggag aaatacatta aagttctccg cgaagaatct tcaaagtaat ctataaaata  15000
gtagggtgca gaaccacttg ggcacttcca tgattcactt tggcagggga ctcgaacgaa  15060
tagtctgaaa cctagcagta agaagcgttt agtatgacgc atactgtggc caaatatgag  15120
ctctgcagct ttcaaaaaac cccactgccc aagtgaatca aaagtgccaa gaataggatc  15180
cggctcccta cttaaagaaa atcccaatac aatcgaggga agaacatctg attgcaatcc  15240
tggaatactt ttgaaacggg tttcaagaag cctataacga ccagtagtat ttgatccacc  15300
taatatgttc atgattaaaa attaataaaa gtttatcaat gttctctaca aagttatagc  15360
tgcacttatt caatgaagta tagtgagata aaaggcatcg gtttcgtatt gcgaggtgac  15420
actgacaatg aacgactcac cgtgtaagtg taaatgaatc ggggacccgt cgcattcgag  15480
tcaagttctg tcactctgtt cttagaataa atttacgctt ctttacggtg tccaaaatta  15540
cccaaaactt ttttcaatgc atatattttg tgctagaacc aacctattag cttcatgaat  15600
ccagggactc tactccttct ggatattgtc caccttgctt gtgaatgatt tcggaacgag  15660
tggccttctg agaatggcta gtgctcatat agtcgatata atccagtcac tgtcgttaaa  15720
atgcttcagc accaggtcga ttgaataggg cacttgcagc ctttgtttag tgtgcccaac  15780
ggacccattt gattttgctg ggaaacgtac cgtaacgtgt tttccgtttc aaaccgttac  15840
ccagcaaaat caaagggagc cgttgggcac acttttgttt gctgcaagcg ccctattgca  15900
ttcttcaatg ctcaactagc gttggcccaa acattggcgt gtcatttcat tcaggtgtgg  15960
cacaaggttc accgttcgat agcctctgaa aacatttttt tttaccttgc ctgattgtcc  16020
tcggcgattc gagcgttatt cgaatttggc actgcatttt cacattcaac tgcaatcaaa  16080
cgatcaacgt tagaatagct gtttcaattt cccttttttgt attacctgtc ccggtgctac  16140
tgttttacaa tgcgctatct ttggttcttc gctcaagctt agctccagct cattattgct  16200
gaacccggcg aatattcttt cattttgctg caaaggaatg tttaatttat tttaaaatta  16260
ctaaaaagtt ttgaaattta cctgaagaaa gataatctgc actcctggag acaaattaca  16320
actagtgatc ctttataaga gagatacgcg gaagctgaca tttctgtcaa agtgtgagcc  16380
```

```
aatcgagcag cgagagctgt caaagcgtga gccaaacgaa catgagccta tagagcttag  16440
tgacatttga acacacgtag actagcatac gctcgtcata cacagtttgt ttttgttttc  16500
ctcaaagaaa cttgcacacg ctttccagac tcatcaaaat gcatatggaa atattaccca  16560
atttgaaaaa tttacacccg gtttctgggt gtttttcgag actgagtgta tattgttttc  16620
ctctaaggtt cacaactaca tctacactag ggcacccata ccattgggcg tgataaccac  16680
tatagtggtt atcacgctca atggtatggg tgccctagtg tagatgtagt tgtgaacctt  16740
agagcaaccg taacggtgcg cgactaaact aaattacata gcgcagtatc attacgctga  16800
tccgtaccgg gcgctgctaa ccagggtagc aaaatgacag cgctgctttc ggaaagcatc  16860
gggtgagcaa atttagcagc gcgatagttg cgctgctatt cgatttgaat tcaagcatac  16920
ggtgtgggat atgaaattct ggttggagtt ttggaaatct gatgcatgat gcatgaagta  16980
gaaatttcaa aattttggga attcgggtaa accttcaaga ttttgataag aatacaggtc  17040
ggactcgatt atccggaggc tcgattatcc ggggactcga ttatccggga ttcgattatc  17100
cggaatttta gactcgatta tccggaattt gtttttcgat gttcttgttt ttcaattttt  17160
atgcatgaat ctgaaataat ttggtattgc aatatacaat atgaatggtt ttgcagtttt  17220
gaacgtattt aagaaaaagg gggtttgaaa aagtggtttt ttgtgtatgc tggtcaaagt  17280
tttgtttttc ttgtaaagac ccctactgtt ccaagaaata atttctggct acgccaccgc  17340
attataaaaa tagaacaaca acaagacgat aatatttaag ttcttttatc gaagatttca  17400
atttttttct cagtgattcg attatccgga gtgaaaaaaa aaatcgatac tccggataat  17460
cgagtccgac ctgtactagg tatctgatgc aattattgga aatctgatag aagtttatga  17520
aatattcgaa aatcctcgta agaatttatc gatttcggag aattatggga ttttgggatt  17580
ccgactggaa tccttgggat tccgactgga atccttggga ttccgactgg aatccttggg  17640
attccgactg gaatccttgg gattccgact ggaatccttg ggattccgac tggaatcctt  17700
gggattccga ctggaatcct tgggattccg actggaatcc ttgggattcc gactggaatc  17760
cttgggattc cgactggaat ccttgggatt ccgactggaa tccttgggat tccgactgga  17820
atccttggga ttccgactgg aatccttggg attccgactg gaatccttgg gattccgact  17880
ggaatccttg ggattccgac tggaatcctt gggattccta ctggaatcct tgggattcca  17940
actggaatcc ttgggattcc gactggaatc cttgggattt cgactgcaat ccttggaatt  18000
ccaactagaa ttccgactgg aatcctcgtg atttcggctg gaatcctcgg gattcagact  18060
ggagtcctcg ggattctgat cagaattgga aagagatttt gataagaaca ccgactggaa  18120
tcctcgggat gccgactgga attataagaa ttttgggatg ccgactggaa tccttgggat  18180
tacgactgga attcttggga ttccgactgg aattcttggg attccgacta taatcctttg  18240
gattccgact ggaatcctcc gaattccgac tggaatcctt gggatatcgt ctggaatcct  18300
cgagatttcg gctggaatct tagggattcc ggctggaatc ctcgggattc agactagagt  18360
cctcgggatt ctgactggta ttccagttcc aaaattctta taattccagt cggaatccca  18420
aggattccag tcggaatccc aaggattcca ataatcccaa gaattccaat aatcccaaga  18480
attccaatcg gaatcccaag gattccagtt ggaatcccaa ggattcaagt cggaatcccg  18540
tgaattccag tcggattcac cataattacg gtcaaatttg caatatttct tgtaagattt  18600
acaaggattc cggtagaatt ggcaagggtt ccaatcaaat tagcatccaa tcaaattcat  18660
aaacaatctc aaaaatttcc gataaaattc ttataattcc gcaccagaat atgatagata  18720
```

```
tcccagcaga gttacaaaaa ttcccaacct gagttgatca ccattatttt cacaactcat  18780
atgttaaccc aaaaagcaac gaccggtacg gaaacgagtt actaaatatg gtagccaccg  18840
gtgtgagaat gagtgactaa actaaaatga caactctggg ggtgatcatt ttaatcaccc  18900
aaatagtcgc ccccgttaaa aatgctctta gaggaaaaca atatgcactc agtctcgaaa  18960
agcacccagc aatcgggtgt aaatttttca aattgggtaa tatttccata tgcattttga  19020
tgagtctgga aagcgtgtgc aagtttcttt gaggaaaaca aaaacaaact gtgtatgacg  19080
agcgtatgct agtctacgtg tgttcaaatg tcactaagct ctatgcatgc tataaaacgt  19140
ttgactttta ctgtgcgccc tgttttcaag tttcccgtaa gagagagcga gacagcacca  19200
acacacggcg cacagtaaaa gtcatgagaa caaaagaatt tatggcacct acagaggctc  19260
atgcgttatg tttgttttga acttttcttg aggagtaatg taatccgctt gaaattattt  19320
cggtgaaaat tgttttgcat tgagcaaaat atatgaaata tttacctttt tttaatgttt  19380
gtcaatgcga tatttagtta gtgttttttt ctgctgttta ttagtttgga aatgtagctc  19440
aaagatctat aacgaaacaa aatacacttt ttagctatgt gaaagtcatg ttcgtgttac  19500
aatattattc tcgacgccga gcaaactcag cactgctggt ctgttgccaa atcattccat  19560
tttacttccg ctaatctctc atataaagga tcacaaatta caacccaaca acgagaccgc  19620
tatcagatgt ttttgttttg attatcgttt tcgtctgacg ttttcgatgc taatatggtg  19680
tgcgtgagtt catgttacaa gcacgcaccc actttacaca taatctcgga ttatctttag  19740
tgccccaaaa tcggcgcact aaagttaata ccggaattta atttttaaaa tcaaggataa  19800
taccgttcgg tgcttaacaa aatcgaggat aatacgtgat cggcgtatca tcttagatgg  19860
agcttaccac catcaaagac atgttacgca aaagaaacga tggatgtgtg ttggtgaaca  19920
gcgaaacaaa agtgacgtca ttgataagct tggtttctta tggcgactgg caggatgaca  19980
cgcacactaa aattttgttt gaatgacctc aattgttgat agtcgttgca aatattgttt  20040
ataaacaaag tcaaaatcct ctccgcgttt ctctagtaat catattctct gactccgact  20100
tatgtatgtt tacgaatggt gtggaaacta tacagagaac agatggaaaa tgtcattttc  20160
ggttttgcct ttatgctggc attctcacat gcacacattc tcaaatttgt gcgtgatgcc  20220
aaaagtggct gcgtcattac ccactttggt gcttaacgaa cgggggtact aattttaata  20280
cccgattttc gaaaatccgg attaaatcag gtatcatctt tcttggagct taccaccata  20340
agtggtaaaa aaaatcgcaa tataccaacg cataacaaac atcacagact cgggaactag  20400
ctaggtgtga gtaagtccgc acccgtctga tcgggagaac agggagaaca tgtcaaaaga  20460
agtagcaaca agctcgggag cgtttactcg cgagtaaccg agcaaggtgt gatttattat  20520
ggttttgaca gacaagttaa ttatataacc atcatatcga cagcaaacta ctattttgta  20580
gtcaaaagcc attggaaacc ataaatctcg gaggggaagc agctttttcc caaaagcaca  20640
atatgactct gaacagctcc gaacaggttc gcgaatcact tttagcttca gttactcggg  20700
agccgacaga tgcgagtaaa ccagtgcact gacgctcggg agtgtttggt tttgtttttg  20760
ttccagttca gaagaaatgt tcgtcacttt ccatcaatgc tgctgaggtc acaaaacaaa  20820
cgaaatattg gtgaaaaata atattgggtg gtttacggtg ctgcttgatt gtcgttcagt  20880
tttagaagta ggaagaatct gcacttttca cctcacatac ctggctattg gatgaatatg  20940
ttcctgacta ggtttctggt cacattccca gcgattgcaa acttgtgctg cttctccagg  21000
atctctataa cgattatacg gttagaatac gttgtagtcc gcggtaaaac ttcgtaaaat  21060
acgtattgtg ctctgcaaga taaatctacg taatgcgatt atctgaaaat gtcgatatac  21120
```

```
cgtcgcagtg ataatgaaaa tcaataaata tttcagattt agcaaatttg atacatttgt  21180
gtccttgaag cacgaaacaa tccaagccta cttgaatttt gacgttgcgt ttgaattgcg  21240
cgcatatctt ctgcgcgtta ccgccgccgc tggatgtgga tttaattttt gtaatttatt  21300
tagtaacaac gatactctgg cggttttacc atttttcagg tcaaggaaaa aataacagtg  21360
tttttaagaa aattacatgt agaaaactag aaatcacaaa agtagttaca aatagttaac  21420
gaaagttaat taaatttaaa gttgaaatga gtatcaacgt gcgttaagcg cattcttgaa  21480
tgaataataa gttggttgct ttttattgct agaggaagcg cattccaggc aacagttccg  21540
gttattagca cactcttccg ttctgaggta gtgtgtcgtg ggacgatgaa gcatcgggag  21600
cgatcctgtt ggcctctttg aaggtggtgc agaagatact cgggaagatt tccatagtac  21660
ccttgtcgca tgaagcagag tatacgattt tggtagttaa cgctgagttc atgtccaaga  21720
accccgtacc gcagcagtcg attctcgctt tcgaagattg tacacgaaac gcaccgccgc  21780
cttgaagccg cggttgagct gctccttctg tgctgcagac aaaccggtat agtacacaac  21840
atcgcagtag gttagaaatg gaactacaac tgcttgtact agcttttttc ttgtggctgt  21900
aggtagaact ggactgaact tcctgaaggt gtgcagtgtt tcaaaaattt ttgctgtggc  21960
gtcattaact tgagccgacc aacgtagatt tctgtccatg tgcaggccca aatttatcac  22020
tttctcagcc actggaatca catcggtaca gaaaacaatt ttcgtattgg gattcaccgc  22080
tccctctttg cagaaaatga tggcttgggt ttttttcggg tttggaaaca aggcgttccg  22140
tctggcccag cgttctattg ctttgaggtc cgagttaatc ttttcgatga gcgtgtcaac  22200
gtcttctttt cgtccagtga tgtatatttg aaggtcatcc gcgtaaagct gatattgaca  22260
cttcggacct tgtgggagac tgttaatata catactgaac agaagggcac tcaagcatga  22320
tccttgaggt gtgccatccg taacaggaag aacagctgat gttgcgttga tggttttaac  22380
gactagggtt cgatgagaga gaaacgagga tactagttgg caagcgttgg ttgtgaaatg  22440
gaactcttcg cgcagtttac ctcctaattt acggtggttt acacagttga acgcgagcga  22500
aaagtcgact agaaccatca cagtacactg accattgtca aaacccttgt agatgtcgtg  22560
agttatctgc gctgttgttg tgctataacg ctttcggtag ccggactggt gtactgccaa  22620
aagtggagga ttcgattgtt ctgcaaagtc aacgatctga ccgagcaaag tttttttccag  22680
gaccttggag atcgctggca agacggagat tggccggaag tcttttggtt gaatgggatt  22740
cgatgttttg gggatcgggg ttacgactcc tttcttccaa atagctggga acgtattgct  22800
atcaatgatg gtattgtaga cgtccaccaa tatcggcaat ataaacgggc atagtagttt  22860
cacgaaagat attgggatgc catctgcccc aatggcatta gattgtatct cagctatttt  22920
tgtggcgact tctacactgt tggtatgctg aaagttgaac cgttgctccc cgtggtgcac  22980
attgggcctg tggtcttccg tggatggact actttgcact gtcgatcgaa gttggcggtg  23040
accgtcgcag aagaaactat tcagttgatc aggtccaagt tccacgccta tcgggttgtg  23100
cttgctgctg atatggatgc cttctcgacg taaattactc cagagtttac gagtcggcag  23160
gttagatgga aagtaacgct caccgtatcg tttcttagaa gcggagatga gagaggcagc  23220
agtatctcgt tttcgaacgt agtcaagcca ttggttgtcg cctcttctac gatttggatt  23280
gcgtgagtag aggttgtggg caagatctct gatgtaaatg gcctcctcga tgtcagcggt  23340
gatccagggg gtcttcttgt ttttgaccct aatcaatttt tctggtgcat gctgattcat  23400
taggctctgc agccgcaaag ttacctgctc agctttgttg ttggcatcgt tacagttggt  23460
```

-continued

```
gatgttctcg aagttactga gttggaaatc cgcttgaagt ctaacagtgt ccacagctcc  23520
gaaatctctt actgtaatac gcagggcttc ttgttttctt attcggacgt cggaaatcaa  23580
gaagattgtt tcatggtctg agatgcagct tgaaattgct ttggcggtta cgatcgaatc  23640
tgaacagtca gtcactagca gatcgatggt agtggcactt acatccgtta tccttgtgag  23700
agacgttggc aataccgaaa gaccgaaaga gtcgtgtatg cgtttcagtg caacttggtt  23760
gcctacggga tggggaacat ttacgttgat attgtagtca cccagtagga ataacctgtc  23820
caggccaagc tcctggatgt caaacagaag tttttcgtat tcttgtgcga aatactgatt  23880
gccactgtag ggattgtaca caatggcaat gccaatgttc aaatcattga ttcgaacttt  23940
cacgacaaga tattcgagcc tttggttgat aggtatgtcg ggattgaaag tggatttcag  24000
tactggaacg gtttttattc cctttcgaac atacaaaccg attcttccgc acgatttact  24060
acctcgacct ctagctgaag gaatgcagtg tttaatgaag ttgtaggatg gtattcgcac  24120
agggccggtt ggattagatg acttcatctt ggtctccgta actccgaaaa agtggtattg  24180
acttttatgt aaagcaagct tcataccatc gatgtggcgt tctaaaccac gcacgttgag  24240
gtggccaagt cgtaaattgg tgtaattgtt tggcatattt gggttgtagt gagaatcgtt  24300
agcgctttgg accgtccagt tagttttgca gagaacattc agcagattcc gcgtcgtaga  24360
aaatggaaga ctcgttgatg cagtaatccg gtttcactaa tccgagaagt tgactgatat  24420
cttcgatggg gatgtacttc ttttgcccag gaagacggac cgatacactg tcgttttgaa  24480
cgtacaccga ttcgactagg tcgttttgtt tcattcgtag cgcgaggtta cgtatccgaa  24540
aactaccgat agatagcatt tcgttaacag tgaaacgata ctccagaggt agtccagatt  24600
tcaagttgca caatttagct tccttgtgct tcttgaagta cttctgaagg acatcggttt  24660
tcaaaccaac gctatcgaat gcgaccagga tggttggcgt gatcgatcga tcggtccatt  24720
tggaaggctt cacgggtagt cgaaagcacg tggttacatg ggacattgag tcttggatgc  24780
ctaagaaact taggaaattt tgaacaatgg accgaacgtt ttccccggtt tggtacggca  24840
ctttgttgat agagattcga aaactgttga cgcttcggga acagatattg gctagtttca  24900
cacctttgtc aattacctcc agcttttgct caacattgct aatagtcatt gtcggcatct  24960
gtttttcagt catcagtacg tttgactgaa tcttattttg cactctatca aactgcttcc  25020
tcacgttgtt ctgaagtgca gcaatttcac tttcgatctt tttgattcga tcaactagtt  25080
cttctatctg ctttgcgatc actttcatac cggtggcact agtattagta ttcttcggta  25140
tcaaactacc aattacagta cactgctcac acaagtacag ataagcactg atgtctgcaa  25200
gcacgtcctg gctaactcgt acacacatgt tgtggaacca cttagaacaa gaatcacaac  25260
agatccaacc aattcctgca tctttcttcg atcgcttctt cgtctttttc ctttgaacag  25320
gcggttcctc acgaccgcag gcctcacaaa tatctccact cataacggtg atacaaccac  25380
tacgctaacg attctaattg gaattaatgc tccattttac agtcgaccgt acgactagag  25440
aagtactaga tcgattggcg ggttggcctg ctgcctgcca aaaattttcc gtcagattag  25500
agccggatcg caaaacggtc aaaacccgcg tcggctgacg atcggggacg aacccccacc  25560
ggaaacccgt gcgctacact tcactcagta gaaatcagct agtatcggaa ataaaaacag  25620
cggaaaacac agaaaatact agggaaaacg ccgcagcaaa aaaagattga aacgcgtcga  25680
aaaacagtgc tgccagaaga tttaatataa gcgccgcaat acttttcttg agctgaacag  25740
catacttagc ttaacttaaa gaacacagcc acgtgagaat gtgtgcgtgc gagaaaagag  25800
ctgcactgca agagagaatg gacttatcca cggtcttctt ttatcctcga ctttcttttt  25860
```

```
cttttctgct gtaaatgcgg gcaatgctta cattaaatga catccggacc aacatccgga  25920
caacgaatgt tcaccggatg aacgtgaatt ggatgaatgt acaacgaaat cgttcatttt  25980
ttgtaaacac ggcccgcagt aaaaggtttt cttcccggcg gaagaagcag cgtgacgtca  26040
ttgtagacta gttcatgaat tgaaacgaca attcaatcgc ttgtttgttt tgttttcata  26100
attccttacc aaaaaagtgt tggattttgt atttttctgc agttttggct ctccagcagc  26160
tttttgatgt gcgtgaagtt tagattaaac atattagaac tattcggctt tcatcgcttt  26220
catataacta gcaacgaacc atcaggtatt cctcaaaaat gtcctgcaaa gtaatggtct  26280
ctgccggttt gcttctggat atccagcaaa actggtttgt ggcagagaat ctgtttatta  26340
gtcaaaaaac gtgtcataat gtagagaaaa actttctcta cgagataaaa atgctcacac  26400
tggcatgtag ggtaaaaaaa cgtcgaaaat aattgaattt tgtattgtgc tttgctttga  26460
taaatggatt attgggaaag ttgtgtatcg cacttcgaag gtcaccaagc agtggttcca  26520
atatgtttct tagcaaatgg atccataccc aaagttcttc aaatgtacat ttacgcgacg  26580
gtttttttta tccaaatgca gatttgcact tgactgcatc attttcacaa ttaattataa  26640
tcgaacaagc ctatttcaaa tggcagacat gctttcacaa atgttttaca agcaagtttt  26700
cgtgaaacaa atgaaacaaa caaactagca accctgctga gagcacatgc ttttgataaa  26760
acataaacaa tttcagttgg cgcgaaaccg attcactgcc ttttcttgcc cgccaacggc  26820
gaaaacaaag ggtttgacgt ttccgcactt atgaacccgc ccgcacttct gaagtgcggg  26880
gtccaataag gtgggaactg cgcaatatca ctggttttca ttattttgga cacaccaatg  26940
cattttggac cctcaaagta tatattttgg acccccggca ttttttatcg cttggcgaca  27000
aagtccatga cactggttgt gtaatatgct tgcccatagt ctaatcaatc gattgacaat  27060
ggaaaaccga agaaattctg cgctcttata agcgatttct tcaccaccgc ttaggtctta  27120
aacctggttt aatcgtatgg gtaaacgtgg tttacggttt aagcgaaggt gaagaaatcg  27180
gcccttagtc cacaaatttg aaaaaagttt ttgtttacgg cttcaatttt tgtgtgtaac  27240
gtgttgtaac ggttgcatga ataaaccgat taaattaaat aaatttctga taaaataaac  27300
actttttctg tgtacaaacg gttgatgcaa gtgcggaata gtcctttctt cccaaatggc  27360
atgcgaattg agttgttctt ttgatttaaa ctgggaaatt tgcaggaaaa tagcccaggg  27420
ggtccaaaat atattggtta ccctagttcc gaaagtaact ggaatcatcc cagggacgaa  27480
gatcgacgtt tcttcttggc cgatccctac tggatttcac cttgcagatc ctgagtttaa  27540
tgttcccaaa ggtatcgata tgttgattgt tgcctctaag tttttcagtc tacttaagtc  27600
aaggcagctt cacctagctg atggtctacc ggaacttcat gaaactcact ttggttgggc  27660
tttctccggt gagattagtg atgttgatag caatgagttg ctatcttatg cagcttccct  27720
tgattctttg gataaaccct taattcaatt tcaggaagtg aaaaatgttc ctgaataaaa  27780
tccattcact tctgacgatc aatgtgtaaa atcgtcccag caaactcacc aacggttgcc  27840
ctcaggttga ttctcaatcc acctacccta tcgagaagat ttgcctgact tgcagaggcc  27900
tctcagtaaa aatccgaatt tcaagccgca atataccaaa atcattggca aatctgaagc  27960
attgagtctc agttttgagg ttaatgatct gaaagacaaa gatcgaattc cgcgtctttc  28020
cgtaatttgg ccgaccaact ccactggtct gcctttgaag tcgaacgatg tttatcacgt  28080
agggaagcct gtcgaaagcg agttgtttag cagccttcgt tttcgtaaac actctgtgct  28140
ggcagaatct tgttgcaact ctcctcgcca aatgccatcg catagtatct ggatgtgatc  28200
```

```
tatcgtggtt gcaattctgc aacgcttgag cacaggtttg cgaggtcact attccacggt  28260
atgtgttttt aaccttgaca atcgctgtaa aaatccacgg ttgcgcagac gcatctgatt  28320
atggggcagt agtttgcgtc cgtatagttc tttccgatag ttcagatcgt ctccacattc  28380
cttgtagaaa ttcgatagta cccttctaaa ggctaccagc ttcctatcta aattcaatga  28440
ttcgtacgtg cagcgattca tccaagctag tcatctaagg aattaatctc ttcaaattcg  28500
atttatcaac ctagagctca ttattaaagt cggtcagtat gaagtcctca gtgctaaaat  28560
ccagagagaa tgaatgaaga aaaatgtaag cgtattgtag acctaaatcc cttgtgtctc  28620
gttggagttc tcaaagtccg agagaggctt aaacactcct cattgttgtt taagaaagcc  28680
atgaaggttc agaaaatctg ctcgtcgtat tgccttggat attctaccca ttcaccatcg  28740
ttcctaaacc cagttgagat ggttttcaat tgaactgtct taatcattgg caatgtgttc  28800
aatgtttgcg tgatgatttt ttcattaaat ggcctcgttt ttgtttgcaa acagtaaccc  28860
atctttaact tgctggccgt ttagttcaca aacattactg ccttccctgg atgatgctga  28920
aactggaact agctgtgcgg acaaaattgt caaaaaagaa agaaaggagt agagcacaca  28980
aggagcaggg gcgcccggat aaaaacgtat cattcagtga atggaataaa gcggtcactg  29040
atcatacaga acctccaact gccaaacaca gtacatgcac tagacagcaa gcacactcat  29100
cgtgttcagt tgctcctgat agttatcact aatacataga ttacacttct gtcattctgc  29160
gaaaaccacg tgctttcaat ttgggcggga aagtttttcc attcatttca ccctgcggct  29220
gtcagttcgc tgtaacggct gcgggcgtac gaccgccgcc ggactctaaa aaaacataag  29280
atgatcaata taccctctca ataaaaatcg tattaaatta cgcccagtat gattgtttag  29340
catgagagta aataaaatac cagtacatat gtggaaattt gaaacaataa ataaccaaaa  29400
ctatcctggg aacagataat ttggtgtata ccgtcgagtg caggtagttt aatagcgtat  29460
aattgataaa attgcattga tatggcaagt ttgattaaac agtcagagaa ttcatctcag  29520
cccggcggga gtatgttggc accaacgcca aagtagcgtc tcagtccgtt aacgaaaatg  29580
tcacattaca aattttgtta ttttcattca tcccgaccgc tcgcgcaaag tacagctgta  29640
taattttcat tcaaaatcac tgaaccaata gaaataataa accatagaag aagaatgtcg  29700
ctggcgtcgc tgtcggaaca tcttttgctg gcggagatag gcggggctat aaatgtcaac  29760
gcgaaaatgt atgcaatttg acagttatgt acccgacatg tttctgagcg agaacaatgg  29820
gaacagcagc gacattcgtc ctctatagtt ttctatctct ataactgaac cataccaccg  29880
ccaagaaaat cataccacca cggcgcagct tgaaaaatag caataataag ctccgccttt  29940
cagctggaag aaggtaatcg tatgttgcca tctccacctt tcttattatg taaggcacat  30000
agcagtaaga ataatcgtca gttttcattt gtatcccgaa aagtaaagat ctcaataaac  30060
aaccagttaa gttaaaagtt cctgttcttt tttgcatcct ggtcaaagca gtcctcctga  30120
gcaaaacccc aatacggcga tccatcctga gacgaagcat ttttcccgag aatacagtcc  30180
acttgagaag acttctgcct gcgaagctgt gtagcattca ccgatttggc ttgagtggtt  30240
cccccccgct gtccttttta ggacaattga gttgctaaga accacaagat agccaccatt  30300
cgctcttgcg agagctcctt gagataaatt tagagctgca cagtttcgag gtcggacagt  30360
tccgattttc ccactggagc cgggctagcg ctccaacagt accgatggta cattttcaaa  30420
caccttgatt tcagtcccta ccagttggtt ttaagacgag agcacgagaa caatgacgat  30480
gactgtaaac atcagaaggc cagctgattt ttttgtgtaa acatgaccag ctggtgagtc  30540
gagaacagag ataaaatggt aaacactgag ccggccggag aaaactgtca tgaatatcag  30600
```

```
gatagttgca tgggcggcgg tgattgaaaa ggggctgcga aatcgaaggc gaaatctgag  30660
aaagacgaaa ttcagatcac taaagtctaa gtggtgatta tgattttttg ttttaagtaa  30720
tggtttcatg agtcgatatc gaactatgga acatcgacta atacaggttt gactgtattt  30780
aaaaatatgg cgatcaaaat cattgccgcg aaaacgtgta agcccaatgc taaaatgact  30840
ttgtttggcc aatgggccaa caggtggcgg tagtgtgtaa acgtcaaaca cgaatgaaaa  30900
cgatgcgagc gctgcagcct gcagttggtc gcatatacac tcagaaacac ggatagtcac  30960
agaatgacta aattttagta atatatgact attttctatc tgcctctctt tcattctgcg  31020
gggaatttta ttcctatttg tcaattcacc tgggttgaag catcgctaag cttcaacccc  31080
gtcgaaatga cagttagtgt gaaagttcac agcagaacga aagagaggca gatagaaaat  31140
agtcattaag gcataaactt tagtaattct gtgactattt ttatttctga gtgtatacga  31200
atcggtcgtt aaaaatatga tcgatggaca ccgatgagag tgtgacgcct ttttgtctgt  31260
gctgaaatca aagaactgtc aatggtggtt acaattgagc aataggcctt ttcacgagtc  31320
gtctcaaatc agctgattcg gaaggtcttt gacagttctt ctatgcaaat gccgaacgtc  31380
tcggtggttc tgaaaggtaa acaataatac aaaataacta tcaaataatg atgaaggcgt  31440
aatcggtttt ctagaaaaca tctattctgt gaattcaact gaattttcgg ataaaattgt  31500
caatggcata ctgcagtagc acgtagtaga aacgtctgct ttcaaacagg catgcaacga  31560
gtgaattcgg caccgctcaa acgtcaaatt agtgaactcg tgcattgatc catggaccga  31620
tacacgtgtt cactaatttg atgtttgagc gggcactggt ttctacgctt acataaataa  31680
cacggcatcg ctaaaatgtc aaataatgaa cttgtgcatt ggtccattgt agctaagtaa  31740
accaaggtgt gtgcatttta ctctgtagct agagtaaggt gtaatcactt ggcgaaagcg  31800
gcttggaggc catctttaac ttgctggccg tttagttcac aaacattact gccttccctg  31860
gatgatgctg aaactggaac tagctgtgcg gacaaaattg tcaaaaaaga aagaaaggag  31920
tagagcacac aaggagcagg ggcgcccgga taaaaacgta tcattcagtg aatggaataa  31980
accattaatg tacaatataa cgtattggat acaatacagc gtattgtaat tgaatgtcga  32040
agcaatatta ttcttgtttg gatatacaat tcaaaaacaa tataatatat tgtaacagaa  32100
cattgtattg cttttaattg gttttatacc ttacaatttc tatcaaattc ctattttcgc  32160
gtaaaacaac tgttgctttt ttttcgatgt agctttgctg aaagaaacaa agaaaacaag  32220
ttcagaaagc aagaaatctc gattactttt tcaaatcgac gtaagtaact tccatacggt  32280
tttgagaaaa ttaattcaga agaatcacaa cctgtcttct aaaactgttt taaaatgaat  32340
caccttttta acatttttc gacgtgtaca ttgcttaact tttgcataca atgagttcgc  32400
gttcaaaaac tatggagttc gtattatttc acacaagaat tttatgacaa aattataagc  32460
cgttttattc agttacttgc gacgtttttc taccagtgta aaatcgactc aagtattgcg  32520
aatattttgt aaaattttac tttagtccag ttagttgcgc gccggccagt tacgcgccag  32580
ggttacgcgc tgcccagatg cattgtgtgt ggccaacgaa aacgaggaca aatgtcaaaa  32640
ttggtctacc agctgaccgt tgtgaagtgt ttatgcatgc tgcaaggtac tgaatttttg  32700
atttttctta aaaactccaa ctttgacata ctgtatcaat taaactatag aagatcttgc  32760
ccttaga                                                            32767
```

<210> SEQ ID NO 117
<211> LENGTH: 971
<212> TYPE: DNA

```
<213> ORGANISM: Aedes aegypti

<400> SEQUENCE: 117

agtgtgcagt gctcaaatgt cactaaggta tatatttttt cttttcatgt tttctccagt     60

ttacgctttt cattcttaag tgatggcttt attacgatca tcttttcagg attattctga    120

ggagcatccc agaaagttga tcccagaact gtgtaaacag ttttataatc ttggatgggt    180

tacagggact ggtggaggta ttagcatcaa gcttgatgat gaaatttaca ttgctccatc    240

aggagtgcaa aaagagcgga ttctgccaga tgacttattt atccaaaata tcgatggaga    300

tgatctgcag ctgccaccgg attataaaaa attaacaaag agccaatgta cacctttatt    360

catgctagcg tatcgtgaaa agaatgctgg agctgtcatt cacactcata gtcaatctgc    420

agtgatagct accctagtat ggcccggtcg tgaatttaga tgcactcatt tggaaatgat    480

taagggaata tacgatcatg aattaggacg gtatcttcga tttgatgagg aattaattgt    540

cccaataata gaaaacacgc catttgaaaa agatttagag caacgaatgg aacatgctat    600

gaaagaatat cctggaagct ctgcagttct agtcagacga catggagtat acgtttgggg    660

acacacatgg caaaaagcaa aggcaatggc tgaatgttac gactatttat ttttctttgac    720

tgtggagatg aaaaaacttg gacttgaccc aaatgatatt ccaaagtact atagaagcaa    780

taaataaaat gtaaaattag aaatgaatat atatactgca aactaattca tattatagct    840

tcacataaat tcatgggtaa gaataataaa aatgtttgta atatgcaaaa taggaagttt    900

tttttagtaa aatgtacgca aataaattgt ttgtaataaa gcatataagt caattctgat    960

tccaatcaca a                                                         971


<210> SEQ ID NO 118
<211> LENGTH: 869
<212> TYPE: DNA
<213> ORGANISM: Aedes aegypti

<400> SEQUENCE: 118

aaatcatcgg catcggatgg agcatcccag aaagttgatc ccagaactgt gtaaacagtt     60

ttataatctt ggatgggtta cagggactgg tggaggtatt agcatcaagc ttgatgatga    120

aatttacatt gctccatcag gagtgcaaaa agagcggatt ctgccagatg acttatttat    180

ccaaaatatc gatggagatg atctgcagct gccaccggat tataaaaaat taacaaagag    240

ccaatgtaca cctttattca tgctagcgta tcgtgaaaag aatgctggag ctgtcattca    300

cactcatagt caatctgcag tgatagctac cctagtatgg cccggtcgtg aatttagatg    360

cactcatttg gaaatgatta agggaatata cgatcatgaa ttaggacggt atcttcgatt    420

tgatgaggaa ttaattgtcc caataataga aaacacgcca tttgaaaaag atttagagca    480

acgaatggaa catgctatga aagaatatcc tggaagctct gcagttctag tcagacgaca    540

tggagtatac gtttggggac acacatggca aaaagcaaag gcaatggctg aatgttacga    600

ctatttattt tctttgactg tggagatgaa aaaacttgga cttgacccaa atgatattcc    660

aaagtactat agaagcaata aataaaatgt aaaattagaa atgaatatat atactgcaaa    720

ctaattcata ttatagcttc acataaattc atgggtaaga ataataaaaa tgtttgtaat    780

atgcaaaata ggaagttttt tttagtaaaa tgtacgcaaa taaattgttt gtaataaagc    840

atataagtca attctgattc caatcacaa                                      869


<210> SEQ ID NO 119
<211> LENGTH: 863
```

<212> TYPE: DNA
<213> ORGANISM: Aedes aegypti

<400> SEQUENCE: 119
agtgtgcagt gctcaaatgt cactaaggta tatatttttt cttttcatgt tttctccagt 60
ttacgctttt cattcttaag tgatggcttt attacgatca tcttttcagg attattctga 120
ggagcatccc agaaagttga tcccagaact gtgtaaacag ttttataatc ttggatgggt 180
tacagggact ggtggaggta ttagcatcaa gcttgatgat gaaatttaca ttgctccatc 240
aggagtgcaa aaagagcgga ttctgccaga tgacttattt atccaaaata tcgatggaga 300
tgatctgcag ctgccaccgg attataaaaa atggcccggt cgtgaattta gatgcactca 360
tttggaaatg attaagggaa tatacgatca tgaattagga cggtatcttc gatttgatga 420
ggaattaatt gtcccaataa tagaaaacac gccatttgaa aaagatttag agcaacgaat 480
ggaacatgct atgaaagaat atcctggaag ctctgcagtt ctagtcagac gacatggagt 540
atacgtttgg ggacacacat ggcaaaaagc aaaggcaatg gctgaatgtt acgactattt 600
attttctttg actgtggaga tgaaaaaact tggacttgac ccaaatgata ttccaaagta 660
ctatagaagc aataaataaa atgtaaaatt agaaatgaat atatatactg caaactaatt 720
catattatag cttcacataa attcatgggt aagaataata aaaatgtttg taatatgcaa 780
aataggaagt ttttttagt aaaatgtacg caaataaatt gtttgtaata aagcatataa 840
gtcaattctg attccaatca caa 863

<210> SEQ ID NO 120
<211> LENGTH: 831
<212> TYPE: DNA
<213> ORGANISM: Aedes aegypti

<400> SEQUENCE: 120
gagcatccca gaaagttgat cccagaactg tgtaaacagt tttataatct tggatgggtt 60
acagggactg gtggagtgat gaaatttaca ttgctccatc aggagtgcaa aaagagcgga 120
ttctgccaga tgacttattt atccaaaata tcgatggaga tgatctgcag ctgccaccgg 180
attataaaaa attaacaaag agccaatgta cacctttatt catgctagcg tatcgtgaaa 240
agaatgctgg agctgtcatt cacactcata gtcaatctgc agtgatagct accctagtat 300
ggcccggtcg tgaatttaga tgcactcatt tggaaatgat taagggaata tacgatcatg 360
aattaggacg gtatcttcga tttgatgagg aattaattgt cccaataata gaaaacacgc 420
catttgaaaa agatttagag caacgaatgg aacatgctat gaaagaatat cctggaagct 480
ctgcagttct agtcagacga catggagtat acgtttgggg acacacatgg caaaaagcaa 540
aggcaatggc tgaatgttac gactatttat tttctttgac tgtggagatg aaaaaacttg 600
gacttgaccc aaatgatatt ccaaagtact atagaagcaa taaataaaat gtaaaattag 660
aaatgaatat atatactgca aactaattca tattatagct tcacataaat tcatgggtaa 720
gaataataaa aatgtttgta atatgcaaaa taggaagttt tttttagtaa aatgtacgca 780
aataaattgt ttgtaataaa gcatataagt caattctgat tccaatcaca a 831

<210> SEQ ID NO 121
<211> LENGTH: 32767
<212> TYPE: DNA
<213> ORGANISM: Aedes aegypti

<400> SEQUENCE: 121

```
gcgagtgcct tatgaatctc tttttgtttc gtagtcgcga attcctatcc tgaacatgtg     60
ctgcttggga aatatttgat tctaaaactt gtgttttaat tttgtattac tgcgtatatc    120
tatagaaaaa agacaatata actataacaa gtcatcaaaa tggatgttga tgtacaggtt    180
atttctacaa gtggcgaaag aacgaaaata aaacagccta agatagaaaa tgatgttcgg    240
aaagtgtttg tacctcgttc caggtaagca atacaaggat tttaaatcta gtatacaatg    300
tttcattatt ttccacagac aatccgcatt gaaggaacaa tggatgaaaa tattcactcc    360
agtcgtggac caacttttac ttcagataag atataatgta aaaagcaagc aagtggaact    420
gcgattggga cccgaatcta aaaatccatc taacttgcaa aaaggagcag attttgtacg    480
cgcatttatt ctcggttttg aggtggaaga cgctttggct ctgcttcgtc ttgacgacct    540
ttttatcgaa tctttcgaag taaatgatgt taagatgttg aaaggtatgt ttataataca    600
tcaaattatc tctttatata tttcagtcta cattgtattg aattctcttg ttaagtatta    660
aataccatac tgcttagcgt tgaaaaatgg gttaaccaac gtgcgaagtt cgatttttga    720
ccaacttcgc cacgtcgcac agtgcgttgc tccatagaca aaaatcaaat ttcaagttat    780
ttttttcggc gataataagt atccacaagt gtttatagat aacatccgtt atcgaaacaa    840
gtatttataa gctttacaaa gcactaaaac atctacaaca agcgtcgaaa gagacagttg    900
tcgaagtagc agaaaaatca aattttgtcg catgttttca gcattccttt caactagcac    960
ggagagtgtc gtaatcaatc tattcaatca aaatctaaaa gagaacatga ctgatggtta   1020
gtaaagtata tttgatgtga taagaacacc aattttaact ttgaatatga gaaattggca   1080
cgttgagttg gctataaaat caaacttatg aaatactaac atgtaatttg taatttattc   1140
attcattcaa cgtaagcctg ttagttacaa acttttgatc aggtcaagga aaggttaaca   1200
ggaaaattta aagtgatcgg aaaaatttgg tgttgtctag agaatttaaa agggaatcag   1260
tacaattaca agtaagattt ctagttccat aaatctacgt gaagcttctc ttaaacgctg   1320
caagcgtcga ttgttgccta agggctaaag gcaaatgatt ccatgttgaa gctccgctga   1380
taagcacact tttcctactg gccgtcgtat ggtgtggcaa gacgaaggag cgtgctcggt   1440
tgttcattct tggttggagg tgttgtagta agtattgggg tagctctcga aggtatccgc   1500
gccgtaggaa gcagcagacg cgcagtctat aattgtctag gagatttctg cctagaatcg   1560
tatgacggat gtcagctgtg gtatcacgtc ggcgaagatt gtagacgaat cgtacggctg   1620
atttgaagct tcggtgtaat tactccttta gcgcttccgt taatgctggg tagtatacca   1680
cgtcgcagta cgtatacagt ggtacgatga cagcttggac aagttttttt tcgtgtgggt   1740
agcgatagta cactccgaaa acgacgaaag gtccgcaggg tgccatagac ctttttcact   1800
atatcgttta cttgatgtgt ccagttgagt ctgttgtcca taacaagtcc caggttagta   1860
accttagcca aaatttggat gggttctcca caaaatacta tacgattttg tgggatgacg   1920
tctccctcct tgctaaacac gattgcttgg gttttcttag ggtttggcgt cagcatattg   1980
ctttgggtcc aggcttcgat cgatctcagg ttctggttaa tgatgtcaac cagcctgtta   2040
acctgatcga taggtcccga aatgtaaacc tggaggtcat cagcatagag ttggtactta   2100
cagttgagat cattcggcag gctattgatg aacaggctga ataacagggc gctcaaacac   2160
gagccctgag gtgttccgtc agtcaaccgc atttctgtag aagtagtatc cccatgcttt   2220
actacttgac tccgctgaat caaaaatgac gagatcagct cgcatgccgc tgcagaaaac   2280
ccgaattctt ggctaagttt ccttaggatg agtccatgct taacgtagtt gaaggctaac   2340
tagaaatcaa ctagcaccat cactgtgcag tggtgattgt caagattagc atagatatta   2400
```

```
tgtgttactt ctgccagtgc agttgtggtg ctataaccgc gtctgtagtc tgattgatgt   2460
gaggccatga ggtgagggtt ggagttgtcc agatgatggg agatctgcgc cagcaaaatc   2520
ttttcaagga tcttcgaaat cgatggaaga acactgatgg ggcggaaatc tttgtgagac   2580
gtagggttgg gcgatttggg gatcggtgtt actactgctt ttttccagga agatgggaaa   2640
gttttgtcag caatgatcgt attgaagaaa tgagtcaata atggtagtat gaatgggctc   2700
agcatcttca cgaaggagat tgggagattg tcacatcctg ttgcatttga acttatctcg   2760
aacatgtgtt tggcaacttc ctctacactg gtgggttgga aacgtagctc ttcttgaacg   2820
atggctggtg cagcttctcg agttgttggc gctgttggag tgacaccact gttttgcagt   2880
gttaggtgtc cttcagtgaa aaaacggtta agttgatgcg cgtcgaagtc gttggaggaa   2940
tctgttttct tcgcattgat atgtactcct tctctacgca tattactcca tagctttttg   3000
gcaggaaggt cagctgaaaa atgtgtatcg ccatactgct tttggcact attaatcagc   3060
gacttcactc gatcacgggc acgttcatat tttcgccact gattgctgtc tctggatcgg   3120
ttgggattac ggacgtataa cgcaaaagca agatctctca cagcgatggc ttgctcaata   3180
tctcgggtga tccaaggtgt tcgtttatca cgcacttgga taactcgctc aggagcatga   3240
gcgtctagta gggactgtaa ttttgcagtt gtcagttcga ctttccgatt gacatcgttt   3300
gcgtcggaga tttcctggag atccgtcgtt tgaaagtcca cctgcagtcg aaccacatca   3360
attcttcgca tgttgcggac ttttactgtt tggggagctg ctcgtggtac tcggatgtcg   3420
gcaataagat aaacaacctc gtgatcggag atggagcttc cgtaatgagt cttagacgta   3480
cggatcgatg atggagaatt ggtcaccagg aggtcaatag ttgttgcgct ttgttcggtg   3540
attcgtgtag cagctgttgg cagaacggtt agattaaaag tagagtgaat gcgagcgagg   3600
gctctgcatt cccacaaagg tgatgtgcgg caacgttaat gttgtagtca ccaaccagat   3660
agactctatc aaaatcgaaa tcttgtaggt cgacgagaag tttttcgtag cgttgggcaa   3720
acaatggatt tgatccgctc ggattataca caaccacaat gcaaatgttg cagttgttga   3780
ttttggtttg tactgcaagg aattcgagtc gagtagcgct attctctcca gcttcgtagg   3840
ttgacttgat tatggtagtt gttttgatcc ctttctggac gtatagtccg acaccaccga   3900
atgctcttac tctgtttcca cgcccagagg atagagaatg tcggacaaag ttgaacccag   3960
ggatccggat tgggccggtg gctaatgaag gacggagcat agtttccgtt acggcaaaga   4020
agtggtattg ggaggaatcg agcaaaactt tgacgccatc gatatggcgt tctaggcttc   4080
tgacgttgag gtgcccgata cgaaggtaag cgtgattgat tctgcacata aggcttggaa   4140
tgtagtcgtc tgtctgcaag tgcttttagg atgtagaaac ggatacggca gaataatccg   4200
aaccaactgc atcaaaaaat actgaagaat tgttcccctt atccgtgggt cagttcgatg   4260
agatggtcga cgtcttttac ttcagtgtaa cggggttggt tcggtagtcg aacagagact   4320
gaaccgttac gaacgaaaac cgactggatc agctttctat gcttcattct caatgctaga   4380
ttacgaatcc gaaacatgta actttgatta tcgattcaaa aaaagttcta ccgagttcca   4440
agctaaatca ctcacagaca tgtttcttaa agtgtcctct aagaggtctg aaagatacag   4500
ctgcaactct ttgaggtttt tgactatttt taggtatact tcttaaccag cacaagcatg   4560
aaaatgagtt gtttgtgata aaaaatccga aaatcttgca tcgctttgta gtcttggctc   4620
aaccaataga aatattagta gtagaacgct aatggcgctg ttctcacaaa actgaattag   4680
tttattatta cctttaactg tatctttaca ttgtttgttc gatgccatgt tgtagtggat   4740
```

-continued

```
gattttaaaa tttatttgac actttgagga ccggtactca agctgtcagc gcgtggcaaa   4800
ctacactgaa aaaaatccac acgtttgatc cgtgtgttca aaattatgga tcgattcatg   4860
aacgtctata tcgatttgtt gtgattttct tacaaacttc gtgtgtgtta cacattcaat   4920
tctttagttt tgcttcatgg actgattcat caaccgacaa catgaattcc aaagttttcc   4980
acatcagttc tgtagaatat agaatccact gcgttgggaa gtgataatag gattgatcac   5040
agcaagcggt ttaatacgtt caaatgtgat gacagtgttg gcgatattgg tttctcttag   5100
taacacgctc ctgtcacttg catactatat gcatgcatgc tctgcctcac ttgagaacaa   5160
acacttgtct tggtaagttg tgtgagcatc gcgtggaggg tgattccttt cccgggtatt   5220
atcgaaactc cacattggcg atcctaccag ttttctacta atttgtggaa agatgcctgg   5280
cttattttac atttttcat tgggcggaat caccctgccg cgttgtgaaa agtgaaatca   5340
aaagtgcagc ccgcagcgtg gtgtttgttg agtgaaaatt tctgactccg tatcagattt   5400
gtttcccgct cgtgaaaaaa aaggttacaa tgaagagaca acccgagaaa gagcattgat   5460
gtgtggacgc ttacagcgtg ttgtttgccg tgggggagga aaattcccgg caatttccgc   5520
tgccgaaaag caaaatttcg tcgatcttgt tgttttgctt ggtgcaaatg tcagatcgga   5580
cgcttacagc gagttgtttg tcgtgaggga agaagagtcc cggcaatgtc cgctgccgaa   5640
aagcgaaatt tattcgatct tgttgttttg ctatttgcaa atgtcagatc agtagcttac   5700
agcgtgttgt ttgctgtggg ggaagaggag cccaggcaat atccgctgct gaaaagctag   5760
aattcgcgga tcttgttgtt ttgctaagtg caaatgtcag gtcagaaaga tagagctatt   5820
gtttgctgtt ggggaagagg agtcccggca atgcccgctg tctaatagca agcattcgtg   5880
gatcttgttg ttttgctgtg tgcaaatgtc agatcggaag atcacagcgt gttgtttgcc   5940
gtgaggaaaa aggagcgtcg gaaatgtccg caaacgaata acgagaattg ttattttttc   6000
tgttcggttt gttcaagtat cagataggat acttttagcg cttgcctgcg tgctgcaatg   6060
ttataaagaa gcaatgtttt attcttatat ttttatgggc aaatgtaatt ccagaacatt   6120
gaagcgtttt gttggaaaga aaactgtcaa tatttgctgt ctagaacgat tatattgttt   6180
tgccttatgc aaacgtcaga gcatgtgtgt acaacgtcta atttgttgta tggtaaataa   6240
cccaacaata ttctttgtag agaaaaggaa aatacgataa atgtgttttt gtgcgaaagg   6300
ccaagtaaca aaaattgaga gtgttgattg tcccaaaagg agactagctg acagatgaat   6360
tttatccttc aattaaactc ttgacaagca taaaaaacac attttttttt gaaaaaaaaa   6420
tcccgctggt cgatgatctt ttcgtaaagg aaattttctc gattcccagg gcatagagta   6480
tctttgtacc tgccacacga tgtacacatg caaaaatggt ccgatgtgcg ttgggaagtg   6540
ataataggat tgatcacagc aagcggttta atacgttcaa atgtgatgca cactgtcatg   6600
ttggcgatat tggtttctct tagtaacacg ctcctgtcac ttgcatacta tatgcatgca   6660
tgctctgcct cacttgagaa caaacacttg tcttggtaac acggattcag tgtgtttaac   6720
ttatgattat cttgtgtcat gatcatcatg ttcaagttgg tctatttgaa ttcgataagc   6780
ttgctgtcga tttccgtgtt ccaaatttct aaattgtctg tgatcaactc atagcgaact   6840
aaattgcggt cggacctcat gtcgaacgac agtcatcatc atgttcgcaa gaaaagaagc   6900
aaattctgaa gctgaaagtg ttagaggaaa atttgcggat ccgtttttct cgctattagc   6960
gaagatgtcc gagtgaaaat gaggagttca ttctaatttt ctaaataaca tgcattactt   7020
ccagcattgg atataacgta tggtgttaaa gaaaaatcgg attccactaa cagattttcc   7080
tagctttcag cttcgaataa aatgaaatat gctaatcccg ggcttcccaa attatggatt   7140
```

```
tgcggcgccc cgcttgttgc tgactcactt gtttgaaaaa aaaacattca agtgagcttg   7200
cgacgagcag aggagcctcg aatccatatt ttggggagca agagttctct atcaaatttc   7260
ttctttcagt ctcatgatat tcatgttcta tcacacctaa ctatctaatg gttctacatt   7320
ttgaattcaa taagcaaatc atttggtttt catgatttaa tatttggaaa ttcatgtttg   7380
tttcacatga caacctaatg ttgatacaca tgttattata ccgtgaagtc aatgatgaaa   7440
tccatatggc taccacactc atatcatgtg gttttcctca ttgcgcaaag ctataagtaa   7500
aacacacgac cttgacgtgt agatttttct cagtgtagat gttggtaaca cgaacagtag   7560
cgacattagc attcttaggt taatgcttct actgctcaac cagacattac accagagcta   7620
gttcatgctt aaaataatat attttaaatg cagttttcaa gattttattc aaatttcata   7680
ttaaaaactg aaaaattaaa aataaatgcg attttgttgc acaaaggcgt ataagtcact   7740
tttgcagcta cgagtgagaa gagacatact tgcaaataac ttcttacatc attataagca   7800
ataaaagtac aaattgcaag acttttctgg gcaaatacag aaattggcgc ttgggacagt   7860
tttgcgatta tgcgtctagt agttgtcatt tatgcaaatt gttgctcttt tgatcagaaa   7920
caacttaccc ttccatacca aggtgctcaa atggcttgat tttcaagctt tgatttttgt   7980
cccgcatctc cataagttca acgcactgtg cgtcgcaact cgattctcaa tagtgcgcat   8040
aatgcacatg gcggagggca tcgatgcgca ctatggactt atccacggtc ttctcttatt   8100
gtcgattttc tttttctttt ccgctctaaa tgcgggccgt gtttacataa aatgacatcc   8160
ggaccaacat ccagtcaagg aatgttcacc ggatgaacat tgagtggatg aatgcgctgc   8220
gaaatcgttc attttttgaa aacacggccc gcagtaaagg ttttcttccc gctggaagtt   8280
gcagcgtgac gtcatcgtag attagttcat agcgaagtga cgcggcgaag ttggtcaaaa   8340
ataaaacttc gcacgaaggt tcacccattt tagcgaagca gtaaatgaat tttttgcctt   8400
attgcaaaaa aaacatttca atacagtacc agatttacgg cctaactgac aaatgtaaac   8460
aaattgagtt ttattcacct aacagtttat ttgataaatt acaatcatat aatgcacaac   8520
tgtttcttaa aaataacatt tttcacgaaa taagtgagaa aaacataaag gcgcatttga   8580
tattctcttt cgatacgaac tctgatgtca atcttccccc tttgcgataa ctgggcgcat   8640
ttgcgattga gtgtggcagc aggtcacatt taaaactgag tgtgcagaag gtcgatagtg   8700
aagaaggttc gtgtgaaaga gcgtagcaaa acgacgaagc tgatgatagt caaaacagaa   8760
ggacgaggtc aaaaggcgca atcgtggctg tcaaactgaa ggagacgaaa aaccgagggg   8820
cgcaacaatc ctcaattttg atgaatggcg catgatgctt ttttatttat ttaaccatgt   8880
tgttcataat atgaaaataa atcaaatggt ttgttacaaa aataatattg taatggatca   8940
tacaaaaatg catcatgcga ttaaatcgat cggaaacata atatagaatt gaaattatat   9000
ccactgaact tcaaaccgat tttactgaca atgtattagt gttcacattc gccctaattc   9060
tgactctgta ttgatttgct ctttaaaact tcaatgaaca tcatatacac tcaaaataat   9120
ccaaacgtca aggctacgtg aaaaatcacg taaaccctta aaaaatgaat ttggccagga   9180
tttacttgac aactgtaact atcaccgtta catggatcaa aattgaatga aatgtcgatc   9240
gtatttactg tggtgcccta tcacccttac gtgaaactca cgtacctagc catgttcatt   9300
ttgacagctt cagttgtttg tattcatttt gtagttcagg taccagtgtg taaagatggt   9360
gtttataaaa agcttgctag tcattgaaat ccatttgttg gtgcaatttt ggagtaaaat   9420
aattgaaatt ggattagatt gctgtaaaag tgtgaaatcg gtatgtggta aatggtattt   9480
```

-continued

```
ttaaaggacg atgcttccga tggaccaact caagaacgaa ccaaaatccg ttcgttaact   9540
tccaactgat tctgttcgat tgtctaatat caaaagtaag taaatttttt aagtttaata   9600
attcaaataa tatagatttt catgttctgc agaaaccgaa aaccaaaaat aacggtgaaa   9660
ctgaagccgg actcccaatt atgggcaaac aatactcgat tacgaatatc cagaccgcac   9720
gtgaaataat aagtcaataa tccagcatat gaaataataa atcaataaac catgcatgca   9780
gaaaaacaca ataaaaatat ctgatacaaa atcacttcga cttaattttg tttcaataaa   9840
cataataaaa tctaatgaaa aacaacttta tttatatatg tatgtctgaa acaatgcact   9900
gaagcctcat ttttgtttta ctcatacatc ctatgaaact cacgaaaaaa acacgtaaca   9960
actaccggat gcttcggtga aatcaaagaa gtccattagt tcatgagttc attcatggtt  10020
gcctttgatt cacgtaagtg ctacgggaaa agtgcgatgg aaaaaaacta cgtatgtttt  10080
cacgtagcct tgacgtttgg attattttga gtgtacgaat agttaaatga gctattatgg  10140
cattggtttg tttttatgaa ttcaagcata attcttcatt ccgacgtaac tgcaaaaata  10200
aacaaatcga gatttgcttt gcatgggctt gacaaacgca taatctacat attgagtcca  10260
aaaaagtaat cctaaaacat ttttttgatt ttttgaaata aatttcaatt ctgccctatg  10320
tgcactttac tcagtatttt taatttggct acatacaccc taccattgca aagcgactca  10380
actgtcaaca tttttcatgc tagcacatac accgtacata tgctcatagc aaagcgacct  10440
atatgcagaa tcaaaacata aaattttaat cagcagatac gtcatactgt tttcgaatta  10500
ctaaacatgt tggaaatcga gagattcgga ttttcacagc tgcagtaagc tgacgggtcg  10560
gcaaactgat gtggaacatc atcagtattc ggttttagac aaatttctca ccaaattttt  10620
cacaagaact gttctccatt tacttttgtt actcacggct ccgtccggtg ctcctgttag  10680
tcgagttgaa attgtaaaca ttcaatattc gttgtagttg aacgtagaaa ctgacgaata  10740
gaacaaactt tattatgttt tatgggaatt tgcaaaccgg tgtatgtgca acttcaaaac  10800
aatactggtg tatatgacgt gacgcatgtg ataaatgaac tgtcaaaccg acgcatcaag  10860
caaggtatga tatcgacgaa tcatcatggt gtatgtgtgc agcacaaagc aaaagggttt  10920
attcgataat ttcaccagtt tttcaatcta attcaaaaca aatcggaatt gtttaatagt  10980
ggttagaaac ggtgttcttt ttttcaactt atagaagaca cagcaataga aaaaatgcaa  11040
aacattttaa acaggattta aaatgcttta caatatattg catcgcatgt ttctcgaatc  11100
cttccaaatg ttagatacgc cgatttgaaa aattaggctt gaattattta aatatgtaat  11160
gttttcaatt attaaaataa tgacatcttt tactgtgata gcgatgtttg ttattcttta  11220
gatatttctc taaaacttat tcaaatagat tcaagtcaaa aaagtataca aacttacttt  11280
atcgattcta cgtgtttcgc agacgaaatt ctacaaattt cgctctaaac caactcgatt  11340
tttcactttt agaacgttta atttccggat ttacaaaacg acgaaagtaa tatttttaac  11400
ttttgcaacc taaccactat tttcgccgct ccgctgtatg gagagacaaa gtgacttaac  11460
cacgaatcaa aacaaaacac tacttgagtc gattttacac tggtacaaaa acgtcgcaag  11520
tacctgaata aatcggctta tcattttttt tttttactta tctcgtttat ttggcaggct  11580
caggcgccgt agggcataac agagccgaaa tcttttcttt ttttttacat tatttacatt  11640
ttgaaatttg aacttatttt aaaaactatg ttagtttgcg gaagttttaa ggttagtgga  11700
tacatttgaa atagggaagg aaaggatttt ttggaattac ttaagctact tagactacta  11760
agctgatgaa gcttgaaggg acaggatgtc cagatctgta atgaaactaa acagaaacgg  11820
tttgtgggag acacgacgag aagaggacaa tttgaatggg aaaaagaaag acagggaacg  11880
```

```
aacacaatca aacccggata ttgatacgct tcaaaaacag atggattaaa ttcatatatt  11940
ctaaatcaag gcccgccaac acttccctga caggtttctg ctgttttcct cggatccgga  12000
gagtttcagt cagctcagat ctgacgccac gatgctcaac gcatccccac acaacatgtt  12060
cgatatcctg gtaagccacg ccgcaaacac agagattgct ttctgagagc ccaatacggt  12120
gggtatgcgc gcttaacgaa tagtgattgg acataagccg acacatgaca cgaatgaaat  12180
cacggctcat gcccaacccc ttaaaccatg gctttttcga cacctgtgga aatatggaat  12240
gcagccatct acccatttct ccgtctctcc atttctgttg ccagctgatc aaggtctccc  12300
gacgggccaa tgcaaaaaat tcttcgaagg cgatttgacg ctcgtaaaca tcgccttctt  12360
tagcgcctac cttagccaga gagtccgctt tctcattgcc aggaatggag caatgcgaag  12420
ggacccaagc tagggtaata gtgtaagagc gaattgacaa agcactcaat gcctggcgta  12480
ttctattcag gaagtacgct gagtgcttca ccggcttcat tgaccgaaca gcctccagag  12540
aacttaaact gtcggaaaaa atgaagatgt gctcgggtgg gagagaactg atgtactcta  12600
aggtgtaatg tatagctgct agttcagcaa catatacaga acatggtttt tgaagcatga  12660
aggaggcgct atgagaaacg ttgtaaacac cgaaaccagt gatatcatcc atttttgacc  12720
catcagtgaa gaactgtcgg ctctcgctga catgcccgaa tttacttgca aacatgggag  12780
ggataaactt tgaacgaaag tgatctggta aaccatggat atcttgcttc atggacaaat  12840
caaatactac agaggaacag tcgaattcta ggaagttatc acgattggtg ttaaccgaag  12900
atgggctaac ctccagcgcc atgtaccagt agtacacact catgaaacga gtttgagggt  12960
tatgttcaag cagcttttcg tagttttcaa taaccaatgg attgagaacc tcacaacgga  13020
tgaggaacct gagtgttaac tccgcgaaac gatctgtcag gggctgtact cctgcaagta  13080
cctctaaact cattgtgtga gtcgagttca tgcagcctag cgcgatgcga agacagcggt  13140
actgaatccg ctgtatcttc agcatatgtg ttttcgccgc ggtttgaaag caaaagctac  13200
cgtactctaa gaccgacaag atggttgttt ggtacagctt gatcagatct tccggatggg  13260
ctccccacca tgttccggtt atagttcgca tgaagttgat tcgtttttgg catttctgtg  13320
tcagatacac aatgtgtttc ccccaggtgc atttggcgtc gtaccagacc ccgagatatt  13380
tagaagacaa gctatgagtg attgtctgta agcggaaact tggcaggttt gtgtttcttt  13440
gaaaagacaa ccatctcagt tttctccgca gagaattcga tacccagctt taaggcccaa  13500
gtagacaaat tgtccagagt atcttgtaag ggtccttgta gttcggctgc tgttggtcat  13560
gtgacagaaa caacacagtc gtctgcaagc tgtcttaacg agcaattttc catgagacag  13620
tcatcaatgt ctctcacata aaaattataa agaaggggac tcagacatga tccctggggg  13680
agacccatgt agctaattcg tgaaactgac aagttgccat gagtaaaact catatgcttc  13740
tcggacaaca aattgtacaa aaaattgttc aaaactgatg aaaggccact tgcgtggagt  13800
ttgtctgaaa ggacatcaac acaaactgag tcaaaagcac ccttaatatc caaaaacact  13860
gaacccatct gttcctttttg ggcaaaggca agttaaattt ctgaagaaag cagcgcaaga  13920
cagtcgttcg ttcctttggc tctgcgaaaa ccaaactgtg tatctgacag catgccattc  13980
gattcaaccc atttatccag ccgaaagaga atcatcttct ctaacaactt gcgaatacac  14040
gacaacatcg caattgggcg gtacgaatta tagttcgacg agggtttccc gggtttttgg  14100
atggctatta ctctcacctg ccgccagtca tccggaacaa tgttacactc cagaaagtga  14160
ttaaacaagt tcaataggcg cctctttgcg acgtcaggta ggcccttaag caaattgaac  14220
```

-continued

```
tttattcgat ccattcctgg agcggaattg ttacatgaaa ggagagcaag tgagaattca  14280
accatcgaaa aaggtctatc catggcgtcc ctatccaccg gaatatctcg tcgcacgcga  14340
tcaacaggaa cggaatccgg acaaactttc ttagcgaaat cgataatcca ccgaggagag  14400
ctctctcgat cttcattaac cgacgatgta ttacgcattc ttcttccgac ggtccaaagc  14460
gttctcaacg aggtctcacg tgataatcct tccacaaaat gacgccaata accgcctttc  14520
ttcgctttga ccaagctttt aaacttgcgt tcaagggaag aatagcgctc atagttgtca  14580
attgaaccac gtttccggaa gcctttaaac gcggcggatt tctcgcgata gagtgcctta  14640
cactcttcat cccaccacgg attgggaggc ttcttgcgaa ccgacggacc aggcacagga  14700
cggcgttggg cttgaagagc gctgttgaga atcaactcgg ataaaaagcg atactcttcc  14760
aacggaggaa gtacttctac cgcttgttct ccatcaatga tcgtttccgc gtacttttcc  14820
cagtctatgt gctttgtgag gtcgtaggcg agatcgatgg atgaagactg ttgtgttcca  14880
ttggaaattg aaactacgat cggcaagtga tcgctaccat ggggatcctg gattaccctc  14940
catgaacaat ccagtgataa cgagcttgaa catattgaga ggtctaaacg gctatcccta  15000
ggacttccat cttgagctgg aggtgccact cgtgtaactt ccccagtgtt gagaattggc  15060
atattgaagt cgtcgcagag gtcatatatc aacgttgatc ggtggtcgtc atacagttcc  15120
ccccagcctg ttccgtggga gttgaaatcc ccaatgaaca accgtggttc aggcattaca  15180
gagcagatgt gagagagatc tctgcgagat atcgccgatc tcggaggaag atatatggag  15240
gcgacactga ggcttttgcc tcggatagtc acctgacatg caacgacttc aatgcctgac  15300
atcggcggca gatcgactct gtagaacgag tgatgctttt tgatccccaa aagcactcct  15360
ccatatgagt cggatcgatc caggcgaata atattaaaat catggaaagg aagggtcaca  15420
tcaggtgtta gccatgtttc tgataacgca aaaacatcgc actgtaaatt actaactaaa  15480
aatttaaaac tatctaattt aggcataata ctacgacagt tccagtgtag aacagaaatc  15540
atatcttcga cctctgtgga taaattatcc atcatgagtt gttgttttgc tctcgtcgca  15600
ttcagacgca gcagcagccg gtacacggag tgctgatgaa tagcacacgg tagtttgttt  15660
ttgcatttta tcaaacggct ttgtattcaa gttcgtatcg ctcgttattt ttgtgcggta  15720
tttcaacacc aatcgattat cgtaatgatt gaaaacacgg tgaaatttcg ttttcctacg  15780
tcggcaccac gtccaacgtg gatcgaaatt tctgtgttcg taaagcagtt aaatgccgat  15840
gtaatggaca tggaaaccgt gtataagatg ggggaggaca ggagtctgtg cattaaattc  15900
agaactactg ccgcaatgga ggatgcactg cagtctaacc tggaatcagc caaatttagc  15960
tattccaatg gaaaaacggt agacgttctt atgtctccgg caggaaccaa cgttcgttac  16020
gtgcggattt ttgatatccc tccagaggtt tctgacgagg atgtggcgtt ggtactagga  16080
gcgtatggaa aaattgaaag agtgattcga gagaagttcc caccgaacct aggcctcgac  16140
catatgttca atggtgtacg aggcgtgtac atggaagttg acaaagacat ccccccgacg  16200
gtggacgttc ttcaatggag agggaaggtg ttctatgagg agctgaaaaa taaatgtttt  16260
ctgtgccaac aggagggtca ccgtagaaat tcctgtccac aaaatgcggc acggaagcaa  16320
catacgaaag aaagacaagg taataaatca gttaatactt atgctgctgc cgttattcag  16380
ggcagtcccg tattaactga accggaaatc atagaagttt tggaggaaga agtagttgaa  16440
gaggtgcagt tggaacctgc ttcaacggag attacacaca tcgaagatca aggagcatcg  16500
atagaaacgg aaccggttgt ttatagaaac aaatatgaaa agaatttggc agaaaattgg  16560
gcgaagcacg aagcagaaaa gcggagacgt caagaagaat accggaaaaa tgaaaaatcc  16620
```

```
atgcagcgac ggtaccaaga aaatttgaga aggcaggaaa aggagcagaa ggagcactgg  16680
gagaaatgtg aagcggagag gaaaagtcgg caagagaaat ataaacaaga tctgtctcaa  16740
catcatcgaa cacttccggt ggaaaatcaa ctgcaatctc cacccaagaa gaatgctaga  16800
aaacaataat tttcaattat caaataattt attttatttg tatgattatc atgatttcgg  16860
ctccgtaatg ccttagggcg cttgagcctt caaataaacg aataagtaaa aaaaaaaaaa  16920
aattatccat caaaagatat gatcgttgca aggaggggca ttctagaagc cagttgcttc  16980
aaaagaggag tcacacatgg aagcaatcct ttgacaatgt tcttcactgg gtcagaagca  17040
ttgaagaaat taaggatgat atctacaatg ccagaaagcg taaacattgg aacgccctga  17100
ggttgcccta ggggctccga atgcgcagag cagtttgaaa ttttggaata tttgggattt  17160
tagattttcc cggtagtggc ggaaagtctc ttttctcttg gagtttgaat ccaggaggtg  17220
aaagctttga gactttcgcg ataggcttag tatttttcat ggctggtggg tcatcactgc  17280
tagacagatt ccgaggcttt tttgtgggtc tctggagtct cacacgcttc ctcgatgaac  17340
ccttgaaaac gaaggaaatt ccttcaccaa cctcagagtc ggagccctga tcatcaagag  17400
acagagaata gtagatattt tggattcag cagacggagc agccttttc aacatctcgg  17460
caaaactacg ccgagagcgc tgctctaatg atcgtcgctg atgttgctgc cggcgtacgt  17520
acgtcgggca gttttcgagg gcatgtggtg gactttcgtt gcaataaacg cattttggcg  17580
gtatactaca tgcaccatcc acatgtctct ccccgcaaga agcacagcga ggtttgttgc  17640
agcaatactg ggcagtatgg cccagctgct tgcaatttgt gcaattcatt accttcggta  17700
cgtacagccg cacaggtaaa cgaagtttgc cgattacaag aaaattcggc aaagcagatc  17760
cggaaaaggt cacacagaag gattcagaat gtgaatagat cttcttttct cccaccaggg  17820
atacggaatg caattgcttg cattccagta tggggacaga tgggagagaa gggtttttga  17880
agcgaccaca accctgcatc aattcttcgc aggtcatact gccttcggtg accactcccg  17940
caatctcaac ccgatggctt ggcagataag tttgatactc cctagtaaag agctcacagg  18000
ccacaatctc attggcctgt ttacggtcac tgacggtgac gcgcagctta ccagaaccca  18060
ctgtgtcaat ggcgacaacg gaagagaatc gcttagtcag atccttactg atctgaatag  18120
tgttcaaccg tttgcctttg gatcgaaaga aaacaacaaa aggcccacca gagtcgggcg  18180
ggtaggcctt gaggcgaggg gacgtcggag atggtagaat attggtgtcc atttgagaca  18240
catcagattg aggggacaca catggattgg gcatagaggt gtttgtgttt tgttggttca  18300
acacattcga agactcagtg aggggatacg acgttccccc gccatcatca tctacaccca  18360
ttgcggtagc ttaacaccgc aaagggcgca cgaataactc aaactaacac tattcacaga  18420
aatggaaatt gaatcaaact gaaaaaaaaa acacatacaa aggggaaagg gaagagggaa  18480
aactttcaca cgcagtaaaa actaatcaaa aaagacgtga agaggagaag aacaacgaga  18540
ggtacttatc ttttactcta tccacgctgg cgtcgtcgat gctgtaaccg atgggcgtct  18600
acgcttgggg agaggtagca agtaacgtac gaccattcgc tgggacgcgt agatgtgtgg  18660
ttgatctccg ctgtccacgc tatacgcaca ccacagacga tgatcgcact gatgaactct  18720
gcactgcaca caggtagcac acgggacggg gtgcgagctg ccttcgatga tacacgtgat  18780
caaaaaagga cggtctggtt cctggttcgc tggtacggtg tatgtgtggt tggtctctca  18840
ctgcctgcca ccaactaaca caggcgtcga taacgatggt gaccactgtc ggcgtggaga  18900
gcgcaccgct gtgcacgcta tatgcacacc acaaacgatg atcactcagg tagcacacgg  18960
```

```
gacgaggtgc aagctgtctt ctacgataca cgtgatcgga aaataaccac gcaatggcga  19020
aaacgttcaa tacttttgcg caaaactcga ttaaacggca acacaatggc ttcgccaaaa  19080
gtgttccgct tccaagccga actaaggctc ttcactgcac taaaaacact ttgcaatagg  19140
cgtcgaaata ccaaagattt ggaaaaacgg gggtgaaccc ggacacacga gaactatcga  19200
ctgtctcgca cggtagctca acaaggaatg gcttatcatt ttgtcataaa aatttttgtg  19260
ggaaataaca gtaactccat agtttttgaa cgcgagcata ttgtatgcaa aatttaagca  19320
atgtacacta cgaaaaaaat attaaaaagg tgattcattt taaaacagtt ttagaagaca  19380
ggttgtgatt cttctgaatt aattttctca aaaccgtaag gaagttactt acgtcgattt  19440
aaaaaagtac cgtggacgta ccatatttga cgcggttaag aaaattctaa attcaaacac  19500
ttgtcaaatc gtctaaatct ttccgatttt gttgaaaatt gaacatatgc tagctcaact  19560
attatagaat tagggaaaaa tcagtaaaaa aatattaaac gtttttttat tcatgtttaa  19620
ccttagtaag gaccttgggt ctttttcgac ccatttcaaa attcaaatca atataacttt  19680
tgattgaaat aatctagcaa tttgaatctt tctgacaatt atttttttgt tggaaatttt  19740
gtttttgcga aaacaaaagt tttgaatgac ccctagggga gcttccataa aaaaagttac  19800
aaattgtgac ttagggtcgt tttcgacccg aaaattcaaa cagctcgcaa aaatcagtgt  19860
gttgaccgaa tttagttctg ttgggcttaa atgaagggca cacatgtcta gtttcagaaa  19920
ccctcccgga gatccggatt tggtcactgt ggccaccggg aacctgctac atatgaaaaa  19980
agtcccttaa gagaccctta ctttgacgac ctgtagtttc gtaactaaac aagtaatctg  20040
aaccgtcctc atattgttga acaggtattc acgtggactg tgaatagaga ttctcaaatc  20100
gcttagttat tcatacccgg ttccggaaac ccggaacatc cgaaaagtaa acttctatcg  20160
tagttttgta tatgtaattc acatcggtgc tattcggttg atggatattt tggcataatt  20220
tttttctgta ataaggaacc aattgccggc gcacattccc tgaagaattc ggtccagtaa  20280
ggtcaaagcg gaaccggttc ctggagtccc gggaggtggc caatctggac aaatcgatga  20340
aattactcag atttgaaccc caaaaccaaa tgaattgtgt ccaattcttt acgatttctt  20400
atgtttggat gtattttgcc gaaaaaatga atgaatggtt attctggtcc ttttggagca  20460
ccggaatggc caccgggaaa cccgtaatat gggaccacaa tattttagca ccaaaaatag  20520
gcatgcgacg gctcaatctt catgattttg catccccgtg acacttatag ttcaattatt  20580
gatgaatgac cactttggtt cttctggctc atcgaaataa cctaggaatg gtcaccggaa  20640
atacccgtat tgtgggacat ttcagttttt gcaccaaaac taggcatgcg acagatcaat  20700
cttcatgatt tgcatccctg agactttgct agttcaatta ttgatgaatg accactttgg  20760
ttctgctggc ccagcgaaat aacccaggaa tgaccaccgg aaatacccgt attgtgggac  20820
atttcagttt ttgtaccaaa actaggcatg cgacggctca atcttcatga ttttgaatac  20880
ctgtgacttt gcttgttcaa ttattgatga atgaccacat tgattattct ggctcatcga  20940
aataacccag gaatgaccac cggaaatacc cgtattgttg gacatttcag tttttgtacc  21000
aaaagtaggc atgcgacgtc tcaatcttca tgattttgaa tacctgtgac tttgcttgtt  21060
caattattga tgaatgacca ctttggttct tctggctcat cgaaataacc taggaatggt  21120
caccggaaat acccgtattg tgggacattt cagtttttgt accaaaacta ggcatgcgac  21180
ggctcattct tcatgatttt gaatacctgt gactttgata gttgaattat tgatgaatga  21240
ccactttggt tcctctggct catcgaaata acccaggaat ggccaccgga aatacccgta  21300
ttgtgggaca tttcagtttt tgtaccaaaa ctaggcatgc gatgtctcaa tcttcatgat  21360
```

```
tttgaatacc tgtgactttg caagttcaat tattgatgaa tgaccgcttt ggttcttctg  21420
gctcatcgaa ataacccagg aatggccacc ggaaatacgc gtattgtgga acatttcaga  21480
ttatgtacca aaaccaggca tgtgacggtt cattcttcgt gattttgaat acctgtgaca  21540
cttctagatc aattattgat gaatgaccac tttggttctt ttggcccatc gaaataaccc  21600
aggaatggcc accggaaata cgcgtattgt gggacatttc agtttttgta ccaaaactag  21660
gcatgcgacg gctcaatctt catgattttg aatacctgtg acttttctat tttaattatt  21720
gataaatgtc cactttgttt cttctggacc accgaaataa cccaggaatg actactggag  21780
atacccgtat tgtgggatat atagtttttt gtgccgaaac taggcatggg acaaataatt  21840
ctttatgatt ttgaatacct gtgactcttc taattcaatt atagcagaat gagcactggc  21900
tcttcgggac cacctaaatt attcaggaat ggccaatgga gtttcccgta ttgtgggaca  21960
tttcagtttt gtaccaaaac taggtatacg aaggctcaat cttcatgact ttgaatacct  22020
gtgacatttt tagtacaatt atagataaat taccactttg gttcttctgt actaccaaaa  22080
taacccaaga attacacctt agatacccat tctatgcgat attgaaatag ttgtgccgaa  22140
actaggcatg cgatggctca atcttcatga tttataatac ttgtgactct tctagttaaa  22200
ttataagtga atgactactc tggctcatta taaccaccgg aaaaccccag gcatgaccat  22260
cggtgttatc tctattgtgg gacatttcag atattgttcc aaaacttgac atgtaacagc  22320
tcaattttcc aaattttctg agcacgtgat ccatctcaca tgctaatgaa tggatggcca  22380
gtctggtctc ttgctgtcac tgaaataacc caggaatgtc caccaaagaa acccgtatcg  22440
tggggtacat tagtgtttga tccataacaa gaaattcgac ggctcaatct tcctagtttt  22500
tcgggcatgt ggcttttctc atacaataat aagtaaaagt ccagtcaggt cctcaggttt  22560
caggttggac gactacgctg tagaatcgtt acccgttctg tggcgtagtt gattaacgtg  22620
cccagtctag cgtattgggg gtcgtgggat cgaagctcac tagaataatt ccattattta  22680
tcgcaaattt tacatctcaa tttgtccaaa ttgactttta tgtctacgaa cttcagattt  22740
tatattcgtt cactattagc cagagtgatt attcgtctat aattgaaaaa gaaaagtcac  22800
aggtattcaa aatcatgaag attgagccgt cgcatggcta gttttggtgc aaaaactgga  22860
atgtcccaca atacgggtat ttccggtggc cattcctggg ttatttcgct gggccagagg  22920
aaccaaagtg gtcattcatc aataattgaa ctagaagtgt caaagggatg caaaatcatg  22980
aagattgagc cgtcgcatgg ctagttttgg tgcaaaaact gaaatgtccc acaatacggg  23040
tatttccggt gaccattcct aggttatttc gatgagccag aagaaccaca gcggtcattc  23100
atcaataatt gaaccagcag agtcacaggt attcaaaatc atgaagattg agccgtcgca  23160
tgcctagttt tggtacaaaa actgaaatgt cccacaatac gggtatttcc ggtggtcatt  23220
cctgggttat ttcgctgggc cagcagaacc aaagtggtca ttcatcaata gttgaactag  23280
caaagtctca gggatgcaaa atcatgaaga ttgatctgtc gcatgcctag ttttggtgca  23340
aaaactgata tgtcccacaa tacgggtatt tccggtggcc attcttgagt tatttcggtg  23400
ggccagaaga accaaagtgg tcattcatca ataattgaac tataagtgtc acggggatgc  23460
aaaatcatga agattgagcc gtcgcatgcc tatttttggt gctaaaatat tgtggtccca  23520
tattacgggt ttcccggtgg ccattccggt gctccaaaag gaccagaata accattcatt  23580
catttttcg gcaaaataca tccaaacata agaaatcgta aagaattgga cacaattcat  23640
ttggttttgg ggttcaaatc tgagtaattt catcgatttg tccagattgg ccacctcccg  23700
```

-continued

```
ggactccagg aaccggttcc gcattgacct tactggatcg aatttttcag gggatgtgcg  23760
ccggcaattg gttccttatt acagaaaaaa attatgccaa aatatccatc aaccgaatag  23820
caccgatgtg aattacatat acagaactac gatagaagct tacttttcgg atgttccggg  23880
tttccggaac cgggtatgaa taactaagcg atttgagaat ctctattcac agtccacgtg  23940
aatacctgtt caacaatatg aggacggttt agattacttg tttagttacg aaactacagg  24000
tcgtcaaagt aagggtctct taagggactt ttttcatatg tagcaggttc ccggtggcca  24060
cagtgactaa atccggatct ccgggagggt ttctgaaact agagatgtgt gcccttcatt  24120
taagcccaac agaactaaat tcggtcaaca cactgatttt tgcgagctgt ttgaattttc  24180
gggtcgaaaa cgaccctaag tcacaatttg taactttttg ttagggacta aggaaggtta  24240
attgactttt tgtggaacac attaggttcc ttaattgacg catcaattct tcaatgtgcc  24300
taatttgacg cactatgttc cttatttgac gcacttacaa ataattgcta aagttcaaaa  24360
tatacaagag tttcagtatt caatagttca attaattgaa aaaagcgctt tagagtggac  24420
ataaaagtta gaagaacctt tggagaaagt tttgaatgac gttatccggt agtacttttg  24480
ctatgcgttt agttagtgta gaaaataaca ccggcgattg agttcaatcc atagttaagc  24540
attattgttt agtttaatgc attttcgtcg cgatatcagg caagggaaag ttttgaaaac  24600
tacgttgcgc tggaacgggg aagatagttt ctaaaataag gaaaaattgg tcaaaaacta  24660
gaacgaaaac aaccggttcc aaaaatatcc gtttaagaat cttcgttact tattacacgt  24720
gaactacgcc tacttgtccc atgttctatg tcacccttat ggaccgcggg acaaatatgc  24780
gtagaactaa cggcagtatg gtcttcgaaa tagatcgaga accatatatg gggtcatcca  24840
taaagtactt catgttatta gggggtagga ggtgttctgc acgatgtgac gaatcatata  24900
agtttttga aggctccata taaaaagtgt gacgtagggc ggatagccgg ggtttttcta  24960
gaaaatggta ttttttggtg actcgtatct catggacacc ccctattgta taaataatac  25020
gaaacaaacc attgaaccta cacctcacct tctgacgcat ttattgaagc ttccttgaaa  25080
cattagggga cgtccataaa ccgcgataaa ttgttcaatt atcaacccct ctcaaccttg  25140
gccacattta ttttatgaaa agtgcgaata ttttgtatga atcgttgcat ttccctgaac  25200
ctcctcctct tcctaaaaac gttacgtaat ctatggatga ccctttacat gtgattacat  25260
aaagcattgg gttgttctgc ggacggattt ttttaattgc aatcaccata aatatttctt  25320
ttgctattat cgattcaaca aaacatgctg aacaaaatag caaataatta ggaacattgt  25380
gtgcctaatt tgacgcacaa gattttcata caaaaatgtg tcttaaacct taaaaataga  25440
aaaaaaatcg acgtcaattt atgaataaaa gaatattact gattgttgtt gatgatattg  25500
ctgtaaaaca gcacaatatt ttcatgaaaa ttgattaata atatttagca cattcactaa  25560
ggaatgaaaa aaattgacgc acttgtcgga tgaattttca aataattttt attttttgcc  25620
tattattaat caaaaataaa cttttttga ttgatatctt acaataacat gtaaatgaag  25680
attaaggaat aaatttttga atgctattct gaactagaat taatttataa taaaaataat  25740
tagaaaatgc gtcaagtttg gacccgcgtc aaatatggta cgttcacggt aatcaagatt  25800
tgatgttttt tagtattttt gcacaaataa caaattatac catgatagta tattttgtta  25860
ttccctggcc acgatcacag ggtttgacgg tgccacagta gaaggtgcac tataataata  25920
ttcgtctgtg aaacatatca ccttcccaat actttggcac acctctaacg gttcatgatt  25980
tatcatgata cggctgcatt caggcggagg atctgttaat atgtttcggc atattatcag  26040
gtcctcttcg aacggaggga ccgccagggc tcagtagtta cttacacacc agtgctggtt  26100
```

```
gttgatgttt cagttcgttt acacgagctg tagcatcctt tgctctaatc agtaatggtg  26160
gttaagtttc aaagctaacg tgtgatcaat cgttttataa tgcaacataa gaatagtggt  26220
tatcacgccc aatggtatgg gtgccctagt gtagttgtag ttgtgaacct tagaggaaag  26280
caatatgcac gctgtctcga aaaacaccca aaatccgggt gtaaattttt caaattgggt  26340
tatattttca tatgcatttt aatgagtctg gaaagcgtgt gcaagtttct ttgaggaaaa  26400
caaaaacaaa ctgtgtatga cgagcgtatg gtagtctacg tgtgttcaaa tgtcactaag  26460
ctccataggt ggaattgtgc attgcattcg tcgttttaaa ataggtgatt gtgagggtgc  26520
taataatgac atttgaagaa atgtgtgatg ataaaaatat ttgtaaattg cattgaaagt  26580
gatggtgata gttttgttga aaatacataa tatgaaccct cagtggtacg tctgtttgtc  26640
tatgctacta gattattgat ggttatagag tgcttcgtaa agcccaagca ggacagttca  26700
gttttgcgtc gtccgataaa ttttgctcac ggtttcgcgc atgttttcgt cgccggagat  26760
tttttttttc ctgttttcaa gcgtcttgct gggtagtgct tcgtaaagcc caagcaggac  26820
agttcagttt tgcgtcgtcc gataaatttg gctcacggtt tcgcgcatgt tttcgtcgcc  26880
ggaaattttt ttttttcctg ttttcaagcg tcttgctggg tagtgcttcg tgaagcccaa  26940
gcaggacagt tcggttttgc gtcgtccgat agatttggct cacgttttcg cgcatgtttt  27000
cgtcgccgga gatttttttt ttcctgtttt caagcgtctt gctgggtagt gcttcgtgaa  27060
gcccaagcag gacagttcgg ttttgcgtcg tccgatagat ttggctcacg gtttcgcgca  27120
tgttttcgtc gccggagatt ttttttagag atgtaccgaa tagcactatt cggcctttgg  27180
ccgaataccg aatagttgta atattattat tcggccaaac gaatattcgg ccgaacattt  27240
ggccgaataa tgacttaata ttcggtcaaa taaaacctaa atattcggcc gaataacacc  27300
cgtatgtgca gttttttaaa tagggaaagc tgaacaatta aacgaagcat aaatggaaat  27360
gaatgatcgt cttcttgagg ttttgaaatc gtttgcagaa atcataagtt ctgaagattt  27420
ctgtatttct gaagctagga agctgtatcc tattgttgat tttagtttaa gaaatttggt  27480
ttactattca accgactttt ggaagtgttt cataaaaatt gaggcaaatt gacggcagac  27540
ccctgactct cataataata gaagaacgta atcagtaggt tttgcaaaga atatagaacg  27600
tagagaaagt cctgataatt gacggacttt aaggtgagga tgcatcgaag ccaaacctgc  27660
atcgaagagc ataaatctag agaatctgac agccgttcgc gctgaatatt ggaatgattg  27720
gtcaacacca gcgattgacc agaaagttaa attttcagca caaacggttg tctggttctc  27780
tagatttgtg ctcttgaaaa tgacgggttt agcttcgatg catctatacc ttgaaaacaa  27840
tttttcaaac gcttctaact agccaagcgg tacgttacag ctcctgcaag atgagataca  27900
atttgatttg cagaaaatgg taacgccata gaacagagaa attctcactt tttcaatatt  27960
tgacatcgaa gtctattcaa agtatccata aaaagaaaaa tacggtcatc atttgaataa  28020
attattgatt ttttaaattt tccttacata aacataatat ttttttttac agtttagttt  28080
attttgttat tattcggtca ctattcggcc tattcggccg aataacggat tttattattc  28140
ggcagaacga atattcggcc aaattaaaaa aatcgagata ttcggcccga atattcggcc  28200
ggccgaatat tcggtacatc tctaattttt ttttcctgtt tccaagcgtc ctgctgggta  28260
gtgcttcgtg aagcccaagc aggacagttc ggttttgcgt cgtccgatag atttggctca  28320
cgttttcgcg catgttttcg tcgccggaga tttttttttt ttttcctgtt ttcaagcgtc  28380
ttgctgggta gtgcttcgtg aagcccaagc aggacagttc ggttttgcgt cgtccgatag  28440
```

```
atttggctca cggtttcgcg cgtgttttcg gctcctaaga ttttttttc tgttttggag  28500
cgtcttgctg ggtaggtatt tggaaggcac aagcaagacg gtttgttttc gggacgccaa  28560
gaagttttgc tgtcagtatc agttttgtgt tcagtcgagg atggattacc tactggtgag  28620
ttcgtttcat tcttgtgata acacatattt tcttgaaagc gtaactttta agtaatttta  28680
aaacaaactt tgtatggttc gtcactataa gtgtcggcat tatgtttttt tcttatacaa  28740
tttcaatata catatatttg tctcttttat atgttattaa aaattatctt ttgaattgtt  28800
cgacattgtg aatgttgacg tattttttaa aacttgtacc atatcgagac aaaatgcaca  28860
gtaatactca tatgtaattt tcaaacaaac tatgtatagt tcgtcactac aagtgtcggc  28920
attattcctg tttcatataa tttaaaatat atacatgtaa ttttcagttt tcgtcattaa  28980
taaaaacatc ttttgaatag agtagtgttt gatccttcga ccttgacgct ggctcctgcg  29040
ggagcgggtg atgagggcag gatcaaatat gtcgcgcgtc ggtagtgaag cggtgaaaaa  29100
gtgatcggtt cgtaagtagt gtttgatcct tcgaccttga cgcttgctcc tgcgggggcg  29160
ggcgatgggg gcaggatcaa acttgtcgcg cgtcgttcgc tcagagaaat gaaaaagcgc  29220
cgcggatcgc tagtagtgtt tgatctattg atcgcgtcgc ttgctcttgc gtgggcgagt  29280
gacgaacact tgttcggcgt ttaatgcgat catcgaatta tttcgcgaat ccggttgggc  29340
gtgattatat catggctcgc atcaccaaac attggtgact cccagatctt taccttatcc  29400
cactaaccca atatcctctc catgacaacc gtggagatgc agaggtgatc tcggtctcta  29460
gtaacaacgg tagtcacact aacattcctt cccttccccg atgaccgtaa ggacgtggcc  29520
ggcgccgtta ttgactttta aatttgagct ctcgatttgt gcacattgaa gaatggtaag  29580
ctaatcccaa gccccattca ttaattccct gtgcaacttc gattgttctg gtcaatcacg  29640
gagtagcaac tacgaattgt acggtcatct atgcttatgc ttatgcttat gctactagat  29700
tattgatggt tataatacat tctgcaacca tttctctgaa tataaaaact attgcctagt  29760
tcttaacaca ttcatgataa gagtgttcat aatgacagtg agtgcagtaa aattaatcac  29820
agtgatttta tttttctact gtaactttat tgatcgtagt gctaaatcgt agtttgaata  29880
ttttttttaa ttatttagtt atgatggtta gatggtaaat ggtaacaaaa atgaattatt  29940
atgaaagtag tgtgatgtta ttttgataaa aaattgtagc agtgaaagtg aagtgatata  30000
atgtaaagta tacatatatg atgtgtatta cgaaagttaa tgagtgataa tcggtgatat  30060
tagtgatagt gttaaaaaag tgacgacagc aaaagtgtgg taattatgtg acagtgactg  30120
atgaaatgaa atggggaacg aggacctttc aataaaacta tttcattctt ctcttcaacc  30180
actttggtag catttcaagt cttatcatag ttttatacta gtctggaata ttagactgca  30240
aaactacggc aagggttgat tgctgctagg gtacacagtg accatttgag caacattgct  30300
taggaacgtc tgtgtgatga atgtaacaga ggcttataaa agtaaatgtt gggcaggagc  30360
ttagggcaga ttaaaagtcc cagtactacc tctatcgcta ctgacaaaaa aaaaaaaaaa  30420
aaaaaaaaaa acaaattata ccatgatagt atattttgtt attgattagt tattgcatga  30480
cataccaatg acaaaatgca aataaaaagc gttcatgata gctcaatcgt ggttggaata  30540
gtaaatttaa aaactcgttc atggttctca ttacttcaac gcttgtttca gtgtacccgg  30600
ttagtgaaaa tgtaaggtct actgcagtgg tccttggggt aacttgttgt atgaaccacc  30660
ccaatgatct cagaatattc tgcggacgac agttcggtga tcactgatcc tctaacatag  30720
tggaagtact aaagtttcgc agctatacag aaaacatcaa aataaagatg ttaaaattga  30780
tattttcctt gaaaacatac aaataaagat atacaactat tcatggaggg aactttgcga  30840
```

attgatgtat aaacatacag gtttgtttca gttctgctca gcagaagttt tttaagtttc 30900
aatacaatct aatgctattc tgaatctatc aaaaacgtgg gtatacatca atacccgttg 30960
aaagaaaaag agatgtggta atttatcaga atcgcagtaa caagattatt acagcgggga 31020
ttcgctggtg ggagtacgac tgccttccat ctaacgaatc cgacccgtta gttggaacga 31080
ctgacagctg gtgaaaatgc tccagactaa cgcatccgga acgcaaatcg tcacgaaacg 31140
cacataaaca tacacatttg ttctatatat ggagatttca atgcgacggt agtcagacgt 31200
caaagtttga catcttctcc tgacattcga gtgctttttg tagttagaat ttttttcaac 31260
cagcgaacat ccaaccatcg agtgattcca tgtagcggac cccaacgag cgaatcccca 31320 cagtatctgc caagttgtca agcaaataga aataataaac catagaagaa taatgtcgct 31380
ggtgttccct ttgttctcgc tcagaaacat gttgggtacg taagtgtcaa actgcataca 31440
ttttcgcttt gcatttatag ccccgcctat ctccgccagc aaaagatgtt cctactgcga 31500
cgccagcgac attcttcttc tatggtttat tacttctatt gtcaagcaat acagttaaga 31560
aactctacac tcaaaaaaat ccgaacgtca ttgctacgtg aaaaatcacg tagatcattc 31620
caaattcatt ttacctccac ttcacctgac caagctaaag atcactaaac cattcataac 31680
caccaaatag tgactcggta atgtttactg aggttaccta tcgcgcttac gtggaattca 31740
cgtaggtgcc tgagttcatt ttgacatttg catagtgtac gtacattcgg tgttgagctc 31800
aaatcctaag atggcgcccg cttgattttt gaagaacttc aaaagctgct gctgcttaaa 31860
cactgtgtaa gattgaattc aattccaaat atgctttgga taccgaagaa tccctgcatt 31920
acttcatatt ttatacgtga tgtataacct ctatcaatag ggtcctaaag ccctgtcccg 31980
attttagtgc caaacgctta aatttaggcc aaaaacacat gtttactcaa ttttctaatg 32040
ttttccgttg gtttaagccc aaaaaacatt ttttttagat tttgtcacat cctttggctt 32100
aaactcaaat tttgggcgta ttttgttttc cgtgtccctt acgaaatgtc agataggaac 32160
aaccccagtg gtcgatccaa aacccctgtg gtgtttttgt cgactaagcg aacgtcaaac 32220
atgatcaaaa gtgtcaaggt tcatttatgg accaaatttt taaattaaag tttaaacatg 32280
atatagccat tatttgagcg ggaaaaattg ctaaagtagt tacagtgaca tgctttttcg 32340
tgttattaaa taaaaacaag atttcattaa aaattttagg acccaattat agcacgcgaa 32400
ggctacaaca aggcagacca aactcacaaa attggggaaa caggattcaa aatgctcaga 32460
ttgacaataa aaatatcaca atcttttaag tttgtttaca ttgggaatta gttttcttcc 32520
aaagcctatt cgaaataaga ttggtattta ttacagttaa atttaaggtc ctattgaaac 32580
gcttcgtaaa ggctaccgga aaatccacgt agctcttacg tttagcgacg gtggaatgga 32640
cgaacttcaa aagttcatgc gttcattctg ggctacctat gattaacgta agagctacgt 32700
ggaaagtgcg atggaaaaaa atcacgtatg ttttcacgta acaataacgt ttggattatt 32760
ttgagtg 32767

<210> SEQ ID NO 122
<211> LENGTH: 840
<212> TYPE: DNA
<213> ORGANISM: Aedes aegypti

<400> SEQUENCE: 122
gcgagtgcct tatgaatctc tttttgtttc gtagtcgcga attcctatcc tgaacatgtg 60
ctgcttggga aatatttgat tctaaaactt gtgttttaat tttgtattac tgcgtatatc 120

```
tatagaaaaa agacaatata actataacaa gtcatcaaaa tggatgttga tgtacaggtt    180
atttctacaa gtggcgaaag aacgaaaata aaacagccta agatagaaaa tgatgttcgg    240
aaagtgtttg tacctcgttc cagacaatcc gcattgaagg aacaatggat gaaaatattc    300
actccagtcg tggaccaact tttacttcag ataagatata atgtaaaaag caagcaagtg    360
gaactgcgat tgggacccga atctaaaaat ccatctaact tgcaaaaagg agcagatttt    420
gtacgcgcat ttattctcgg ttttgaggtg gaagacgctt tggctctgct tcgtcttgac    480
gacctttttta tcgaatcttt cgaagtaaat gatgttaaga tgttgaaagg ggatcattta    540
agtcgcgcta ttggaagatt agctggaaaa ggaggacgaa ccaagtttac tctggaaaac    600
tcaactaaaa cgcgaattgt tctacaggac tctaagattc atattctggg aaattacaaa    660
agcatacagc atgcaaaacg tgcagtcagc catctcatct taggatcgcc tgccagcaaa    720
gtgtatggaa atttgcgaac agttgctgga aaaatatctg agcgaattta atacttttga    780
cgttgagtgt ttcattttta tatgcttttg tatagtatcc attaaatatt aatacctgta    840
```

<210> SEQ ID NO 123
<211> LENGTH: 663
<212> TYPE: DNA
<213> ORGANISM: Aedes aegypti

<400> SEQUENCE: 123

```
cgtgtattcg accttttgtc gacaaaggtc ccatgagcga cagctgtcaa aataaatgga     60
aaagtttata cgacgcacct gtaatattga ttctgcctcg tttaacagtt tttttgcacc    120
atgttaatcc acccattcat tgcttggtaa gtttctcata gataaaacat tgtttcagtg    180
taataatgtt tcttttacag atgctgcgat tctccgaaaa caaaccgttt ggtttgccta    240
tggaaagacc tcaactgaag acccgccaga tcgcagcttt gttatctctt cacttgatgg    300
ttccagtgga gaaacagcat cgggatcgat tccatggatg agaatgagca tccattcgcc    360
atccaacctt caagcgaatc agtgtattcc atggcaaaat cggtccgcac cggcttggca    420
cctggaaaca tcaatggatc attcttccca tgccaatcaa tcccttcgtc tttcctgaca    480
cgtcttcatt cgttgaatca ccagcttcgt cagacgatag cccaggcctt gaaaccgagt    540
ccataaaaac gagttatgga gagttgactg ttgtactaaa ttcggttttt gtttactaac    600
tactaaacag ctcgaagatt tattatcaaa aactattttt tgaaatgtgt taacttattt    660
cta                                                                  663
```

<210> SEQ ID NO 124
<211> LENGTH: 609
<212> TYPE: DNA
<213> ORGANISM: Aedes aegypti

<400> SEQUENCE: 124

```
cgtgtattcg accttttgtc gacaaaggtc ccatgagcga cagctgtcaa aataaatgga     60
aaagtttata cgacgcacct gtaatattga ttctgcctcg tttaacagtt tttttgcacc    120
atgttaatcc acccattcat tgcttgatgc tgcgattctc cgaaaacaaa ccgtttggtt    180
tgcctatgga aagacctcaa ctgaagaccc gccagatcgc agctttgtta tctcttcact    240
tgatggttcc agtggagaaa cagcatcggg atcgattcca tggatgagaa tgagcatcca    300
ttcgccatcc aaccttcaag cgaatcagtg tattccatgg caaaatcggt ccgcaccggc    360
ttggcacctg gaaacatcaa tggatcattc ttcccatgcc aatcaatccc ttcgtctttc    420
ctgacacgtc ttcattcgtt gaatcaccag cttcgtcaga cgatagccca ggccttgaaa    480
```

ccgagtccat aaaaacgagt tatggagagt tgactgttgt actaaattcg gtttttgttt 540
actaactact aaacagctcg aagatttatt atcaaaaact attttttgaa atgtgttaac 600
ttatttcta 609

<210> SEQ ID NO 125
<211> LENGTH: 654
<212> TYPE: DNA
<213> ORGANISM: Aedes aegypti

<400> SEQUENCE: 125 gacctttgt cgacaaaggt cccatgagcg acagctgtca aaataaatgg aaaagtttat 60
acgacgcacc tgtaatattg attctgcctc gtttaacagt ttttttgcac catgttaatc 120
cactcattca ttgcttggta agtttctcat agataaaaca ttgtttcagt gtaataatgt 180
ttcttttaca gatgctgcga ttctccgaaa acaaaccgtt tggtttgcct atggaaagac 240
ctcaactgaa gacccgccag atcgcagctt tgttatctct tcacttgatg gttccagtgg 300
agaaacagca tcgggatcga ttccatggat gagaatgagc atccattcgc catccaacct 360
tcaagcgaat cagtgtattc catggcaaaa tcggtccgca ccggcttggc acctggaaac 420
atcaatggat cattcttccc atgccaatca atcccttcgt ctttcctgac acgtcttcat 480
tcgttgaatc accagcttcg tcagacgata gcccaggcct tgaaaccgag tccataaaaa 540
cgagttatgg agagttgact gttgtactaa attcggtttt tgtttactaa ctactaaaca 600
gctcgaagat ttattatcaa aaactatttt ttgaaatgtg ttaacttatt tcta 654

<210> SEQ ID NO 126
<211> LENGTH: 600
<212> TYPE: DNA
<213> ORGANISM: Aedes aegypti

<400> SEQUENCE: 126 gacctttgt cgacaaaggt cccatgagcg acagctgtca aaataaatgg aaaagtttat 60
acgacgcacc tgtaatattg attctgcctc gtttaacagt ttttttgcac catgttaatc 120
cactcattca ttgcttgatg ctgcgattct ccgaaaacaa accgtttggt ttgcctatgg 180
aaagacctca actgaagacc cgccagatcg cagctttgtt atctcttcac ttgatggttc 240
cagtggagaa acagcatcgg gatcgattcc atggatgaga atgagcatcc attcgccatc 300
caaccttcaa gcgaatcagt gtattccatg gcaaaatcgg tccgcaccgg cttggcacct 360
ggaaacatca atggatcatt cttcccatgc caatcaatcc cttcgtcttt cctgacacgt 420
cttcattcgt tgaatcacca gcttcgtcag acgatagccc aggccttgaa accgagtcca 480
taaaaacgag ttatggagag ttgactgttg tactaaattc ggtttttgtt tactaactac 540
taaacagctc gaagatttat tatcaaaaac tattttttga aatgtgttaa cttatttcta 600

<210> SEQ ID NO 127
<211> LENGTH: 1106
<212> TYPE: DNA
<213> ORGANISM: Aedes aegypti

<400> SEQUENCE: 127
tctcttgctg gcggagatag gcggggctat aaatgtcaac gcgaaaatat atgcagtttg 60
acatttatgt acccgacatg tttctgagcg agaacaaagg gaacaccagc gacattcgtc 120
ctctatagtt ttctatctct attaattatc ctgatattca tgacagtttt ctccggccag 180

```
ctcagtgttt accatttctg gagctcgatt tgaaaaggtc gtaagtaaca aaagtaaata    240
aatcatgcta atttcaccat taggtagatt ctactcagct taatatgtgg ttaaaatatc    300
atttcgatat gatatttctt caaaaataaa ttaaaagtta acacttcgac gtaattaacg    360
aaaactagaa acagtgcaaa tttgttcatt cgtcctattg cgcataaggt cgaaagtagc    420
aaaaatgact aaacccgaaa aatcgtgtat tcgacctttt gtcgacaaag gtcccatgag    480
cgacagctgt caaaataaat ggaaaagttt atacgacgca cctgtaatat tgattctgcc    540
tcgtttaaca gtttttttgc accatgttaa tccacccatt cattgcttgg taagtttctc    600
ataaataaaa cattgtttca gtgtaataat gtttctttta cagatgctgc gattctccga    660
aaacaaaccg tttggtttgc ctatggaaag acctcaactg aagacccgcc agatcgcagc    720
tttgttatct cttcacttga tggttccagt ggagaaacag catcgggatc gattccatgg    780
atgagaatga gcatccattc gccatccaac cttcaagcga atcagtgtat tccatggcaa    840
aatcggtccg caccggcttg gcacctggaa acatcaatgg atcattcttc ccatgccaat    900
caatcccttc gtctttcctg acacgtcttc attcgttgaa tcaccagctt cgtcagacga    960
tagcccaggc cttgaaaccg agtccataaa aacgagttat ggagagttga ctgttgtact   1020
aaattcggtt tttgtttact aactactaaa cagctcgaag atttattatc aaaaactatt   1080
ttttgaaatg tgttaactta tttcta                                         1106
```

<210> SEQ ID NO 128
<211> LENGTH: 1052
<212> TYPE: DNA
<213> ORGANISM: Aedes aegypti

<400> SEQUENCE: 128

```
tctcttgctg gcggagatag gcggggctat aaatgtcaac gcgaaaatat atgcagtttg     60
acatttatgt acccgacatg tttctgagcg agaacaaagg gaacaccagc gacattcgtc    120
ctctatagtt ttctatctct attaattatc ctgatattca tgacagtttt ctccggccag    180
ctcagtgttt accatttctg gagctcgatt tgaaaaggtc gtaagtaaca aaagtaaata    240
aatcatgcta atttcaccat taggtagatt ctactcagct taatatgtgg ttaaaatatc    300
atttcgatat gatatttctt caaaaataaa ttaaaagtta acacttcgac gtaattaacg    360
aaaactagaa acagtgcaaa tttgttcatt cgtcctattg cgcataaggt cgaaagtagc    420
aaaaatgact aaacccgaaa aatcgtgtat tcgacctttt gtcgacaaag gtcccatgag    480
cgacagctgt caaaataaat ggaaaagttt atacgacgca cctgtaatat tgattctgcc    540
tcgtttaaca gtttttttgc accatgttaa tccacccatt cattgcttga tgctgcgatt    600
ctccgaaaac aaaccgtttg gtttgcctat ggaaagacct caactgaaga cccgccagat    660
cgcagctttg ttatctcttc acttgatggt tccagtggag aaacagcatc gggatcgatt    720
ccatggatga gaatgagcat ccattcgcca tccaaccttc aagcgaatca gtgtattcca    780
tggcaaaatc ggtccgcacc ggcttggcac ctggaaacat caatggatca ttcttcccat    840
gccaatcaat cccttcgtct ttcctgacac gtcttcattc gttgaatcac cagcttcgtc    900
agacgatagc ccaggccttg aaaccgagtc cataaaaacg agttatggag agttgactgt    960
tgtactaaat tcggtttttg tttactaact actaaacagc tcgaagattt attatcaaaa   1020
actatttttt gaaatgtgtt aacttatttc ta                                 1052
```

<210> SEQ ID NO 129
<211> LENGTH: 917

<212> TYPE: DNA
<213> ORGANISM: Aedes aegypti

<400> SEQUENCE: 129
agttaattct ggagctcgat ttgaaaaggt cgtaagtaac aaaagtaaat aaatcatgct 60
aatttcacca ttaggtagat tctactcagc ttaatatgtg gttaaaatat catttcgata 120
tgatatttct tcaaaaataa attaaaagtt aacacttcga cgtaattaac gaaaactaga 180
aacagtgcaa atttgttcat tcgtcctatt gcgcataagg tcgaaagtag caaaaatgac 240
taaacccgaa aaatcgtgta ttcgaccttt tgtcgacaaa ggtcccatga gcgacagctg 300
tcaaaataaa tggaaaagtt tatacgacgc acctgtaata ttgattctgc ctcgtttaac 360 agttttttg caccatgtta atccacccat tcattgcttg gtaagtttct catagataaa 420
acattgtttc agtgtaataa tgtttctttt acagatgctg cgattctccg aaaacaaacc 480
gtttggtttg cctatggaaa gacctcaact gaagacccgc cagatcgcag ctttgttatc 540
tcttcacttg atggttccag tggagaaaca gcatcgggat cgattccatg gatgagaatg 600
agcatccatt cgccatccaa ccttcaagcg aatcagtgta ttccatggca aaatcggtcc 660
gcaccggctt ggcacctgga aacatcaatg gatcattctt cccatgccaa tcaatccctt 720
cgtctttcct gacacgtctt cattcgttga atcaccagct tcgtcagacg atagcccagg 780
ccttgaaacc gagtccataa aaacgagtta tggagagttg actgttgtac taaattcggt 840
ttttgtttac taactactaa acagctcgaa gatttattat caaaaactat tttttgaaat 900
gtgttaactt atttcta 917

<210> SEQ ID NO 130
<211> LENGTH: 863
<212> TYPE: DNA
<213> ORGANISM: Aedes aegypti

<400> SEQUENCE: 130
agttaattct ggagctcgat ttgaaaaggt cgtaagtaac aaaagtaaat aaatcatgct 60
aatttcacca ttaggtagat tctactcagc ttaatatgtg gttaaaatat catttcgata 120
tgatatttct tcaaaaataa attaaaagtt aacacttcga cgtaattaac gaaaactaga 180
aacagtgcaa atttgttcat tcgtcctatt gcgcataagg tcgaaagtag caaaaatgac 240
taaacccgaa aaatcgtgta ttcgaccttt tgtcgacaaa ggtcccatga gcgacagctg 300
tcaaaataaa tggaaaagtt tatacgacgc acctgtaata ttgattctgc ctcgtttaac 360 agttttttg caccatgtta atccacccat tcattgcttg atgctgcgat tctccgaaaa 420
caaaccgttt ggtttgccta tggaaagacc tcaactgaag acccgccaga tcgcagcttt 480
gttatctctt cacttgatgg ttccagtgga gaaacagcat cgggatcgat tccatggatg 540
agaatgagca tccattcgcc atccaacctt caagcgaatc agtgtattcc atggcaaaat 600
cggtccgcac cggcttggca cctggaaaca tcaatggatc attcttccca tgccaatcaa 660
tcccttcgtc tttcctgaca cgtcttcatt cgttgaatca ccagcttcgt cagacgatag 720
cccaggcctt gaaaccgagt ccataaaaac gagttatgga gagttgactg ttgtactaaa 780
ttcggttttt gtttactaac tactaaacag ctcgaagatt tattatcaaa aactattttt 840
tgaaatgtgt taacttattt cta 863

<210> SEQ ID NO 131
<211> LENGTH: 637
<212> TYPE: DNA

<213> ORGANISM: Aedes aegypti

<400> SEQUENCE: 131
ctcccctgcg acgtagtttt taactatttg gagccgggca cccaagtgaa gtagcctgct 60
ccggtaaact tccttgttcg gacacctata ccccaaatcc tccttcatgg actcaaattt 120
accactacaa atggacaatt cagtttctac attcccttga aacgaacgga tgacaggttc 180
ggagctgctc tgctccatgg acaaaaatcc ccgcaatcga cgacgcctct tcgaacccga 240
ttgatccgat tcaggaggga taataacacc acgggagttc agttcaaagt cgatctcatc 300
gagttctaaa tgatcggcac gcaattgaaa ataggcgacg ttgaactccc ccaacgtcaa 360
agtatggagt gccattttga tgaatgaaca acaaaagtct tcaaaatatg gacgaaattg 420
agacttacca actgatcagt gacgtacaaa tacggtaaat aataatttat gattactaac 480
ggttccaaaa tgattttagg ttgccaaatt aagtcagatg tcaccccaaa tcagcccaga 540
agaatcaaaa atcccgccct gagaacaaag agacccaaaa tgtcccaatt cgttccgcag 600
acgagacggt tcaccgattt agtttaaaaa cgaacaa 637

<210> SEQ ID NO 132
<211> LENGTH: 576
<212> TYPE: DNA
<213> ORGANISM: Aedes aegypti

<400> SEQUENCE: 132
ctcccctgcg acgtagtttt taactatttg gagccgggca cccaagtgaa gtagcctgct 60
ccggtaaact tccttgttcg gacacctata ccccaaatcc tccttcatgg actcaaattt 120
accactacaa atggacaatt cagtttctac attcccttga aacgaacgga tgacaggttc 180
ggagctgctc tgctccatgg acaaaaatcc ccgcaatcga cgacgcctct tcgaacccga 240
ttgatccgat tcaggaggga taataacacc acgggagttc agttcaaagt cgatctcatc 300
gagttctaaa tgatcggcac gcaattgaaa ataggcgacg ttgaactccc ccaacgtcaa 360
agtatggagt gccattttga tgaatgaaca acaaaagtct tcaaaatatg gacgaaattg 420
agacttacca actgatcagt tgccaaatta agtcagatgt caccccaaat cagcccagaa 480
gaatcaaaaa tcccgccctg agaacaaaga gacccaaaat gtcccaattc gttccgcaga 540
cgagacggtt caccgattta gtttaaaaac gaacaa 576

<210> SEQ ID NO 133
<211> LENGTH: 1539
<212> TYPE: DNA
<213> ORGANISM: Aedes aegypti

<400> SEQUENCE: 133
gcataatggt gaaccgattc caggaactca ttgagtccgg ttccttcatc gttcccagca 60
tatttttgga ttttccaatc ggccactcgt tggggccgcc gatagtaacc ggtgatctcc 120
accgagtctg tactctcagg ctgacgagaa ggtacgtgat ttggaaaaga aggacgcgaa 180
aacacatttt gcggcggatg agtcggctcg ggcttctcaa aagttctgga attgttaaca 240
aaggcggagc tgaaaggttt ctgatttgac tgttttggta ttccaaactc tttagtaggt 300
attgagaaac gcctcgaaga gttctctgga acacctaagc cttctaacgt cgccggatcg 360
aaatcgggca aatccggtag atctggactt gttctcaaac gaatctcatc cagttctact 420
ggcaaacttt gggagtttac gttagggact atgctattca cgatgccctg taactctgaa 480
accgctacgc gaagtgtttg cacatcccga ttcgttttct gaagttcaga agcaatcgtg 540

```
ctgatagaca caagtccgtt accgagcttt ttcactgcag cttccaggga atcaactcta    600
gaagaactgc gagcctcgct tagcttaatt tgggcttgtg tcttttggat ctccgccctt    660
atttcaaaca agacatctcg aatatcacct acggcatggc tgttggatac tttttcggct    720
ggaatttgag agttctcgtc cgacacagca tccgtccccg tggcaatgtg gatttgcaaa    780
tcatcaccac catcttcctt atcttcctca atcggcgtta ggggcggcgc cgacacattc    840
gcgaagtggt agttgtgaag agcaaccaca tcgctcaaaa gatctacgaa ggccttatta    900
ttctcccctg cgacgtagtt tttaactatt tggagccggg cacccaagtg aagtagcctg    960
ctccggtaaa cttccttgtt cggacaccta taccccaaat cctccttcat ggactcaaat   1020
ttaccactac aaatggacaa ttcagtttct acattccctt gaaacgaacg gacgacaggt   1080
tcggagctgc tctgctccat ggacaaaaat ccccgcaatc gacgacgcct cttcgaaccc   1140
gattgatccg attcaggagg gataataaca ccacgggagt tcagttcaaa gtcgatctca   1200
tcgagttcta aatgatcggc acgcaattga aaataggcga cgttgaactc ccccaacgtc   1260
aaagtatgga gtgccatttt gatgaatgaa ctacaaaagt cttcaaaata tggacgaaat   1320
tgagacttac caactgatca gtgacgtaca aatacggtaa ataataattt atgattacta   1380
acggttccaa aatgatttta ggttgccaaa ttaagtcaga tgtcacccca aatcagccca   1440
gaagaatcaa aaatcccgcc ctgagaacaa agagacccaa aatgtcccaa ttcgttccgc   1500
agacgagacg gttcaccgat ttagtttaaa aacgaacaa                          1539
```

```
<210> SEQ ID NO 134
<211> LENGTH: 1478
<212> TYPE: DNA
<213> ORGANISM: Aedes aegypti

<400> SEQUENCE: 134

gcataatggt gaaccgattc caggaactca ttgagtccgg ttccttcatc gttcccagca     60
tatttttgga ttttccaatc ggccactcgt tggggccgcc gatagtaacc ggtgatctcc    120
accgagtctg tactctcagg ctgacgagaa ggtacgtgat ttggaaaaga aggacgcgaa    180
aacacatttt gcggcggatg agtcggctcg ggcttctcaa aagttctgga attgttaaca    240
aaggcggagc tgaaaggttt ctgatttgac tgttttggta ttccaaactc tttagtaggt    300
attgagaaac gcctcgaaga gttctctgga acacctaagc cttctaacgt cgccggatcg    360
aaatcgggca aatccggtag atctggactt gttctcaaac gaatctcatc cagttctact    420
ggcaaacttt gggagtttac gttagggact atgctattca cgatgccctg taactctgaa    480
accgctacgc gaagtgtttg cacatcccga ttcgttttct gaagttcaga agcaatcgtg    540
ctgatagaca caagtccgtt accgagcttt ttcactgcag cttccaggga atcaactcta    600
gaagaactgc gagcctcgct tagcttaatt tgggcttgtg tcttttggat ctccgccctt    660
atttcaaaca agacatctcg aatatcacct acggcatggc tgttggatac tttttcggct    720
ggaatttgag agttctcgtc cgacacagca tccgtccccg tggcaatgtg gatttgcaaa    780
tcatcaccac catcttcctt atcttcctca atcggcgtta ggggcggcgc cgacacattc    840
gcgaagtggt agttgtgaag agcaaccaca tcgctcaaaa gatctacgaa ggccttatta    900
ttctcccctg cgacgtagtt tttaactatt tggagccggg cacccaagtg aagtagcctg    960
ctccggtaaa cttccttgtt cggacaccta taccccaaat cctccttcat ggactcaaat   1020
ttaccactac aaatggacaa ttcagtttct acattccctt gaaacgaacg gacgacaggt   1080
```

tcggagctgc tctgctccat ggacaaaaat ccccgcaatc gacgacgcct cttcgaaccc 1140
gattgatccg attcaggagg gataataaca ccacgggagt tcagttcaaa gtcgatctca 1200
tcgagttcta aatgatcggc acgcaattga aaataggcga cgttgaactc ccccaacgtc 1260
aaagtatgga gtgccatttt gatgaatgaa ctacaaaagt cttcaaaata tggacgaaat 1320
tgagacttac caactgatca gttgccaaat taagtcagat gtcaccccaa atcagcccag 1380
aagaatcaaa aatcccgccc tgagaacaaa gagacccaaa atgtcccaat tcgttccgca 1440
gacgagacgg ttcaccgatt tagtttaaaa acgaacaa 1478

<210> SEQ ID NO 135
<211> LENGTH: 1539
<212> TYPE: DNA
<213> ORGANISM: Aedes aegypti

<400> SEQUENCE: 135
gcataatggt gaaccgattc caggaactca ttgagtccgg ttccttcatc gttcccagca 60
tatttttgga ttttccaatc ggccactcgt tggggccgcc gatagtaacc ggtgatctcc 120
accgagtctg tactctcagg ctgacgagaa ggtacgtgat ttggaaaaga aggacgcgaa 180
aacacatttt gcggcggatg agtcggctcg ggcttctcaa aagttctgga attgttaaca 240
aaggcggagc tgaaaggttt ctgatttgac tgttttggta ttccaaactc tttagtaggt 300
attgagaaac gcctcgaaga gttctctgga acgcctaagc cttctaacgt cgccggatcg 360
aaatcgggca aatccggtag atctggactt gttctcaaac gaatctcatc cagttctact 420
ggcaaacttt gggagtttac gttagggact atgctattca cgatgccctg taactctgaa 480
accgctacgc gaagtgtttg cacatcccga ttcgttttct gaagttcaga agcaatcgtg 540
ctgatagaca caagtccgtt accgagcttt ttcactgcag cttccaggga atcaactcta 600
gaagaactgc gagcctcgct tagcttaatt tgggcttgtg tcttttggat ctccgccctt 660
atttcaaaca agacatctcg aatatcacct acggcatggc tgttggatac tttttcggct 720
ggaatttgag agttctcgtc cgacacagca tccgtccccg tggcaatgtg gatttgcaaa 780
tcatcaccac catcttcctt atcttcctca atcggcgtta ggggcggcgc cgacacattc 840
gcgaagtggt agttgtgaag agcaaccaca tcgctcaaaa gatctacgaa ggccttatta 900
ttctcccctg cgacgtagtt tttaactatt tggagccggg cacccaagtg aagtagcctg 960
ctccggtaaa cttccttgtt cggacaccta taccccaaat cctccttcat ggactcaaat 1020
ttaccactac aaatggacaa ttcagtttct acattccctt gaaacgaacg gacgacaggt 1080
tcggagctgc tctgctccat ggacaaaaat ccccgcaatc gacgacgcct cttcgaaccc 1140
gattgatccg attcaggagg gataataaca ccacgggagt tcagttcaaa gtcgatctca 1200
tcgagttcta aatgatcggc acgcaattga aaataggcga cgttgaactc ccccaacgtc 1260
aaagtatgga gtgccatttt gatgaatgaa ctacaaaagt cttcaaaata tggacgaaat 1320
tgagacttac caactgatca gtgacgtaca aatacggtaa ataataattt atgattacta 1380
acggttccaa aatgatttta ggttgccaaa ttaagtcaga tgtcacccca aatcagccca 1440
gaagaatcaa aaatcccgcc ctgagaacaa agagacccaa aatgtcccaa ttcgttccgc 1500
agacgagacg gttcaccgat ttagtttaaa aacgaacaa 1539

<210> SEQ ID NO 136
<211> LENGTH: 1478
<212> TYPE: DNA
<213> ORGANISM: Aedes aegypti

<400> SEQUENCE: 136

```
gcataatggt gaaccgattc caggaactca ttgagtccgg ttccttcatc gttcccagca     60
tatttttgga ttttccaatc ggccactcgt tggggccgcc gatagtaacc ggtgatctcc    120
accgagtctg tactctcagg ctgacgagaa ggtacgtgat ttggaaaaga aggacgcgaa    180
aacacatttt gcggcggatg agtcggctcg ggcttctcaa aagttctgga attgttaaca    240
aaggcggagc tgaaaggttt ctgatttgac tgttttggta ttccaaactc tttagtaggt    300
attgagaaac gcctcgaaga gttctctgga acgcctaagc cttctaacgt cgccggatcg    360
aaatcgggca aatccggtag atctggactt gttctcaaac gaatctcatc cagttctact    420
ggcaaacttt gggagtttac gttagggact atgctattca cgatgccctg taactctgaa    480
accgctacgc gaagtgtttg cacatcccga ttcgttttct gaagttcaga agcaatcgtg    540
ctgatagaca caagtccgtt accgagcttt ttcactgcag cttccaggga atcaactcta    600
gaagaactgc gagcctcgct tagcttaatt tgggcttgtg tcttttggat ctccgccctt    660
atttcaaaca agacatctcg aatatcacct acggcatggc tgttggatac tttttcggct    720
ggaatttgag agttctcgtc cgacacagca tccgtccccg tggcaatgtg gatttgcaaa    780
tcatcaccac catcttcctt atcttcctca atcggcgtta ggggcggcgc cgacacattc    840
gcgaagtggt agttgtgaag agcaaccaca tcgctcaaaa gatctacgaa ggccttatta    900
ttctcccctg cgacgtagtt tttaactatt tggagccggg cacccaagtg aagtagcctg    960
ctccggtaaa cttccttgtt cggacaccta taccccaaat cctccttcat ggactcaaat   1020
ttaccactac aaatggacaa ttcagtttct acattccctt gaaacgaacg gacgacaggt   1080
tcggagctgc tctgctccat ggacaaaaat ccccgcaatc gacgacgcct cttcgaaccc   1140
gattgatccg attcaggagg gataataaca ccacgggagt tcagttcaaa gtcgatctca   1200
tcgagttcta aatgatcggc acgcaattga aaataggcga cgttgaactc ccccaacgtc   1260
aaagtatgga gtgccatttt gatgaatgaa ctacaaaagt cttcaaaata tggacgaaat   1320
tgagacttac caactgatca gttgccaaat taagtcagat gtcaccccaa atcagcccag   1380
aagaatcaaa aatcccgccc tgagaacaaa gagacccaaa atgtcccaat tcgttccgca   1440
gacgagacgg ttcaccgatt tagtttaaaa acgaacaa                           1478
```

<210> SEQ ID NO 137
<211> LENGTH: 520
<212> TYPE: DNA
<213> ORGANISM: Aedes aegypti

<400> SEQUENCE: 137

```
ttaattcatt ccgaacgtgt tcattcttcg attcatttag tgttgtgatc aattgtaaag     60
atggcgtcaa gtgaaaataa acatcaagat ttggtggact tcccattttt tgattgattg    120
aaaggtatat tttaatttgt tgtagtaaag cttaaattga tttgaatttt acttctcaat    180
agatcatcgg gccatttttc tgagtcgcat ctttgctagc aatgcgggtc agattggtac    240
gtggtattgg aagagctggc gcaggtcaac tatggttatc ccgttttttt tttaatttaa    300
gcgtgagtaa acatttactt tgtgatgctt ttaaaaataa ctattcttgt ttccgatatt    360
ctttctctga aacagaaacg ttggctgtaa ttgtgtgccg aaggatttcc gagaatatcg    420
agctgaaaac atacaacaaa accagacttg ttaccagatt ttccgatact ccagcattgt    480
gtgaaatatc gatggttcaa taaataaaag taagaattaa                          520
```

<210> SEQ ID NO 138
<211> LENGTH: 389
<212> TYPE: DNA
<213> ORGANISM: Aedes aegypti

<400> SEQUENCE: 138
ttaattcatt ccgaacgtgt tcattcttcg attcatttag tgttgtgatc aattgtaaag 60
atggcgtcaa gtgaaaataa acatcaagat ttggtggact tcccattttt tgattgattg 120
aaagatcatc gggccatttt tctgagtcgc atctttgcta gcaatgcggg tcagattggt 180
acgtggtatt ggaagagctg gcgcaggtca actatggtta tcccgttttt tttttaattt 240
aagcaaacgt tggctgtaat tgtgtgccga aggatttccg agaatatcga gctgaaaaca 300
tacaacaaaa ccagacttgt taccagattt tccgatactc cagcattgtg tgaaatatcg 360
atggttcaat aaataaaagt aagaattaa 389

<210> SEQ ID NO 139
<211> LENGTH: 459
<212> TYPE: DNA
<213> ORGANISM: Aedes aegypti

<400> SEQUENCE: 139
gattgcgtca agtgaaaata aacatcaaga tttggtggac ttcccatttt ttgattgatt 60
gaaaggtata ttttaatttg ttgtagtaaa gcttaaattg atttgaattt tacttctcaa 120
tagatcatcg ggccattttt ctgagtcgca tctttgctag caatgcgggt cagattggta 180
cgtggtattg gaagagctgg cgcaggtcaa ctatggttat cccgtttttt taaatttaag 240
cgtgagtaaa catttacttt gtgatgcttt taaaaataac tattcttgtt tccgatattc 300
tttctctgaa acagaaacgt tggctgtaat tgtgtgccga aggatttccg agaatatcga 360
gccgaaaaca tacaacaaaa ccagacttgt taccagattt tccgatactc cagcattgtg 420
tgaaatatcg atggttcaat aaataaaagt aagaattaa 459

<210> SEQ ID NO 140
<211> LENGTH: 328
<212> TYPE: DNA
<213> ORGANISM: Aedes aegypti

<400> SEQUENCE: 140
gattgcgtca agtgaaaata aacatcaaga tttggtggac ttcccatttt ttgattgatt 60
gaaagatcat cgggccattt ttctgagtcg catctttgct agcaatgcgg gtcagattgg 120
tacgtggtat tggaagagct ggcgcaggtc aactatggtt atcccgtttt tttaaattta 180
agcaaacgtt ggctgtaatt gtgtgccgaa ggatttccga gaatatcgag ccgaaaacat 240
acaacaaaac cagacttgtt accagatttt ccgatactcc agcattgtgt gaaatatcga 300
tggttcaata aataaaagta agaattaa 328

<210> SEQ ID NO 141
<211> LENGTH: 642
<212> TYPE: DNA
<213> ORGANISM: Aedes aegypti

<400> SEQUENCE: 141
accatccact gactttacct gactaaggta acagttaccg gttcataaat gaaagtaata 60
tgtttcttcg ataattttca ctgcgtcaac ctatcgacct tacgtgaaat ctacgtacat 120
gctttaattc attccgaacg tgttcattct tcgattcatt tagtgttgtg atcaattgta 180

```
aagatggcgt caagtgaaaa taaacatcaa gatttggtgg acttcccatt ttttgattga    240

ttgaaaggta tattttaatt tgttgtagta aagcttaaat tgatttgaat tttacttctc    300

aatagatcat cgggccattt ttctgagtcg catctttgct agcaatgcgg gtcagattgg    360

tacgtggtat tggaagagct ggcgcaggtc aactatggtt atcccgtttt ttttaaatat    420

aagcgtgagt aaacatttac tttgtgatgc ttttaaaaat aactattctt gtttccgata    480

ttctttctct gaaacagaaa cgttggctgt aattgtgtgc cgaaggattt ccgaaaatat    540

cgagccgaaa acatacaaca aaaccagact tgttaccaga ttttccgata ctccagcatt    600

gtgtgaaata tcgatggttc aataaataaa agtaagaatt aa                       642
```

<210> SEQ ID NO 142
<211> LENGTH: 511
<212> TYPE: DNA
<213> ORGANISM: Aedes aegypti

<400> SEQUENCE: 142

```
accatccact gactttacct gactaaggta acagttaccg gttcataaat gaaagtaata     60

tgtttcttcg ataattttca ctgcgtcaac ctatcgacct tacgtgaaat ctacgtacat    120

gctttaattc attccgaacg tgttcattct tcgattcatt tagtgttgtg atcaattgta    180

aagatggcgt caagtgaaaa taaacatcaa gatttggtgg acttcccatt ttttgattga    240

ttgaaagatc atcgggccat ttttctgagt cgcatctttg ctagcaatgc gggtcagatt    300

ggtacgtggt attggaagag ctggcgcagg tcaactatgg ttatcccgtt ttttttaaat    360

ataagcaaac gttggctgta attgtgtgcc gaaggatttc cgaaaatatc gagccgaaaa    420

catacaacaa aaccagactt gttaccagat tttccgatac tccagcattg tgtgaaatat    480

cgatggttca ataaataaaa gtaagaatta a                                   511
```

<210> SEQ ID NO 143
<211> LENGTH: 493
<212> TYPE: DNA
<213> ORGANISM: Aedes aegypti

<400> SEQUENCE: 143

```
tcacaatcta cccatatttg gatgaaaaaa aacattagct tcatcatcat caacgaaatt     60

ttcgtgaagg aactaagagt ggttgcctga taaaggtaaa ttgcaattaa aataattatt    120

cataactatt tctagctgat ttgttttaca gcattcattc cgctacttag gaatctgcgc    180

caaggggaac tagcgatgaa ttttcatccg agctgttccc atttcactcg tttccggaag    240

attggattga aaacgtgcgt tttggtactc tggttggcag gttcccggtt aacatttctg    300

gatccactag ggcgaaggtt tattaccgca atccgttatc catcgtggaa aactcggctc    360

caaattaatg caatgtggaa tatgtctttg atattcattg gcatttcagt ggcacgaatc    420

ttcaatctat catattgatt aaagttgtag attcaatatt gattcattaa ataaatgaga    480

tatgtaccta cta                                                       493
```

<210> SEQ ID NO 144
<211> LENGTH: 437
<212> TYPE: DNA
<213> ORGANISM: Aedes aegypti

<400> SEQUENCE: 144

```
tcacaatcta cccatatttg gatgaaaaaa aacattagct tcatcatcat caacgaaatt     60
```

```
ttcgtgaagg aactaagagt ggttgcctga taaagcattc attccgctac ttaggaatct    120

gcgccaaggg gaactagcga tgaattttca tccgagctgt tcccatttca ctcgtttccg    180

gaagattgga ttgaaaacgt gcgttttggt actctggttg gcaggttccc ggttaacatt    240

tctggatcca ctagggcgaa ggtttattac cgcaatccgt tatccatcgt ggaaaactcg    300

gctccaaatt aatgcaatgt ggaatatgtc tttgatattc attggcattt cagtggcacg    360

aatcttcaat ctatcatatt gattaaagtt gtagattcaa tattgattca ttaaataaat    420

gagatatgta cctacta                                                   437


<210> SEQ ID NO 145
<211> LENGTH: 582
<212> TYPE: DNA
<213> ORGANISM: Aedes aegypti

<400> SEQUENCE: 145

aactctcgat tttttcgggc gaacggtttg tagaatgtga acgacccacg gtacccacgc     60

tcatttgacg ttttccacag ttccataatt tttgtttgtc cctttttatt cgatcggttt    120

tgtttttatt gtttgcatca acagtttgtt gttgttgcaa attttgcatc caattcgcaa    180

cgatccgaaa gtgattttat tacaaactcg gtcaccgaag ttccccagta agtaagtatt    240

gtgataactt gaattgagta cgttcactct ctgtaggtgc atacaataat ctgaatttat    300

ttccaaatct aatcaaagcc taccacacaa cgatagcaca aatatcttca acaaattcat    360

ccggccttcc gggacatcaa ggtgctaacg tcttccgagc gcaagacgct cttcgccaac    420

attgtccccg tgcacgagtg ctccgattta gaaaactgtt agcaggacaa catcatgctc    480

ctgggcctca gtcgcagtat gtacaagcac gccgagaaac acttccacgt gtacgttaac    540

tactgcgagc accaagcgaa gatcgatcgc accctaaaga ac                       582


<210> SEQ ID NO 146
<211> LENGTH: 495
<212> TYPE: DNA
<213> ORGANISM: Aedes aegypti

<400> SEQUENCE: 146

aactctcgat tttttcgggc gaacggtttg tagaatgtga acgacccacg gtacccacgc     60

tcatttgacg ttttccacag ttccataatt tttgtttgtc cctttttatt cgatcggttt    120

tgtttttatt gtttgcatca acagtttgtt gttgttgcaa attttgcatc caattcgcaa    180

cgatccgaaa gtgattttat tacaaactcg gtcaccgaag ttccccagta acctaccaca    240

caacgatagc acaaatatct tcaacaaatt catccggcct tccgggacat caaggtgcta    300

acgtcttccg agcgcaagac gctcttcgcc aacattgtcc ccgtgcacga gtgctccgat    360

ttagaaaact gttagcagga caacatcatg ctcctgggcc tcagtcgcag tatgtacaag    420

cacgccgaga aacacttcca cgtgtacgtt aactactgcg agcaccaagc gaagatcgat    480

cgcaccctaa agaac                                                     495


<210> SEQ ID NO 147
<211> LENGTH: 480
<212> TYPE: DNA
<213> ORGANISM: Aedes aegypti

<400> SEQUENCE: 147

taaagttaca cgctaacttt gaagtaccca ttaaatgggt ttcttgtacc catttttatt     60

gcttgtactg agttgtcaaa aaaagggtat tattttctga cattaaaaag ggtacatttt    120
```

```
actcttcttg aggaatgact tcagtcagca ataatgggtg aaataatgtc gttattttga    180

gcagaaagat tgaaattatt accacgaatt atatttcatt aattaactga aagcatcatg    240

gtaagtagct atttcttgaa gaaactattt acatcgaaga ctaaattgac tattccttat    300

aacaggaccc tcgaagaagc acaaaaagcg gcaatttagg agcgattttt catccgggat    360

ctggaacagg aagatacgga gcaagcgcca cggattcaga tggaccaatg ttattaatac    420

tccaattaac actttattta aaagtaataa tctaataaaa ttattttcat tagactctta    480
```

<210> SEQ ID NO 148
<211> LENGTH: 415
<212> TYPE: DNA
<213> ORGANISM: Aedes aegypti

<400> SEQUENCE: 148

```
taaagttaca cgctaacttt gaagtaccca ttaaatgggt ttcttgtacc catttttatt     60

gcttgtactg agttgtcaaa aaaagggtat tattttctga cattaaaaag ggtacatttt    120

actcttcttg aggaatgact tcagtcagca ataatgggtg aaataatgtc gttattttga    180

gcagaaagat tgaaattatt accacgaatt atatttcatt aattaactga aagcatcatg    240

gaccctcgaa gaagcacaaa aagcggcaat ttaggagcga tttttcatcc gggatctgga    300

acaggaagat acggagcaag cgccacggat tcagatggac caatgttatt aatactccaa    360

ttaacacttt atttaaaagt aataatctaa taaaattatt ttcattagac tctta         415
```

<210> SEQ ID NO 149
<211> LENGTH: 567
<212> TYPE: DNA
<213> ORGANISM: Aedes aegypti

<400> SEQUENCE: 149

```
gctaactttg aagtacccat taaatgggtt tcttgtaccc atttttattg cttgtactga     60

gttgtcaaaa aaagggtatt attttctgac attaaaaagg gtacatttta ctcttcttga    120

ggaatgactt cagtcagcaa taatgggtga aaacgcccct tgtcgttatt ttgagcagaa    180

agattgaaat tattaccacg aattatattt cattaattaa ctgaaagcat catggtaagt    240

agctatttct tgaagaaact atttacatcg aagactaaat tgactattcc ttataacagg    300

accctcgaag aagcgggatc tggaacagga agatacggag caagcgccac ggattcagat    360

ggaccaatgt tattaatact ccaattagca ctttatttaa aagtaataat ctaataaaat    420

tattttcatt agactcttat atgttgtgtc gtcggatatg tttaaaaaat ttctttagaa    480

tccttgtttt ccgtatgtgc cggcaagagg ggggtatttt ttacccattt ttgtaaaatc    540

aatgaggggt aaataatacc catttta                                        567
```

<210> SEQ ID NO 150
<211> LENGTH: 502
<212> TYPE: DNA
<213> ORGANISM: Aedes aegypti

<400> SEQUENCE: 150

```
gctaactttg aagtacccat taaatgggtt tcttgtaccc atttttattg cttgtactga     60

gttgtcaaaa aaagggtatt attttctgac attaaaaagg gtacatttta ctcttcttga    120

ggaatgactt cagtcagcaa taatgggtga aaacgcccct tgtcgttatt ttgagcagaa    180

agattgaaat tattaccacg aattatattt cattaattaa ctgaaagcat catggaccct    240
```

```
cgaagaagcg ggatctggaa caggaagata cggagcaagc gccacggatt cagatggacc    300

aatgttatta atactccaat tagcacttta tttaaaagta ataatctaat aaaattattt    360

tcattagact cttatatgtt gtgtcgtcgg atatgtttaa aaaatttctt tagaatcctt    420

gttttccgta tgtgccggca agaggggggt attttttacc catttttgta aaatcaatga    480

ggggtaaata atacccattt ta                                             502


<210> SEQ ID NO 151
<211> LENGTH: 438
<212> TYPE: DNA
<213> ORGANISM: Aedes aegypti

<400> SEQUENCE: 151

ctaactttga agtacccatt aaatgggttt cttgtaccca tttttattgc ttgtactgag     60

ttgtcaaaaa aagggtatta ttttctgaca ttaaaaaggg tacattttac tcttcttgag    120

gaatgacttc aatcagcaat aatgggtgaa aaagcccctt gtcgttattt tgagcagaaa    180

gattgaaatt attaccacga attatatttc attaattaac tgaaagcatc atggtaagta    240

gctatttctt gaagaaacta tttacatcga agactaaatt gactattcct tataacagga    300

ccctcgaaga agcgggatct ggaacaggaa gatacggagc aagcgccacg gattcagatg    360

gaccaatgtt attaatactc caattagcac tttatttaaa agtaataatc taataaaatt    420

attttcatta gactctta                                                  438


<210> SEQ ID NO 152
<211> LENGTH: 373
<212> TYPE: DNA
<213> ORGANISM: Aedes aegypti

<400> SEQUENCE: 152

ctaactttga agtacccatt aaatgggttt cttgtaccca tttttattgc ttgtactgag     60

ttgtcaaaaa aagggtatta ttttctgaca ttaaaaaggg tacattttac tcttcttgag    120

gaatgacttc aatcagcaat aatgggtgaa aaagcccctt gtcgttattt tgagcagaaa    180

gattgaaatt attaccacga attatatttc attaattaac tgaaagcatc atggaccctc    240

gaagaagcgg gatctggaac aggaagatac ggagcaagcg ccacggattc agatggacca    300

atgttattaa tactccaatt agcactttat ttaaaagtaa taatctaata aaattatttt    360

cattagactc tta                                                       373


<210> SEQ ID NO 153
<211> LENGTH: 675
<212> TYPE: DNA
<213> ORGANISM: Aedes aegypti

<400> SEQUENCE: 153

agttgtaagc aatcacgcac tcaggcaaat aaattaacta atttcataaa ttttccctta     60

tgaagcgttg aaaaatctat aaaaacctat ttcagaaggc taatatggat ttcataccgt    120

tgaaataata atcataattg ataaaatagt taattataat gaacgttctc aaatttcatt    180

gcgcgcctta tgatttccat tgctgtcatt agtcatttcc tcaatgatac catcattcat    240

aaggctatta tggatttcat attagttcaa tgaaaaccat aattgcgaag catgttatcc    300

ctcattaacg aatatcaatt tcattgggcc accttatgaa gcacatagct gtcgctagtg    360

tgaaaaactc ataaggttgt tattatgaaa atttgcaaat ggaaaaataa ctggacgcgg    420

atccatttac ggaagcatca taaatttgtt cgaatatttt caaaggtaat aagttggttt    480
```

```
ttctgataat ttgaaattaa tacggaattg aattttcaga tagaatttta taggcaggat    540

cgtcattcga ctggagagca gcatgaaatc accgccatcg ttgacatccc gcatactgca    600

gtcaactttt ttataagtct ggttatgggg aaggaagtac agcgatggaa gattgtaaaa    660

atcgaaaaaa aaaaa                                                      675


<210> SEQ ID NO 154
<211> LENGTH: 621
<212> TYPE: DNA
<213> ORGANISM: Aedes aegypti

<400> SEQUENCE: 154

agttgtaagc aatcacgcac tcaggcaaat aaattaacta atttcataaa ttttccctta     60

tgaagcgttg aaaaatctat aaaaacctat ttcagaaggc taatatggat ttcataccgt    120

tgaaataata atcataattg ataaaatagt taattataat gaacgttctc aaatttcatt    180

gcgcgcctta tgatttccat tgctgtcatt agtcatttcc tcaatgatac catcattcat    240

aaggctatta tggatttcat attagttcaa tgaaaaccat aattgcgaag catgttatcc    300

ctcattaacg aatatcaatt tcattgggcc accttatgaa gcacatagct gtcgctagtg    360

tgaaaaactc ataaggttgt tattatgaaa atttgcaaat ggaaaaataa ctggacgcgg    420

atccatttac ggaagcatca taaatttgtt cgaatatttt caaagataga attttatagg    480

caggatcgtc attcgactgg agagcagcat gaaatcaccg ccatcgttga catcccgcat    540

actgcagtca actttttat aagtctggtt atggggaagg aagtacagcg atggaagatt    600

gtaaaaatcg aaaaaaaaaa a                                               621


<210> SEQ ID NO 155
<211> LENGTH: 1172
<212> TYPE: DNA
<213> ORGANISM: Aedes aegypti

<400> SEQUENCE: 155

gtaagctcca tcgaggttaa tacggcaatc gtgtattatc ctcgattttg ctaagcatcg     60

aacggtatta tcttcgattt taatcccggt attaacttta gtgcgccgat tttggcgtac    120

taaagataaa acgagatttt ccaaatacag gctgcgtgct ttaatttgcc taaacgcacc    180

caggaaccaa ctagtggaga aatcggactg aaccaaatga ttgtggtacg ctgtttctga    240

ctcgcaatgg tgcttcgcgg tggatatttt ttttaaacca ccacactctt cgatccgcga    300

gctcgcacaa acagtggatg gtcaataatg cacataagta ttttcctgtg gttgaccccc    360

tttagctgaa ggaaattcgt caatccggat ccatggatac tccaaacatg aggattggac    420

cgtaaaaacc atttccgagg gaactttagg catagacctt tgcgctgccg ccaccgaaac    480

cggacaaggt atcggcgggc gcaatacgcc gcatcactca ggcaaataaa ttaactaatt    540

tcataaattt tcccttatga agcgttgaaa aatctataaa aacctatttc agaaggctaa    600

tatggatttc ataccgttga aataataatc ataattgata aaatagttaa ttataatgaa    660

cgttctcaaa tttcattgcg cgccttatga tttccattgc tgtcattagt catttcctca    720

atgataccat cattcataag gctattatgg atttcatatt agttcaatga aaaccataat    780

tgcgaagcat gttatccctc attaacgaat atcaatttca ttgggccacc ttatgaagca    840

catagctgtc gctagtgtga aaaactcata aggttgttat tatgaaaatt tgcaaatgga    900

aaaataactg gacgcggatc catttacgga agcatcataa atttgttcga atattttcaa    960
```

```
aggtaataag ttggtttttc tgataatttg aaattaatac ggaattgaat tttcagatag   1020

aattttatag gcaggatcgt cattcgactg gagagcagca tgaaatcacc gccatcgttg   1080

acatcccgca tactgcagtc aacttttttta taagtctggt tatggggaag gaagtacagc   1140

gatggaagat tgtaaaaatc gaaaaaaaaa aa                                  1172
```

<210> SEQ ID NO 156
<211> LENGTH: 1118
<212> TYPE: DNA
<213> ORGANISM: Aedes aegypti

<400> SEQUENCE: 156

```
gtaagctcca tcgaggttaa tacggcaatc gtgtattatc ctcgattttg ctaagcatcg     60

aacggtatta tcttcgattt taatcccggt attaacttta gtgcgccgat tttggcgtac    120

taaagataaa acgagatttt ccaaatacag gctgcgtgct ttaatttgcc taaacgcacc    180

caggaaccaa ctagtggaga aatcggactg aaccaaatga ttgtggtacg ctgtttctga    240

ctcgcaatgg tgcttcgcgg tggatatttt ttttaaacca ccacactctt cgatccgcga    300

gctcgcacaa acagtggatg gtcaataatg cacataagta ttttcctgtg gttgaccccc    360

tttagctgaa ggaaattcgt caatccggat ccatggatac tccaaacatg aggattggac    420

cgtaaaaacc atttccgagg gaactttagg catagacctt tgcgctgccg ccaccgaaac    480

cggacaaggt atcggcgggc gcaatacgcc gcatcactca ggcaaataaa ttaactaatt    540

tcataaattt tcccttatga agcgttgaaa aatctataaa aacctatttc agaaggctaa    600

tatggatttc ataccgttga aataataatc ataattgata aaatagttaa ttataatgaa    660

cgttctcaaa tttcattgcg cgccttatga tttccattgc tgtcattagt catttcctca    720

atgataccat cattcataag gctattatgg atttcatatt agttcaatga aaaccataat    780

tgcgaagcat gttatccctc attaacgaat atcaatttca ttgggccacc ttatgaagca    840

catagctgtc gctagtgtga aaaactcata aggttgttat tatgaaaatt tgcaaatgga    900

aaaataactg gacgcggatc catttacgga agcatcataa atttgttcga atattttcaa    960

agatagaatt ttataggcag gatcgtcatt cgactggaga gcagcatgaa atcaccgcca   1020

tcgttgacat cccgcatact gcagtcaact tttttataag tctggttatg gggaaggaag   1080

tacagcgatg gaagattgta aaaatcgaaa aaaaaaaa                           1118
```

<210> SEQ ID NO 157
<211> LENGTH: 1836
<212> TYPE: DNA
<213> ORGANISM: Aedes aegypti

<400> SEQUENCE: 157

```
acaaaggaca cgggatatac tacaatagat caaatattgg tcgcagtggt ttatgttccg     60

aacagaaaaa aaaggctctc atgggtcaat ttgtttccag gatgcatatt atctctgatt    120

cccttaccat gctaattcca aacatatcca cagctgtcag cccctggtga tttattatca    180

acaaaaataa ttaaagtcca attattttca cttttcagct cagaagttta ccaacgcttc    240

attggtctac ataactgaga cagttttaga ggaaatcgga ataattgaaa aaggcccgca    300

agtggtaatt ctaaccgtgg tagcaaaact gaaaaaagct catcatgaca gtacatcgga    360

tacaaaccct acccaagctg gaccatcacg aagattaact gagtctccga gtgaagctgt    420

aacagtaagt taatagcata tgagactgca aagaaacgtt actatatctt gccctgcctt    480

agatccgaca aaccctggaa cgagatgcta cttgttgaaa aatactttac actaaagttg    540
```

```
atgctggaaa tgtaccgaca catactgaac tgttgtcagt ggttcgagtt ctttgtaata    600
atatggtatc gaaattgctg aatgagaaaa tgtaagtata ttataaacga gatccattaa    660
acaacgaaac atttaaggaa gaaagggttc aaatttcata tcaatcaatt caaataaaat    720
cgattgaaga atcagtgaat gaactctatg ctattcttga gaaatttgcg aaggaatctt    780
tagatgtatt tctgaagaaa ttcgaagtag agtctctaga ataatttcta ggatagtcct    840
tttagaatga taagttgaat tcttgaaaat atttagagta tctttttgat ccctgctcgg    900
tctttttttt cccattcggt tcatttttgg tctcttctat caagcataag gtctctacag    960
ttcctatttt aaaaagcagt catccgctac cagccttgaa aagattgaaa cacattttta   1020
ttaccttttt ctgatcctgt ttttaaagtt tatttatttt tgcattcatt tcagttatcc   1080
atcaactgaa gagaaaaaag cgttggcaaa gcgagttatt gaaacttttt ccatattggc   1140
ttccacaaaa ataacggaaa actctcccga ccatgtaagt atctaaacat tacattataa   1200
ttataatctt tgaggtgata atcgttgtag tacgatgtag tagattgtaa aacgacatga   1260
taactaataa tattcttttt ttcatttgat tttagtcata cttttttttgg agaaatggag   1320
gcaaaggacc aaatcatgaa cattcgggac tcattcatac tcacttacgg aacaaagcca   1380
aaaagcttaa ggccgaagac cgaaaataca ctcataagaa aaaagctgac aaagtcagca   1440
gcattccgac tggaatagtt gagctagctg aagaatgtgc tcacaaggaa gctacagtcg   1500
ccaatttcaa tacaatcgta aagttcatgg aaaaaacgca cactcttcac atcatgatgc   1560
tgcaagataa gaagccattc gatttcattc ttcaaacatt tccgcatttc aaatcatttg   1620
atggactttt ggtaagtatc ttcatatcta tgttttgaaa attatcttta atttttcatt   1680
ctacacctgc attacagaat caaaaagcat atcaatacag agtcagaatt aaggcgaatg   1740
tgaacactaa tacattgtca gtaaaatcgg tttgaagttc agcggatata atttcaattc   1800
tatattatgt ttccgatcga tttaatcgta tgatgc                             1836
```

<210> SEQ ID NO 158
<211> LENGTH: 1657
<212> TYPE: DNA
<213> ORGANISM: Aedes aegypti

<400> SEQUENCE: 158

```
acaaaggaca cgggatatac tacaatagat caaatattgg tcgcagtggt ttatgttccg     60
aacagaaaaa aaaggctctc atgggtcaat ttgtttccag gatgcatatt atctctgatt    120
cccttaccat gctaattcca aacatatcca cagctgtcag cccctggtga tttattatca    180
acaaaaataa ttaaagtcca attattttca cttttcagct cagaagttta ccaacgcttc    240
attggtctac ataactgaga cagttttaga ggaaatcgga ataattgaaa aaggcccgca    300
agtggtaatt ctaaccgtgg tagcaaaact gaaaaaagct catcatgaca gtacatcgga    360
tacaaaccct acccaagctg gaccatcacg aagattaact gagtctccga gtgaagctgt    420
aacaatccga caaaccctgg aacgagatgc tacttgttga aaaatacttt acactaaagt    480
tgatgctgga aatgtaccga cacatactga actgttgtca gtggttcgag ttctttgtaa    540
taatatggta tcgaaattgc tgaatgagaa aatgtaagta tattataaac gagatccatt    600
aaacaacgaa acatttaagg aagaaagggt tcaaatttca tatcaatcaa ttcaaataaa    660
atcgattgaa gaatcagtga atgaactcta tgctattctt gagaaatttg cgaaggaatc    720
tttagatgta tttctgaaga aattcgaagt agagtctcta gaataatttc taggatagtc    780
```

```
cttttagaat gataagttga attcttgaaa atatttagag tatctttttg atccctgctc    840
ggtctttttt ttcccattcg gttcattttt ggtctcttct atcaagcata aggtctctac    900
agttcctatt ttaaaaagca gtcatccgct accagccttg aaaagattga aacacatttt    960
tattaccttt ttctgatcct gtttttaaag tttatttatt tttgcattca tttcagttat   1020
ccatcaactg aagagaaaaa agcgttggca aagcgagtta ttgaaacttt ttccatattg   1080
gcttccacaa aaataacgga aaactctccc gaccattcat actttttttg gagaaatgga   1140
ggcaaaggac caaatcatga acattcggga ctcattcata ctcacttacg gaacaaagcc   1200
aaaaagctta aggccgaaga ccgaaaatac actcataaga aaaaagctga caaagtcagc   1260
agcattccga ctggaatagt tgagctagct gaagaatgtg ctcacaagga agctacagtc   1320
gccaatttca atacaatcgt aaagttcatg gaaaaaacgc acactcttca catcatgatg   1380
ctgcaagata agaagccatt cgatttcatt cttcaaacat ttccgcattt caaatcattt   1440
gatggacttt tggtaagtat cttcatatct atgttttgaa aattatcttt aatttttcat   1500
tctacacctg cattacagaa tcaaaaagca tatcaataca gagtcagaat taaggcgaat   1560
gtgaacacta atacattgtc agtaaaatcg gtttgaagtt cagcggatat aatttcaatt   1620
ctatattatg tttccgatcg atttaatcgt atgatgc                            1657
```

<210> SEQ ID NO 159
<211> LENGTH: 1272
<212> TYPE: DNA
<213> ORGANISM: Aedes aegypti

<400> SEQUENCE: 159

```
acaaaggaca cgggatatac tacaatagat caaatattgg tcgcagtggt ttatgttccg     60
aacagaaaaa aaaggctctc atgggtcaat ttgtttccag gatgcatatt atctctgatt    120
cccttaccat gctaattcca aacatatcca cagctgtcag cccctggtga tttattatca    180
acaaaaataa ttaaagtcca attattttca cttttcagct cagaagttta ccaacgcttc    240
attggtctac ataactgaga cagttttaga ggaaatcgga ataattgaaa aaggcccgca    300
agtggtaatt ctaaccgtgg tagcaaaact gaaaaaagct catcatgaca gtacatcgga    360
tacaaaccct acccaagctg gaccatcacg aagattaact gagtctccga gtgaagctgt    420
aacagtaagt taatagcata tgagactgca aagaaacgtt actatatctt gccctgcctt    480
agatccgaca aaccctggaa cgagatgcta cttgttgaaa aatactttac actaaagttg    540
atgctggaaa tgtaccgaca catactgaac tgttgtcagt ggttcgagtt ctttgtaata    600
atatggtatc gaaattgctg aatgagaaaa tttatccatc aactgaagag aaaaaagcgt    660
tggcaaagcg agttattgaa actttttcca tattggcttc cacaaaaata acggaaaact    720
ctcccgacca ttcatacttt ttttggagaa atggaggcaa aggaccaaat catgaacatt    780
cgggactcat tcatactcac ttacggaaca aagccaaaaa gcttaaggcc gaagaccgaa    840
aatacactca taagaaaaaa gctgacaaag tcagcagcat tccgactgga atagttgagc    900
tagctgaaga atgtgctcac aaggaagcta cagtcgccaa tttcaataca atcgtaaagt    960
tcatggaaaa aacgcacact cttcacatca tgatgctgca agataagaag ccattcgatt   1020
tcattcttca aacatttccg catttcaaat catttgatgg acttttggta agtatcttca   1080
tatctatgtt ttgaaaatta tctttaattt ttcattctac acctgcatta cagaatcaaa   1140
aagcatatca atacagagtc agaattaagg cgaatgtgaa cactaataca ttgtcagtaa   1200
aatcggtttg aagttcagcg gatataattt caattctata ttatgtttcc gatcgattta   1260
```

atcgtatgat gc 1272

<210> SEQ ID NO 160
<211> LENGTH: 1128
<212> TYPE: DNA
<213> ORGANISM: Aedes aegypti

<400> SEQUENCE: 160
aactacctat ttatgggtaa actgatctta gcgtgtacgg tccgtctacc ttgctacgac 60
catgtgtgtt atttttgtat aagcgtttga ccacaatgtt ttcgttagtg aaaaactctc 120
agcatttgga caaatcaata cagtactaaa acaacggcct aactgacaaa tgtaaacaaa 180
ctgtgtttta ttcaccaaac agtttatttg ataaattaca attatataat gcatatctgt 240
tccttaaaaa taacattttt cacgaaaaga gtgagaaaaa cataaagacg catttgatgt 300
tttgtttcga tacaaactct catgtcaatt tcgcacatct tctcctccag cggtaaccgg 360
gcgcatttga gattgagtgt ggcagcaggg cgcatttcaa actgagtgtg cagaagggcg 420
atattgataa aggttcgtgt gagagagcgt agcagaacgg cgaagctgct gaatgtcaaa 480
ccagaaggac gaggtcaaaa ggcgcactcg ctgttgtcaa actgaagaag acgaaaaacc 540
gaggggctca acagctctaa attttgatga acggcgcatg atggtttttt atttatttta 600
acgtgttatt cataatatgt aaataaatta aatgttttgc tacaaaagtg catcatgtga 660
taaaatcgat cggaaacata atatagaatt aaaattactt ccgctaaact tcaaaccgat 720
tttactgaga attcgcccta attatgactc tgtattgaaa tggttgtaaa gtccgtgtaa 780
tgctatttcg gggtcatcgt cgtctacggt tttttttttct ctcacagtag cgtgacagtt 840
aatgggtgaa aaaataccca ttttcgctag aagtacctcc acccatttaa tgagtaaacc 900
cggtttaccc agagaggtct acaagtgaac tgtcacgaac gccaacgcac gatcacaatc 960
ttacagaagt cgatttcctc caacccggga gcatcatgac agctgcagta caacgtcaat 1020
gtaccgaaaa attttggtcc gtggtactgt caaactcaat gaaatcatgg agtgtgctca 1080
aaatagggcg taaactagaa ttatgtttga tggacatata aaaaagtt 1128

<210> SEQ ID NO 161
<211> LENGTH: 949
<212> TYPE: DNA
<213> ORGANISM: Aedes aegypti

<400> SEQUENCE: 161
aactacctat ttatgggtaa actgatctta gcgtgtacgg tccgtctacc ttgctacgac 60
catgtgtgtt atttttgtat aagcgtttga ccacaatgtt ttcgttagtg aaaaactctc 120
agcatttgga caaatcaata cagtactaaa acaacggcct aactgacaaa tcggtaaccg 180
ggcgcatttg agattgagtg tggcagcagg gcgcatttca aactgagtgt gcagaagggc 240
gatattgata aaggttcgtg tgagagagcg tagcagaacg gcgaagctgc tgaatgtcaa 300
accagaagga cgaggtcaaa aggcgcactc gctgttgtca aactgaagaa gacgaaaaac 360
cgaggggctc aacagctcta aattttgatg aacggcgcat gatggttttt tatttatttt 420
aacgtgttat tcataatatg taaataaatt aaatgttttg ctacaaaagt gcatcatgtg 480
ataaaatcga tcggaaacat aatatagaat taaaattact tccgctaaac ttcaaaccga 540
ttttactgag aattcgccct aattatgact ctgtattgaa atggttgtaa agtccgtgta 600
atgctatttc ggggtcatcg tcgtctacgg tttttttttc tctcacagta gcgtgacagt 660

```
taatgggtga aaaaataccc attttcgcta gaagtacctc cacccattta atgagtaaac    720
ccggtttacc cagagaggtc tacaagtgaa ctgtcacgaa cgccaacgca cgatcacaat    780
cttacagaag tcgatttcct ccaacccggg agcatcatga cagctgcagt acaacgtcaa    840
tgtaccgaaa aattttggtc cgtggtactg tcaaactcaa tgaaatcatg gagtgtgctc    900
aaaatagggc gtaaactaga attatgtttg atggacatat aaaaaagtt                949

<210> SEQ ID NO 162
<211> LENGTH: 827
<212> TYPE: DNA
<213> ORGANISM: Aedes aegypti

<400> SEQUENCE: 162

tttattttca tattatgaac aacatgttta aataaataaa aaagcatcat gcgccattca     60
tcaaaattga ggattgttgc gcccctcggt tttcgtctc cttcagtttg acagccgcga    120
ttgcgccttt tgacctcgtc cttctgtttc gactacacgg agaaaagcga ttatactagt    180
tagcatgcat attattattt ttcaaacatt ttcctcattt aatcgttgcg atacttaaaa    240
aatattctct ggattatttt attttatact ttgtcatgca tttttctttt atatatttta    300
ccatgcatat gtagccaccc atgctactct ttggactttt gcaaaatcaa tctcgttctg    360
ttcggttact taattcatgc tattcaagta agtcgcgtcg cgttcattaa aaatatcata    420
atattcacga aaaggtgcct aaataccccg agtatgtttt catcctgttc agcagcatgt    480
gaaaactctt ggagacaaaa taacaaacca acctcaaata aaggaaatct tccgaagttc    540
cagcgtgtcg taaaactgta caaattacag ccgaaaaagc tgttgaaagg taagttggct    600
ggctataata tttaaaccat tcagtaaaag tgatatgaaa ccttttcagt tgattttgtg    660
cggaagaaac ccatcgcgat aatcgtgaag aaatcggaaa aaaatcggga cactattctg    720
gaactgaatt caccgagcat gatggatttt gcgagatcga agtggcattg cgcaggagac    780
cggatcagtc aatgtcggga agcaaaataa atttgaaaaa gcagctg                  827

<210> SEQ ID NO 163
<211> LENGTH: 767
<212> TYPE: DNA
<213> ORGANISM: Aedes aegypti

<400> SEQUENCE: 163

tttattttca tattatgaac aacatgttta aataaataaa aaagcatcat gcgccattca     60
tcaaaattga ggattgttgc gcccctcggt tttcgtctc cttcagtttg acagccgcga    120
ttgcgccttt tgacctcgtc cttctgtttc gactacacgg agaaaagcga ttatactagt    180
tagcatgcat attattattt ttcaaacatt ttcctcattt aatcgttgcg atacttaaaa    240
aatattctct ggattatttt attttatact ttgtcatgca tttttctttt atatatttta    300
ccatgcatat gtagccaccc atgctactct ttggactttt gcaaaatcaa tctcgttctg    360
ttcggttact taattcatgc tattcaagta agtcgcgtcg cgttcattaa aaatatcata    420
atattcacga aaaggtgcct aaataccccg agtatgtttt catcctgttc agcagcatgt    480
gaaaactctt ggagacaaaa taacaaacca acctcaaata aaggaaatct tccgaagttc    540
cagcgtgtcg taaaactgta caaattacag ccgaaaaagc tgttgaaagt tgattttgtg    600
cggaagaaac ccatcgcgat aatcgtgaag aaatcggaaa aaaatcggga cactattctg    660
gaactgaatt caccgagcat gatggatttt gcgagatcga agtggcattg cgcaggagac    720
cggatcagtc aatgtcggga agcaaaataa atttgaaaaa gcagctg                  767
```

<210> SEQ ID NO 164
<211> LENGTH: 32767
<212> TYPE: DNA
<213> ORGANISM: Aedes aegypti

<400> SEQUENCE: 164
tcctcgtggt gatagaatgt gacttatcag tgtgtcactg catgtctgtg ctatttgcgt 60
ttgatgttac gttccaaacc gcttgtgtac ataaaaaatt agtattagat atcgtcaatg 120
ctagagatcc agtatagatg cattgtgttg cagtttaaca aaacaagtct tttgactcat 180
cagccttttc tgaagtcatt gtcagtgaac cagccaagtt gattgtaata caatggaaag 240
gtaaatcatt ttctatattt tcgtcaatgt tgttcccata ttttaagtat tgtgcccaca 300
cagtttttac gtgagagaaa gaaccgtatc ttattcttgg cattttttcgt tcttattttt 360 ttaaaaccta ttgggctcat gtttcaactg ttgcttctca ttgcaatgtt tcaaatagtt 420
cagccaagaa agccctctat gccaatctga atcatggagg tacccaattt gatctgtata 480
tttaacaaaa aatattaatt tcaaaattcg ttgtatgcag taaactttaa cataatcgta 540
aattgcacgt aaaatttgat atacctctag aactatctaa aaagtgcgca tttcttcatg 600
cgctttgttt tgcggcgctc attttaaatc gtatactatc agagcccggg tacactagaa 660
taccgattgc gtgtctttgc ggaagtctct ggcaacttcc agacttcgct gacgaactta 720
actaaagcac acaaaacagg taaccgattg atgaatggga atcaatacaa tttattcttg 780
aagagtggtc ttggatgtga gtaaacggtc tgactagtta ccaataattg aacaaaactt 840
aagagccagt tcgcgagagc cgcaacccct tcttgtatcg atgttctccg actaggctga 900
aattttcagg gattgttctt ctatataaaa gaagatgttt cacaaaattt tagattttta 960
tattaggggg aagtgggaca aaatgacccc caatgatttc atgtcactaa acatgtaaaa 1020
tcacaaaaac tgatataact atagtaaaag tgtacggatt gtgttgaaat ttggcatgat 1080
tactctacgt tatataaact tttagattga catggtattt ggattttaaa agtacttcaa 1140
agcgagaaaa atgagttttt cataaatatt ttagtgattt tcaaatcgat ttttttctta 1200
ccaaccgaac taggtcaaaa atctaaatat gacgttttgt agggcaactc atgggctttc 1260
atttgaggtg taatccagat atgccgtttc aaaaaaattc gaaaaaaaat tttgtttcgg 1320
ggtagtgttt gaacttgagc cattttgcga gtaccgcaac cctcttgcat agagaggttg 1380
tattgatgtt cttcgatcga tctaaaattt acaggaattg ttttcctata taaaagaagt 1440
tatttcgcaa aacttcagat aataaccgct aatgatttaa tttgaaaaca aatattcaaa 1500
atgaattaaa ctgctatagc tatagtaaaa atgcacgaat ttgtatgaaa tttggcattt 1560
ttgctttacg ttacatgaac ttcaaaatga acatgatatt tggattgaaa aaaatgttaa 1620
aaatcgaaaa aaaaaactta attatttttt tatcaaatcg gcttatcttt tgtcaaccga 1680
actaggtcaa aaaacaatat atgtaaagtt ttgtagggct actcaaggac tcattggtgg 1740
tgtaccgtgg tgaatcaaaa tccggacggt accaatatcc ggacattttg ataatattta 1800
caaaaaaaaa tgctaaattg aaggttaata tgtttatttt aattctttac ttgttttaaa 1860
cgtgattact tattttacgc gcatttataa ttcagtaacc atttataaat aattaataaa 1920
aatgaaaaag ttactgcaga cgtggtgtat tttccgtggt gaacttgtat tagtgatagt 1980
gccaacgaat acacccacaa cgtttataca attattgaat gaaaaatatg ctttctatat 2040
agtgattgta acataataac atacaaagtt atagtttaaa agtttagtga caccacattg 2100

```
aaaaattatg atgtaaatac agtttaaaat agtaaaaaga ggctgtctgg aatggagcca   2160
aatatttttt aaatccggac attgtattgg aatcgtatgt ttagatgccg taagtacaca   2220
attttcaaat aaaactgaaa taatactttg atcattatca acacatgagt aatatgtaat   2280
aagaacaata ctgtgcgtcg ttcaatgcgg attcattgaa caaatcagtg atgattgcag   2340
tttaaaccac aaacatgtct gtccaaacaa ttaaatcaca aacattgctt tgtttttgta   2400
tttttaaacg aatacagaac acatgcattc tacaagttat taaaggcgtg atatatttag   2460
ttgattttga aaagctttgc atggttcaat tttacaattt tatgttgaaa taaagttgat   2520
cggattttga ttgttcgatt ttgaagtgtt cggatttata gcaatgacaa acagttaacc   2580
aagttacaat aagcacaatt tgtagcttgt caactatctc ataataatct atagtttttc   2640
aatatgtttt cattactatt caaagtggta cacattttgc agaagtacac ttttcataag   2700
ttaaaagtga atcaaaatga cccaatcaat taaaatacct aattttcgtg agaaaatgca   2760
atttactctt ttcgtgaaat ttgtgaacat caaggccggt aaaagtcaaa attctattca   2820
agatataaac agtacaatgt ctcataacag ccatatgtgc agtcagtcta aactaagctc   2880
aactcaatta tttacaaaat gatctctatc aaacaaacca tcatataagg tacacacata   2940
tgtggccctc ccaatcgaac ccatcaaaac attacccaaa ttaataaaat gtggtagttc   3000
attcccaacc aaacagcgtg agaagaaaca acgcttactg ccgaccgaaa gcattggtgc   3060
aatgccttat tgttatccac ataatcactt ttgcaaggaa atgacatttc tttcagatat   3120
ggcagcggca acacggtatg atataatcgg aggccttcac acgctcctta taccgtccgg   3180
attttttaaa tttttaata tttagttttt tgacctagtt cggttgacaa aatataagcc   3240
gatttgataa aaaaataatt ttgcaaagaa aaaaaggttt ttctcgattt gaaacatttt   3300
ttcaaaccca aataccataa tcattttgaa gtttatgtaa cgtaaagtaa acataccaaa   3360
tttcatacaa atccgtgcat ttttactata gctatagcag tttacttggt tttgtatata   3420
tttttatatt aaatcattag tggttatttt gtaccacttc cccctaatat aaaaaaattga  3480
atttttgcga aataacttct tttatatagg aaaacaactc ctgtaaattt cagctcgatc   3540
gaagaacatc aatacaacct ctctatgcaa gaaggttgcg ggaatggcaa aatagctcaa   3600
gttcatacac tacaccgaaa aaaaattttt tttcgaaaat ttttgaaacg gcatatctga   3660
attacacctc aaatgaaagc ccatgagttg ccctacaaaa cgtcatattt agatttttga   3720
cctagttcgg ttggtaagaa aaaaatcgat ttgaaaatca ctaaaatttt catgaaaaac   3780
tcattttttt agatttgaag tacttttaaa atccaaatac catgtcaatc tttaagttta   3840
tataacgtag agtaatcatg ccaaatttca acacaatccg tgcactttta ctatagttat   3900
atcagttttt gtgattttgc atgtttagtg acatgaaatc attggggatc attttgtccc   3960
acttccccct aatataaaaa tctaaaattt tgcaaaacat cttcctctat atagaagaac   4020
aatgcctgaa aatttcagcc tgatcggaaa aacttccctg gaaagggggt tgcggttctc   4080
gcgaactggc tcttaatgaa agtatacgaa tagaagtcgg agagtttcgc ggtcaattcc   4140
gtaaccttga acagtgttgg tggtttttag acttagtaat aaaacaccaa acaagaacga   4200
aacgtttatt gaaactaaac gagctaaaac taggatattt tttcaattta ttgctgcgat   4260
aaggagtgtt aacaaatttt atttcgagct ctcgaacaag tggaagtgtt tccatcatta   4320
ggattttaaa gttggttcag tggaagcacc agtttttagt ttcttttcaa attgtattct   4380
aagattttct taattgtaag agaagaaatg gcgatgtcca attttgcatc gtggaaccac   4440
gcgatgaatc ccggccatct gaccacagat gagctggagt acgagatgga aatccgtgat   4500
```

```
tttccgttgg atatctctcg tagcgctgcg gaacaaacat tgcgtagcca cctaaaagag   4560
gaaaaaagca aatcggacgt tagaatgaaa tttgtgagtg aatcggtagt tgatgagtta   4620
gaggtttgtg acgataaaca gaatgggata aaaaattacc aagaaaagcg ccagatcatt   4680
tgtagaaaac gaaattgatt catacatttt tgcagtgatt gcaagctcac actaaggaag   4740
aagacgaatt gaatagcctc gagttgattg ctggcgaatg tgcaaaattt ctcaacgtgt   4800
attattcacc cacctcccac cttctagaag ttcgagaggc tgaattggtg attttaaacg   4860
aaagtttgaa tcaaattagg caagagctag taccgagtga tggtagccaa cctgagaaga   4920
cgacggatag tgagaaagag agatagcatt agagatccga cagctaacgg cgctagtgag   4980
ccaactttg tcggcgcgat aaaaagttag aaaaggttcc tcgccgaagt tggatttttc   5040
ttagaagcta tgcgagatac atataagtta tcacttcgga tgtggtgcat tcgattcgca   5100
tctggatgcg ctcgaatgcg tcctacttcc gaagtagggt ttcttgcatg gatttcgaga   5160
aaaatcttac ttcgacgaaa ttaattttct aacaattggc ctaacttaca atacagtaac   5220
gcatcacggt acttgctcat caaaatgttg ctgaaccgct gaatcttcat acaggtgcag   5280
ccaatagtac tcagattgag atgaatatgg tggtagagaa agaggtacct agaagaggtt   5340
cagggaaagt ctgtagattg tttaggctgg ttgaaacaga ggaataagtc gttagatacg   5400
ctgaaaaatt cggatgaaga ctagcacgtc ggtagcaagg tgaatggaag aaccgaaagg   5460
agagttgaaa atagcaggtc tttgagtatt ggaaataaat ttccgattca taaatggtca   5520
gtgagatatg acgaaatgaa taatggaagg cgattgaatg aattcttgaa agaggtggaa   5580
ttcaacgccc ggtctgattt ttttttctga attggagatg ttgtagggag ccatctgttt   5640
aaaaaaagag gaggtcctgg ttcataaata tcagtggaga gatagcgtca tggagcgagt   5700
tagttaggga gctcaagaaa gagttcttac cagtcgatat agactatgtc tatgatcggc   5760
aggctaataa ccgaaagcag ggtctctggg agaaattcca ggctttgaca ttaggccggg   5820
acaattttgg caaattttcg aaatcgaaaa agcacataat cacaaatggt agcaaataag   5880
cccaaacgaa accctgcaaa atttaaaaat tctaaaaaat cgtttagcta ctcggcaagc   5940
gacttgaagt ttagtatggg gaaatgattt attcagtagg atgccggtgc catatgtgga   6000
ctacctaagc tataaaaaat cataacaaaa caacggaaag ccttaacaaa gatcttttga   6060
cgtcaacaga aagatttcaa cctctactat ataggaaaaa tatgaaaaga gtgataaaac   6120
tatttttta acatgaaatc gcttgagcca ctattggtac acgtgctcca gtagttgcgc   6180
tagtgctcct gaaactcgct agctcaatga aaataagatc agggtcgttt ttccaattgg   6240
aacgaagttc ccttttccct acactctctc tcaaaacgtc attcatttat caatggaaca   6300
cgagcaaacg gatcacttgt tcacagtggg ggaatgcaaa ctccaaaatt tgtacttacc   6360
aagtatttca actatttctc tcaaaggctg ttcgaaaact caacttttcg ccaaatcaaa   6420
ggaagacgag gattgattgc tcccttttga gcacggggaa acgaaatcaa caaaatatag   6480
cttattacct caaggatgcg cctcttaaga aaaacagcga ccaccttttc aacttaatac   6540
attattggtt ttatttgccc aatagggccc tatctgacgt cacaatttct aagggagtac   6600
ttgccgaggg catcgtcatg cctgggtgcg gatcctggtc gctttgatgc atgcagaggt   6660
ggttgcaggg tgggttgacg ggatgtggtg tcttgtgggt gcctagcagg tgagcggatg   6720
ctccgacgct gctatcctag caaaatggcc gccggtgccg caacgttgat gaatggtgcg   6780
gattacgacg gtctagcggg ggagctgcta ctccgaaagt tgacaaacgg gccggcggga   6840
```

-continued

```
cacaagcgtt gatgaacggg atggcttaca gagggcgtcg gttcaaagcg gcgatattgc   6900
agtcacaggt ctgggaatca cggtattgcg gctcaacgat ggagtcttgt ggggcacggc   6960
cttcaattgt ctggatgccg tagaaaatgg ccgacactaa tactcctatc ggatggctgg   7020
aaacttttct gccgaacttc taacgggtcg gacgaccaca atggctagtg gttttccaat   7080
cgagtgcgca aaatagccaa ccttgatgac accggagatt cctgcggaaa tacccggaac   7140
tagttccgga atgatgaaaa agaaaaaggc ccttgataag gacctttttc cgattttgct   7200
gatcacaata aagattttag cacaatagca attcttcaca atagcgaact cgatttttga   7260
cgtacgtact attttcttcg ccgtactatt ttaactgccg tactattttt aggttttaac   7320
tttttagcac ctaggaattt tcctggagaa aatttagaat ttatcacgcc gcgcactact   7380
atttcgtcca atggttcgaa cagaaaagat ggtttttcga tgtccgccga gtagttttaa   7440
tctaattgtt gaacatacgg agggcaaact tcgtaccaaa tccgaagttt gacattttaa   7500
atacctccta ccttggggtt gtagtatctt gataatttac ataacgaccc ctatgagtga   7560
ttttttctg cgtgtagtga gcaagcgttc gcttcgctac gcgtaagccg ctgacaacaa   7620
actagtgagt tagagatgga atgttgggga aattagaacg tgagtgttcc acctgtcgga   7680
ttgacccgtg agagctgcca ctcacttctt ctcaaatagg atacacggaa aactctacta   7740
atatttttc tttgtgctgg aggcaacaaa taggaatatt gtgaccaccg gttacactcc   7800
agtagtaggc gttcgggaat gatacaaggc attttaaaca aaatggtaaa tttttacata   7860
ggttcaacat ttttccctcg gaatatcaat taatatcttt cgaatgaagc ataaaggtca   7920
tctctagggc tttttttaa tttttataca tccattttaa aaactgcttc catccgttga   7980
tcaactactg gaatacgacg gcaactgttg gtgcaaggga gcattttttt gcgtaaactt   8040
atttatttat atgacttttt gataaaataa aaagctaaaa tttggcaaat cgactaaact   8100
agagacgatc tatttaccaa taatagcaca cgttgttttt atcgaaaaat gttcgtttta   8160
ttccatagtc caatctactg gtacattaca attattggta ccggcaccct aataaaaaaa   8220
tctctcccta gctgataatt taggccatga aacagtgaac atttcgttag aagacatctt   8280
tctagtacag taattcccaa agtgggcgaa ttcgcccccc tgggggcgat tttcaggctc   8340
aagggggcga aaatttgtaa aacagaattt gggggcgaa aaattcagaa agggggcgaa   8400
aaggggagca cggaagcatt taaaaataat tactgataat ttttttagga cacacatctg   8460
aaggttaatc aattccaaac ttaacaaatt cgaggaatat tttaccttat atcgatatac   8520
atgtcggact cgattattcg gagtatcgat ttttttcac tccgaataat cgaatcacta   8580
agaaaaaaaa aatgaaatct ttgacaaaaa aactgaaata ttgtcttttt tcgtcatttt   8640
atttatatga ggcggtggcg tagccagaaa ttttttctag gaagagcagg atctttgtac   8700
aagaaaaaaa atttgatcgg catacataaa accacttttt caaacccccc ttttcttaaa   8760
tacgttataa actgctaaac cattcatatt gtatattgca atatcaaatt atttcaaatt   8820
tatgcataca aattgaaaaa caagaacatc aaaaacaaat tccggataat cgagtctaaa   8880
attccggata atcgaatccc ggataatcga gtccccggat aatcgaatct ccgcataatc   8940
gagtctgacc tttatctcca atcagggtta ttttaaaatt atgatagact tcacttgata   9000
attgtcaaat acatgtattc aggtttttaa tatcatgtga gttttaagaa tggtcggtat   9060
ttaagatttt cacaagattg gatgattagt aacagataac atttaaaaca caacatatgt   9120
tgaatgtaca agaattttta gtacttttta tggcaattcc caatattata tatggatttt   9180
tttatgtggg aactttgagg ttaggaagct aatatgtctt tcattggcat ccagcttttt   9240
```

```
acagaaaaaa aggagattcg gttgcactct ttcttataat tcttatggta caaatcattt    9300
tagagacaaa tttttctggt gttagaaaaa atactctttt ttatattaca ttggaatatg    9360
agttaaaaaa cattctggat tttcatatat ttgttcagtt tttttttgga ttgaatgaaa    9420
acaatcgttc cctgaaacgt caaacattta ttatttacaa tttctgaaaa ttattggagt    9480
aatattatga acaaatgata aatcagtata ataatcccca actacgtcaa ctacggcgcc    9540
tatgcattta ttatattcaa atagtttaaa ctgggctaag cttgtatcaa aaactaattc    9600
agtagcctgt aatgcacgca aaatactgtt aaaattgcta ttataaattt cagcctagtg    9660
catcattcct aataatttg ggatatcgat atttaagaga atatttttaa atgtgcataa    9720
tagtttttgt accatgattc tgcagatatg cgagtcaaag acatgtgttg acgtacagca    9780
ccaaattaca taaaatattg aaatcacata tcagggggc gattccagat aaatgttggc    9840
ctcaagggag cgaaagttga aaaagtttgg gaagcactat ctagtagctc ttcaaataaa    9900
cgagttataa atttggaagc actgggaatt gtatacgact gttttgtcat tttttaatct    9960
ggcatcacgg tgcattttat gtaggaaaca gagaatttgt ttattgtgct ttgctttgat   10020
aaatggatta ttgggaaagt tgtgtatcgc acttcgaagg tcaccaagca gtggttccaa   10080
tatgtttcta agcaaatgga aaattcttca aatgtacatt tacgcgacaa attacactgg   10140
ttttgctatg caaatgcaga tttgcacttg actgcatcat tgccacaatt aattataatc   10200
gaacaagcct atttcaatgg ctgactttta caaatgtttt acaagcaagt tttcgtgaaa   10260
caaatgaaac aaacaaacta gcaaccctgc tgagagcaca tgcttttgat aaaacgtaaa   10320
caattttcgt tggcgcgaaa ccgataggcc ttttcatgtg acaggtccgt ctatgcattt   10380
gtttacatcg gtggaggacc ggtgcataca cgaggctgtc attttcatag aagaactgtc   10440
aaagagcttc ccgatcagct gttttggaac gtcatgtgaa taggcctatt cactgccttt   10500
tcttgccccg ccaacggcga aaacaaaggg tttgacgttt ccgcacttat gaacccgccc   10560
gcacttctga agtgcggggt ccaataagga gggaactgcg caatatatat atagagaagc   10620
gcggattctg aaaccaaagg ttccaattga accgtcaaac gtggttccaa tcgagcaaat   10680
tcaatgagaa tcaaagagat gttacgcaaa agagacgatg gatgtgtgtt agtgaaaagc   10740
gatacgaaag tgacgtcatt gataagcttg gtttcttatg gcgactgaca ggatgacacg   10800
ccacactaaa atgttgtttg aatgacctca attgttgata gtcattgcaa atattgttta   10860
taacaaagtc aaaatcctct ccgcgtttct ctagtataat catatctctg gtaggaaagt   10920
gggtggcaaa gccgtcttcc gcatcaccga cttctggatg gaggggccaa gtagttgtta   10980
aaactggttt tacttcaatg ttaaaatatt cttgtgattt tcactagata gaggaacggt   11040
ccatgtaacc acaagtatta aggtattacc gtattttaac tttaattcaa cgagtgcaat   11100
gcatcattgc ttttattctg caatttgcgt gcagtaatgc tttaattcca ttttatgaat   11160
acaatgtagc atcgatttaa ttcatcaatg aaatgtgcat taataggtga tatacggtca   11220
ccattcaatg cttaattgca tcatcttact caatgcttca tcgcaacaaa aacggcaaga   11280
ttgcaatgct ctatttatcg tcaatccttc cttcactcag gcaaataacc tatagaaata   11340
cttaaatatc gcttatgaaa attcgtcaca agaaatcggg ttgaaattcg tagatttgtc   11400
ttatgagaaa ccagaatttg aaaaaaaaaa gcatctactt ggtattgaac caaaaacctt   11460
acgattgata ggtccgtgca tacactacac gcctatcgac gactcaatgt gccgagatgc   11520
taaacggtat acataaaacg tgaagatgag caacttttta gccccacaca ctgaaaacaa   11580
```

-continued

```
aacataatct caacagcaaa aaagcgacag ccgcggtaaa cttagaagtg caacagtcca  11640
cggtaaaaaa tcagcacgtt cgatggaatg gattgatcac ttgactcaat tcaaaaaacc  11700
tatcaccatg atttgaagag ttttaacttt ggatgtgctc tactgtctta gcactggact  11760
ctaaagtgaa aagtttttga ttttgaacac catgtctttt gtatgaaagc aatcattgac  11820
agctcgttgt agaaagtgat tgacatcaat tcgattccat tcaacagatg cgatttgttg  11880
tcgaggttag atacaagact tgcactccga agattgaagg tacaaatcta agtcaggctg  11940
aaacgtttat aaaacttttt tttattttca aatcaaaact tgcaaacgtt gaattcaagt  12000
gctgttactt gatattgtca agatttaaca gtagtgcaaa tccaagtgca gaactattga  12060
tggcatcgtg cttattttta ccgtgtcgtg tccataccaa cttattgcgc acttcacccc  12120
aaattggact atcacaaatt tgtggagtgc agaaatgtgt gataagggtg cacgcttgca  12180
tcggattatc tcaatgtatt cggtgcactt gttctttgaa ccacaaggaa taagtgcact  12240
aaaaacacca tcatgattcg acgtaaccct gagctgctat cacactttga gggagcttac  12300
acacttgggg cttggagtga aatcgacaat atttatcact ggcaacgaaa gggcgctgct  12360
tgaagttgca caattttccc ggccaagaca tgcggcattt atggtccgga ggataggcgc  12420
ggcgagtcat cgaaaacatc tcaaaaaatt tggggctatt gctgttctta tttttttctt  12480
gaaagttcag ttaattttac gtttactgtc aaattttcag cgatgtatgt ttttagtttt  12540
ttgagatttt ttttttgaa aataaaaaat cagtcatttt tcatcggcac acctgtaggt  12600
ctcggtgcaa tagatttttt atttaaaaaa aaaccataac ttttgaacag cttaaccgat  12660
ttccaatctt ttttttata gaatgaaagc ttaagatttc aacttttcag acaatatcga  12720
aaaatctgct atcgacttga atttttattt acaagcaaat atgtttattg aacaggattt  12780
agagtagttt catgggtaaa ataaatactg aatgaaatca gaataactat atcaactcaa  12840
acaactttac ttctacaatc aattttttgt tcctaatatt aaaatattgt ggctttgaat  12900
atttatttac aagcataaat atttattgaa ctaggtctcg cgtagttttt taagtaaagt  12960
aaaatttgag tgtaataaaa aaatgtatta ctccccaaac atatctacca tcagtgcacc  13020
agtttcctgg tttccgctca ctagtataaa aattgatttt cgtgtcaaag accaacattt  13080
ttcggtcatc tgacattatt ttcatatgat aaaacacaag aaaaacacaa gacctcgggg  13140
gtggttattg gaccactagt aatatttgta tgttacaata accgctcatg caaaaaaata  13200
acaaaatttt aaagaaatgt cgaatttagt atacagcctt ctttctttct tgacaacaaa  13260
aaatatcagg ataaataaca attcgaaata atgcattttt tagcagttcg ggcacgaaat  13320
ctgttaccgt gagcggaaat aggaaacata gatgcagtaa tcaacgaaaa taaaatattt  13380
ttcatggaag tttttcaaat tctttttat ttcgcccgtt gattgtctat acttggagct  13440
ccattgccat aaaaaatagt attgatcgac gcaatagtta ctttataata aacatttgaa  13500
cacataactt ccttaaatga gtgaaatctg gtgcactgat ggtaacacga cttctaaaat  13560
caattttgtg ttgtaaaaca gcatactatc gatttgaata tttatttaca agcagatatg  13620
tttattaaac aagggtttac gtagtctctt gggtataaac aattaagttg taatcgaaat  13680
gtctatttct actcaaacgt gtaaccctaa cttctatatt atgaaaattt attggctttt  13740
atcggtgaat gcaatactgt actcagagtg aaagggagta acgaaagtaa tgaaatgaca  13800
agatggatag aatcgcaagc gagcgacgag agaaatgaat agaagttgaa aatttgtttt  13860
taacagaggg ccatatgtgt gaacaacaca atcgaaacga caaatcgttg cctaacgtcc  13920
tggtcttgaa cggctagatg tgtgttggtc actactaaca ctagacaggc aaaaaatttg  13980
```

```
tcgcctcgac ctgttaacta tattgttcgg cgtatataac agttctatcg atcgttggca  14040
tattttcgga gattgatacg aaatgacgtt acttattgga tttttcgcgt ctaatctcgc  14100
atacccctaa tttgcccaag tgatcctatt cgaactgacg ttaaatttct ttgccaaatt  14160
gattctacat ttataaggtt taatcaccgc atgactttaa tattatgaaa atttttggct  14220
tttatcggtg aatgcaatac ttactcagag tgaaagggag taacgaaaat aatgaaatga  14280
caagatggat agaatcgcaa gcgagcgacg agagaaatga atagaagttg aaaatttttt  14340
ttaacagagg gccatatgtg tgaacaacac aatcgaaacg acaaatcgtt gcctaacgtc  14400
ctggtcttga acggctagat gttgtagtgt tggtcactac taacactaga caggcaaaaa  14460
atttgtcgcc tcgacctgtt aactatattg ttcggcgtat ataacagttc tatcgatcgt  14520
tggcatattt tcggagattg atacgaatga cgttacttat tggatttttc gttcgcgtca  14580
attaatctcg gcataacccc ctaatttgcc caagtgatcc taattctatt aaatacgttt  14640
ttgcctgtca gtgtttagta tgaccaacac tacaacatct atcgttcaag accaggacgt  14700
tataacgatt ggtttcgatt gtgttgtgtt tcacatatgg ccctctgtta aaaacaattt  14760
tcaacttcta ttcatttctc tcgtcgctcg cttgcgattc tatccattgt catttcatta  14820
ctttcgttac tccctttcac tctgagtaca gtattgcatt caccgataaa agccaataaa  14880
ttttcataat attaaagtca tgcggtgatt ataccttata aatgtagaac cctaacttct  14940
atacacgcta gtttggaagt actcattaat gggtaaaata atacccattt ccaagttaag  15000
tggtttaact cagagaatat gattatacta gagaaacgcg gagaggattt tgactttgtt  15060
tataaacaat atttgcaatg actatcaata attgaggtca ttcaaacaat attttagtgt  15120
acgtgtcatc ctgtcaatcg ccataagaaa accaagctta tcaatgacgt cactttcgta  15180
tcgcttttca ctaatacaca tccatcgtct cttttgcgta acgtctcttt gagtctcatt  15240
gaatttgctc gattgggacc acgtttgacg gttcaattgg aacctttggt ttcagaatcc  15300
gcgcttctct atataaacaa attctctggt ttaactcatt taatgagtaa agtcgattta  15360
ctcattaaag ggtaagtgcc ttgaacttca aaacatgggt atttatcact cttgattttt  15420
attatggaaa tgggtaaaaa accctcatta tttcgaaaac ttttttgtag attgaggtta  15480
tgatggattt cctcagtaag attttcactg aaatacactg ttttaatgta ggaaataagg  15540
cgactgttct ctacaggtag taacggataa ctgtttattc aactcatgag actactacga  15600
ttaatactat aacatctcct cctccatgat tgttagcggt aattgaaaaa atctcttagt  15660
ctatttctta acggatatcg ggtactgaac gatgtatctt ctataacaga tggttcatct  15720
ggatgatgtt gcttcctctg aagtaggtgt tttcttcttc tgtaaaggtc tcttcatctg  15780
tttcgtgaga atttcttaat gcaggttcaa cgatttcttc tacattttgc gataccgtag  15840
atgtaccatt ccttgtttca tcacgtgtgt cgttattttg atttgcacta caatcattat  15900
catttccatt caagtcctca gcactaccat ggagttcgct ttcattgttt tgttctgaac  15960
taatcacgat ttcttcctgt tcatcgactg gcacgggcat ggttgttgga taatctttgt  16020
ttgatggttg ttgtggttca tcgaaaatat aatcgaatat ttcgtttcgt ttttgatgtg  16080
aatgtggtaa tctatcatgg acatcgaaat tttgctcgat cggaacgtgg ttctgcctca  16140
cttgatatag tatttcttgc aggcctaatg aaaatacgat tatagactcg gttatcgtct  16200
gtaactatcc aatatgatct gtcgtctcgt cggtataatt attctacagt ttgtccattt  16260
aatgttttgt tggatatatt ttcacataaa ctctttcatc attttcaaat ctctcagatt  16320
```

```
aacagtgcct ttgtcgtaat gttctgctgt tttcgatctt ctttctgcta tttttgcgct  16380
tacgttctct tctatttttg gcttcaatgt tgatgaatcg ttggaaggtg agttcttgtt  16440
cgtctagcaa ataatcgttg agttgggcta ctgtcaattt tatttggcgt gtttctccac  16500
atcaatagag cttcatagaa atccgtctcg ctatcttcac atttcttcaa caaatttttt  16560
acatattttt acggctgatt cgtcgtagta gtctcatgag ttgaataaac agttatccgt  16620
tactacctgt agagaacagt cgccttattt aagtccacgg gatcaatgca gagtctcagt  16680
ttgtcattgc gtcgtactat aagaatgtta ctagtccact ctgaatattc atttaccttt  16740
gcaataacac ccatattttc catctcatcc agctgctttt tcatctcagc tcgcaatttt  16800
tgaggaactc gtcttggaat ttgctgtttg ggtggaactg atttatcgat ttctaagctg  16860
acttctcctt ctacacaacc taagccatca aatacgtccg gaaattcagc gattatttgt  16920
tctgctccgc ttttattcga gaatatcgtg ttgatagctt ccttgtttac agtgatgaat  16980
ccgaatttca aacatgtttg taacgataat aacggaagat actccttgta ttcacctccc  17040
accacttcga acatcagcgt tgactcttga ccatcttgaa taactgtgag ttcacatcga  17100
ccttctggta ttattacacc tccaccataa actctaagct ttgtcgttgt agttttcagt  17160
tctttcctag ctgcgattct ggtaaaacag gatattccca tcaacattac aggacgctcc  17220
agtatctagt tggcatttaa ctttctcaca cttatcgcca gtggacgaaa gaataacgaa  17280
gcgtgtagct gggttggtga ttcatttcgg actgcgagga tgttctcata actttctttc  17340
gatcagtttt acttcattat ttgattgttt cgatctgcat acgctagcaa agtggttcat  17400
caatccgcat tgaaggcatt tcttcccatt cgctggacat tttctctttt tctcttgcgt  17460
gttcgtatcc acagtaattg catttagatt tgttgtacga tgcggtatag tttgatcttc  17520
ttcctttgtt ctggacttta tcgacatgtg cttcaattga catcttggaa tcggaattga  17580
gttgtttcat ctgtttttct gtaagttcag ctgcgcgaca tttttgtatt gcttcgttca  17640
acgtaatttc ttggttctcc caaagacgtt gacgcaggct cacgtctctt acagacacca  17700
cgattctgtc caacaatagt tcatcttgca tatctccgta ttgacaattc ttgatcagcc  17760
ctcgcaaacg atgtatatat tgatctatat tttcttcttg ttcttgaacg gcgctgttga  17820
aaatagctct ctcgtaacgc ttatttatct tcgggagtag atgtgcttct aaagcagaca  17880
atattgtttc acaagattgg ttgtcttcaa acacctaacg gtaagttctg ataaagcttc  17940
aaacaatctt ttccaatgca cgacagaagg gttgcaattt gttgtttcat gggcctggtt  18000
gaaaggttgc ttgcaataca gtaatattcc catgatgatt tgaaagaact tgacgctttg  18060
gcaaatatct ccatgaatgt caatggcctc aggtgtaggg atattttggg ctcgaaagga  18120
atattgcagg ggcctctgga atgccagcgc ttgttaccgt ggaccatttc cgcgctcctt  18180
aattttcccg caaagcagtt tgcaattcga taatttgcaa tttcagctct tccatttttt  18240
ctgttattcc tgttgctatg gatctgacac catgttttaa tgtaggaaat aaggcgactg  18300
ttctctacag gtagtaacgg ataactgttt attcaactca tgagactact acgattaata  18360
ctataacata caccttcaag ttggtccgag ccaactcctc catacattca attcggaata  18420
gaaacttcag caaagcgcag atgccggatc gtttgtgacg atctaataga gaagttgttt  18480
tcaatccaat catcctcagg gacgtccaaa tcgctgcagc tgcaagataa atgtaacaaa  18540
aatgatttta atcagctaaa agaaaccaaa ctaataaatc gactttttac ttgcttcgaa  18600
aggcaacaat ggttatatta tcccaaacaa ccatgcgtac tatttaccca cttttatcag  18660
cagaacaaat acttcgaaat gaggttttag taccctttt atgtcatcgg aaaataccct  18720
```

```
ttatttgaca acttagtact gatcataaaa atgggtacaa gaaactcatt taaagggtac  18780
tttcaagtta gcgtgtaagc aaattataat caaaaaaagc caggagcgtt ttggatttcg  18840
atttacaggt aaacaagctc atgccatttt cgtagttctt aggttaaata aatttgaagt  18900
gttatcagaa atgtctgttt cttctcaaac atgtccactt aacttctata tgcaagttca  18960
tgccgaaaaa actaattgtc atttctttgg atttcgattt acatgcagac atacacggag  19020
ccgcaaatca acccaacttt gacttctttt gacgcaattc ggctcttccg tgggataacc  19080
caaataactg atatatacct atcattaggt tgttttctga agaagtaggc cttgctgagc  19140
aagccatgag attctgacaa gcgctagtgg agttcattac gaaccaagcc ttcaaactgt  19200
atagaccatt ctctcctaat aaacgttctt tagttgtttg agattgagtc tttctattgg  19260
cccatccgcc cagtccttaa tattacaata ggttatgggc tcgtcaaagg aaggaatccc  19320
gcagctgacg gaccgaatta cgagaattgg cgcttccgag tcaagcttca catggatgca  19380
gtggaagtat cgtccgtgtt gtcggaacca gctccgggtg taggcgatgc aggtcgtgca  19440
aaatgggagc aaacggacag gaaggctaaa tcggtgctgg tgggattcgt ggcggatgaa  19500
attcttgaag ttgtccggga aaaggaaacg gcgtctgaaa tgtggaaggc tctggaagaa  19560
acctttgcga agcggtcagt ttcaagccaa acgttgctga ggaaaacaat tggcccgttt  19620
acgtaagatg gagggaactt caatgcgagc tcatttcaat gtattcgatg accttgtccg  19680
gcaactcaag tccgcaggag ccaaactgga ggaaggtgat ttggtatgtc aattattctt  19740
aaccctgccc gatagttatg accccttggt gacggcactc gagaatctgg cggagaagga  19800
cctgaagcta gagacagtca agcagcggct gctggctgaa gaaagcaagc gtgaagaccg  19860
tctggatgac tcgagtgaag acaacggggc agcgttcatt ggtggcaaga agaagaacca  19920
gaagaagttt actggcaagt gtcatcggtg tggaaaactt ggccacatga agaaggactg  19980
tcggtcaaag aagcagaaag gtaacgcaaa tgcagcagtc ggcagtaagg cggtcgcctt  20040
catggcaaac ggtgaccaga cgaagtctga agcagggaag atccacttct gcgtagactc  20100
gggatgcagt gatcatctcg tgaatgatgc aaaacatctg cgatccatgc ggaaattgaa  20160
ggatcccttc gtaatcgatg tagccaagaa tgatgtggca ctcgtcggga agttcgcagg  20220
agatataaaa ggtatgtcca acaaaggaat tgaatttcag ataaaaaatg ttgtgctcct  20280
gccggatctc cgagaaaacc tgctctcggt gagaagctct cgcatgctgg aatcgatgtt  20340
ctattactgg tcgtggaggt caagaccgtg cggagttcaa gaaaaatgga gaactcattg  20400
gcgtggcata ccttcgcgga aacttgtaca actggaattg gatgtcggat ctgtagccaa  20460
tatcagcgtg gctggatgag caagttgtgg catcgtcgta tgggacatgc aagtcaacaa  20520
gcattgaaca ctctcgttaa gcatgaaatg gccacggggt ttacgaagaa gcttgaaacg  20580
attggttttt acgatacatg cgtgatggcc aagcagtgcc gggaatcatt cgatggtgtt  20640
cgagaacgtg ccacacgtcc actggaacga gttcattcag acgtgtgtgg ccctattgat  20700
ccaccggcct gggacggatc gcggtacttc gtatcgttca tagacgactg gacgcatttt  20760
gctgtaatct atccaataaa gcgcaaagtc tgaggtatac cgatgtttta aggagtatga  20820
agcgatggct acaactcaat ggcagacaag aatatgcaag tttactgtgg accaaggccg  20880
ggaattcttt tccaacgaac aaagaagcta ctacaagaag cgaggcattc agggacaacc  20940
cacagtagct tattccctca acaaaatgga gtagctgaac ggttcaaccg aactttggtg  21000
gagaaggtaa gatcaatgct cattgattca aaagctccga agaaccagtg gtcagaagcg  21060
```

```
gcactgactg cgacgtacct cctgaaccgt tgtccgacgg tggcagtgcc tgaaaaagtt  21120
accccggcag aaagatggac gaatgcaaaa ccggaccttg acaagataag gattttcgga  21180
tgtaaggcca tggcgtggat cccgagccaa caaaggaaga aatggacccc aaaagccgtg  21240
agacggtgat gattggatac gctccaaacg gataccggct ttgggacaga gcgtcaagaa  21300
aaataataat agcgagagac gtgaagttca acgacgaatg ttttccatac gcagagcaaa  21360
ctgatgaatc aagtcaagtt ccgttggtag tccccacgct atacgagcca gagggggagc  21420
tgtttgaata atcctggtga agaggaacca catgctgatg ttgtcgatca tgaatctgat  21480
gaagaaacca tatttgaaga agttgaagag gaagcaaatc ctggggcgct cccttcgcaa  21540
catagaggtg acggctgttc agagtcaaac accaggcgca gcgaacggga gcgcaggctc  21600
ccaggtaagt ttttcgattt tttaactgga ttcagagcaa tctctgctgc tgacaattcc  21660
gattcttcag atccgccgtc ctcctatgaa gagatcgatg gacgcaacga tcgagactgt  21720
tggttggcgg ctgtccgtga cgagctgcgt tcgatggata ccaaccatgt gtggcgacta  21780
gtgaagcgac cctccggagt gaaaccattg cagccaaaat gggtattctg cgttaaagaa  21840
gatgctgatg gaaatgtcgt taggcataag gcaagattgg tcgtaaaggg cttccttcaa  21900
aaatctggca tcgattatca agaaacctat gcgccggtag ccaaactgac gacgattcga  21960
gtggcattag ctgtggcgct gcaaagaggc atggttatac accaaatgga tgtgcagacg  22020
gccttcctgc atggtgagct gcaagagact atttatatgg caatacccga aggcgtcgaa  22080
gcggatgctg aaacagtctg cctgttgaaa aaatcattat atggtctgaa acaagctccg  22140
aagtgctgga acgagaaatt gaatcaggta ctattgaagc ttgggttcaa gagatcgaag  22200
catgactatt gtgtatatac ccgcatcgac gagaggggga acgatgatgt ctacattgtc  22260
atatacgtcg atgatttgct aatcatggga gtacaacggc aaaacggtgg acgatatcaa  22320
aaaagaagtt atcccagttc ttcaagatga ccgattgtgg tgagttacaa cacttccttg  22380
ggatgaagat cgtctatgac cgagtattgg gaacaatgtg tctttttttt ttttttgtaa  22440
aatttggttt tattcgtcag tttatttgat tttgtttaca atttaaaatt ctagatctaa  22500
gtgaaaattg agttcattta catcaattct tccattacac tcgttaacaa agcagatgta  22560
ttttacgaac aatttcaaaa tttctaagcg tctagttcta tttattcctg tcaaggcagg  22620
tctcaccagg tcctcgaaag atagccgcct ccaaccattc attacgactg ccagccctct  22680
gctgcaggac cgtccaagcc gggccgacac gagcacagtc gcaaaatttg tgctgaagcg  22740
tttcagcttg ttgtccatcg caatgtgtac agaactcgct gtctgatctc cgcatcacga  22800
agaggagttt tagatgctcc aactttccat tcaccaaaat gtagagcttg gatcgctcca  22860
gcgaagagag ctttttgtct tgaatattgc gccacgcacg tggccagtca atcactgggt  22920
tgcttatttc caccttgggc agatctgtct gcgtgacgaa atgccgatgg atgagatcgg  22980
cggaggggtt ttcttggata tggggtggaa tgtgggaata gttcggaagg attattttaa  23040
ggtcgggatg gtctatggag attgctgggc agggattatc gtggaataga agggatttat  23100
aataaggaag ggaatcgatc tccttgagat gacgattgat tgcaagcgat ttcgccttca  23160
acgcaggcaa gtgcaaattg agtccgccgt gctccttgct tcgcgcaagc tgcatcatcg  23220
ggacgcgggc gggcattcct ctccacaaga acgtgcccat cgtggaggtc actttcgcgt  23280
gtgtacgcct aaaggaggta acaccgacga aacataccat aacttgctgg tgccgaacgt  23340
attcagcatt atcaccttct gatggagggt catcaaacgc agtgagtgca gccacatctg  23400
ttgcgcaaac ttccccacca gcgcattcca gttttaaggt cgtcatcagc cgtatggagt  23460
```

```
tagcgaatgt gatacccaaa attttaacta catcggctgt ttgtagccac tgggtattta  23520
tcgcattgcc ctcataaagc ccaacgttga ttgcgaccgt tttccgcaag tttaaaacgt  23580
gcgccggcaa cagcctcgaa ccggatgaat atttcattca tcagttcaat ctgctcggct  23640
gacgtcacga tgacgctaat atcgtcagca tatgcgacca acaaatcgtt gccacatgct  23700
tgttcgagcc tacacaccag ggggtggagg tagagaacga agagatgcat ggacaacggg  23760
tcgccttgcc ggaccgaacg ttggatctca aacggacgcg agagacgccc gttgatgagc  23820
agccgagagg tggcaatgcg cgcgagaaga gcgacgagat cccgactgaa accgagcgag  23880
cacatggtgc cgaagaggaa tgagtggcga acccgatcga atgcgttctc caaatcgaaa  23940
ctgatcaatt taccggcgcg ccggtgatga cggagactcg ctatccggtc tttcagggag  24000
agtgtcttga aaaatattac gctccgagtt ggagcatttc tgcccgtcgc tcagcacgtg  24060
gtgggctcgc atgacgcact ctagcctggt cttggagaat gcgcgagaga agtttataat  24120
cgctgttgag cagcgaaatg ggtcggtacg atcgggccgt gttgtcgcct cccttcttct  24180
tcaccagcac gatgatgccc tccacaaaag caggggggaag gttgcctgct agtgcttcgt  24240
tgagcaggag attgagctcc cgatggatca cgtcgaagag acgcaaataa aattctcgtg  24300
ggataccatc attgccgggg gaacgccgtg gggcactcgc tcggatggca gagaggattt  24360
ttgcggtggt gatttcgtcc gtgcaggttt ggttgatggg atcatcgggt gggatcacac  24420
gctcgcatgc aaacccgtca tcgttgttgt tatccgctgc ttcttccgtg tacagaccag  24480
agaagaagtt gagcagattc gcttcgatcg ctgctggctc ggcaatggtt tcgttctcct  24540
ccgttcgcaa ctgggtgatg acggttcttc tccttcgtct ctcccccaac tgaaatatag  24600
aaacgggttc tcccgccacg tacgtttcgt tcattcgcat aaacatgtgc gaaaagttgc  24660
gttgaagcgc caacatttcg ccttttaaac ggttgatggt gggtggtatt tcgggatgct  24720
ggtagtaccc gtcgtacgct agccgcagct ccgcgtattg acgctgatgc gcgtcatgga  24780
attcgtcgaa gacgatccgt gatttacgtt taaaaaacgt tttgattctg ggcttagcat  24840
acgtgatcca ccaatcgatc cacgagccgt agtttctacg ttgccgggtc caatattgcc  24900
actgtgtttg gaactcggca acgttttcgt cggtcaggag atgcggtcga agggaccaga  24960
aaccacggcc cggctcatgg cctagctggc ggaggcacag acggagtgtc agcgctttgt  25020
ggtccgtgaa cgagcagaca tgcgtatgtg ctgtacgcaa atgctcccgc aatccgctgc  25080
tcacataaat gcggtcgagg agcgattgtg cgtttcggca aacgtacgta aagccgccat  25140
cccgcgggcg caacttttcc cacgcatcgt ggagttgcag ctgctgaacg gcagttttga  25200
gtgcagggct tgtgtttggg ctggacgaat cgcatgagcg aagcacgcaa ttgaagtcgc  25260
cagcgaggat gacgtgctga gtggcatgac ggagatagta ggcgagagtg ccgttgaaaa  25320
aatcttcccg tgccgcgcgc tgtgcagagc cggagggagc gtagaggtta caaatcgtgg  25380
tatcatgcac tcgcagagca attaggcggc tatccaggct tttctcaatg tgagatacct  25440
gaatgtaatc cttcagagca acagctgttc ctcttctcgt gtggtctaca ttcgtgtgta  25500
cgacgaagcc aggcaaggag agctgatcgt tttccacttc ttgcagacac acaatatcga  25560
ggctttggct gtggatgaag gtgcgcagcg ccgctagttt cgtggggttg gtgatggtgc  25620
cgatgttgat ggatgcgata ttgtaggatg tgagagccat tacggttggg aatcctcatc  25680
ctgctcgtcg tcatcgtctt ctcggcgggg ctttttgccg ggtggttggc ctctgcttcg  25740
cctgctgctc gtggatgccg atgatttgtc ggtttcgttg ccgttgccat tcttgctgtg  25800
```

```
cgatcgcagc gcatggatcg gctttttgaa caagtccacc acagcaacat tgggttggtt  25860
agcttcggtg gcttgttgag tcgaacggtg agacgacgac gaaccgtgcg cgcgttgcat  25920
gctgagggac accgttaagt caattttatc agaatgactg tttgttttcg tcaccggggc  25980
agactgttcg gtccgactcg gaggcttcgg cagctcgggg aaagcagccg aagaggtgag  26040
tgatggcgcg gtaggaccta ccggtttcat gttcggtggt ttcacaccgg acgatttttt  26100
cggtggctga cggttgccac tctgcttcgc tacgttggcg tagctcttct gcacaagcag  26160
tttttattc tggacacatg atatgccaga atgtgcctgc tctttgcagt gtttgcatga  26220
gagcacctgc cccttgtaca ccacgtacgc ctgctgccca tcgatggtga ctcacgagtc  26280
gatgtttcgg ttgagtagca tacgggccga ccatatgccg agcggtacac tggcgaactc  26340
gtagctctcg ccccacgtta gttcgtgaat cgagatcact tcaccgaacg cacgcaagaa  26400
ctccacgatc ttctccttcg tcacgttttc ggggaggtca tggaccttca cttcgacact  26460
tccatcctcg atggttattc gaagcttgtg cttcttcccg tctatttcca cttcgtgatg  26520
tccatcgtgt tcttcaacaa ttttctgtgc gagcgtcagg tcgccgacct tgacgaacgc  26580
acattgttca cctctactac actgtagtct caacacatct tccttcttca ggccgagcac  26640
tgtacggcaa aagccgtgga ccttttcgaa cgacggcttc acggggaagt tcgaatagtc  26700
gatccgaaag gtgttttctc gcctcatcgt gtaatcacca cacacgcgac gcggcacaac  26760
ggaatatcga tagaacgatc tgaaaaaaat gcctgactaa tgaggagcgc aaatcgcaaa  26820
cacgtctttg cgtctcataa gctgagcgat aactgatttc gcaagaagct agtattgaaa  26880
aagttttgaa gaagtttggt atggatgatt gtaatccaac aaaaactccc atggagaagg  26940
ggatacagct gacactaagc aataccggaa tggttggcga accgtatcgt gaacttctcg  27000
gaagcttaat gtatataatg atgtcaactc gaccggatgt ttgtttccca gtaggatttc  27060
ttggacgttt tcagcaacaa ccagaacagc aacactggac cgccttgaaa cgagtagtac  27120
aatacatgaa agggacgaag aacatatgtt tggaatactc tcgaaataag gaagcggaac  27180
ctttggtcgg atttgctgat gcggactggg cgacggatac aatggacaga aaatcggtga  27240
gtggattctt gttccaggtt tatggcaata cgatctcctg gtcaagcaag aaacaaacga  27300
ctgttgctac ctcgtccagt gaagccgagt atatagcgtt gagcgcaggt gttgcagaat  27360
cgatttggat atctggactc ttgactgacc ttggagtaaa gatgacgaag ccggtgacca  27420
tctatgagga caatcgtggt tgtataggaa tggcccaaaa cctggagtgc aaacgggcaa  27480
agcatattga cattaaacat cattttattc gcgatcacat tgcagccgga cgcattcggg  27540
tggaaccagt ctgcacagac aggcagttag cagacatttt tacaaaagcg ttggacattg  27600
caagatttga aaatctacgc cgaaccattg ggctccacaa tcgagagggg gtgaagaagt  27660
aggccttgct gagcaagcca tgagattctg acaagcgcta gtggagttca ttacgaacca  27720
agccttcaaa ctgtatagac cattctctcc taataaacgt tctttagttg tttgagattg  27780
agtctttcta ttggcccatc cgcccagtcc ttaatattac aatattttca tttgacagcg  27840
gcaaaacaaa caactcagtg caaaaaaaaa tctacccagc gttagctttc gaagtctccg  27900
tgatgggtta aaacaactta acgttaggta aactcgaaag aacccaaatt tggcttattc  27960
cattgaactt cgacgctggg ttggtgtgtc tctttctgtt tttgacaaca ttgctgttgc  28020
gagagaggca aaacaaccca accgtgggta aaaactaaat gcagtttacc caaatttgag  28080
taaaaagaac ttattttttg ggaagtctga tttctccgtg tattcactaa ataggttttt  28140
agcactttct agggtaaaat aaatgttgag tgtaatcaga agtttttttt tctttttcaa  28200
```

```
acatcttcac gtcaattata agccatttta cgagacgttc gaatgacgtt ttctggcgaa  28260
ccgctcattg ttgttgttca aaaaactagc atgatatctg aatggcgctg gacacatttt  28320
ggttgccgat gacttccccg tctctttcag cgcatgtttc tacccggttt acatgtatta  28380
cagacaacgt agatgaaaaa tatcttcccc gcctactgat tgaaatttta catgagaaca  28440
ttaaaaactt tgttgcattg ccaccagcgc cattgttgaa tatgctcctt ccaaatgtgg  28500
cgctagaaga aacgtaaata aatcggcccg ccagaaactt tcaaagctgg taaacaaacg  28560
gaaaccatat gattcgaaac gtctcataaa atggcttatt aattttatat ggcgaaaaaa  28620
gtatacactg taaggtcaaa gtacccttta aagagtaaaa aagtacccac tttgagagaa  28680
actagtttaa ctcataaaaa gagtaaaggc cctgtaccca ttaaagagta aacggcttgt  28740
acgtcagatc aacgaatgaa ttttacccac tatccgaaag acatgttttg aggaacagag  28800
taaaatttac tctttttata tatgggaatt gattatgatt tgtatggtat tttcgtagaa  28860
aaattaacaa tgaaatccta ttaatataga aacatcaatt tattcaatta aatattaaca  28920
ataaacaatt gtttttggtc taatgcaaga gaatcattta ttatcagcat ttggggttgc  28980
aagcctggaa aatggggctg cttctccggc aggccattct tatgcgggat atacccggaa  29040
ttgaaatcat cctgtaaaat ttgatttttc atctagttag cgcacacggc agggaaaagt  29100
atttatttaa tgcacctact ttgaccttct agtgtttctg agcacttatt tctttgttgt  29160
ggaaacaaac tactgctgca cagcctacac gctaagatca gtttacccat aaataggtaa  29220
gtgattcacc catttatgag tttttcatat taaacccata atatgggtaa aatttaccaa  29280
taaaaattgg taaatttcac tcatattatg agtgaagtca ctttacccaa atatgggtaa  29340
tctcatttac ccatatttgg atgaaaaatt agacatcaac aataatcggc gtgatgatat  29400
ccggttgctg tctttaaaaa tgtttgtgca agaactattt agctaaggta agtatatatg  29460
tttatttaca ttgcaaaaaa cagaaatata caaagaagaa ttactacttt tgtattatta  29520
tttgtttcag ttcacattgg cgatatatgc tggatcgtag aactttttcc ttttgcattt  29580
tggagatcaa cggatgcaga agttgattct tgaatcactc aactgtagca gccttttaca  29640
accaactgcg ttctatgtgt gtccagaaga tatgttattt ttcctaatct tgtatatgat  29700
taaccacact attctaatat aatattttat aaaatcagta taaaacgttt gattgtaaca  29760
atttcattta attttatcaa tataattatt gaaaatcaac agagaaaagt aaaataaagt  29820
actcatattt gggtactttt ccaataattt tgctcacaat aatataccca tttatgggtt  29880
ttgggactta acctatttat gggtaaaacc cactttaccc ataaaatgag tgtgtgcact  29940
tttcatcgat tatgggtaaa ctttacccat atttgggtag actgatctta gcgtgtaatg  30000
gggaattcca ctattattat tgacaattcg agtgacaatt agaagttcgg tagtcaaaac  30060
ttcggcgaag ttcggcgtcg gcattctaat ttggtgcttc gccgacgcat aaggattgtc  30120
tttgtcggcg tagcacttcg gtagaatacc gacgccgaac ttcggcgaac tttcggtgat  30180
atttcatttg tcttatgaac ttcggtctaa agttaatctg aatgcacaat aaatcgcaag  30240
gattttttca cccattatag agtaaaagaa cgcaacatat aaaagggcaa aaattaccca  30300
ttatctggaa aaataaaata cccctttttt tacgtttcca tatatcagaa aataatgggt  30360
acttttccca cattaaagag taatgtcgag ttaacagtgt atgtcattgc tttgcatttt  30420
gcacgctaac tttgaagtac ctattaatgg gtactttcgt actgtaacct ctcaaaatga  30480
ttacatttgt ttttttttgt aaatattccc tgtaaatagt ttttttgttc attattatta  30540
```

```
tcattattat tattattctt attgtgcttt gctttgataa atggattatt gggaaagttg  30600
tgtatcgcac ttcgaaggtc accaagcagt ggttccaata tgtttctaag caaatggaaa  30660
attcttcaaa tgtacattta cgcgacaaat tacactggtt ttgctatgca aatgcagatt  30720
tgcacttgac tgcatcattg ccacaattaa ttataatcga acaagcctat ttcaaatggc  30780
taacttttac aaatgtttta caagcaagtt ttcgtgaaac aaatgaaaca aacaaactag  30840
caaccctgct gagagcacat gcttttgata aaacgtaaac aattttcgtt ggcgcgaaac  30900
cgattcactg ccttttcttg cccgccaacg gcgaaaacaa agggtttgac gtttccgcac  30960
ttatgaaccc gcccgcactt ctgaagtgcg ggtccaata aggtgggaac tgcgcaatat  31020
tattattcct atcattattc tacatattat tcttattatt attatttttc ttattactac  31080
ccttattact attatcattt ttattaaaat tacggctgca aaaatataat gaatttaaaa  31140
ttgaaatacc tacatctaaa ataaaatgaa attaaaatgt gaataaataa gaaaaatcga  31200
atgcgcttcc cttgagcatc cctatcccaa tcataacgcc tactacccac acaccaccaa  31260
caccggtacc aaacaagaag gagaaactga tagcaccgtt ggtaatcacc gaagccaacg  31320
gaggaataaa actgcttgta atcattgcag cagtggctag taagtgaaca ctcttttcgc  31380
cgtcggtggt gcattttaag tggctgatgt tcgacgccct gtgcaccgat cctatcgcta  31440
ccatgctacc gccatctggt tttgaaggaa gccctagccg gtgttccggc atgccccgaa  31500
gactcggcgg accgacaggc ggaagcctcc ctcaatgacc atctatggta ctatgaacgg  31560
gtatgtggaa tccctctata accttttttcc attcttgaaa taaggaattt tgaatatata  31620
atgttaaatt gaactagatt atttctcatt tcaccaagct aagccctgat ttttgacctt  31680
tctattgtta atagctccac tttggttttc ttgttaaggg aagtctttcc gctaacccca  31740
atttcctctt ggagcagcat aaacgaccct gaggcccagg acaaaagcct gggtgggaac  31800
aacagaggtt cccaaccttt agaatctcta acagtaccca tttcaaagaa aagtggttta  31860
actcatttaa tgagtattgg ccatttactc attaaagagt atttgcctcg aactgcaaaa  31920
catgggtatt atttacccct catcgatttt acaaaaatgg gtaaaaaata ccccccctctt  31980
gccggcacat acgggaaaaa cggttccaaa tgaagtttta aaatatttca ggccaaataa  32040
caatacagtc taataaaaat cattttattg gatcatttaa ttaagggtca attcgaacat  32100
taatacggtg acttgctcgt gagtccatct gtattcctgg gtcttgctgc gtgtcttccg  32160
gttccagatc ttggatgaaa aataacactt aaattgctgc ttctcatgct tcttcgaggg  32220
gtttgctgta gagaaaagtc aatttagtcc ttaatgtaaa tagtttgtta aaaaaatatt  32280
gtcgcgcgcc caccaaatcg gaacgcgcgt gtgggacacg cgacgtgtga ctcgttcccg  32340
acataactgt cataatgaca tgtgtgccgc tgcattctta cgatgtttat gaacacagtg  32400
cactattcaa atattagtcg cgacgcttgt agattgagaa aaacaatatt taaagaaaat  32460
tgtttgtcct tatttctgtc ggatccataa tagctactta ccattgttct ttcaattaat  32520
taatacaata tgatccgtgg caaaaaaatt taatgttgct gctccaaaca acgacaagtg  32580
gctttttttac ccattattgt tgacggaact cattcttcaa gaagagtatt atggatccga  32640
cagaaataag gacaaacatt tttattaaat atattttttc tcaatctcca agcgtcgcga  32700
ctaatatttg aatagtgcgc tgtgttcata aacatcgtaa gaatgcagcg ccacacatgt  32760
cattttg                                                            32767
```

<210> SEQ ID NO 165
<211> LENGTH: 2239

<212> TYPE: DNA
<213> ORGANISM: Aedes aegypti

<400> SEQUENCE: 165
tcctcgtggt gatagaatgt gacttatcag tgtgtcactg catgtctgtg ctatttgcgt 60
ttgatgttac gttccaaacc gcttgtgtac ataaaaaatt agtattagat atcgtcaatg 120
ctagagatcc agtatagatg cattgtgttg cagtttaaca aaacaagtct tttgactcat 180
cagccttttc tgaagtcatt gtcagtgaac cagccaagtt gattgtaata caatggaaag 240
gaaatcgtat acggggtact tgttcactac tgaaatattc cagaagaagc aactaaacat 300
taaggaaacg cagaaacatt acaagtctaa tttattacga tttgtaacaa agcggtttca 360
cgtattttgc ataggctctc tgtttgccat tgcatttatg tattttcaaa aaccgccaca 420
gattattcga caatccgagt catcccgcca acttataccg ccaaaccctc aaagtacgga 480
cacgaaagtg acaccatcat acacaccttt acatattttc cagaaagctg cagtgtgctc 540
tgattcagaa atatgcagtg gcattggaag agatatcctt caaaaaaatg ggaccgtagt 600
ggatgcagca ctagccacaa tgttttgtgc aggtctttca aacatgcaat caatgggtat 660
aggtggagga ttcattatga acatttacat taagaaggaa aacaaagcct acacattgga 720
tgcaagagaa ataactgcta tagcggcgac gcaaaatatg catttacatg atcccttaac 780
aacaaatgaa ggaccattgt ctattgccac acctggggaa cttaaaggtt attgggaagc 840
acataaacgg ttcggaaagc tgaaatggaa agaagttatg gaaccaacgt taaatatttg 900
cagaaatggc ttcgaaatgt ccaaacatat gtcagattcc ttgcatgtaa atctaaatgt 960
caaaaatgac caagggttgc gacaaatgta tttcgacgaa gcaactggta cattccacaa 1020
accaggaacc gtaattaagc cagagcagct ctgtaacacg ctccaatata tagcagaaaa 1080
tggaggtaat tcgttatatg agggggagct tttagaccag tttgcagaag atttgaaaga 1140
catgggaagc ataattacaa aggaagatct tgaaaaatat gaggttcgat ggagtaattc 1200
cattcctatc gatatcaatg gtgatattat gtatgtagtt ccaccaccag cgagtgggat 1260
tctgctcagt tttataatga atattctgaa aaattataat ttcgagccaa acgatctctc 1320
aaccgttaat tcgacaattt taacatacca tcgcataata gaagcattca aacatgctta 1380
cggcagacgc tctcagatag gcgatccaaa atttgtagat attgaagatc ttgttcagaa 1440
aatgacgtcg cctgattatg gagaaaaaat aaggaaaaca atagacgatt ccagtactaa 1500
gctacaccct catgactacg gaggtcattt cttcatcaaa gaaagtcatg gaacagcgca 1560
tttatccttg ataggttcta atggagatgc agtttctgta acgagttcca tcaactttta 1620
ctttggagct gctctttccg gtaaaaggac tggtattatc gttaacagtg gtatggatga 1680
cttttcatcg ccgggtttac aaaactattt tggacttcct ggatcgaagc gaaactatat 1740
acaaccacaa aagcgcgcgc tttcgtcaat gtctcccact attatagtag gtaacgatgg 1800
taacgttaaa ctcatagttg gtgcggctgg aggtacaaaa attacaacag cagtggttat 1860
gacaattatg aaatatttgt ggtttggcag cgatatcaaa gaagctgtag attcccctcg 1920
catacatcat caattaattc cgatgacatt gcagtacgaa tttggaaatt tggaggacgt 1980
tttgctgggc ttagaagcaa aaggacacgt tacaaagcgg tatcgtgaac gaggatcgat 2040
agtttgtgca atcgctcaga ataatacggg catttacgcc aatgcagatt tcaggaaagg 2100
tggtgacgtc gttgggtttt gaacaaaaat gtctaatgta gtatcaatga attattattg 2160
ctgcaatagt tttcgataat acaaaacctt ttatgacctg caaatgatga ataaaataat 2220

```
tgagtaaagt ggtgcaaaa                                                2239


<210> SEQ ID NO 166
<211> LENGTH: 2118
<212> TYPE: DNA
<213> ORGANISM: Aedes aegypti

<400> SEQUENCE: 166

tcttctaaac attacacata tggtgaaaga tgcgtatatt attagacaac gtcttaataa     60

ataattgaag ataaatagta tatccttcta aacgttaaac agactataca attatacatg    120

aaatcgtata cggggtactt gttcactact gaaatattcc agaagaagca actaaacatt    180

aaggaaacgc agaaacatta caagtctaat ttattacgat ttgtaacaaa gcggtttcac    240

gtattttgca taggctctct gtttgccatt gcatttatgt attttcaaaa accgccacag    300

attattcgac aatccgagtc atcccgccaa cttataccgc caaaccctca aagtacggac    360

acgaaagtga caccatcata cacaccttta catattttcc agaaagctgc agtgtgctct    420

gattcagaaa tatgcagtgg cattggaaga gatatccttc aaaaaaatgg gaccgtagtg    480

gatgcagcac tagccacaat gttttgtgca ggtctttcaa acatgcaatc aatgggtata    540

ggtggaggat tcattatgaa catttacatt aagaaggaaa acaaagccta cacattggat    600

gcaagagaaa taactgctat agcggcgacg caaaatatgc atttacatga tcccttaaca    660

acaaatgaag gaccattgtc tattgccaca cctggggaac ttaaaggtta ttgggaagca    720

cataaacggt tcggaaagct gaaatggaaa gaagttatgg aaccaacgtt aaatatttgc    780

agaaatggct tcgaaatgtc caaacatatg tcagattcct tgcatgtaaa tctaaatgtc    840

aaaaatgacc aagggttgcg acaaatgtat ttcgacgaag caactggtac attccacaaa    900

ccaggaaccg taattaagcc agagcagctc tgtaacacgc tccaatatat agcagaaaat    960

ggaggtaatt cgttatatga gggggagctt ttagaccagt ttgcagaaga tttgaaagac   1020

atgggaagca taattacaaa ggaagatctt gaaaaatatg aggttcgatg gagtaattcc   1080

attcctatcg atatcaatgg tgatattatg tatgtagttc caccaccagc gagtgggatt   1140

ctgctcagtt ttataatgaa tattctgaaa aattataatt tcgagccaaa cgatctctca   1200

accgttaatt cgacaatttt aacataccat cgcataatag aagcattcaa acatgcttac   1260

ggcagacgct ctcagatagg cgatccaaaa tttgtagata ttgaagatct tgttcagaaa   1320

atgacgtcgc ctgattatgg agaaaaaata aggaaaacaa tagacgattc cagtactaag   1380

ctacaccctc atgactacgg aggtcatttc ttcatcaaag aaagtcatgg aacagcgcat   1440

ttatccttga taggttctaa tggagatgca gtttctgtaa cgagttccat caacttttac   1500

tttggagctg ctctttccgg taaaaggact ggtattatcg ttaacagtgg tatggatgac   1560

ttttcatcgc cgggtttaca aaactatttt ggacttcctg gatcgaagcg aaactatata   1620

caaccacaaa agcgcgcgct ttcgtcaatg tctcccacta ttatagtagg tagcgatggt   1680

aacgttaaac tcatagttgg tgcggctgga ggtacaaaaa ttacaacagc agtggttatg   1740

acaattatga aatatttgtg gtttggcagc gatatcaaag aagctgtaga ttcccctcgc   1800

atacatcatc aattaattcc gatgacattg cagtacgaat ttggaaattt ggaggacgtt   1860

ttgctgggct tagaagcaaa aggacacgtt acaaagcggt atcgtgaacg aggatcgata   1920

gtttgtgcaa tcgctcagaa taatacgggc atttacgcca atgcagattt caggaaaggt   1980

ggtgacgtcg ttgggttttg aacaaaaatg tctaatgtag tatcaatgaa ttattattgc   2040

tgcaatagtt ttcgataata caaaaccttt tatgacctgc aaatgatgaa taaaataatt   2100
```

gagtaaagtg gtgcaaaa 2118

<210> SEQ ID NO 167
<211> LENGTH: 2239
<212> TYPE: DNA
<213> ORGANISM: Aedes aegypti

<400> SEQUENCE: 167
tcctcgtggt gatagaatgt gacttatcag tgtgtcactg catgtctgtg ctatttgcgt 60
ttgatgttac gttccaaacc gcttgtgtac ataaaaaatt agtattagat atcgtcaatg 120
ctagagatcc agtatagatg cattgtgttg cagtttaaca aaacaagtct tttgactcat 180
cagccttttc tgaagtcatt gtcagtgaac cagccaagtt gattgtaata caatggaaag 240
gaaatcgtat acggggtact tgttcactac tgaaatattc cagaagaagc aactaaacat 300
taaggaaacg cagaaacatt acaagtctaa tttattacga tttgtaacaa agcggtttca 360
cgtattttgc ataggctctc tgtttgccat tgcatttatg tattttcaaa aaccgccaca 420
gattattcga caatccgagt catcccgcca acttataccg ccaaaccctc aaagtacgga 480
cacgaaagtg acaccatcat acacaccttt acatattttc cagaaagctg cagtgtgctc 540
tgattcagaa atatgcagtg gcattggaag agatatcctt caaaaaaatg ggaccgtagt 600
ggatgcagca ctagccacaa tgttttgtgc aggtctttca aacatgcaat caatgggtat 660
aggtggagga ttcattatga acatttacat taagaaggaa aacaaagcct acacattgga 720
tgcaagagaa ataactgcta tagcggcgac gcaaaatatg catttacatg atcccttaac 780
aacaaatgaa ggaccattgt ctattgccac acctggggaa cttaaaggtt attgggaagc 840
acataaacgg ttcggaaagc tgaaatggaa agaagttatg gaaccaacgt taaatatttg 900
cagaaatggc ttcgaaatgt ccaaacatat gtcagattcc ttgcatgtaa atctaaatgt 960
caaaaatgac caagggttgc gacaaatgta tttcgacgaa gcaactggta cattccacaa 1020
accaggaacc gtaattaagc cagagcagct ctgtaacacg ctccaatata tagcagaaaa 1080
tggaggtaat tcgttatatg agggggagct tttagaccag tttgcagaag atttgaaaga 1140
catgggaagc ataattacaa aggaagatct tgaaaaatat gaggttcgat ggagtaattc 1200
cattcctatc gatatcaatg gtgatattat gtatgtagtt ccaccaccag cgagtgggat 1260
tctgctcagt tttataatga atattctgaa aaattataat ttcgagccaa acgatctctc 1320
aaccgttaat tcgacaattt taacatacca tcgcataata gaagcattca aacatgctta 1380
cggcagacgc tctcagatag gcgatccaaa atttgtagat attgaagatc ttgttcagaa 1440
aatgacgtcg cctgattatg gagaaaaaat aaggaaaaca atagacgatt ccagtactaa 1500
gctacaccct catgactacg gaggtcattt cttcatcaaa gaaagtcatg gaacagcgca 1560
tttatccttg ataggttcta atggagatgc agtttctgta acgagttcca tcaactttta 1620
ctttggagct gctctttccg gtaaaaggac tggtattatc gttaacagtg gtatggatga 1680
cttttcatcg ccgggtttac aaaactattt tggacttcct ggatcgaagc gaaactatat 1740
acaaccacaa aagcgcgcgc tttcgtcaat gtctccccact attatagtag gtagcgatgg 1800
taacgttaaa ctcatagttg gtgcggctgg aggtacaaaa attacaacag cagtggttat 1860
gacaattatg aaatatttgt ggtttggcag cgatatcaaa gaagctgtag attcccctcg 1920
catacatcat caattaattc cgatgacatt gcagtacgaa tttggaaatt tggaggacgt 1980
tttgctgggc ttagaagcaa aaggacacgt tacaaagcgg tatcgtgaac gaggatcgat 2040
agtttgtgca atcgctcaga ataatacggg catttacgcc aatgcagatt tcaggaaagg 2100
tggtgacgtc gttgggtttt gaacaaaaat gtctaatgta gtatcaatga attattattg 2160
ctgcaatagt tttcgataat acaaaacctt ttatgacctg caaatgatga ataaaataat 2220
tgagtaaagt ggtgcaaaa 2239

<210> SEQ ID NO 168
<211> LENGTH: 1097
<212> TYPE: DNA
<213> ORGANISM: Aedes aegypti

<400> SEQUENCE: 168
aaaacaagcg tagccagcgc gtcagacgcg ttgtttttga aaaaaatcaa aattgacgct 60
gtgattccgg ttgcatgttg gttttgtgct acgggttatt tcaaaagaaa aatcaaattt 120
gaaatggatt tcgaaagtac gtgtgctttg attaacaagg tgaagcagca tgagtgtttg 180
tgggcgaaga ctaataaaca ttaccgaaat gtgctgatga aggagaaaat ttggctgcaa 240
attgctactg atttgatgca aaccggtaag tactgaaatc cctaagaaaa aaaaaaagtt 300
ttggatggaa actcccattc gtatatttaa cacgttcctt acttatgtgt agcctatgca 360
tcataatcat ctcattttgt tcattacagt cgattccgtc aaaagccgct ggaagagctt 420
gcgagataag tttgttcgcg aacagaatga actatcgcaa ataacaacat ccggatcagc 480
tgctcccgaa aaggcaaagt ggaagttttt cgacgaacta ctttttctga aagggcattg 540
ccaaagaaga ccgtaagttt ttgcttaatt tattgtatgg caatattttg aattgttaat 600
ttatgttata acaggacagc ttcaaactac cggaacacag aatcatcgca gcttgcggaa 660
aaggaggcag acaattatgc aacaaatgat cccttcatcc cggaaatggc tcccgtcaac 720
gatgagaatt ttgatgaacc agaacaatta gatacaccga ctacgcgaaa gagggttaaa 780
atggatagca ggttcaacga aatgctggac aaagtcgaat ccctgtgttc ttcaggacct 840
gccgctccat ccaggcatga atcatttgcc aaatacctct gtgaccggtt ggaaatattt 900
ccgcttccgg ttgcacggtc tcttgaaatt gaaatcctat cgcgtgttca taatgtaatt 960
gatgaatttg aggagatgga gataattgat aacccgaagc tctaaagcgt caaatttata 1020
accaatgggt attcgaacaa ttcgtaattg tctctattga ctgaatgatg ttcaatatat 1080
gaaaactcca tacatta 1097

<210> SEQ ID NO 169
<211> LENGTH: 1035
<212> TYPE: DNA
<213> ORGANISM: Aedes aegypti

<400> SEQUENCE: 169
aaaacaagcg tagccagcgc gtcagacgcg ttgtttttga aaaaaatcaa aattgacgct 60
gtgattccgg ttgcatgttg gttttgtgct acgggttatt tcaaaagaaa aatcaaattt 120
gaaatggatt tcgaaagtac gtgtgctttg attaacaagg tgaagcagca tgagtgtttg 180
tgggcgaaga ctaataaaca ttaccgaaat gtgctgatga aggagaaaat ttggctgcaa 240
attgctactg atttgatgca aaccggtaag tactgaaatc cctaagaaaa aaaaaaagtt 300
ttggatggaa actcccattc gtatatttaa cacgttcctt acttatgtgt agcctatgca 360
tcataatcat ctcattttgt tcattacagt cgattccgtc aaaagccgct ggaagagctt 420
gcgagataag tttgttcgcg aacagaatga actatcgcaa ataacaacat ccggatcagc 480
tgctcccgaa aaggcaaagt ggaagttttt cgacgaacta ctttttctga aagggcattg 540

```
ccaaagaaga ccgacagctt caaactaccg gaacacagaa tcatcgcagc ttgcggaaaa    600

ggaggcagac aattatgcaa caaatgatcc cttcatcccg gaaatggctc ccgtcaacga    660

tgagaatttt gatgaaccag aacaattaga tacaccgact acgcgaaaga gggttaaaat    720

ggatagcagg ttcaacgaaa tgctggacaa agtcgaatcc ctgtgttctt caggacctgc    780

cgctccatcc aggcatgaat catttgccaa atacctctgt gaccggttgg aaatatttcc    840

gcttccggtt gcacggtctc ttgaaattga aatcctatcg cgtgttcata atgtaattga    900

tgaatttgag gagatggaga taattgataa cccgaagctc taaagcgtca aatttataac    960

caatgggtat tcgaacaatt cgtaattgtc tctattgact gaatgatgtt caatatatga   1020

aaactccata catta                                                    1035
```

<210> SEQ ID NO 170
<211> LENGTH: 32767
<212> TYPE: DNA
<213> ORGANISM: Aedes aegypti

<400> SEQUENCE: 170

```
gcggcgctca agatggaaat tcatttttca gcagtactga ataaattgtt ttaggatcaa     60

gaagaaaaat gatgattcct atcggaggtg agtaggtata gtcatttatt cattgttatt    120

aggtgttata tattccagtt tcttcatcga tgtgcaccaa tgtttttctt catggcgaca    180

aaaaactgaa catttcgggc tggttaaatt gtgctgtact aaccaagatg caacaactac    240

aaaactgaat cgaaattggg agacagcaat tccaaataag aatgtcgttc cgtttatttg    300

tcacgatata catatttcac aactcttggt tgacaataat tttactctat tttataatat    360

atctttattt ctcaataaag tttgcatttg tatgttaatg acaaaattca atttaattca    420

aaatagtcat aaagaaattt aataaaaaag ctagtcgaaa agtctatgaa actactcatt    480

tttgcgtatt ttttagaata attgcttcca agcttgaata cccaaatatg ggtattgtca    540

gtttacctat ttatgagtaa acccgctttt tggcgattat gggcaaactt tacccatatt    600

tgggtagact gttcttagcg tgtacatcta gggcacccat acccaatgtg atctataaga    660

ggtgaagaga aagtcattgt gtgattgtat tagtacaata aaaatcaaaa caaacattga    720

ggggaaaatg agtgacgtca taccgtttca acgaaatgct gtgagtggat gtaaaacact    780

ccatatcgtg gaacaaatca agatcacacc gtataaatct gcaactaaca cctagatgaa    840

agagtcgaat gggtagattc caggaattat gtttttttcac tatattcacg gatgaaagaa    900

agcacttttc ttactttttt ctaattatat tcaatttgag cactacattt atggatgaat    960

tacgcaaaat atcctttgga agaaagaaca atttcagcct attccagcac attatcagtt   1020

ttgatgatat ttgggttgcc ttccgttgtt atatttcctc tgttttataa tagatttcat   1080

cctaaaataa agcaaaactt agcatgaagc aaacaacgca tgaattacct gaaatgccat   1140

ctttctgcga cgaatttttt catgttgttg tttgaacaac agcacacagg acaaccttgg   1200

taacgatagg gttgctagta acgatacctc gaaataaatc gataacaaac tgtatgacgt   1260

cacgcagtgg tggaatgcaa tgggttgctg tgtgaaaatt taagcgaccc actaacacat   1320

gcaagcagtt gtgtattaca caaaatcatc tcctcacctc taataaagca cattgaccca   1380

taccattggg cgtgataacc actataatcg agtaaaaata agagagaaca gtggcacgca   1440

acatgatttt tcccattttt ccacctgagc aaactaagaa cattgactac ggagctcagt   1500

ccagcaataa tgttaatcat aaaaagatgt gatctttttc aaagaaaatt ttattagtgt   1560
```

-continued

```
tttctaagtt ttatattgat ttttgttttt gtcgtgcaaa tgtgtaaaaa aagaaatgct   1620
gagatcaatg cagaatttga tatcatcaaa aaatattgta tatatatagg aaatattcca   1680
ttctttgcat caaagaatga tgtggttgtc aaatttgccg aatacggcga aacatgtaac   1740
atatatatgc aatcaaataa accacattgc gacgttaaac ctgcaattgt tcgatatcgt   1800
tcgagaaaaa gtgtagacaa gtctttgtgt ttaaacaatt caaaattcgg caacacgata   1860
ttaatagttc taccactaag tttgccttat tcaagatatc tgctgaccta tgatacttgc   1920
attgtggtat atattaatga taagaattct tgtaagacat caatggctga gctatatgat   1980
gaatttcaaa aaattggtga tattcaaaac atgtttaaaa cgacaaataa tatgatttat   2040
ataaactttg agtctgaaaa gtctatgcaa ttatctttag ctactaagcc ctttttaata   2100
aataataata ttttcaaaat caaaaaagtt gaacgaaaca ttaacatgtg cggtctaaat   2160
tcagaaagcc aggatttctc cacaaatcta aaaaaaaaac ttttgtataa tcgctctatt   2220
ggaatatttg gattgccatc aaatgccacg gaagagcgaa ttgcacaaat attttcaagg   2280
tgagtatgtg caaattaaag cgtgcttcag aataattacg gcgctcatat taaatacaca   2340
acgcgcaaac aatatatgca caaatgcaac ctaacattca aaaacacgca gtaaacttga   2400
ctatcggaat tcatacattt tgcccattgc acggtgacgt catcagaata tagctttttt   2460
ctcttcggga aatccgaaaa caactctttc ggcactcacc gcatcaaaac agcaatgtca   2520
ccgtataatg cagccaatgc agcccacaga cgctcagacg gtttgactaa agaaacgaaa   2580
gaaactataa gcaaagaagc gaaatgttcc aatggaccaa tgcacgagtt cacgaatttg   2640
acatttgagc ggtgccgaat tcactcgttg ctatggccac acaaataaca cggcaccgct   2700
caaacgtcaa ataacgaact cgtgcatagg ccttttcatg tgacagatcc gtctatgcat   2760
ttgtttacat cggtggagga ccggtgctaa cacgggcctg tcattttcat agaagaactg   2820
tcaaagtgct tcccgatcag ctgatttgag acgtcatatg aataggccta ttggtccatt   2880
ggaatttcaa gtttactgtc aatgtcattc caatcgagta ggagacttgt caaacacttt   2940
ttcacacaag ctgaaaacca agggtgaagg gcggctgtca aatgggagta aaattgaaaa   3000
gcccccaacc tatgtccaga accagttttg aggcttaaag cctgattcgc tgctgacaag   3060
taatttctcg gcctatcttg atgcatggga aattcctgca aggaatcgat caagaaagtt   3120
ttttttctga tcgcagtctt caccattgtt tggtagaaat gttgtacact caggcaaaaa   3180
tactatgaat atccattgtt ttcccttatg tttatttgcc acaagaaatc ggtaagtatt   3240
tcattgattc accttatgaa tttatctgaa tcatgccaat gtggtgtctt gctcatttca   3300
taaaacagcc ttatgaacat tgatatgata atttaagaat ttcttctttc agtagtataa   3360
acaacattac tttttataac acttattatt atttctttac tcgtttttta tacctcatgg   3420
acaatacatt ccattttgaa tatttacaga attttcaatg ctttcatttt cttaatatta   3480
ggtaattaat tacctaacgt gtagaaatca aatttccacc tactttctcg tgctgttgca   3540
tattatgcag taaagtttgc atatcgaact gtaacgcaac gaagaatgaa aattcgattt   3600
ttaaacgttg gttaagccat ttttctaagg caaaattgat attaattgaa ccattactct   3660
ctttttatta atctgttctt ttgttttttt tttcgatttt tacaatcttc catcgctgta   3720
cttccttccc cataaccaga cttataaaaa agttgactgc agtatgcggg atgtcaacga   3780
tggcggtgat ttcatgctgc tctccagtcg aatgacgatc ctgcctataa aattctatct   3840
gaaaattcaa ttccgtatta atttcaaatt atcagaaaaa ccaacttatt acctttgaaa   3900
atattcgaac aaatttatga tgcttccgta aatggatccg cgtccagtta tttttccatt   3960
```

```
tgcaaatttt cataataaca accttatgag tttttcacac tagcgacagc tatgtgcttc   4020
ataaggtggc ccaatgaaat tgatattcgt taatgaggga taacatgctt cgcaattatg   4080
gttttcattg aactaatatg aaatccataa tagccttatg aatgatggta tcattgagga   4140
aatgactaat gacagcaatg gaaatcataa ggcgcgcaat gaaatttgag aacgttcatt   4200
ataattaact attttatcaa ttatgattat tatttcaacg gtatgaaatc catattagcc   4260
ttctgaaata ggtttttata gatttttcaa cgcttcataa gggaaaattt atgaaattag   4320
ttaatttatt tgcctgagtg aatgatacca tcattcataa ggctattatg gatttcatat   4380
tagttcaatg aaattatcat atcaatgttc ataaggctgt tttatgaaat gagcaagaca   4440
ccacattggc atgattcaga taaattcata aggtgaatca atgaaatact taccgatttc   4500
ttgtggcaaa taaacataag ggaaaacaat ggatattcat agtatttttg cctgagtgtt   4560
gaggaaatga ctaatgacag caatggaaat cataaggcgc gcaatgaaat ttgagaacgt   4620
tcattataat taactatttt atcaattatg attattattt caacggtatg aaatccatat   4680
tagccttctg aaataggttt ttatagattt ttcaacgctt cataagggaa aatttatgaa   4740
attagttaat ttatttgcct gagtgtatgg ttgtttagtt tttagaacca gcgacacgtt   4800
ggggtagcag taaagagccg ccagttccac ccttgctgaa aacggctcac acaaaaatgt   4860
taccgcccac gaaaattttg cttcttctga agtagcatat tttctgaata cttgagtgtc   4920
gattgcaatt ttcatgcttt gcataaagaa tgctctactc attacattgg ttttccacac   4980
attcagtcaa tttttcattc gttacccaaa cctgtgaaaa ctcaacacat aaaacctgtg   5040
actcactttt agcgtgggat tcaacattgg cagtgctacg taatagatta tggacttatc   5100
cacggtcttc tcttatcctc gactttcttt ttcttttctg ctctaaatgc gggcaatgtt   5160
tacattaaat gacatccgaa ccaacatccg gacaacgaat gttcacagga tgaacacgaa   5220
gtggatgaat gcacaacgaa atcgttcatt ttttgtaaac acggcccgca gtaatggttt   5280
tcttcccgct ggaagttgca gcgtgacgtc atcgtagatt agttcataca gtgctacgta   5340
ataggcatag ttgctagcag atttctggac taacatttga aaagggccca agaggtcttg   5400
agcctttttt tagaaacgtt gttgttgagc cctcctcagc ccgcccacgc aaactaacac   5460
cactattaga aagattggtg ttagctcttc ctgatagtgg tattggtgag cgtgatcgag   5520
ttgaattggg ctcaacagcg tcttgcaaag ccaatgttta ccaatgtcga tgtgcccttt   5580
tcaaatgttt gtccagattt attttgaata tgatcagatt tcgtctcttt ataatttaga   5640
ttctttaggt ttgaccaaca taggcctttt catgtgacaa atccgtctat gcatttgttt   5700
acatcggtgg aggaccggtg ctaacacggg cctgtcattt tcaaagaaga actgtcaaag   5760
tgctatgcat ttgtttacat cggtggagga ccggtgctaa cacgggcctg tcattttcat   5820
agaagaactg tcaaagagct tcccgatcag ctgatttgag acgtcatgtg aataggccta   5880
ttgactccgc cccccaggtt gatgctcaag ttggtgctat gtttgaccgt gctgtttgac   5940
gaaccaattt gacagtttgt gaaaccgatt tgacggttga cgaatcggtc ggccaaaatc   6000
aaacgagttt gattttgctc aaaccaccgc acagtggaca aaaaccgacc caaaatcgca   6060
cttatttcgt gccgctgatt tctgaaggtg ggaagtagct attttcatta aaaaacatgc   6120
gaggaatcga atggcgccat tttcattcac cgcacgccat cggaagtacc tcattttgcc   6180
ccgttttccc ctttctgata tgaaaactag agtttttagt agtttatttg cttctgctga   6240
ttaaaatcga tgaattatat aattgaaaac ccatcggcaa accaaatatg tatatgaaaa   6300
```

```
ataatatttt tggacaaact tgatcaatgt accagtttac ccctttttccc ctataattta   6360
gacattttga tagtttcaat aaatttttca aaactaacac ttaatttaca attcataact   6420
cgcaaaccct tccattgaaa gtttgcgaaa tggactgagg gatatatcga actatgtaga   6480
ccacgacgaa tagctcattt catccctttt cccctaatat ttcttcatat atggcagttt   6540
tacgatattt catattactg ccgccagatt ttcaattcaa accgacaaac cctattgtaa   6600
aacagtagta tgtgaaagcg acatatgcgt gaatcatggt ttacgaacca tcataaatag   6660
ctcattttgc cctttttccc ctataattag ctttatacga aggttttact atatttctga   6720
atactgcagt tagattttaa actttaaaca tataatttat tttgtaaaat agtatggaaa   6780
tttgacagat gcatatatca agcttagcgt accactgtga atagcccatt ttaccccatt   6840
tcccctaata tttcttcata taatgcagtt ttacgatatt tcatattact gccgccagat   6900
tttcaactca aactaccaaa tccttacgca atacagtaag taaaagcaac atatgcgtga   6960
atcatgattt acgaaccatg gtaaatagct cattttgccc cttttcccct ataattagct   7020
ttatacgaag atttactatt tttctgaata ctgcagttag attttaaact ttaaacatat   7080
aatttatttt ataaaatagt atggaaattt aacagatgca tatataaagc ttagcgtacc   7140
atggtaaata gtccattttc ccctttttccc ctatacttcg gtatacatga aagttttacg   7200
atattttaca ttgttgccgc tagatttaca actcaaacta ccaaaccctt tcgtaataaa   7260
atatgtgtac agcaatctag ccacggggct aaggcccaat cttttaaaat tctaagactc   7320
aatcttttaa aattctcaat gtacaattat aaccacccaa gtaaccacta agccgtataa   7380
aacggcacca agttggttct atagtcgatt taaaggcttg gcaatcaggg cttattggaa   7440
ctatatcgca attaagggct gctatagagc cacttttggc gaattatttg gctgataaac   7500
ggcctactcg ttccgagtct ctgaagcgag aggtgtcaaa attttatagc acatggatca   7560
aagaaaaagg aaaaaaaatc tttgtttatt tttcgtcctt ttctaccttt ttatgttcct   7620
aatcgaagtt gatttttttg ttacgtgatc caggttcgaa ctaatgtttc cgaggctcct   7680
attacatgat tttccctaga ttttccaact gctccaccta tgcattgatg gtttagtttg   7740
cccaggatag tatttaaagc ataagagatt acctaggtgt ccagatagcc tcggtaagat   7800
tgttagcaaa ctcatggaag aggccacgga cttcattgca gtatacaata atggtggaag   7860
ttaaatccct aaacaactaa tcgaagaagg atttcaatgc gatgatctcg tgaaataacc   7920
ccaaaaacgc tttcatgatt cattttgtat ttcctctcgc tgctcttgca atggttcgga   7980
atgggaaagt tctttatcag gagtgttgca aatcggaagc attcaaatcc tcagtgtttc   8040
cactactcat gaatttctat ggactttttc cgctgcggaa tcgtttactt tctgcaatca   8100
ttctgctgtt caaaatacat tttaaccaaa tttgatcatc gaatctacat ttgttttgat   8160
tgaaatctgt atcgactttg ttgtcataaa cgtcatgtca caagccgttt ataagcattc   8220
acagcccttg tgtactgcta ataggcacag ggtttacaag ccctgtaaca tagcgttata   8280
tacccgtata cggctaatat cagggcttgt ggaacacaat gcctaaaagc atttgaaaat   8340
gttatatgct gccagttggc actgacatgc tgttgaacag ctcatttacc gcttataaca   8400
gtgcttactg gttacctggg caataccaaa aacgaaaggt cataatgtgt ttgaacgtct   8460
aaaaatatat cggtttggca ttcggttgca gtttttgaaa tgatgccgaa agaaaatcaa   8520
gtgcgtaaac atattttgca caaacgcgtg aaaaaaataa tgatgatgga tgtccgatga   8580
cgttgaagcc cacttcaaac ggctttctgg tctaactttt tacactgcaa ttcaacgagg   8640
gaaagttgac gattatttta aaattaaaaa ttgtcaaagt ttgctgacaa gtacaagagt   8700
```

```
tcgccagttc tatttagttc agtgtggagt gcttgatttt gcgatgctca ggagtggtac   8760
ctttaaaatt gctgtaaatt tcacgaaatt gcctcaaaag actacagtct cctaaacact   8820
ctaaagttat gactaattca catttttga ccatattgta gcgaaaccta gtaaaatcga    8880
aaggagtagc gaataatgat gaaaatattt ttacaattag gaaaaatctc ctaatgaaat   8940
ttttaggaga ctgtgcaaaa ttgtattgca gtgttaacat aaagaaattc ttttccgttt   9000
aggcctaccc aagtaattct tttagcagaa tattcggtga aagtttgctt gatgctatgt   9060
tcatactacc ctctttatta agaaactagt ggtcccggca aacttcgtct tgccatcaag   9120
taggctgttg aatacgctat agatcgtccc atacaaaatg acagtttcgt ccactctcgt   9180
ttttccgact ttcccggtga atatcctgag atttttatac acacaaacac gtcggaaccc   9240
ctgacgaaca aaacggagaa ataatcgttc aaatccgtta acccgttcgt aagccatttc   9300
gtgaggcggc atccacaaat tacgtaacgc tctaggggga gggggagta ggctcaagcc    9360
ttacggctca tacgaaaatt tgaaattttt catacaaaaa gcgttacaga gggggggggg   9420
gggggtgagg tggtcaaaaa tttccaattt tagtgttacg taataaatgg atgctgcctg   9480
acatacgaac acattttttt tatatagata gaagatagat agatataggc tttcttgaca   9540
tgggagatca tgtatctagt tttcacagga aatggggctc tgcactgttt tgattttgta   9600
tgtgattttg acgtttactg gtcttgttgt ttactaattt catgtgagag agaaagagag   9660
aaaatgattt ttgcgcagag ccccattgta tgatgtttga atcaagttga cctttcgttt   9720
ttggtattgg ttataattgt acattgagaa ttttaaaaga ttgagtctta gaattttaaa   9780
agattgggcc ttagcgccgt agctagattg ctgtacacat attttattac gaaaggattt   9840
ggtagttaga gttgtaaatc tagcggcaac aatgtaaaat atcgtataac tttcatatat   9900
accgaagtat aggggagaaa ggggaaaatg gactattcac catggtacgc taagctttat   9960
atatgcatct gtcaatttc catactattt tacaaaataa attatacacc ccaacctctt   10020
tttacgaccg ttatcggggg gtcgtaaaaa aaatcggtcc aaaatggccg ttcaggtttt  10080
catattttgg caaaatatgg caacactgct cgattgttat caaaagagct aattttatgg  10140
gggtgtgata tgcaaatacc aaacaattta aagataacga taccgaatat tcaccaaagt  10200
tgaaggaagt gttgcgtgtc atacagtcgg ccaaatcaca aatgttcatg tgactggcaa  10260
cgctgtttaa aaagaataaa atagagatca aaaccatcaa acttgagcgg aacagaaaaa  10320
tataatgctt agcaacatag caatactctt cagctgtaat ccagtttttc atgaagggtt  10380
caaacttttt tcgtagctgg caacactgct taagtgaaat tgcgccacca ggcagtacaa  10440
gtgtgcatgc aactattgtt ttgcgtatat atcaggatcc tgaccactta gaaagatggc  10500
gtcttcggca aagttgttca gtagctcaag gactatcatt ataagagctg tgagattcta  10560
aattttgcca ccaggcggcg ctagtgagca taaaattttc gttttgcgga tatctcagga  10620
tcctggtcac ttagagagat ggcgccttcg gcaaagttgt tcagtagctc aaggactatc  10680
attataaaag ctatgagttt cgaaattttg ccaccaggcg gcgctagtaa gcatgaaact  10740
tttgttttgc ggttatctta ggatcctagc tacttagaaa gatggtgcct tcggcaaagt  10800
tgttgagtag ctcaatcgct atcattataa aagttatgag attcgaaatt ttgccaccag  10860
gcggcgctag tgagcataga atttttgttt tgcgaatagc tcaggatcct ggccacttag  10920
aaagatggcg tcttgggcaa agttgttcag tagctcaagc gctatcatta taaaagttat  10980
gagattcgaa attttgccac caggcggcgc tagtgagcat gaaacttttg ttttgcggtt  11040
```

```
atcttaggat cctagccact tagagagatg gcgtcttcgg caaagttgtt cagtacctca  11100
agcggtatca ttataaaaga tatgagattc gaaattccgc caccaggcgg cgctagtgcg  11160
catagagttt ttgttttgcg gatagctcag gatcctggcc acttagaaag atggcgcctt  11220
tggcaaagtt gttcagtagc tcaaggacta tcattattct agccaagaga ttcgagattt  11280
ggccaccagg cggcgctagt gcgcatagat tatttgtttg ccggatagct caggatcctg  11340
gccacttaga gagatggcgt cttcggcaaa gttgttcagt agctcaagcg ctatcattat  11400
aaatgttatg agatttaaaa ttttgccacc aggcggcgct agtgagcata gaatgtttgt  11460
tttgcagata gctcaggatc ctggccactt agaaagatgg cgtcttgggc aaagttgttc  11520
agtagctcaa ggactatcat tataaatttt gccaccagac ggcgctagtg agcatagaat  11580
gtttgttttg cggttatctt aggatcctag ccacttagaa ggtgcgcctt cggcaaagtt  11640
attgagtagc tcaatcgcta tcattataaa agttatgaga ttcgcaattt tgccaccagg  11700
cggcgctagt gagcataaat tttgttttg cggatagctc aggatcctgg ccacttagaa  11760
agatggcgtc tttggcaaag ttgttcagta gctcaaggac tatcattatt ctagccaaga  11820
gattcgagat ttggccacca ggcggcgcta gtgcgcatag atttttgtt tgccggatag  11880
ctcaggatcc tgatcactta gagagatggc gtcgtcggca aagttgttca gtagctcaag  11940
cgctatcatt ataaatgtta tgagattcga aattttgcca ccaggcggcg ctagtgagca  12000
tacaattttt gttttgcgga tagctcagga tcctggccac ttagaaagat ggcgtcttgg  12060
gcaaagttgt tcagtagctc aaggactatc attataaatt ttgccaccaa acggcgctag  12120
tgagcataga atgtttgttt tgcggttatc ttaggatcct agccacttag aaagatggcg  12180
ccttcggcaa agttattgag tagctcaatc gctatcatta taaaagttat gagattcgaa  12240
attttgccac caggcggcgc tagtgagcat aaatttttgt tttgcggata gctcaggatc  12300
ctggccactt agaaagatgg cgcctttggc aaagttgttc agtagctcaa ggactatcat  12360
tattctagcc aagacattcg agatttggcc accaggcggc gctagtgcgc atagattttt  12420
tgtttgccgg atagctcagg atcctgacca cttagagaga tggcgtcgtc ggcaaagttg  12480
ttcagtagct caagcgctat cattataaaa gttatgagat tcgaaatttt gccaccaggc  12540
ggcgctagtg agcataaaat tttgttttg cgaatagctc aggatcctgg ccacttagaa  12600
agatggcgtc ttcggcgaag tcgatcagta gctctagcgc tatcattata aaagttataa  12660
gattcgaagt tttgccagtg aaaacggaga aataatcgtt caaatccgtt aacccgttcg  12720
taagccattt cgtgaggcgg catccacaaa ttacttatga aacttttgtt ttgcggttat  12780
cttaggatcc tagccactta gagagatggc gtcttcggca aagttgttca gtacctcaag  12840
cggtatcatt ataaaagata tgagattcga aattccgcca ccaggcggcg ctagtgagca  12900
tagagttttt gttttgcgga tagctcagga tcctggccac ttagaaagat ggcgcctttg  12960
gcaaagttgt tcagtagctc aaggactatc attattctag ccaagagatt cgagatttgg  13020
ccaccaggcg gcgctagtgc gcatagatta tttgtttgcc ggatagctca ggatcctggc  13080
cacttagaga gatggcgtct tcggcaaagt tgttcagtag ctcaagcgct atcattataa  13140
atgttatgag attcaaaatt ttgccaccag gcggcgctag tgagcataga atgtttgttt  13200
tgcagatagc tcaggatcct ggccacttag aaagatggcg tcttgggcaa agttgttcag  13260
tagctcaagg actatcatta taaattttgc caccagacgg cgctagtgag catagaatgt  13320
ttgttttgcg gttatcttag gatcctagcc acttagaagg tgcgccttcg gcaaagttat  13380
tgagtagctc aatcgctatc attataaaag ttatgagatt cgaaattttg ccaccaggcg  13440
```

```
gcgctagtga gcataaattt ttgttttgcg gatagctcag gatcctggcc acttagaaag  13500
atggcgcctt tggcaaagtt gttcagtagc tcaaggacta tcattattct agccaagaca  13560
ttcgagattt ggccaccagg cggcgctagt gcgcatagat tttttgtttg ccggatagct  13620
caggatcctg accacttaga gagatggcgt cgtcggcaaa gttgttcagt agctcaagcg  13680
ctatcattat aaaagttatg agattcgaaa ttttgccacc aggcggcgct agtgagcata  13740
aaatttttgt tttgcgaata gctcaggatc ctggccactt agaaagatgg cgtcttcggc  13800
gaagtcgatc agtagctcta gcgctatcat tataaaagtt ataagattcg aagttttgcc  13860
agtgaaaacg gagaaataat cgttcaaatc cgttaacccg ttcgtaagcc atttcgtgag  13920
gcggcatcca caaattacgt aacgctctag ggggaggggg gagtaggctc aagccttacg  13980
gctcatacga aaatttgaaa tttttcatac aaaaagcgtt acagaggggg gggggggggg  14040
gggtgaggtg gtcaaaaatt tccaatttta gtgttacgta ataaatggat gctgcctgac  14100
atacgaacac attttttta tatagataga agatagatag atataggctt tcttgacatg  14160
ggagatcatg tatctagttt tcacaggaaa tggggctctg cactgttttg attttgtatg  14220
tgattttgac gtttactggt cttgttgttt actaatttca tgtgagagag aaagagagaa  14280
aatgattttt gcgcagagcc ccataactta tgatgtttga atcaagttga cctttcgttt  14340
ttggtattgg ttataattgt acattgagaa ttttaaaaga ttgagtctta gaattttaaa  14400
agattgggcc ttagcgccgt agctagattg ctgtacacat attttattac gaaaggattt  14460
ggtagttaga gttgtaaatc tagcggcaac aatgtaaaat atcgtataac tttcatatat  14520
accgaagtat aggggagaaa ggggaaaatg gactattcac catggtacgc taagctttat  14580
atatgcatct gtcaattttc catactattt tacaaaataa attatacacc ccaacctctt  14640
tttacgaccg ttatcggggg gtcgtaaaaa aaatcggtcc aaaatggccg ttcaggtttt  14700
catattttgg caaaatatgg caacactgct cgattgttat caaaagagcc aattttatgg  14760
gggtgtgata tgcaaatacc aaacaattta aagataacga taccgaatat tcaccaaagt  14820
tgaaggaagt gttgcgtgtc atacagtcgg ccaaatcaca aatgttcatg tgactggcaa  14880
cgctgtttaa aaagaataaa atagagatca aaaccatcaa acttgagcgg aacagaaaaa  14940
tataatgctt agcaacatag caatactctt cagctgtaat ccagtttttc atgaagggtt  15000
caaacttttt tcgtagctgg caacactgct taagtgaaat tgcgccacca ggcagtacaa  15060
gtgtgcatgc aactattgtt ttgcgtatat atcaggatcc tgaccactta gaaagatggc  15120
gtcttcggca aagttgttca gtagctcaag gaccatcatt attctagcca aaagatgcga  15180
gattttgcca ccaggcggcc ctactgagcg tagaattttt gttttccgga tagctcagga  15240
tcctgaccac ttagaaagat ggcgtcttcg acaaagttgt tcagtagctc aaggactatc  15300
attataagag ctgtgagatt ctaaattttg ccaccaggcg gcgctagtga gcataaaatt  15360
ttcgttttgc ggatatctca ggatcctggt cacttagaga gatggcgcct tcggcaaagt  15420
tgttcagtag ctcaaggact atcattataa aagctatgag tttcgaaatt ttgccaccag  15480
gcggcgctag taagcatgaa acttttgttt tgcggttatc ttaggatcct agctacttag  15540
aaagatggtg ccttcggcaa agttgttgag tagctcaatc gctatcatta taaaagttat  15600
gagattcgaa attttgccac caggcggcgc tagtgagcat agaatttttg ttttgcgaat  15660
agctcaggat cctggccact tagaaagatg gcgtcttggg caaagttgtt cagtagctca  15720
agcgctatca ttataaaagt tatgagattc gaaattttgc caccaggcgg cgctagtgag  15780
```

```
catgaaactt ttgttttgcg gttatcttag gatcctagcc acttagagag atggcgtctt  15840
cggcaaagtt gttcagtacc tcaagcggta tcattataaa agatatgaga ttcgaaattc  15900
cgccaccagg cggcgctagt gagcatagag tttttgtttt gcggatagct caggatcctg  15960
gccacttaga aagatggcgc ctttggcaaa gttgttcagt agctcaagga ctatcattat  16020
tctagccaag agattcgaga tttggccacc aggcggcgct agtgcgcata gattatttgt  16080
ttgccggata gctcaggatc ctggccactt agagagatgg cgtcttcggc aaagttgttc  16140
agtagctcaa gcgctatcat tataaatgtt atgagattca aaattttgcc accaggcggc  16200
gctagtgagc atagaatgtt tgttttgcag atagctcagg atcctggcca cttagaaaga  16260
tggcgtcttg ggcaaagttg ttcagtagct caaggactat cattataaat tttgccacca  16320
gacggcgcta gtgagcatag aatgtttgtt ttgcggttat cttaggatcc tagccactta  16380
gaaggtgcgc cttcggcaaa gttattgagt agctcaatcg ctatcattat aaaagttatg  16440
agattcgcaa ttttgccacc aggcggcgct agtgagcata aatttttgtt ttgcggatag  16500
ctcaggatcc tggccactta gaaagatggc gcctttggca aagttgttca gtagctcaag  16560
gactatcatt attctagcca agagattcga gatttggcca ccaggcggcg ctagtgcgca  16620
tagatttttt gtttgccgga tagctcagga tcctgatcac ttagagagat ggcgtcgtcg  16680
gcaaagttgt tcagtagctc aagcgctatc attataaatg ttatgagatt cgaaattttg  16740
ccaccaggcg gcgctagtga gcatacaatt tttgttttgc ggatagctca ggatcctggc  16800
cacttagaaa gatggcgtct tgggcaaagt tgttcagtag ctcaaggact atcattataa  16860
attttgccac caaacggcgc tagtgagcat agaatgtttg ttttgcggtt atcttaggat  16920
cctagccact tagaaagatg gcgccttcgg caaagttatt gagtagctca atcgctatca  16980
ttataaaagt tatgagattc gaaattttgc caccaggcgg cgctagtgag cataaatttt  17040
tgttttgcgg atagctcagg atcctggcca cttagaaaga tggcgccttt ggcaaagttg  17100
ttcagtagct caaggactat cattattcta gccaagacat tcgagatttg gccaccaggc  17160
ggcgctagtg cgcatagatt ttttgtttgc cggatagctc aggatcctga ccacttagag  17220
agatggcgtc gtcggcaaag ttgttcagta gctcaagcgc tatcattata aaagttatga  17280
gattcgaaat tttgccacca ggcggcgcta gtgagcataa aatttttgtt ttgcgaatag  17340
ctcaggatcc tggccactta gaaagatggc gtcttcggcg aagtcgatca gtagctctag  17400
cgctatcatt ataaaagtta taagattcga agttttgcca ccaggcggcg ctagtgagca  17460
tagaatgtat gttttgcgga tagctcagga tcctggccac ctagcaagat ggcgtcctcg  17520
gcaaagttgt tcagtagctc aaggactatc attataaaag ctaggagact caaaattttg  17580
caaccaggcg gcgctagtga gcatgaaact tttgttttac aattatctta ggatcctagc  17640
cacttagaaa gatggcgtcg tcggcaaagt tgttcagtgg ctcaagcgct atcattataa  17700
aagttatgag attcgaaatt ccgtcaccag gcggcgctag tgagcataga atttttgttt  17760
tgcggatagc tcaggatcct ggccacttcg aaacatggca tcttcggcaa agtttttcag  17820
tagctcaagg actatcataa ttctagccaa gagattcgag atttggccac caggcggcgc  17880
tagtgagcat agattatttg tttgccggtt agctcaggat cctgaccact tagagagatg  17940
gcgtcttcgg caaagttgtt ctgtagctca agcgctatta ttataaaagt tatgagattc  18000
gaaattttgc cttcaggcgg cgctagtgag catagaattt ttgttttgcg gatagctcag  18060
gatcctggcc acttagaaag atggcgtctt ctgcaaagtt gttcagtagc tcaaggacta  18120
tcattattct agccaagtga ttcgagattt ggccaccagg cggcgctagt gagcatagat  18180
```

```
tttttgtttg ccggatagct caggatcctg accacttaga gagatggcgt cttcggcaaa  18240
gttgttcagt agctcaagcg ctatcattat aaatgttatg agattcaaaa ttttgccacc  18300
aggcggcgct agcgagcata aaatttttgt tttgcgaata gctcaggatc ctggccactt  18360
agaaagatgg cgtcttgggc aaagttgttc agtagctcaa ggactatcat tataaatttt  18420
gccaccaggc ggcgctagtg agcatgaaac ttttgttatg cggttatctt aggatcctag  18480
ccacttagaa agatggcgcc ttcggcaaag ttatttagtt gctcaatcgc tatcattata  18540
aaagttatga gattcgaaat tttgccacca ggcggcgcta gtgagcataa atttttgttt  18600
tgcggatagc tcaggatcct ggccacttag aaacatggcg tcttcggcaa agttgttcag  18660
tagctcaagg actatcataa ttctagccaa gagattcgag atttggccac aaggcggcgc  18720
tagtgagcat agattatttg tttgccggat agctcaggat cctgaccact tagagagatg  18780
gcgtcgtcgg caaagttgtt ctgtagctca agcgctatta ttataaaagt tatgagattc  18840
gaaattttgc catcaggcgg cgctagtgag catagaattt ttgttttgcg gatagctcag  18900
gatcctggcc acttagaaag atggcgtctt ctgcaaagtt gttcagtagc tcaaggacta  18960
tcattattct agccaagtga ttcgagattt ggccaccagg cggcgctagg gagcatagat  19020
tgtttgtttg ccggatagct caggatcctg accacttaga gagatggcgt cgtcggcaaa  19080
gttgttcagt agctcaagcg ctatcattat aaatgttatg agattcaaaa ttttgccacc  19140
aggtggcgct agcgagcata gaatgtatgt tttgcgaata gctcaggatc ctggccactt  19200
agaaagatgg cgtcttcggc gaagttgatc agtagctcaa gcgctatcat tataaaaaat  19260
atgagatttg aagttttgcc accaggcggc gctagtgagc atgaaacttt tgttttacgg  19320
ttatcttagg atcctatcca cttagaaaga tggcgctttc cgcaaagttg ttcagtagct  19380
caagcgctat cattataaaa gctatgagat tcgaaatttt gtcaccaggc ggcgctagtg  19440
agcatagatc atttgtttgc cggatagctc agaatcctgg ccacttagaa aggtggcgtc  19500
ttcgacaaag ttgttcagta gctcaaagaa tttcattatt ccagccaaga gattcgagat  19560
ttggccacca ggcggcgctt gtgagcaaag attatttgtt tgccggaaag atcaggatcc  19620
tgaccactta gagagatggc gtcttcagca aagttgttca gtagctcaaa gactatcatt  19680
attctagcca agagattcga gattttgaca caagacagtc ataatcaaga gctatccgca  19740
aaacaaaaat tctatgctca ctagagggga ctggtggcgg aattttgaac atcatagctt  19800
ttataatgat agcgcttgag ctactgaaca actttgccga agacgccacc tttctgaata  19860
gtcataattc agagctatcc acaaaacaaa aattatatgc tcactagcgt cgcctggtgg  19920
cggaactttg aatctcaaag catctgttat gatagcgctt gagctaccga acaacttttc  19980
cgaagacgcc atctctaagt ggtcaggatc ctgagctatc cgaaaaacaa aaattatgtg  20040
ctcactagcg ccgcctgaag gcggaaattc aaatctcata gcttttataa tgatagtcct  20100
tgagctactg aacaactctg ccgaagacgt tatccttcta agtagctagg atccggagct  20160
atccgtaaaa caaaagttct atgttcacta gcgccgcctg gtggcggaat tttgaatctc  20220
atagcttcta taatgatagc gcttgagcta ctgaacaact ttgccgaagg caccatcttt  20280
ttaagtggcc gggatcctga gatatccgca aaacaaaagt tccatgctca ctagcgccgt  20340
ttggtggcaa aattttaaat ctcatagctt ttataatgat agcccttgag ctactgaaca  20400
actttgctga aggcgccatc gctctaagtg gtcaggatcc tgagctattc gaaaaacaaa  20460
aattgtatgc tcactagcgc tgcctgaagg caaaatttcg aatctcataa cttttataat  20520
```

```
gatagcgctt gagctactga acaactttgc cgaaggcgcc atcgttctaa gtggccacga  20580
tcctgagata tctgcaaaac aaaggtttca tactcactag cgccacctat tggcaaaatt  20640
ttgaacctca tagcatttat aataatagcg cttgagctac tgaacaactt tgccgaagac  20700
gccatttatc taagtggtca ggatcctgag ctattcgcaa aacaaacatt ttatgcacac  20760
tagcgccgcc tggtggcaaa attttgaact tcatagcgtt tataataata gcgcttgagc  20820
tactgaacaa ctttgtcgaa gacgccatct ctctaagtgg tcaggatcct gagctatcgg  20880
gaaaaataaa aatctatgct cactagcgcc gcctggtggc aaaatcttga atttcttggc  20940
tagaataatg ataaaccttg agtaactgaa caactttgcc gaagacacca tctttctaag  21000
tggccagaat cctaggctat ccgcaacaca aaaattctat gctcactagc gccacctggt  21060
ggccaaatct cgaatctctt ggccaaaata atgatagcgc ttgagctact gaacaacttt  21120
gtcgaagacg ccatctctct atgtggtcag gatcgtgagc tattttttt ttacttatct  21180
cgtttatttg gcaggctcag gcgccgtagg gcgtaacaga gccgaaatct ttcttttttt  21240
tttttacatt atttacattt tgaaatttga tcttatttta aaaactatgt tagtttgcgg  21300
aagttttaag gttagtggat acatttgtaa cagggaagga aaggattttt tggaatttct  21360
taagctactt agactactaa gctgatgaag cttgaaggga caggatgtcc agatctgtaa  21420
tgaaactaaa cagaaacggt ttgtgggaga cacgacgaga agaggacaat tgaaggggaa  21480
aaagaaagac agggaacgaa cacaatcaaa ctcggatatt gatacgcttc aaaaacagat  21540
ggattaaatt catatattct aaatcaaggc ccgccaacac ttccctgaca ggtttctgct  21600
gttttcctcg gatccggaga gtttcagtca gctcagatct gacgccacga tgctcaccgc  21660
atccccacac aacatgttcg atatcctggt aagccacgcc gcaaacacag agattgcttt  21720
ctgagagccc aatacggtgg gtatgcgcgc ttaacgaata gtgattggac ataagccgac  21780
acatgacacg aatgaaatca cggctcatgc ccaacccctt aaaccatggc tttttcgaca  21840
cctgtggaaa tatggaatgc agccatctac ccatttctcc gtctctccat ttctgttgcc  21900
agctgatcaa ggtctcccga cgggccaatg caaaaaattc ttcgaaggcg atttgacgct  21960
cgtaaacatc gccttcttta gcgcctacct tagccagaga gtccgctttt tcattgccag  22020
gaatggagca atgcgaaggg acccaagcta gggtaatagt gtaagagcga attgacaaag  22080
cactcaatgc ctggcgtatt ctattcagga agtacgctga gtgcttcacc ggcttcattg  22140
accgaacagc ctccagagaa cttaaactgt cggaaaaaat gaagaagtgc tcgggtggga  22200
gagaactgat gtactctaag gtgtaatgta tagctgctag ttcagcaaca tatacagaac  22260
atggcttttg aagcatgaag gaggcgctat gagaaacgtt gtaaacaccg aaaccagtga  22320
tatcatccat ttttgaccca tcagtgaaga actgtcggtt ctcgctgaca tgcccgaatt  22380
tacttgcaaa catgggaggg ataaactttg aacgaaagtg atctggtata ccatggatat  22440
cttgcttcat ggacaaatca aatactacag aggaacagtc gaattctagg aagttatcac  22500
gattggtgtt aaccgaagat gggctgacct ccagcgtcat gtaccagtag tacacactca  22560
tgaaacgagt ttgagggtta tgttcaagca gcttttcgta gttttcaata accaatggat  22620
tgagaacctc acaacggatg aggaacctga gtgttaactc cgcgaaacga tctgtcaggg  22680
gctgtactcc tgcaagtacc tctaaactca ttgtgtgagt cgagttcatg cagcctagcg  22740
cgatgcgaag acagcggtat tgaatccgct gtgtcttcag catatgtgtt ttcgccgcgg  22800
attgaaagca aaagctaccg tactctaaga ccgacaagat ggttgtttgg tacagcttga  22860
tcagatcttc cggatgggct ccccaccatg ttccggttat agttcgcatg aaattgattc  22920
```

```
gtttttggca tttctgtgtc agatacacaa tgtgttttcc ccaggtgcat ttggcgtcga  22980
accagacctc gagatattta gaagacaagc tatgagtgat tgtcttaccc atcagtgtaa  23040
gcggaaactt ggcaggtttg tgtttctttg aaaagacaac catctcagtt ttctccgcag  23100
agaattcgat acccagcttt aaggcccaag tagacaaatt gtccagagta tcttgtaagg  23160
gtccttgtag ttcggctgct gttggtcctg tgacagaaac aacacagtcg tctgcaagct  23220
gtcttaacga gcaattttcc atgagacagt catcaatgtc tctcatataa aaattataaa  23280
gaaggggact cagacatgat ccttgggga gacctatgta gctaattcgt gaaactgaca  23340
agttgccatg agtaaaactc atatgcttct cggacaacaa attgtacaaa aaattgttca  23400
aaactgatga aaggccactt gcgtggagtt tgtctgaaag gacatcaaca caaactgagt  23460
caaaagcacc cttaatatcc aaaaacactg aacccatctg ttccttttgg gcaaaggcaa  23520
gttgaatttc tgaagaaagc agcgcaagac agtcgttcgt tcctttggct ctgcgaaaac  23580
caaactgtgt atctgacagc atgccattcg attcaaccca tttatccagc cgaaagagaa  23640
tcatcttctc taacaacttg cgaatacacg acaacatcgc aattgggcgg tacgaattat  23700
agttcgacgc gggtttcccg ggtttttgga tggctattac tctcacctgc ctccagtcat  23760
ccggaacaat gttacactcc agaaagtgat taaacaagtt caataggcgc ctctttgcga  23820
cgtcaggtag gcccttaagc aaattgaact tgattcgatc cattcctgga gcggaattgt  23880
tacatgaaag gagaacaagt gagaattcaa ccatcgaaaa aggtctatcc atgacctccc  23940
tatccaccgg aatatctcgt cgcacgcgat caacaggaac ggaatccgga caaactttct  24000
tagcgaaatc gataatccac cgaggagagc tctctcgatc ttcattaacc gacgatgtat  24060
tacgcattct tcttccgacg gtccaaagcg ttctcaacga ggtctcacgt gataatcctt  24120
ccacaaaatg acgccaataa ccgcttttct tcgctttgac caagcttttg aacttgcgtt  24180
caagggaaga atagcgctca tagttgtcaa ttgaaccacg tttccggaag tctttaaacg  24240
cggcggattt ctcgcgatag agtgccttac actcttcatc ccaccacgga ttgggaggct  24300
tcttgcgaac cgacggacca ggcacaggac ggcgttgggc ttgaagagcg ctgttgagaa  24360
tcaactcgga taaaaagcga tactcttcca acggaggaag tacttctacc gcttgttctc  24420
catcaatgat cgtttccgcg tactttcccc agagtatgtg ctttgtgagg tcgtaggcga  24480
gatcgatgga taaagactgt tgtgttccat tggaaattga aactacgatc ggcaagtgat  24540
cgctaccatg gggatcctgg attaccctcc atgaacaatc cagcgataac gagcttgaac  24600
atattgagag gtctaaacgg ctatccctag gacttccatc ttgagctgga ggtgccactc  24660
gtgtaacttc cccagtgttg agaattgtca tattgaagtc gtcgcagagg tcatatatca  24720
acgttgatcg gtggtcgtca tacagttccc cccagcctgt tccgtgggag ttgaaatccc  24780
caatgaacaa ccgtggttca ggcataacag agcagatgtg agagagatct ctgcgagata  24840
tcgccgatct cggaggaaga tatatggagg caacactgag gcatttgcct cggatagtca  24900
cctgacatgc aacgacttca atgcctgaca tctgcggcag atcgactctg tagaacgagt  24960
gatgcttttt gatccccaaa agcactcctc catatgagtc ggatcgatcc aggcgaataa  25020
tattaaaatc atggaaagga agggtcacat caggtgttag ccatgtttct gataacgcaa  25080
aaacatcgca ctgtaaatta ctaactaaaa attttaaact atctaattta ggcataatac  25140
tacgacagtt ccagtgtaga acagaaatca tatcttcgac ctctgtggat aatttatcca  25200
tcaaaagata tgatcgtcgc aaggaggggc attctagaag ccagttgctt cagaagagga  25260
```

-continued

```
gtcacacatg gaagcaatcc tttgacaatg ttcttcactg ggtcagaagc attgaagaaa  25320
ttaaggatga tatctacaat gccagaaagc gtaaacattg gaacgccctg aggttgccct  25380
aggggctccg aatgcgaact ttcttttgac tgagcagttt gaaattttgg gatatttggg  25440
attttagatt ttcccggtag tggcggaaag tctctttcct cttggagttt gaatccagga  25500
ggtaaaagct gtgagacttt cgctacaggc ttagtatttt tcatggctgg tgaatcatca  25560
ctgctaggca gattccgagg ctttttttgtg ggtctctgga gtctcacacg cttcctcgat  25620
gaacccttga aaacgaagga aattccttca ccaacctcag agtcggagcc ctgatcatca  25680
agagacagag aagagtagat attttgtgat tcagcagacg gagcagcctt ttacaacatc  25740
tcggcaaaac tacgccgaga gcgctgctct aatgtgaagt attgaaacac agtggagagc  25800
tttgagtgat ccgtcttgta tatttggcgt ctcgaggatt aatgaataac aaaacattga  25860
atgtccctat tctgctaatc atagcctgct tcaattatat aatacctcat tgcctactta  25920
aatctcctac aactcggcca tcctgacatt cacatcgtcc cgatgtgcat ttaattcgtt  25980
tttcatatcc cataacttca tatttacagg atcaaaaact ccggtaaagg gtacacgtgt  26040
aagctgaata ccatcaacat cactaacaac ataacgatta tttggaagcg tttttctgac  26100
aatataagga cctttgaatt gtgcttgtaa cttagatgaa ctcccaggta taacatgatg  26160
tggtatataa actaggtcac cttcttgata ttttgtgtta atcttacatt cggagtcgta  26220
tttctttttg ttgtaaattt gaattgctct atttatggca attgcttttt ctctaacttt  26280
aatcaaatct ctttcaatgt ctttattttt attaatactt ctctcgataa tactaatagt  26340
tgatttcttt tggtttattc caaatagtac ttgcgaaggg gtattaccta ttgaccgaca  26400
gaaagtatta ttaataaaat gttcagcatc tgacaaaatt ggaccaaaac ctcttgtagg  26460
ataactttca acaagtttag ctattactgg tgttaaaact ctgttaaacc gttctacctg  26520
accatttgct cttggacatg cagtagctat taaaatatgt tttatttcac attcgacatt  26580
aaattctcta aaactatttg aagtgaaaca acttccacga tcagaaataa tttgatcagg  26640
tattgaatat acactaaaat aatgtttaag atgcttaatt acttcactcg tgtttgttgt  26700
tttacaagga taaagtttta aatattttgt aaaggcgtct actaccacaa aaatatatct  26760
ataattacaa tttcttagcg ttattggtcc ataatggtca atgtgtatcg tatgaaaagg  26820
tctatttcct ttctctacta tattcaaagg gccatccttc ttaaaatttt tcttagaata  26880
tacgatacat tttaaacaat tatttatata cttcttaatt tgctctttca tgtttggaaa  26940
ccagtatgat ttgttgataa gttcataaac tttttgtgca ccaaaatggc cgaaatcatc  27000
gtgatacatt ttcaaaattt gacttatcat attttgtgga acatagaaca atattttatt  27060
atctttgctt ttcctataca cgactccatc tcgtaaatca taatttttat cttcgctatt  27120
ttctaactga gctctaactt cttcaatttt agaatccaac atctggctag ccaataatgc  27180
tctttcaaaa ctattatttt cattccctaa tgcacaaata attggcaaac gtgataaggc  27240
atctacatgc ttcatatttg aagaactacg gtgaattata tcatagtcgt attcagaaag  27300
aaaaatttcc catcgagcaa tcttcgcatt aatgtcctat ttatttagtg tttctttcaa  27360
tgcaatacaa tcggtaacta tggtaaattt aattccctgt aaataaatgt aaaatctctt  27420
tatactgttt actactgcca atgtttcaag ttcaaaagaa tgtagctttg attcatggga  27480
atctgttctt ttgctatagt acattactgg atgtaaaact ccatctgatt gttcctgcat  27540
taaaacacca ccgaatccaa gagcacttgc atctgtgtgc agttcagtcc tagcaaaagg  27600
agaataaatt tttaatactg gttctgcaat aagtttttct cgaaggattt cgaaggaagc  27660
```

```
catttcctct tttgcaaacc taaaatcctt tttatccttt tttactaaat cataaagtgg  27720
ttttgcaata actgaaaaat ttgggataaa ttttctaaag taacttgcta atccaatgaa  27780
tttatgaaca tcatgcacat ttttaggaac tggaaagttt tttatgcatt caacatgttt  27840
ctcacttgga cttattcctt ccgaatcaat attgtatccg agatactcta ctttagattt  27900
caaaaattta catttagtta attgtaattg taaatggttt tccactaaga ttttgaatac  27960
ctgtttgagt accacgaaat gctcctcaat tgtttcagtt gcaataataa tgtcgtcgat  28020
ataaattctt atcacgcctt ttttaattaa atctttgaaa attgtattaa taaatctcat  28080
aaatgctgaa ggtgcgttgc aaaggccgaa aggtactctc ttatattcaa actgacccat  28140
atgacttaca aatgctgtat acttttgaga gctttcatca atcaatagat gatgataccc  28200
gcttttgaga tctaaagtac taaaatattt cttacttctc aggctatcta aatggtcttc  28260
aatgtgtgga attggatacc gtcgtgcggg gtgacattgg tccataaggg tgactttggg  28320
ccaatatttt tacagcaaac taatgccaga ataatgggaa caatgtgtca agcttcaaga  28380
atacgttaca aatagccaat tgattgtcat agattagatt tttggcgttc ataccagcca  28440
ggaggttcat ggaaagaggc ggtcaaagtc accccctagg cccaatgtca ccccgcacgg  28500
cggtacctat cttttaccgt aattttattt aattctctat aatccacaca cattctccac  28560
gaattatctt tctttttttac caatactatt ctactagcgt aaggtgaatt actttcttgt  28620
attactcctt cctgtaaaag tttatttatt tgcgattcta cttctaactt ctgagaataa  28680
gacaaccgac gtggtggaaa attaaaaatt ttgttatttt gcaattcaaa tttcatagta  28740
tacgagtttt taggtttaac tggtcttaat ccgtttttat acacgttgtt aaaaagagat  28800
ctgacatctg taacatattt gaaaggaata cttgtatctc ctatatctaa atgatccaaa  28860
tcagtattca agaaagtgcc tgagcttacc tccacatcat aaatatccgg acgaatgtca  28920
tcttctattg taaccacgtt caaaagtttc ctattttctc cattttctta ccaaaagtta  28980
tcgcgttacc gtcatattca gccaacaagt tattccgttt tacgaagtcc gaccccaaaa  29040
tgcacatcgg ttccatggta gagtctttta caattttaag ctgcaatttg taaatataat  29100
tattaataac aatttctgta tcaaatgttc ctaaaatatc aatctttgaa ttatttaggc  29160
cggagtatgt ttgttcagaa tatttaaaaa ttttagaatt acttggaaca acgctacttt  29220
ttatcaaaca aatggggctc cctgtgtcaa ataaagttat acattcttta taaaaacttg  29280
aaaatctaac taaaatattg aaaaatgatt tttctagaat attcctacct ctaaactcaa  29340
tactacctcg agaacgctca aaatcatcag ttttcattcc tcggtggtct gcatcaattt  29400
ctcctatggc cgaaatcgaa ttaggttcct tcatcgtgta acgttcttgc tttcgtcggt  29460
tttccccatc gctcctatac tgttggtttc taaatttttc ttcaccatga tcgtcgtgag  29520
aacctgctcc tcctgaacta ttaatttgct gatcgttgct tgtgtaagat gctctatatc  29580
ttgcatcttc atcataacgt tgtcgaaaat tactgccact tccttgaaat cgttgttcat  29640
ttttccaaaa gcacgttctt gccaaatgtc cacgttctcc acagttgtag cagcaacgat  29700
ttttattatt cattcgcaca tgatcttgaa aatgttttga aaattttaca tcttccgctg  29760
attgcatatt tgtttgattt tcgtaccgta aaattgcttc caacaatgta ttaacagatg  29820
tatgtccagc tgtactcaac gccagcctca aatttgagtt cggaatgcca ttgataatgt  29880
acttgataat aactgcatca gttaggtcca ccatgcttgc tatagccaca acgtcataaa  29940
taaacttctc atatgtttct tccggttgct tcacccttct tatcaaagta ctatggatat  30000
```

```
ccacttcatc gactcttgat ggaaacgcct gtacgattct tcgtttaaaa tcattccagt  30060
cgtcgacagc ttgttcaaca ccttcgtacc aaatccgagg aaccgtaccc agccgtattg  30120
ttgcataatg aagcgccact cgttcttccc agctatacac attcttcaaa ttttcgattt  30180
ttcttagcca tttctgtaca gtgatcttct ccggggtgaa ttcaggaatc aaactacgaa  30240
catcttcagg atgtaaatat agttgaacgc tgttcgtacc cgtactgccg atcatcgatc  30300
ttgaattact tccaactcca ttcttgttca caacattcgt aacaactccg cgttcaccaa  30360
caaccgttga atcggtttcg gctcgcgtta tatcctctgc agtaccgctg tctatatttc  30420
ttgggtttga caatttcatt tggttttcat tcgaaacgcc tttgacggtt gaaaaattct  30480
catcatcagc tcctcgtctt aaaaaacccc gcgtgatcat catcccactt ctgaattgaa  30540
gtattgaaac acagtggaga gctttgagtg attcgtcttg tatatttggc gtctcgagga  30600
ttaatgaata acaaaacatt gaatgtccct attctgctaa tcatagcctg cttcaattat  30660
ataatacctc attgcctact taaatctcct acaaatgatc gtcgctgatg ttgctgccga  30720
cgtacgtacg tcgggcagtt ttcgagagca tgtggtggac tttcgttgca ataaacgcat  30780
tttggcggta tactacatgc accatccaca tgtctctccc cgcaagaagc acagcgaggt  30840
ttattgcagc aatactgggc agtatggccc agctgcttgc aatttgtgca atttattacc  30900
ttcggtacgt acagccgcac aggtaaacga agtttgccga ttacaagaaa attcggcaaa  30960
gcagatctgg aaaaggtcac acagaaggat tcagaatgtg aatagatctt cttttctccc  31020
accagggata cggaatgaaa ttgcttgcat tccagtatgg ggacagatgg gagagaaggg  31080
tttttgaagc gaccacaacc ctgcatcaat tcttcgcagg tcgctggtac ggtgtatgtg  31140
tggttggtct ctcactgcct accaccaacc aacacaggtg tcgataacga tggtgaccac  31200
tgtcggcgtg gagagcgcac cgctgttcac gttatacgca caccaataaa cgatgatcac  31260
tcaggtagca cacgggacga ggtgcaagct gtcttctacg atacacgtga tcggaaaata  31320
accacgcaat ggcgaaaacg ttcaatactt ttgcgcaaaa ctcgataaaa cagcaacaca  31380
atggcttcgc caaaagtgtt ccgcttccaa gccgaactaa ggctcttcac tgcactaaaa  31440
acactttgca ataggcgtcg aaataccaaa gatttggaaa aacgggggta aacccggaca  31500
cacgagaact atcgactgtc tcgcacggta gctcaacaag gaatgaggat cgtgagctat  31560
cgggaaaaca aaaattatat gctcactagc gccgcctggt ggcaaaatct cgaatctctt  31620
ggctagaata atgatagtcc ttgagctact gaataacttt gccgaagacg ccatcttcct  31680
aagtggtcag gatccggagc tatccggaaa acaaaaaatc tatgttcact agcgccgcct  31740
ggtggccaaa tctcgaatct cttggctaga attatgatag tccttgagct actgaataac  31800
tttgccgaag acgccatctc tctaagtggc caggatcctg agctatccgc aaaacaaaaa  31860
ttatatgctc actaacgccg cctgttggca aaatttcgaa tctcataact ttaataatga  31920
tagtccttga gctactgatc aactttaccg aaggcgccat ctttctaagt ggccaggatc  31980
ctgagatatc cgcaaaacaa aagttttatg ctcactagtg ccgcctggtg gcaaaatttt  32040
gaacctcata gcgtttataa taatagcgct tgagctactg aacaactttg tcgaagacgc  32100
catctctcta agtggtcagg atcctgagct atcgggtata tggcctggtg gccaaatctc  32160
gaatctcttg gctagaataa tgatagtcat tgagctactg aataactttg ccgaagacgc  32220
catttttcta agtggccagg atcctgagct atccgcaaaa caaaaatttt atgctcacta  32280
gcgccgcctg gtggcaaaat ttcgaatctt ttggctagaa taatgatagt ccttgagcta  32340
ctgaataact ttgccgaaga cgccatcttt ctaagtggcc aggatcctga gatagcttga  32400
```

```
gcttgagctt gagcttgatt ggccgcccgt ggatgctact ccagtatcgc cagatcagct  32460

gcacttacac aaggaaccaa ccgaatgact gcttgggact aacaggcatc ctcagtgtat  32520

aagtgctggt gatcttctat ttttaggcaa caatggcacc tgccacgtca gaatgcagac  32580

caatgagggg aagggggagg aattgatgat gcattgaact gactcccacg tagaccgtat  32640

attccactgc atctacgcca gttcatgcgg gagtgtatgg attgggggaa aggcatggca  32700

gagaggtttg cttttgtggt tagcagactg cctatgtatc aggcgtaagg aaggcgtgcg  32760

cgtggaa                                                            32767

<210> SEQ ID NO 171
<211> LENGTH: 2421
<212> TYPE: DNA
<213> ORGANISM: Aedes aegypti

<400> SEQUENCE: 171

gcggcgctca agatggaaat tcatttttca gcagtactga ataaattgtt ttaggatcaa     60

gaagaaaaat gatgattcct atcggagttt cttcatcgat gtgcaccaat gtttttcttc    120

atggcgacaa aaaactgaac atttcgggct ggttaaattg tgctgtacta accaagatgc    180

aacaactaca aaactgaatc gaaattggga gacagcaatt ccaaataaga atgtcgttcc    240

gtttatttgt cacgatatac atatttcaca actcttggtt gacaataatt ttactctatt    300

ttataatata tctttatttc tcaataaagt ttgcatttgt atgttaatga caaaattcaa    360

tttaattcaa aatagtcata aagaaattta ataaaaaagc tagtcgaaaa gtctatgaaa    420

ctactcattt ttgcgtattt tttagaataa ttgcttccaa gcttgaatac ccaaatatgg    480

gtattgtcag tttacctatt tatgagtaaa cccgcttttt ggcgattatg ggcaaacttt    540

acccatattt gggtagactg ttcttagcgt gtacatctag ggcacccata cccaatgtga    600

tctataagag gtgaagagaa agtcattgtg tgattgtatt agtacaataa aaatcaaaac    660

aaacattgag gggaaaatga gtgacgtcat accgtttcaa cgaaatgctg tgagtggatg    720

taaaacactc catatcgtgg aacaaatcaa gatcacaccg tataaatctg caactaacac    780

ctagatgaaa gagtcgaatg ggtagattcc aggaattatg ttttttcact atattcacgg    840

atgaaagaaa gcacttttct tacttttttc taattatatt caatttgagc actacattta    900

tggatgaatt acgcaaaata tcctttggaa gaaagaacaa tttcagccta ttccagcaca    960

ttatcagttt tgatgatatt tgggttgcct tccgttgtta tatttcctct gttttataat   1020

agatttcatc ctaaaataaa gcaaaactta gcatgaagca aacaacgcat gaattacctg   1080

aaatgccatc tttctgcgac gaatttttttc atgttgttgt ttgaacaaca gcacacagga   1140

caaccttggt aacgataggg ttgctagtaa cgatacctcg aaataaatcg ataacaaact   1200

gtatgacgtc acgcagtggt ggaatgcaat gggttgctgt gtgaaaattt aagcgaccca   1260

ctaacacatg caagcagttg tgtattacac aaaatcatct cctcacctct aataaagcac   1320

attgacccat accattgggc gtgataacca ctataatcga gtaaaaaataa gagagaacag   1380

tggcacgcaa catgattttt cccatttttc cacctgagca aactaagaac attgactacg   1440

gagctcagtc cagcaataat gttaatcata aaaagatgtg atctttttca aagaaaattt   1500

tattagtgtt ttctaagttt tatattgatt tttgtttttg tcgtgcaaat gtgtaaaaaa   1560

agaaatgctg agatcaatgc agaatttgat atcatcaaaa aatattgtat atatatagga   1620

aatattccat tctttgcatc aaagaatgat gtggttgtca aatttgccga atacggcgaa   1680
```

```
acatgtaaca tatatatgca atcaaataaa ccacattgcg acgttaaacc tgcaattgtt   1740

cgatatcgtt cgagaaaaag tgtagacaag tctttgtgtt taaacaattc aaaattcggc   1800

aacacgatat taatagttct accactaagt ttgccttatt caagatatct gctgacctat   1860

gatacttgca ttgtggtata tattaatgat aagaattctt gtaagacatc aatggctgag   1920

ctatatgatg aatttcaaaa aattggtgat attcaaaaca tgtttaaaac gacaaataat   1980

atgatttata taaactttga gtctgaaaag tctatgcaat tatctttagc tactaagccc   2040

tttttaataa ataataatat tttcaaaatc aaaaaagttg aacgaaacat taacatgtgc   2100

ggtctaaatt cagaaagcca ggatttctcc acaaatctaa aaaaaaaact tttgtataat   2160

cgctctattg gaatatttgg attgccatca aatgccacgg aagagcgaat tgcacaaata   2220

ttttcaaggt ttggcgacat tcaaaaaatt acattgatat gcgacgtagt cggcaactcg   2280

aagcaatatg gttttatata ttacaagaaa cgtacttctg ctaatgctgc taaagtgata   2340

atggatggag aaaattttga aggaaataaa atttccgttc gatttgtccc agaaaaaaaa   2400

gtgtttaaaa attaataaag t                                             2421
```

<210> SEQ ID NO 172
<211> LENGTH: 1000
<212> TYPE: DNA
<213> ORGANISM: Aedes aegypti

<400> SEQUENCE: 172

```
cagtccagca ataatgttaa tcataaaaag atgtgatctt tttcaaagaa aattttatta     60

gtgttttcta agttttatat tgatttttgt ttttgtcgtg caaatgtgta aaaaaagaaa    120

tgctgagatc aatgcagaat ttgatatcat caaaaaatat tgtatatata taggaaatat    180

tccattcttt gcatcaaaga atgatgtggt tgtcaaattt gccgaatacg gcgaaacatg    240

taacatatat atgcaatcaa ataaaccaca ttgcgacgtt aaacctgcaa ttgttcgata    300

tcgttcgaga aaaagtgtag acaagtcttt gtgtttaaac aattcaaaat tcggcaacac    360

gatattaata gttctaccac taagtttgcc ttattcaaga tatctgctga cctatgatac    420

ttgcattgtg gtatatatta atgataagaa ttcttgtaag acatcaatgg ctgagctata    480

tgatgaattt caaaaaattg gtgatattca aaacatgttt aaaacgacaa ataatatgat    540

ttatataaac tttgagtctg aaaagtctat gcaattatct ttagctacta agcccttttt    600

aataaataat aatattttca aaatcaaaaa agttgaacga aacattaaca tgtgcggtct    660

aaattcagaa agccaggatt tctccacaaa tctaaaaaaa aaacttttgt ataatcgctc    720

tattggaata tttggattgc catcaaatgc cacggaagag cgaattgcac aaatattttc    780

aaggtttggc gacattcaaa aaattacatt gatatgcgac gtagtcggca actcgaagca    840

atatggtttt atatattaca agaaacgtac ttctgctaat gctgctaaag tgataatgga    900

tggagaaaat tttgaaggaa ataaaatttc cgttcgattt gtcccagaaa aaaaagtgtt    960

taaaaattaa taaagtgata tatgacacac atttgttttt                         1000
```

<210> SEQ ID NO 173
<211> LENGTH: 1190
<212> TYPE: DNA
<213> ORGANISM: Aedes aegypti

<400> SEQUENCE: 173

```
cagatcgaat ctgtcgcttc ggcaaccctt cttcgaacga gtttgatata aacttacagt     60

tttacaaact tttaatagga cgcacgcgcg agtcaaccat gcacttttga caaccacccg    120
```

```
ccgagactcg cgagacgaag cactttcggg aaaaacgctg tcagtctgag ctgtaaaaca    180
aaatggataa tgtttgagag cggtgctttc gagtgaaaaa agttgaaatt attgtgcaaa    240
aaccgtgtta tttctagtgg gaaagtattc taaactgttt agctgttttt ggaaaatagg    300
ttttcaccga aacttccagc tgaatcgtgt gaattgaggt aaaattgtgt ttttttctct    360
gcgctgttta ccccctctat atttccacat tgatcggttt ttgtagattt actgtctcgc    420
aggagagtga tgtcttggcc aaacagttgg caagtgcaac caggttatgc gggatacgct    480
acggcagctg cgcctccatc ggtggctccg gttgcgtctg ctgcggccgc tgcgcttcct    540
ggtggttact cggccatgac tccggaacaa tacgcccaat ggcaacagtg gcaacagtac    600
cagcagcaat acgcccaatg gcatgcccaa tacggggagc agtatgcccg tcaaatgggc    660
aaaccgttgc cggcagtgcc ggctccgatg cccttgcagc atatgggcct agccaccaat    720
gttcctccgc cggcagtggc catggcacaa cccgttcctg ccccggtagt agcccccacc    780
gttgttccta cagcacctcc ggctattgcg gccgttgtgg ggcccgttcc tccggttgct    840
gccgtcgctc cacctatacc aaccatctca gctgcaccgc cgccgcctcc ggaaccccac    900
ccggatagtg ttgctagcca aggtatgtgg aataatttgt gttttccctt atggacaatg    960
aatgaaaaaa aaaagttttg gaagtgtttg acctggaaca tgggaatatc gatagtctaa   1020
tgtgcagtaa ttttgtgtag aacaacaaac agtagagtac aattgaaatt tgtatcaaat   1080
cttgccttta agtttctgt caaggatcgt tcaaaagtta tgtaacgcta taatgtctga   1140
tgagagatcc agtccagttt aatcgaagtg cgttttgtta acatttctaa              1190
```

<210> SEQ ID NO 174
<211> LENGTH: 1122
<212> TYPE: DNA
<213> ORGANISM: Aedes aegypti

<400> SEQUENCE: 174

```
cagatcgaat ctgtcgcttc ggcaaccctt cttcgaacga gtttgatata aacttacagt     60
tttacaaact tttaatagga cgcacgcgcg agtcaaccat gcacttttga caaccacccg    120
ccgagactcg cgagacgaag cactttcggg aaaaacgctg tcagtctgag ctgtaaaaca    180
aaatggataa tgtttgagag cggtgctttc gagtgaaaaa agttgaaatt attgtgcaaa    240
aaccgtgtta tttctagtgg gaaagtattc taaactgttt agctgttttt ggaaaatagg    300
ttttcaccga aacttccagc tgaatcgtgt gaattgagat ttactgtctc gcaggagagt    360
gatgtcttgg ccaaacagtt ggcaagtgca accaggttat gcgggatacg ctacggcagc    420
tgcgcctcca tcggtggctc cggttgcgtc tgctgcggcc gctgcgcttc ctggtggtta    480
ctcggccatg actccggaac aatacgccca atggcaacag tggcaacagt accagcagca    540
atacgcccaa tggcatgccc aatacgggga gcagtatgcc cgtcaaatgg gcaaaccgtt    600
gccggcagtg ccggctccga tgcccttgca gcatatgggc ctagccacca atgttcctcc    660
gccggcagtg gccatggcac aacccgttcc tgccccggta gtagccccca ccgttgttcc    720
tacagcacct ccggctattg cggccgttgt ggggcccgtt cctccggttg ctgccgtcgc    780
tccacctata ccaaccatct cagctgcacc gccgccgcct ccggaacccc acccggatag    840
tgttgctagc caaggtatgt ggaataattt gtgttttccc ttatggacaa tgaatgaaaa    900
aaaaaagttt tggaagtgtt tgacctggaa catgggaata tcgatagtct aatgtgcagt    960
aattttgtgt agaacaacaa acagtagagt acaattgaaa tttgtatcaa atcttgcctt   1020
```

```
taagttttct gtcaaggatc gttcaaaagt tatgtaacgc tataatgtct gatgagagat   1080

ccagtccagt ttaatcgaag tgcgttttgt taacatttct aa                      1122


<210> SEQ ID NO 175
<211> LENGTH: 870
<212> TYPE: DNA
<213> ORGANISM: Aedes aegypti

<400> SEQUENCE: 175

tattgcaatg ccaacaatgt tcattccaga ctagacgtcg ttggtgtaag acgtagttaa     60

gatttgttat tgtgtttttt aattatataa tatcaatatg cttcgctgtt attcctgaag    120

ctgtttcata tggaactcct gcaactgagc tgtaaatatt ccgagatccg gatttactaa    180

aggtaaacat ctttgaacta ttccccaccg atgaaatcgg tgagcaaaat gttaattggt    240

ctctttttc aggaattcag ttatcgattg gtttgatgca cgattgccgg aatcgaaaaa     300

tgcctgatcc cgataaactt aatgttccct gctcccgata gctactaccc tgttcgaagc    360

actgtttgcc gcttccgcca cccaacattc acgattcctg gaaccgagca gctggttatt    420

gttactgaaa aaaaaatccg cgctactccc gacagtagcc actccgtccc gactttggct    480

ccattgaccg ttccagatgc ccttcagggt ttgataaagg cggatatgaa ggttagtgat    540

ttcttctggt cccgagaaaa aaaaaaaaaa caaatcctct tctgtttaaa ggtgtcgagc    600

tttccaatgg cgttcccagt acatgattgc cggccccagt tggttgctat atgtgttttc    660

acccgatcca aattgtttcc tgcaccgatg acgtcgttcc tgccgcccac gctattggct    720

atgcaaacca attcaaaatc aatatatttt ttatgtgttt cctaatgcat cctaataata    780

tttgttttag taatatttta gatgcaattt cattgcattg attccttccg taaattaaag    840

aaaataaatt attttattag tcaagttgaa                                     870


<210> SEQ ID NO 176
<211> LENGTH: 740
<212> TYPE: DNA
<213> ORGANISM: Aedes aegypti

<400> SEQUENCE: 176

tattgcaatg ccaacaatgt tcattccaga ctagacgtcg ttggtgtaag acgtagttaa     60

gatttgttat tgtgtttttt aattatataa tatcaatatg cttcgctgtt attcctgaag    120

ctgtttcata tggaactcct gcaactgagc tgtaaatatt ccgagatccg gatttactaa    180

aggaattcag ttatcgattg gtttgatgca cgattgccgg aatcgaaaaa tgcctgatcc    240

cgataaactt aatgttccct gctcccgata gctactaccc tgttcgaagc actgtttgcc    300

gcttccgcca cccaacattc acgattcctg gaaccgagca gctggttatt gttactgaaa    360

aaaaaatccg cgctactccc gacagtagcc actccgtccc gactttggct ccattgaccg    420

ttccagatgc ccttcagggt ttgataaagg cggatatgaa ggtgtcgagc tttccaatgg    480

cgttcccagt acatgattgc cggccccagt tggttgctat atgtgttttc acccgatcca    540

aattgtttcc tgcaccgatg acgtcgttcc tgccgcccac gctattggct atgcaaacca    600

attcaaaatc aatatatttt ttatgtgttt cctaatgcat cctaataata tttgttttag    660

taatatttta gatgcaattt cattgcattg attccttccg taaattaaag aaaataaatt    720

attttattag tcaagttgaa                                                740


<210> SEQ ID NO 177
<211> LENGTH: 398
```

<212> TYPE: DNA
<213> ORGANISM: Aedes aegypti

<400> SEQUENCE: 177
tgatgtgcgc aacagtggca ttaatgcagc aaataatcac cgagtgggct aaaggaatgg 60
aaaaggcaca atttgccata ttaacgaact aactgaagtg aaataaaacg gacaaggagc 120
gttagaacag tgtagtttga gtgaatcagc aacatgggca ctacggagtc caagaacacg 180
gaaaataaag gtgacccaca ggtccaagta ctcaatagat tagaagtaca cgaaagttta 240
caccagaaaa acgatattaa actgaacatt attctaatac tactaacaac tactaatcat 300
gttttaccgc atgtataagg aacattcacg gaagcaagct ttaaaagctg cgaagagtgt 360
gtcggcttta aataaactaa gtgaggttta aaaaaaaa 398

<210> SEQ ID NO 178
<211> LENGTH: 269
<212> TYPE: DNA
<213> ORGANISM: Aedes aegypti

<400> SEQUENCE: 178
tgatgtgcgc aacagtggca ttaatgcagc aaataatcac cgagtgggct aaaggaatgg 60
aaaaggcaca atttgccata ttaacgaact aactgaagtg aaataaaacg gacaaggagc 120
gttagaacag tgtagtttga gtgaatcagc aacatgggca ctacggagtc caagaacacg 180
gaaaataaag gaacattcac ggaagcaagc tttaaaagct gcgaagagtg tgtcggcttt 240
aaataaacta agtgaggttt aaaaaaaaa 269

<210> SEQ ID NO 179
<211> LENGTH: 1088
<212> TYPE: DNA
<213> ORGANISM: Aedes aegypti

<400> SEQUENCE: 179
acgaatatga cccggcaaaa aataggctgg gatcatatta cattctgaac acgcaaacag 60
cgtgtggtcg tcaagcgcaa ttcggtttgg cgcaattagc cttctccgta tctctctctc 120
tgagcattct cttttccggt gtcgatcact gattggtgat caaatacata acaatacata 180
agtgctttca agtgtctccg aactaaataa gtgtcagaat aattttggat aactgaataa 240
atcaattctg tcttgaccct caaaccgaga ggttcgtttg ccattttaat tatcgaggat 300
gatgacaacc aaaaaggaga tttctctaca tggctaccaa agtgacaggc taccaaagtg 360
aaaaagtgtg aaaaacagtt gtgaagattt tgaagtgaag attttgcacc atgacggtga 420
catcgatctt aattataatg ctagcattaa ttttgatgtg cgcaacagtg gcattaatgc 480
agcaaataat caccgagtgg gctaaaggaa tggaaaaggc acaatttgcc atattaacga 540
actaactgaa gtgaaataaa acggacaagg agcgttagaa cagtgtagtt tgagtgaatc 600
agcaacatgg gcactacgga gtccaagaac acggaaaata aaggtgaccc acaggtccaa 660
gtactcaata gattagaagt acacgaaagt ttacaccaga aaaacgatat taaactgaac 720
attattctaa tactagtagt actacaacta ctaatcatgt tttaccgcat gtataaggaa 780
cattcacgga agcaagcttt aaaagctgcg aagagtgtgt cggctttaaa taaactaagt 840
gaggtttaaa aaaaaaaaaa aagtacaaac agtgtcgaac tcgaaaaacg gtcagttttt 900
tttttcaggc atctatctcg cctctaagag ataaacagtg gggcagtagc ccataattaa 960
gaaagtagcc gaatctaaca tgatgaatga acgcgagacc cttgcctaag gccggcaaca 1020
gtagcagcga atagcagcag aaaagtgaat catcattaaa agcgagcgta gaggagtgcg 1080
cctccgcc 1088

<210> SEQ ID NO 180
<211> LENGTH: 954
<212> TYPE: DNA
<213> ORGANISM: Aedes aegypti

<400> SEQUENCE: 180
acgaatatga cccggcaaaa aataggctgg gatcatatta cattctgaac acgcaaacag 60
cgtgtggtcg tcaagcgcaa ttcggtttgg cgcaattagc cttctccgta tctctctctc 120
tgagcattct cttttccggt gtcgatcact gattggtgat caaatacata acaatacata 180
agtgctttca agtgtctccg aactaaataa gtgtcagaat aattttggat aactgaataa 240
atcaattctg tcttgaccct caaaccgaga ggttcgtttg ccattttaat tatcgaggat 300
gatgacaacc aaaaaggaga tttctctaca tggctaccaa agtgacaggc taccaaagtg 360
aaaaagtgtg aaaaacagtt gtgaagattt tgaagtgaag attttgcacc atgacggtga 420
catcgatctt aattataatg ctagcattaa ttttgatgtg cgcaacagtg gcattaatgc 480
agcaaataat caccgagtgg gctaaaggaa tggaaaaggc acaatttgcc atattaacga 540
actaactgaa gtgaaataaa acggacaagg agcgttagaa cagtgtagtt tgagtgaatc 600
agcaacatgg gcactacgga gtccaagaac acggaaaata aaggaacatt cacggaagca 660
agctttaaaa gctgcgaaga gtgtgtcggc tttaaataaa ctaagtgagg tttaaaaaaa 720
aaaaaaaagt acaaacagtg tcgaactcga aaaacggtca gttttttttt tcaggcatct 780
atctcgcctc taagagataa acagtggggc agtagcccat aattaagaaa gtagccgaat 840
ctaacatgat gaatgaacgc gagacccttg cctaaggccg gcaacagtag cagcgaatag 900
cagcagaaaa gtgaatcatc attaaaagcg agcgtagagg agtgcgcctc cgcc 954

<210> SEQ ID NO 181
<211> LENGTH: 417
<212> TYPE: DNA
<213> ORGANISM: Aedes aegypti

<400> SEQUENCE: 181
atcatactct tgatgatctc ggctcggagt attgcttgga gaatgccaat aacgaatcca 60
ctgaagcgtt tccaacgaaa caagttatcg ttgaaggtga gttggttttc tttttatata 120
acaaagcata taaccacggc ataaaaatta acaaggcagt ctcttcactg atgtaaatat 180
cgagtttcat tataaacatg tgacgtcact cctatcgtac catatacctt ccggaccact 240
agatcatttt tttcgcaaat ttgttcgagg tggataggaa tgacgtcgtc aagtagctgt 300
cagttttcgg agtatatcac cttcttaatt ttagtacacc gtgcatataa catgtaatat 360
attccatgca aaccataaag gagagacagc aacgcttcca gaacatacgg gaaacac 417

<210> SEQ ID NO 182
<211> LENGTH: 133
<212> TYPE: DNA
<213> ORGANISM: Aedes aegypti

<400> SEQUENCE: 182
atcatactct tgatgatctc ggctcggagt attgcttgga gaatgccaat aacgaatcca 60
ctgaagcgtt tccaacgaaa caagttatcg ttgaaggaga gacagcaacg cttccagaac 120
atacgggaaa cac 133

<210> SEQ ID NO 183
<211> LENGTH: 1302
<212> TYPE: DNA
<213> ORGANISM: Aedes aegypti

<400> SEQUENCE: 183
gtcccatgag cgacagttgt caaaataaat gaaaaaagtg gatacgacgc tcgtgtaata 60
ttgattttat ttcattaaac atattgttta tcaatatttt cacgtctaca ccaagccaca 120
caatcaacaa gacaaaaaca gctatggttc cgaataagct actacacgat gaacgtaagc 180
gtaagactgt ctgtacatat aatatatttg tataactatt tgcatttaca gatcacgaag 240
ccttcgcatc cgttatacct tctagtaatc catatttaat ttcaaacaca tccgaagata 300
tggttcaaga tgcgtctttc atcaatatcg tcacttcaac accgagctca acacctcttc 360
ccgaacctcg cccggaatat caacagacta ctttctctgc tctggccaac gaatcagcga 420
caacaaacaa agagtttata tcgaaaaaac gattatttga ttgtgaagac agtaagcgat 480
tgttcaagga aaatgatctg gatgtacgat tcgagtagcg attgtgacga ttctgattgg 540
aatttggata aagtatccga tacaacagac ggtagcgacc aggaaggtga tgcatctgat 600
ttagctgacc tttctattta cgagtatttc caaaagtatc atactcttga tgatctcggc 660
tcggagtatt gcttggagaa tgccaataac gaatccactg aagcgtttcc aacgaaacaa 720
gttatcgttg aaggtgagtt tgttttcttt ttatatataa caaaacatat aacatgtaat 780
atattccatg caaaaccata aaggagagac agcaacgctt ccagaacata cgggaaacac 840
tccgaggatc aacataagta tccaagtcgt cgacgatatg gtcaaagaat gtttggaacc 900
aatcattagc aaggccgaaa tgcgagcaac aaacagaaga cgaaaggaaa gaggcttgga 960
atacactcgg ccagatggcg taatcgtacg agcgagagaa cttagacctc cttttaattg 1020
taagcgtaaa tgcagcgaaa agtatcccga ctccatccgc tcaaagcttt tagaacagtt 1080
attgagtgtg aagctatccg gacagaacca gttcttggcc aaccatatgg tggtgtccaa 1140
aacagcacga tcgaaggaaa atattgtaaa tttttcagca attccataaa aaaagcaggg 1200
ttgatagcag gtctcttcga agagacattg tctctatttt aatgcaagtc tcttaaaagt 1260
accgttttga ttcatattac ggacagcttc aaattccgga ca 1302

<210> SEQ ID NO 184
<211> LENGTH: 1175
<212> TYPE: DNA
<213> ORGANISM: Aedes aegypti

<400> SEQUENCE: 184
gtcccatgag cgacagttgt caaaataaat gaaaaaagtg gatacgacgc tcgtgtaata 60
ttgattttat ttcattaaac atattgttta tcaatatttt cacgtctaca ccaagccaca 120
caatcaacaa gacaaaaaca gctatggttc cgaataagct actacacgat gaacatcacg 180
aagccttcgc atccgttata ccttctagta atccatattt aatttcaaac acatccgaag 240
atatggttca agatgcgtct ttcatcaata tcgtcacttc aacaccgagc tcaacacctc 300
ttcccgaacc tcgcccggaa tatcaacaga ctactttctc tgctctggcc aacgaatcag 360
cgacaacaaa caaagagttt atatcgaaaa aacgattatt tgattgtgaa gacagtaagc 420
gattgttcaa ggaaaatgat ctggatgtac gattcgagta gcgattgtga cgattctgat 480
tggaatttgg ataaagtatc cgatacaaca gacggtagcg accaggaagg tgatgcatct 540

```
gatttagctg acctttctat ttacgagtat ttccaaaagt atcatactct tgatgatctc    600

ggctcggagt attgcttgga gaatgccaat aacgaatcca ctgaagcgtt tccaacgaaa    660

caagttatcg ttgaaggaga gacagcaacg cttccagaac atacgggaaa cactccgagg    720

atcaacataa gtatccaagt cgtcgacgat atggtcaaag aatgtttgga accaatcatt    780

agcaaggccg aaatgcgagc aacaaacaga agacgaaagg aaagaggctt ggaatacact    840

cggccagatg gcgtaatcgt acgagcgaga gaacttagac ctccttttaa ttgtaagcgt    900

aaatgcagcg aaaagtatcc cgactccatc cgctcaaagc ttttagaaca gttattgagt    960

gtgaagctat ccggacagaa ccagttcttg gccaaccata tggtggtgtc caaaacagca   1020

cgatcgaagg aaaatattgt aaatttttca gcaattccat aaaaaaagca gggttgatag   1080

caggtctctt cgaagagaca ttgtctctat tttaatgcaa gtctcttaaa agtaccgttt   1140

tgattcatat tacggacagc ttcaaattcc ggaca                              1175
```

```
<210> SEQ ID NO 185
<211> LENGTH: 306
<212> TYPE: DNA
<213> ORGANISM: Aedes aegypti

<400> SEQUENCE: 185

tttatggagt gaaaactttg aatattttgc cacgaattat atatcattaa tttgtagaaa     60

gaatcatggt aagtaactgt tttttgaaca aactatttac atcaaaggct taattcactt    120

ctcctcaaca cagaaccctc gaagaaacat ggaaagcggc aattagagag cgtttttttc    180

atccgggatc tggaacagga agatatggag taagagacac ggacaatgaa aaattcaacg    240

taaaagtatc ccaattagca gtttattcat aagtaatcat ctaataaaat gatgttcatt    300

agacta                                                               306
```

```
<210> SEQ ID NO 186
<211> LENGTH: 241
<212> TYPE: DNA
<213> ORGANISM: Aedes aegypti

<400> SEQUENCE: 186

tttatggagt gaaaactttg aatattttgc cacgaattat atatcattaa tttgtagaaa     60

gaatcatgaa ccctcgaaga aacatggaaa gcggcaatta gagagcgttt ttttcatccg    120

ggatctggaa caggaagata tggagtaaga gacacggaca atgaaaaatt caacgtaaaa    180

gtatcccaat tagcagttta ttcataagta atcatctaat aaaatgatgt tcattagact    240

a                                                                    241
```

```
<210> SEQ ID NO 187
<211> LENGTH: 468
<212> TYPE: DNA
<213> ORGANISM: Aedes aegypti

<400> SEQUENCE: 187

actttaaagt acccattaaa tgggtttctt gtacccattt ttattgttag tactgagttg     60

tcagaaaaag ggtattattt tttgacatta aaaagggtac attttactct tcttgaagaa    120

tgagatccgt caacaataat gggtaaaaaa gccacttgtc gttatatgga gtgaaaactt    180

tgaatatttt gccacgaatt atatatcatt aatttgtaga aagaatcatg gtaagtaact    240

atttttgaa caaactattt acatcaaagg cttaattcac ttctcctcaa cacagaaccc    300

tcgaagaaac atggaaagcg gcaattagag atcgtttttt tcatccggga tctggaacag    360
```

```
gaagatatgg agtaagagac acggacaatg aaaaattcaa cgtaaaagta tcccaattag    420

cagtttattc ataagtaatc atctaataaa atgatgttca ttagacta                 468


<210> SEQ ID NO 188
<211> LENGTH: 403
<212> TYPE: DNA
<213> ORGANISM: Aedes aegypti

<400> SEQUENCE: 188

actttaaagt acccattaaa tgggtttctt gtacccattt ttattgttag tactgagttg     60

tcagaaaaag ggtattattt tttgacatta aaaagggtac attttactct tcttgaagaa    120

tgagatccgt caacaataat gggtaaaaaa gccacttgtc gttatatgga gtgaaaactt    180

tgaatatttt gccacgaatt atatatcatt aatttgtaga aagaatcatg aaccctcgaa    240

gaaacatgga aagcggcaat tagagatcgt ttttttcatc cgggatctgg aacaggaaga    300

tatggagtaa gagacacgga caatgaaaaa ttcaacgtaa aagtatccca attagcagtt    360

tattcataag taatcatcta ataaaatgat gttcattaga cta                      403


<210> SEQ ID NO 189
<211> LENGTH: 336
<212> TYPE: DNA
<213> ORGANISM: Aedes aegypti

<400> SEQUENCE: 189

acaataatgg gtaaaaaagc cacttgtcgt tatatggagt gaaaactttg aatattttgc     60

cacgaattat atatcattaa tttgtagaaa gaatcatggt aagtaactat tttttgaaca    120

aactatttac atcaaaggct taattcactt ctcctcaaca cagaaccctc gaagaaacat    180

ggaaagcggc aattagagag cgtttttttc atccgggatc tggaacagga agatatggag    240

taagagacac ggacaatgaa aaattcaacg taaaagtatc ccaattagca gtttattcat    300

aagtaatcat ctaataaaat gatgttcatt agacta                              336


<210> SEQ ID NO 190
<211> LENGTH: 271
<212> TYPE: DNA
<213> ORGANISM: Aedes aegypti

<400> SEQUENCE: 190

acaataatgg gtaaaaaagc cacttgtcgt tatatggagt gaaaactttg aatattttgc     60

cacgaattat atatcattaa tttgtagaaa gaatcatgaa ccctcgaaga aacatggaaa    120

gcggcaatta gagagcgttt ttttcatccg ggatctggaa caggaagata tggagtaaga    180

gacacggaca atgaaaaatt caacgtaaaa gtatcccaat tagcagttta ttcataagta    240

atcatctaat aaaatgatgt tcattagact a                                   271


<210> SEQ ID NO 191
<211> LENGTH: 663
<212> TYPE: DNA
<213> ORGANISM: Aedes aegypti

<400> SEQUENCE: 191

ggcagtccta gacgttcagc gcgtggagaa gtaagccaac cggaagttgg cgtaccctgg     60

gggactgttg gcctacccta ttaggtcagc gcgcacgtct atcattgtgg cctctttaat    120

gcttgcaatc ctgcatgcaa gactggggct gtaatggtat gacagaggag tgacaggtac    180
```

```
gcgacctgtc accgggtgag tcaacaatga aaaataagta ttaactgaac tatgcagagt    240

tgattacctt atgctatatt attagaaact tgaaagtagt gtaaaaatca ttgaaatcga    300

acttaaatct agtggacgaa acttctacat atctacaacc agaatcggta aaaatattta    360

aatttacagt gaaattagat caaaaacatt atgcttacat attaggtaac ctaaattgtg    420

cctcgttgcc ccacttcatt gctacacaaa ggacagtttc ctactatcaa aaccggtaag    480

gactaaactt aacgaacatc tttgaaacat atcaaacata tattgtaatt actaggacta    540

ccactaattt gctttgaacg gacacaatgt tacacaaagg gaactaaacg taagtaaaca    600

ttgttacagt taaggtcctt taccctatga gagaggctct agtaggtaga gaaggtgagc    660

gcc                                                                  663

<210> SEQ ID NO 192
<211> LENGTH: 545
<212> TYPE: DNA
<213> ORGANISM: Aedes aegypti

<400> SEQUENCE: 192

ggcagtccta gacgttcagc gcgtggagaa gtaagccaac cggaagttgg cgtaccctgg     60

gggactgttg gcctacccta ttaggtcagc gcgcacgtct atcattgtgg cctctttaat    120

gcttgcaatc ctgcatgcaa gactggggct gtaatggtat gacagaggag tgacaggtac    180

gcgacctgtc accgggtgag tcaacaatga aaaataagta ttaactgaac tatgcagagt    240

tgattacctt atgctatatt attagaaact tgaaagtagt gtaaaaatca ttgaaatcga    300

acttaaatct agtggacgaa acttctacat atctacaacc agaatcggta acctaaattg    360

tgcctcgttg ccccacttca ttgctacaca aaggacagtt tcctactatc aaaaccggac    420

taccactaat ttgctttgaa cggacacaat gttacacaaa gggaactaaa cgtaagtaaa    480

cattgttaca gttaaggtcc tttaccctat gagagaggct ctagtaggta gagaaggtga    540

gcgcc                                                                545

<210> SEQ ID NO 193
<211> LENGTH: 728
<212> TYPE: DNA
<213> ORGANISM: Aedes aegypti

<400> SEQUENCE: 193

tgcatattga ccaccggaca ccggatgttg gcctacccta ttaggccagc gcgcacgtct     60

atcattgtgg cctctttaat gcttgcaatc ctgcatgcaa gactggggct gtaatggtat    120

gacagaggag tgacaggtat gcgacctgtc accgggtgag tcaacaatga aaaataagta    180

ttaactgaac tatgcagagt tgattacctt atgctatatt attagaaact taaaaatagt    240

gtaaaaatca ttgaaatcga acttaaatct agtggacgaa acttctacat atctacaacc    300

agaatcggta aaaatattta aatttacagt gaaattagat caaaaacatt atgcttacat    360

attaggtaac ctaaattgtg cctcgttgcc ccacttcatt gctacacaaa ggacagtttc    420

ctactatcaa aaccggtaag gactaaactt aacgaacatc tttgaaacat atcaaacata    480

tattgtaatt actaggatta ccactaattt gctttgaacg gacacaatgt tactcaaagg    540

gaactaaacg taagtaaaca tgagaattga aattcatatg cacacttccc acaggggttc    600

acaaacttat cgtggcgtac cacacgccct aaactatatt tattttaaga aattaaaatg    660

atactaaaat gaatttatac gttccaacta ggaaaattat attctccttt gcaaccacaa    720

ctggatcg                                                             728
```

<210> SEQ ID NO 194
<211> LENGTH: 610
<212> TYPE: DNA
<213> ORGANISM: Aedes aegypti

<400> SEQUENCE: 194
tgcatattga ccaccggaca ccggatgttg gcctacccta ttaggccagc gcgcacgtct 60
atcattgtgg cctctttaat gcttgcaatc ctgcatgcaa gactggggct gtaatggtat 120
gacagaggag tgacaggtat gcgacctgtc accgggtgag tcaacaatga aaaataagta 180
ttaactgaac tatgcagagt tgattacctt atgctatatt attagaaact taaaaatagt 240
gtaaaaatca ttgaaatcga acttaaatct agtggacgaa acttctacat atctacaacc 300
agaatcggta acctaaattg tgcctcgttg ccccacttca ttgctacaca aaggacagtt 360
tcctactatc aaaaccggat taccactaat ttgctttgaa cggacacaat gttactcaaa 420
gggaactaaa cgtaagtaaa catgagaatt gaaattcata tgcacacttc ccacaggggt 480
tcacaaactt atcgtggcgt accacacgcc ctaaactata tttattttaa gaaattaaaa 540
tgatactaaa atgaatttat acgttccaac taggaaaatt atattctcct ttgcaaccac 600
aactggatcg 610

<210> SEQ ID NO 195
<211> LENGTH: 753
<212> TYPE: DNA
<213> ORGANISM: Aedes albopictus

<400> SEQUENCE: 195
agttttccat acaagaagga tggcgtcagc acggtcatct atttaccaag attagcacgg 60
tcatctattt accaagatta ttcggaggaa catcccagaa aattgattcc agagctgtgc 120
aaacaatttt atcatcttgg atgggttaca ggaactggtg gaggcatcag catcaagctt 180
gatgatgaaa tttatattgc tccctctgga gttcaaaagg aacggattct gcctgatgat 240
ttattcattc aaaatatcga cggcgatgat ctgcagctgc caccggatta taaaaaattg 300
acaaaaagcc aatgtacgcc tctattcatg ctagcgtatc gtgacaggaa tgctggagct 360
gtcattcaca cccatagcca gtctgccgtg atggccactc tcttgtggtc cggacgcgaa 420
tttcgatgca ctcatttgga aatgataaag ggaatttacg atcatgaatt agaacgtaac 480
ctacggttcg acgaggaatt aattgttcca ataattgaaa atacgccatt tgaaaaagat 540
ttagaagaac ggatgggata tgtaatgaac gaataccctg gaacctccgc agttcttgtc 600
aggcgacatg gagtatatgt atggggtcaa acttggcaga aggctaaagc aatggcagag 660
tgctacgatt acttgttttc tctggctgta gaaatgaaga agcttggact tgaccctaat 720
gaagtaccaa agtactatag aagcaccaaa taa 753

<210> SEQ ID NO 196
<211> LENGTH: 4947
<212> TYPE: DNA
<213> ORGANISM: Anopheles gambiae

<400> SEQUENCE: 196
ggtgcgaggg gggagttgac gtcgtataaa cagttgcccg tgtcgggctg tcagtcgttc 60
gcaccgtgtc gcagcttcca tatcgctcag cacacaatcc gaagccttct ccggcttctt 120
ccaggcttct cccgggacaa gcaagtgtgt gtgcttgagt gcgtgcgtgt gtgtgtgtgt 180

```
acgagtttgt gttgtcgctt atctcctagg gtctccccag cccctccccc caaaagcatc    240
gcgagggcat ggcatcggga aggtcatcca tctatcagga tctgtccgag gtacgttcga    300
ttccggagtt cgggtgagtc caggaagtgg ggaccgtgct tgtagtgcga acccaaaagc    360
agcatataaa agcaaaaaaa aagaaggaaa ttgggaggac gtacacggga cgggggattt    420
tatttgaacg cacctctctc tctatctctg cttaggaaag gaatgaatga aacagacacg    480
gtttttactt tccgttctcc aatatttaat cttttgttta accacttgta ccacatcctc    540
cctgccccaa ccacctccct ctcaatgtat ctctctctat ctctatatcc cggtgttgcg    600
taggatatgt ttgttctagc aatgtctgat aatttagact agaaatctca cctttaagcc    660
ggtctttagc agccacagac acatacacac acaggtacac ccagtacatt tcctgagaat    720
taaggctatc aattaagagg cacacgttgt cgcaaaactc ccccgcattg attggagcaa    780
attgtggtgt tttttttttg ttttccggga aaatccgcgg acgctcgatt ggttccagcg    840
ccaccgaaca aatcgtttcg caaccaacgc ggagctattg aggtttcgat aagtgggtcc    900
ttattgtggg atgggattgg gggaggagga ggaggaggag gaggaagaga agatggggag    960
gagctgaagg agtcgatcga ttttggggct gatgtgatgt aaggcaccga ccggggaacc   1020
ggacggagaa atcaataatg cgcgttccgc ggcgccgcta accaggatga gcacacgagc   1080
acgtgcgccg agacaggtgt atgtgtgttt gtatgtgtgt ggctgtgtgt gtgtgtctcg   1140
taaaagattt ttcctttcct taagcagtag ggtaattcta gacacaatag ccacttgttt   1200
cccgaccgtt ctttttggtt ttcttcttct ttgttccttt ttctggttgg tttttcaaca   1260
ctttcttccc ttcctttggt ggagcccctt ctgtctgtgt gtgtgtgtgt gtttgtgtta   1320
aattcacaca aaatagtaca accgttcgac caacacgacc acgtgcgctg tgcaggggct   1380
gacggtaagg gtccgaacta atgttgggtt tgatgtatat ttcgatgaaa ttcattcgta   1440
tgaatcttca gtgatgagtg attcaaactt tgaattgaat cttcaaagag tcatgaatct   1500
ctcaaaatag gcgaatgagg ccaatgcccg cgtacagacg acgcccacgg gtctgcccag   1560
gcccgagggc agagccgata gcatacgatt atatcttctc catgaacgta agagggatag   1620
ctgaagtgct gctatttgat acgcgcacat gtttaacgaa caaatctatt cggttcgggt   1680
cggtaatcgt cgggtggacg ccggaacgca agggagttga ctttttcatg attttgtatg   1740
acgtctgttg ttttggacct catgtgtgga cgcttgcaat cggctcaaaa tgagtgtaaa   1800
aataaataaa aacaaatgaa tctctaaaga tccatgaatc ttcaagaatc atgaatctct   1860
aagtattcat gaatcttcaa gaattcgtga atctgtaagt atacatgaat ttccaaaaat   1920
tcatggatct ccaagaattt catgaatttc caagaattca tgactctcca agaattcatg   1980
aatctcttga gattcatgga tctgtaagat tcataaatcc attaaaattg atatatctgc   2040
agggattcat gagcctttag agatgtataa tttccaaaat attgaatttg tccaattcct   2100
cctaaaactt gcccgttgtt ggttcaagcc tagcatggac cgcccccccc cccccccctcc   2160
cgtagcaata caaactatcc ggttgcgtgg tattttccaa gaagtctcga aagcctctat   2220
aggctggcat gaccacgtag gttgttacgt caagaagatg aataaaaaag tcaaagtttt   2280
tttcggtatt tagagattta tgaatcccac gagattcatg gatctttaga gattcttgaa   2340
tctttcgaga cataagagtc tgtcgagata taagaatctt tcgagattta tgatcctttc   2400
gaagttgatg aatcttacga gattaatgta tctctgaagt tcatgaatct tttaaaattc   2460
attaatgttt gagattcatg aatctttcca tccaagattc agattcattg aaagatttca   2520
acgattcatt cagaatcatg aatcggaatc agatgtaccc aatactagtt cgaaccgaac   2580
```

```
cgcaattctt gtcgtcgctg ttatcgccgc tgtgcttcct gcatgcttat gctaacatac   2640
aaaagcaaca tacaaaaaac acccacacac acacacccac acacacacac acacacacac   2700
acacacacac acacacacac acacacacac acacacacac acacacacac acacacacac   2760
acacacacac agagttgagt ctcttgtcca acaatcaaat ccaatctaaa acgccctacc   2820
gcttcccact atcctccctg tctaaaaaga ctgacataat cgttccacaa aaaccctctt   2880
cccctccctt ccgcggatcg cccgcacggc agccacaaat aacacaagca cttaacttaa   2940
aataacacta aaaaaataaa gatcaccctt ggtaatgaat gtaccttttc ttttcttgat   3000
ttgcctctgt tgtgtccggt tattctcctc gctcgtatta gatttatgat aatgtaatca   3060
ataaggtaaa tttcatatac acacattgcc actgtttttt ttttgttttt cgttgtttag   3120
ttcaccatgc gcgatttatg cgatggcttt tcgtttcgtt gttctgtgtg tttttttttt   3180
agttttctct tgactgtttg ttgtgttttt ctgttgattt atttttttatt tcgttgtcgt   3240
ttgtcggctg agaaaaccag cgctctaact tacaatctct ttgctgtctg ttctgtcttt   3300
cccacccatt gtcaacttaa tcatcatgga tgccaaacat cggcgctggc gttcccttgt   3360
cctgtgcagg agcatccccg caagctgata ccggagctgt gcaaacagtt ctacaacctc   3420
ggatgggtga ccggcaccgg tggcggtata agtattaagc tggagttcgt atagttcttg   3480
ccttttggtc cctccgtaca cctcatcacc tggaatgccg tattttctaa tgttttcttt   3540
tttttctttg cttttttgct tcttccctct tccgtttcag cgatgaaatc tacattgccc   3600
cgtccggcgt gcagaaggag cggatccagc cggacgatct cttcatacag aacatcgagg   3660
gggacgatct gcaaacgcca ccggactaca aaaagtaacg ctgcccgggc gaaagcaaaa   3720
acccccattg gcccatatta tattttgccc gtttgtttga tgtttttttt tttttttttg   3780
tcgccagact aacgaagagc cagtgcacgc cactgtttat gctcgcgtac aaggagcgca   3840
gcgccggggc ggtaatccac acgcacagcc cggccgccgt catgaccacg ctgctctggc   3900
cgggcaagga gttccgctgc acgcatctcg agatgatcaa gggcatctac gactacgagc   3960
tgaaccgcaa tctcatgtac gacgaggagc tggtggtgcc gatcatcgag aacacgctgt   4020
tcgagaagga cctggaggag tcgatggcga acgcgctgcg cgactacccg gggacgtctg   4080
cgatcctggt gcgccgccac ggcgtgtacg tgtggggcca caactggcag aaggcaaaga   4140
cgatgtacgt tttcgagggt catttttgtg tgtgtgtgtg tgtctttttt ccaatagaat   4200
gtaattttat gttttctttc taccccttc tagggcggag tgctacgact atctgttctc   4260
gctcgccgtg gaaatgcaca aggtgggcct ggacgcgaac gccgtcccga aacggtacta   4320
gatgcgacga acgcattcac acaccctgcc tcctcccgca aaaacaaaac cccccgcaag   4380
gataatcacc gactcccgcc tcgtgagcca cgtggatgca tgataatcga atagtggacg   4440
tagcgaatta gttgttatca tggcctagcc gtgaattttt tcctaccaca cgatcaaaca   4500
cacagaaaga cacacacaca cacacacacg cattgcgcca atttttctca ggcctttacc   4560
gaatacccgt acccagaggt gttttgcctt ccgtttgtcg tgcgttgttg tattaattat   4620
tgattttaaa caaaaaaatg taaccacaaa cacacacgca cccccacagg cacaagtagg   4680
gaaaagttgc acaaccacag tgatttttac agaatgcaaa tgtggtagca aaagaaagaa   4740
agagagagga agagagagag agagagagag agagagagag agagagaaag agagagaaga   4800
gggaaaggcc acattcgctc atcgaggctt tttgcatacg acaaaacgaa ccgtgataga   4860
agcgcgcgcg cacacaccca caccctcaca catacacaca cacaatacac atttttgtac   4920
```

```
gaacggtttt tagtgtaggt actttttt                                    4947

<210> SEQ ID NO 197
<211> LENGTH: 1570
<212> TYPE: DNA
<213> ORGANISM: Anopheles gambiae

<400> SEQUENCE: 197

ggtgcgaggg gggagttgac gtcgtataaa cagttgcccg tgtcgggctg tcagtcgttc     60

gcaccgtgtc gcagcttcca tatcgctcag cacacaatcc gaagccttct ccggcttctt    120

ccaggcttct cccgggacaa gcaagtgtgt gtgcttgagt gcgtgcgtgt gtgtgtgtgt    180

acgagtttgt gttgtcgctt atctcctagg gtctccccag cccctccccc caaaagcatc    240

gcgagggcat ggcatcggga aggtcatcca tctatcagga tctgtccgag gagcatcccc    300

gcaagctgat accggagctg tgcaaacagt tctacaacct cggatgggtg accggcaccg    360

gtggcggtat aagtattaag ctggacgatg aaatctacat tgccccgtcc ggcgtgcaga    420

aggagcggat ccagccggac gatctcttca tacagaacat cgagggggac gatctgcaaa    480

cgccaccgga ctacaaaaaa ctaacgaaga gccagtgcac gccactgttt atgctcgcgt    540

acaaggagcg cagcgccggg gcggtaatcc acacgcacag cccggccgcc gtcatgacca    600

cgctgctctg gccgggcaag gagttccgct gcacgcatct cgagatgatc aagggcatct    660

acgactacga gctgaaccgc aatctcatgt acgacgagga gctggtggtg ccgatcatcg    720

agaacacgct gttcgagaag gacctggagg agtcgatggc gaacgcgctg cgcgactacc    780

cggggacgtc tgcgatcctg gtgcgccgcc acggcgtgta cgtgtggggc cacaactggc    840

agaaggcaaa gacgatggcg gagtgctacg actatctgtt ctcgctcgcc gtggaaatgc    900

acaaggtggg cctggacgcg aacgccgtcc cgaaacggta ctagatgcga cgaacgcatt    960

cacacaccct gcctcctccc gcaaaaacaa aaccccccgc aaggataatc accgactccc   1020

gcctcgtgag ccacgtggat gcatgataat cgaatagtgg acgtagcgaa ttagttgtta   1080

tcatggccta gccgtgaatt ttttcctacc acacgatcaa acacacagaa agacacacac   1140

acacacacac acgcattgcg ccaatttttc tcaggccttt accgaatacc cgtacccaga   1200

ggtgttttgc cttccgtttg tcgtgcgttg ttgtattaat tattgatttt aaacaaaaaa   1260

atgtaaccac aaacacacac gcacccccac aggcacaagt agggaaaagt tgcacaacca   1320

cagtgatttt tacagaatgc aaatgtggta gcaaaagaaa gaaagagaga ggaagagaga   1380

gagagagaga gagagagaga gagagagaga aagagagaga agagggaaag gccacattcg   1440

ctcatcgagg ctttttgcat acgacaaaac gaaccgtgat agaagcgcgc gcgcacacac   1500

ccacaccctc acacatacac acacacaata cacatttttg tacgaacggt ttttagtgta   1560

ggtacttttt                                                          1570

<210> SEQ ID NO 198
<211> LENGTH: 2571
<212> TYPE: DNA
<213> ORGANISM: Culex quinquefasciatus

<400> SEQUENCE: 198

atggcactat ccgccgtaat actgggactg tacgtagtgg aggcgataat ggcgagaatc     60

ggagcaggga gcgtagcggt tcacaccgga cgagccactg cgagaaagag caggagcgat    120

cgcgtaggca gcagagtggg tatgaagaag aagaagatga gactagctta gcctaaggcg    180

agagtaccta gaacagccct ctgtcacgac ggccatgttt atgaaaccta aatgtttgac    240
```

```
gcgaacatga aaacaacaaa gaagatgaag aacgcagttg ctgtcaaaat ttgaaaataa    300
acaaaccgcg tggtaaaaaa aagcataatt tcataatgtt gaaatgattt ccatgaaaaa    360
ataacgacat gggacggatt tccaaacaca agttcccgaa ggaccctatc caccagagac    420
tatggataaa tgccccgcgt agtggcgatg aagacggttt tgcaagttca aagttcagat    480
ttgttcggac cacttcgcga tgaacttctt gtgagtccac aataggtcgg attctacaca    540
agcacgcgat tccttcgact ccctaggcga gtcgacagcg ggagtgggcc agtcctcgaa    600
gaaggttatc gaaggatgct cggagagacc agctccgcca caatcaccgt aatcacggat    660
gtttctgcac atggtcggtt atccctgccg gagattgcag cgagttgttc ggaaggatca    720
acagcgggac ttggccagtc cccggtccag tactacccgg caaatcttcc cggtcaatcg    780
gaagcaacag ttctcatcat ttttcgtaac agatttgcac acacaaaaag tgatgtttct    840
tgaagatgtg gtgtaaacaa acagacaaca ccaatattgc tacactcaca gagcccacgc    900
agtaatatta gtgaagagcc cacgataaac aacgtgggct cttcaccaat actactacgt    960
gggctcttcg aggttttggt gactgcagcc ctctgtcacg acggccatgt ttatgaaacc   1020
taaatgttcg acgcaaacat gaagacaaca aataagacga agaaggcatt tgctgtcaaa   1080
atttgaaaat aaacaaaccg cgtggtgaaa aaaggcataa tttcataatg ttgaaatgat   1140
ttccatgaaa aataacgaca cgggacggat ttccaaacac aagttcccga aggaccctat   1200
ccgccagaga ctatggataa atgccccgcg aaattgcgat aaagccggtt ttgcatgctc   1260
gaagttcaga tttgttcgaa ccacttcgcg atgaacttct tgtgattcca caaaaggtcg   1320
gattctacac aagcacgcga ttccttcgat tccctgtgcg agttgatagc gggagtggga   1380
cagtcctcag agaaggttat cgaaggatgc tcggaaagac cagctccgcc acaatcaccg   1440
gaatcacgga tgtttctgca catggtcggt taatccctgc cagagattgc agcgagttgt   1500
tcggaaggat ctacagcggg acttgaccag gccccggtcc agtactaccc ggcaaatctt   1560
cccggtcaat cggaagcaac agttctcacc tttttcgcaa cagatttgca cacacaaaaa   1620
gtgatgtttc ttgaagattt ggtgtaaaca aacagacaac accaatactg ctacactcac   1680
agagcccacg cagcagtatt agtgaagagc ccacgataaa caacgtgggc tcttcactaa   1740
tactattacg tgggctcttc gaggttttgg tgactgtcaa acgttctagc catttacagt   1800
ggtgccagag ggttgggtga ctgtcaaacg ttctagccat ttacagtggt gccagatggt   1860
tgacctagaa gaataagagg aaggccatgg atagcacagt attaatgttc gtaggaaata   1920
cagtcccgat ggacagatat ctggttccgg acaccgttcc taagcaacct aggtgaatag   1980
tcttcgacga tattaggtgc cttacgggca caatctattc tttatgtaaa ctaatgtcaa   2040
aaacataaac aatgactttt aaaacccgcc gtttggcatg caagattttt aaaacccgcc   2100
aaacaaatcc cagcacactg ggggttgctg ggggaaaatc ggaaaagtcc ttgtcaaaaa   2160
ttttgtgttt tcttctggaa aggtggggtt ttttcggagt cctgaggggg tgaaccgagc   2220
accaacagcg gcagcgcgtg tccgtgtcgt tgtctgccgg cagcagtaaa agcagcggct   2280
cgttggccgc caagaaaaag tccagcctgt tgatcggttc cggtgccaca agttcatcca   2340
aggaaacaaa caaagagcag cgcgattcct cgccggtgga ctatttgggg agatgatggc   2400
cgcgtgacag cgggacaact cggatacgcc gctgatccta atttgggtgc catctttttg   2460
tcgtaccaat ccacagcgtt gagctttctg aagaagccca tctcgagcat cgatcgaatg   2520
ctggagaagg cgccggagga tttgaagaac ctcaagaagg aagacctgtg a            2571
```

<210> SEQ ID NO 199
<211> LENGTH: 351
<212> TYPE: DNA
<213> ORGANISM: Culex quinquefasciatus

<400> SEQUENCE: 199
atggcactat ccgccgtaat actgggactg tacgtagtgg aggcgataat ggcgagaatc 60
ggagcaggga gcgtagcggt tcacaccgga cgagccactg cgagaaagag caggagcgat 120
cgcgtaggca gcagaagcag cgcgattcct cgccggtgga ctatttgggg agatgatggc 180
cgcgtgacag cgggacaact cggatacgcc gctgatccta atttgggtgc catctttttg 240
tcgtaccaat ccacagcgtt gagctttctg aagaagccca tctcgagcat cgatcgaatg 300
ctggagaagg cgccggagga tttgaagaac ctcaagaagg aagacctgtg a 351

<210> SEQ ID NO 200
<211> LENGTH: 7524
<212> TYPE: DNA
<213> ORGANISM: Culex quinquefasciatus

<400> SEQUENCE: 200
atggaagagg acagtctgct ccgaaaacgc gccaacaagc cgaacgacct tctgctggac 60
gagtgctgca tcctcccgaa ccgggtgcgc atcgcccagt tgcagtcagg catcagtcgg 120
tagttaaagg tacttaacga ccgctcaaat atcgcatcac ggtggccaga atatggtgaa 180
tgaaattgct ttgaaatata aactagggtt taaaacaact tgtatttatt tataacaatg 240
ggacaatcgc gtacgcttcg tactccccg atcggttcag cctgccacga tggtgttgca 300
tctttttctg gttctgctgg taattttaca gtttttgggc tgctgctgac agggattctg 360
accctgctgc tgctgttgat gataacggtg ctgattcaac accggatgat tttgctgaac 420
ctcctgaacc agcctctggt tgaagttcaa cggcggcaac catgttaaac gccggaggaa 480
agtttactgg aatcgtaaac gtcggctggt tcgttatgcc ggtaattcgt ccgccaaaaa 540
gatacgcatc taagcgggtt tcgacaacgg aaagtttggc tgaagaccga tgaagaaacc 600
acctacaata aacataaaat taatcaacaa tctcccatca ttcaaaatcc cctccttact 660
tttctccccg ctgctgcgat ttctccaaat gatgctgctg cattgccgga tgtgacgtcg 720
gatgctgcgt ttctagcatg ttcggcatca tcaacacgtt cagatccagc tgcaacctcg 780
cttccctctg tttcaaccgg actaaatctt cgtgcactct tcccagtcgt tcagttcgtc 840
gaactccaaa tcgtccggca tactgccgat gccttcgcct ccgcaatcct ctactagatg 900
cgtgtcgaag caaaagaatg gtggcacctc gaatcgcaag ttttcataaa aaattctaat 960
taaactcgcg acatattttc tttctaaaac taaatcaaaa caaacttgac agttctgcca 1020
gcgaaagtga cacgaggcaa atcaatgttt tcaaagcagg tgtggtgctg tcaaatatta 1080
aatgacgcga gaaatttaat tccttaatta attaaacgcg aaaattaata cattaaggcc 1140
aatgtcacgc ccctcgctta taaacttagt taacttaaca taaacattga tttttttctt 1200
acaaactata tcagctactt tagtgatggt acatttaacg taaaaataaa atttgaatat 1260
cttaaatatg attttaacaa gaaaaactat gactatcaaa gtcaccccgg aattaaaact 1320
aagaattttt aacgtaacta tttttctaaa cactattgaa aaaacttttt tttccaaaat 1380
tgtgcatgga ctttgtgtgg cctaccccac acagaaaaaa atatgtgaat taactcgaaa 1440
cggaaaaaat gaatcacatg taaactcagt tgatgtaaac ttgagatttg acgtaaacgg 1500
ttgaatcaaa cgtaaaatca cgtttttacg tataatttgt cgcaaattta catcaaattg 1560

```
catttaaatt taaatgttta atgacgtgca aaagtgttac atcataaatg atgtaacatt   1620
cggaaatatt tttttgtgtg cagtacatgt tttaaaaata ataatattga gaaaaccctt   1680
acctgttgga aaatattcta aaaacaaatt gaaatcaaag tcaccccggt ttacggtagc   1740
ttggaaaatt atatatcttg gcctgttata taacttggca cattaggata gggtagtcat   1800
tagggtggtc caaatccggg ctttttgggg gctacccccct gaaattaaag attaacccat   1860
cactaggcta aattccaaat ttgaactcat tctgaccacg ggaacccctc cctccaatcg   1920
cttaaagttt gtatgggaaa aatcgtcaaa atgtatggag aaaagcaact gttttacttt   1980
tttacctatg gaaggcgcca tagttatccg attcttacca tttctcaaat gtagaacctt   2040
cattaaattt agaacaactt tcccgaagac accatatttt tataattttt ccccgcgaag   2100
ttattagcgc ccaaaactga ccatttttgc gcggctagct gtaaggggct acctaacaac   2160
gatgtttaat tccaattcgt acacgcacgt agcagtgcgt ggccgaatgg ttacgctgtc   2220
cgctttgtaa gcggatgatt ctgggttcga ttcccatctg ctccaacctg tcggtcccgg   2280
ccttagtgcg gcggttggac tcgcaatcaa aaggtcgtca gttcaaacaa gatatatata   2340
tatatatgtt tttttttttt gggagggtga tccagccgca catcgttgat gtcgaaacct   2400
ctaaactggg ccctcgtttt gtcatgtccg tcagtagtct tgtcgtacat tacaactaga   2460
atcagatctg ccaatgaatt agtacacttc gaccaaataa acactgacgc tgtatggatc   2520
tgactctaga ataaatgcac agttgtgtgt tattcataag tccaaaatgt tcaattattc   2580
atataagtcc aattttcatt tgcggataac tacctaactt gaattgaata cgctggtggt   2640
ggtggtggtg ttaaaaaaac aaacgttcaa tttactaaca ttgagtccaa aacctcccta   2700
caaacatcta taccactagg tgacgtacac agaaaaaaat attcctgtaa atttacatta   2760
tttatcatgt accaaaaagt atcatgataa atgatgtata tttacattag gttcattgga   2820
aatttacatt agatttattg gaaatttaca ttagttttga aaatttacat tagttttaaa   2880
atttacatta ctttagcaat ttacattagt tcaaagcaac taattctgat tggccaatgg   2940
gaatgagaag cttgacttgg attgcagtag gaaaaggatg tggcctatgt tctattttaa   3000
aattattgaa gcgggcatca aaaggaaatt ctgattttaa aaagttgctt cacaggtagg   3060
ggacgctttc tcgtcgacgg ccaagtggaa taacgctgga ctggaatcga acggacgacg   3120
ggtaggatgt tcgatgttac tgctgctacc cgctgccgac tgagccatct tcgcatttta   3180
ttaacgagcg gctaaagcat caacttgttc aggtcgaggc tcaggcagtg ggccagcgaa   3240
gtatgagagc gatagaaaga gaaccaaata taactatttt tagttcgggt agttttgaag   3300
tcaacgtttg gcagaaatac attggatata tgatttacat taaataggaa tttacaggaa   3360
gccgaacacg ggtagaaatt catcagattt gagtttccat gctcaacgtt tccatttgat   3420
tcatgattta cattagattt agatttacat tagagtaatt tccatgactt tttgcgcttt   3480
acatcatatc tcaacattac attgagtgag tttacataag aaacagtaat tacgtgctgt   3540
gtaaatttac atattttttt ctgtgtagag atctctgcgc attctagata gatgtttact   3600
aacatacctt ccaatccccg aggttagcaa ggtaccggcc aggagcccct tatcttactg   3660
gatagtaata cacgctcatc taaagaggaa aacatggtat ctcccgtgtt ggaatattgt   3720
aaccggatga gagtctagtg ctatcatacg tttaattaca gttaaacagc aagataagcg   3780
ttgtgcagcc atccggaatt gtgcgacctt tattgctaat gctaatgcta atgctaaacc   3840
taataaaagg actttgtagc ccaactcatg ccctatgaaa tgacgaaaga aaattggaga   3900
```

-continued

```
aatattagtt tttgtgttaa tggtagccta tgagcaaaaa tgtaattttt agtcaaaatt   3960
tacttttaca ccccagagtc aaacacgtat gaataacttt gcaagggagc gtccataacc   4020
aaagtcacta ttatggcaga cgcgtatcta gtagacactc ctttccccca aatatgagcc   4080
agattggttg aaactacgtc ttgtgagatc cattttatca ttgttccatt gattgttcat   4140
tgtctcattc atgactactc tacccttgct gcctgaaata ccaccaccac tcaataaaag   4200
aattgttccg attggttgat ttatggctga gaaccagcgc acagtgggat gaaatcggga   4260
aaaagacgat ttacgtccac agtaattaca gaattggcca caggaaccat gttccgggac   4320
cccggtggaa tattgaccag gaatgtccag gaattttggc atgttgcatt gcaatcgtca   4380
tgatttcaac agagaaacct actactaggg accatccata aaccacgtgg acactttttt   4440
ttaatttcaa cccccccccc cattcttggg caaatgacaa tcaccatacc ccccaccccc   4500
ctctaaggcg tccacgtggt ttatggatag tcccctagtt tccaatcagt caaacaagca   4560
attttgagct acacagaaaa aaatatgtaa atttacacag cacgtaatta ctgtttctta   4620
tgtaaactca ctcaatgtaa tgttgaaata tgatgtaaag agtaaaaagt catggaaatt   4680
actccaatgt aaatctaaat ctaatgtaaa tcatgaatct aatggaaacg ttgcgcatgg   4740
aaactcaaat cagaagaatt tctacccgtg ttcggcttcc tgtaaattcc tatttaatgt   4800
aaatcatata tccaatgtat ttctgccaaa cgttgacttc aaaactaccc gaactaaaaa   4860
tagttatatt tggttctctt tctatcgctc tcatattttg cttgcccact gcctgagcct   4920
cgacctgaac aagttgatgc tttagccgct cgtttataaa atgcgaagat ggctcagtcg   4980
gcagcgggta gcagcagtaa caccgaacat cctacccgtc gtccgttcga ttccagtcca   5040
gcgttattcc acatggctgt cgacgagaaa gcgtccccta cctgtgaaac aactttttaa   5100
aatccgaatt tccttttgct gcccgcttca aacattttaa aatagaacat aggccacacc   5160
cttttcttac tgcaatccaa gtcaagagct tctcattccc attggccaat cagaattagt   5220
tgatttgaat taatgtaaat tccaaaagta atgtaaattc caaaactaat gtaaattttc   5280
aaaactaatg taaatttcca atgaaaataa tgtaaatttc caatgaacct aatgtaaata   5340
tacatcattt atcatgatac cttttggtac atgataaata atgtaaattt acaggaatat   5400
tttttctgt gtactgtaac cggttccagg cggcccgggg gaagaattgg ccactttgga   5460
tataaagtga aaacggtaat ttaagtgata aggctagcac tagtaatggc ctaggagtat   5520
ggacaaacca aaaaaagtta gaataggtta agtagttttg gtataatatt tgaaagattc   5580
taaaggccgg ttggcactgc ctaaagttct aatatttgag ggttgggaaa taaggttttg   5640
caggggttat atagcaaaaa aattgacaat ttttgttcaa gggggttgct tggatatata   5700
cgtatacaaa ttgtgcttat ccattttttt catcaaaaat tgcaatttat gatagaatat   5760
actatgggca cgtctgtttg tctgtgccct agatataaca tcactaagct tgagtttcat   5820
tggttccagt gtgtgaagta attattttgt ataaaatatg tacttctgga gagatccaat   5880
gtttgttaac atcggtaaga taaaagtgtt ccgaatttgt ggaattcaag ggtcaatgtt   5940
tttcttagaa aacatgatat ataacgtaaa aatttacagt cggtcaatac atcaatcgaa   6000
agatctcaag aaaagctttc acatgaaggt aaaagcgtac cattatgttc aattatcgat   6060
ttgctatgat tttttgaaca ttggccgatc tgtgaactgt cacttagtca ctcacttgaa   6120
aaataatccc gataaatgtg aataattagc aagaaccatc aaaaaaacaa acgcgctatg   6180
tcttttgacg tttcaatttt gaccacccat tcctaacgaa ggctgaagaa aaccgagcga   6240
gaagcgaaga caaataaaga acaaagggtg gccaccaaca ccaccagcag cgcttgtggt   6300
```

gttgccagga aactttctct ataaatgcta cttttcgtga gtgttcgctc aaaatttcat 6360
caattttggc agcactaagc agacccaaac gagcgttgga agaaaaaaag aactaagctg 6420
aaaatagaaa aatgggcgtg gcccaatgca cacgactgat tagaatgcgt ttttgaaata 6480 ttttttttaaa atgcttgtaa aaggaatagc ataactttta ttaaaagtga aaataaacag 6540
aaatgttcac aaaaagttgt tctactcgtt ggtgtacttg gttttactga atttcaagga 6600
acactccaga ttatccagca tcattcaaac aagaccgctt attaggctta aaatgggttt 6660
atttccccta ataataaaaa ttatcgtttt gatataaaaa atttatcaac acgataaata 6720
aaggttatta aatcaataac taaaaattat taatgttgat aatgttattt atcaaactga 6780
taaggctgaa tttttctgcg tgaatttttc accggggttc cggatcatgg tttctgtggc 6840
caaatctgta ctgtattatc ttgggggatc ttaattcgtc atatcttgtc atgagcgaca 6900
tttttcgttg atatttggct ccgagggttt tttttaaatc attggaataa aagttccggt 6960
ggaaatccgg ccatatctcg gttccccgtg gtgcacccag gatgaaacca cctccaatag 7020
attcccagga cttatttaca taagaaaagt cttggccgaa cttggggaac cagccgcgtt 7080
ccaagatgtg gacgtaatcg tctttttccc gatttctcc cactgtgcag cgagtttacc 7140
gttctgattt ttttaagggt tctaaatttt ttaagaaact gcagttttgt ttaaatgatc 7200
aatagtgatt ttattttcgt ttttcttacc agtgatgaaa tttatattgc tccttctgct 7260
gttcaaaagg agagaattca gccggacgat ttgttcattc agaatatcga tggagatgat 7320
ctgcagagtc ctccagatta taaaaagtaa gtgagcttaa ccaattcgat ttgatttcat 7380
gtactaaaac ggtttttttt ttctccctaa aggttgtcca aaagccagtg cactccgttg 7440
ttcatgctag cttatcgcga gaagaacgcc ggagcggtta tccacaccca ttccccttct 7500
gcggtcatag caacgttact gtaa 7524

<210> SEQ ID NO 201
<211> LENGTH: 345
<212> TYPE: DNA
<213> ORGANISM: Culex quinquefasciatus

<400> SEQUENCE: 201
atggaagagg acagtctgct ccgaaaacgc gccaacaagc cgaacgacct tctgctggac 60
gagtgctgca tcctcccgaa ccgggtgcgc atcgcccagt tgcagtcagg catcagtcgt 120
gatgaaattt atattgctcc ttctgctgtt caaaaggaga gaattcagcc ggacgatttg 180
ttcattcaga atatcgatgg agatgatctg cagagtcctc cagattataa aaagttgtcc 240
aaaagccagt gcactccgtt gttcatgcta gcttatcgcg agaagaacgc cggagcggtt 300
atccacaccc attccccttc tgcggtcata gcaacgttac tgtaa 345

<210> SEQ ID NO 202
<211> LENGTH: 439
<212> TYPE: DNA
<213> ORGANISM: Culex quinquefasciatus

<400> SEQUENCE: 202
atgattaagg ttagatagaa aaaaaaaaca gccggaccat ccgaacccaa acttatttct 60
tttttctcat agggcatcta tgatcatgag atggagcgca acctgcagtt cgacgaagaa 120
ctagttgtgc caatcatcga aaatacaaat aacgaaagtg atcttgagga tagaatggca 180
aacgcaatga aggagtaccc tggtacatcc gcgattctcg tcagaagaca cggtgtttat 240

-continued

```
gtttggggaa gcagctggca gaaagcgaag gcaatgtaag catgagatta gtgtttttct    300

tcaaaaagtg gcacctttat aatttaaact tctttttagg acggaatgct acgactatct    360

attttcctta gccgtcgaga tgaagaaact tggcctcgac ccaaatgatg tccccaaata    420

ttacagaaac aatcattag                                                 439


<210> SEQ ID NO 203
<211> LENGTH: 312
<212> TYPE: DNA
<213> ORGANISM: Culex quinquefasciatus

<400> SEQUENCE: 203

atgattaagg gcatctatga tcatgagatg gagcgcaacc tgcagttcga cgaagaacta     60

gttgtgccaa tcatcgaaaa tacaaataac gaaagtgatc ttgaggatag aatggcaaac    120

gcaatgaagg agtaccctgg tacatccgcg attctcgtca gaagacacgg tgtttatgtt    180

tggggaagca gctggcagaa agcgaaggca atgacggaat gctacgacta tctattttcc    240

ttagccgtcg agatgaagaa acttggcctc gacccaaatg atgtccccaa atattacaga    300

aacaatcatt ag                                                        312
```

SEX-LINKED RNAi INSECTICIDE MATERIALS AND METHODS

GOVERNMENT SUPPORT CLAUSE

This invention was made with government support under AI144256 awarded by National Institutes of Health. The government has certain rights in the invention.

CROSS-REFERENCE TO RELATED APPLICATIONS

This application is a national stage entry of International (PCT) Patent Application Number PCT/US2019/058232, filed Oct. 26, 2019, which claims priority under 35 U.S.C. § 119(e) to U.S. Provisional Application Ser. No. 62/751,052, filed Oct. 26, 2018, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 25, 2019, is named IURTC-2019-031-02-WO_SL.txt and is 409,936 bytes in size.

BACKGROUND

Mosquito-borne infectious diseases continue to be a serious global health concern. Viruses that cause Zika, chikungunya, yellow fever, and dengue are spread by the bite of female *Aedes aegypti* mosquitoes. Given poor progress in vaccine development and distribution, mosquito control is the primary mechanism for disease control. The current pesticide repertoire will soon reach its expiration date, and it is imperative that new methods for mosquito control are identified. Most animal species display sexually dimorphic behaviors, the majority of which are linked to sexual reproduction. Disease vector mosquitoes are excellent subjects for studies that explore the biological basis of sexual dimorphism. Only adult female mosquitoes, which require blood meals for reproduction, bite humans and transmit pathogens. Females differ from males in morphological, physiological, and behavioral traits that are critical components of their ability to spread diseases. Researchers have therefore had a long-standing interest in the potential to manipulate genetic components of the sex determination pathway and sexual differentiation for vector control. Moreover, success of the sterile insect technique (SIT) and other genetic strategies designed to eliminate large populations of mosquitoes is dependent upon efficient sex-sorting of males and females prior to large-scale release of male mosquitoes. Likewise, Wolbachia-infected sterile male *A. aegypti* mosquitoes have also been sorted from females and released en masse. Unfortunately, affordable methods for sex-sorting mass-reared animals that can be pursued in remote or resource-limited regions have yet to be developed. Many have argued that sex-sorting, as well as insect sterilization itself, is best achieved through large-scale genetic or transgenic approaches. Although the genes that regulate sex-specification and development of mosquito sexual dimorphism may represent novel targets for vector control, a majority of these genes have yet to be characterized in vector mosquitoes, and affordable genetic methods of effective sex-sorting have not yet been established for mass-reared insects.

SUMMARY

The present disclosure provides use of interfering RNA technology to specifically kill either female or male mosquito larvae, thereby allowing the isolation of all male or all female populations and/or the targeted reduction or killing of male or female mosquitoes. The iRNA may target lnc RNA genes at the M locus region or protein-encoding genes in the regions that are described herein that play a role is sex-specific growth and reproduction.

In one aspect, the present disclosure provides at least one interfering ribonucleic acid (iRNA) able to target and silence expression of at least one sex-linked gene required for maturation of at least one mosquito species from larvae to adult or required for reproduction of at least one mosquito species.

In another aspect, the present disclosure provides at least one iRNA able to target and silence expression of at least one sex-linked gene required for reproduction of at least one mosquito species.

In another aspect, the present disclosure provides a mosquito insecticide composition for preventing and/or controlling a mosquito infestation comprising: (i) at least one interfering ribonucleic acid (iRNA) described herein, (ii) a bacterial cell expressing the iRNA described herein, or (iii) a yeast cell as described herein, and at least one suitable carrier, excipient or diluent.

In some aspects, the insecticide composition comprises or consists essentially of: a) a synthetic iRNA; b) a DNA construct encoding the iRNA; c) a yeast cell engineered to produce the iRINA; or d) a bacterial cell expressing the iRNA; wherein the insecticide composition is able to inhibit larval maturation, adult reproduction or adult mosquito survival.

In another aspect, the present disclosure provides a sugar bait comprising the insecticide composition described herein.

In yet another aspect, the present disclosure provides a dried inactivated yeast composition comprising the insecticide composition described herein.

In yet another aspect, the present disclosure provides a method for controlling, reducing, or treating a mosquito infestation comprising exposing at least one mosquito larva or adult to the at least one interfering ribonucleic acid (iRNA) described herein, or the composition of described herein in an effective amount to control, reduce, or treat the mosquito infestation.

The foregoing and other aspects and advantages of the invention will appear from the following description. In the description, reference is made to the accompanying drawings which form a part of the description, and in which there are shown, by way of illustration, certain embodiments. Such embodiments do not necessarily represent the full scope of the invention, however, and reference is made therefore to the claims and herein for interpreting the scope of the disclosure.

BRIEF DESCRIPTION OF THE SEVERAL VIEWS OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 7 depicts a gene tree for gene AEEL011830.

DETAILED DESCRIPTION

Figure 1:
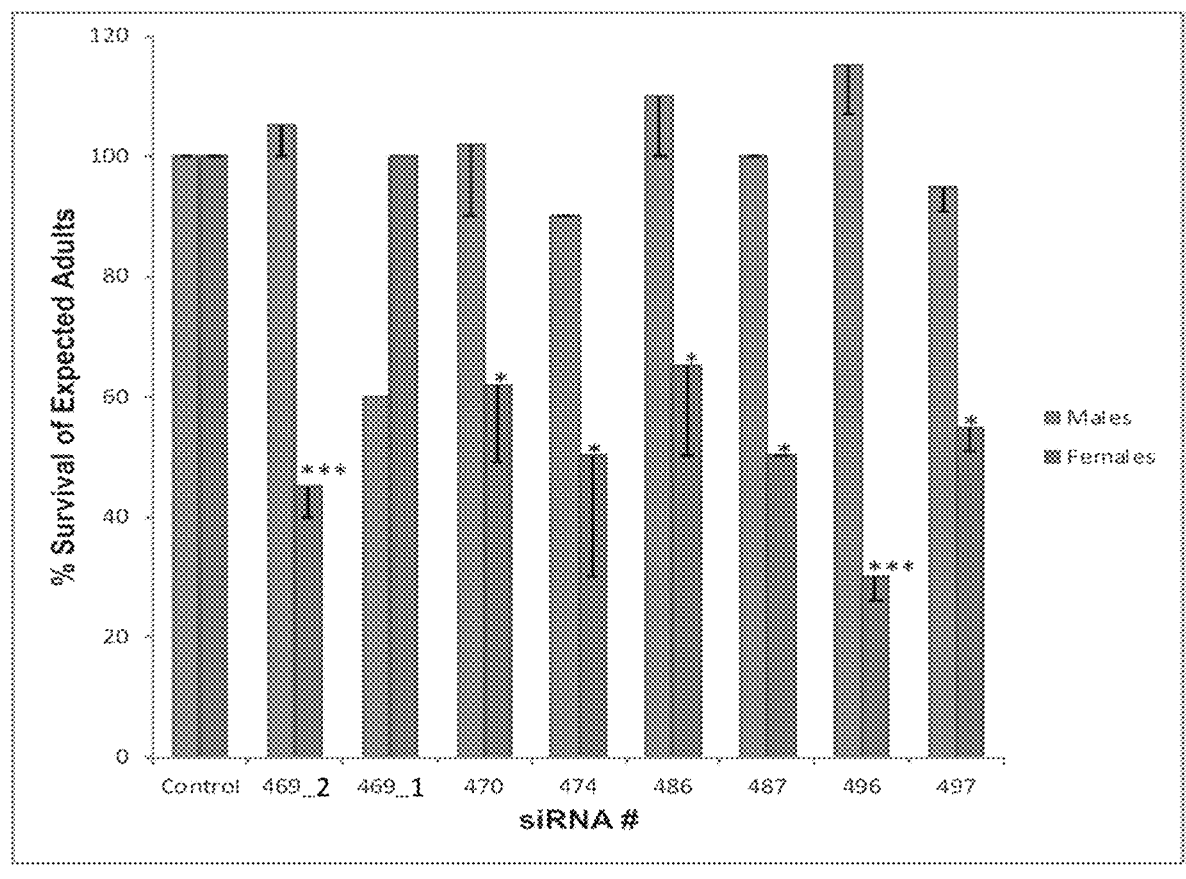
FIG. 1 is a bar graph representing the sex-linked targeting of the siRNA of the present invention. Sex-specific lethality induced by brief siRNA soaking treatment in the pilot screen. The percentage of expected male and female adults that survived is shown for each siRNA treatment. *=p<0.01; ***=p<0.001 reduced survival with respect to control survival.
Figure 2:
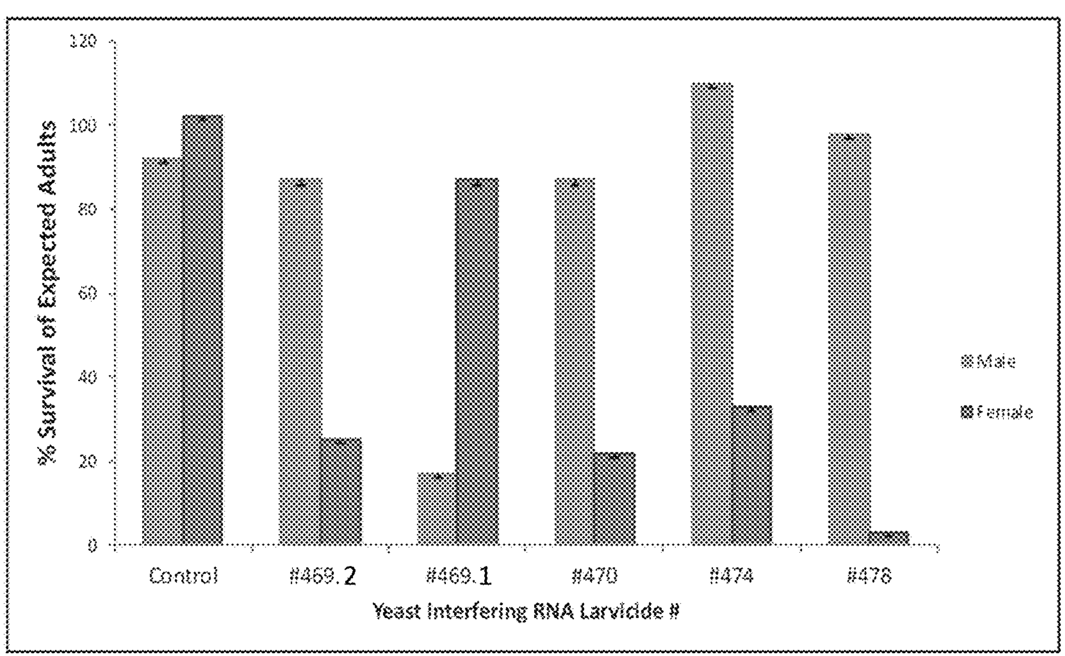
FIG. 2 demonstrates sex-specific larval lethality induced by yeast interfering RNA larvicides. The percentage of expected male and female adults that survived following oral feedings with the indicated yeast interfering RNA larvicides is shown. Larvicides #469.1, 470, 474, and 478 induced significant female-specific larval lethality (p<0.001), while larvicide #469.2 resulted in significant male-specific larval lethality.

The present disclosure provides methods and insecticides for control of disease vector mosquitoes by specifically targeting mosquitoes based on their sex (e.g., female or male mosquitoes). The present disclosure provides female-targeting and male-targeting interfering RNA (iRNA) that regulate sex-specific development. These methods and insecticides may be used to permit mass-rearing of same-sex mosquitoes (for example, a population of male mosquitoes) or used as specific insecticides targeting female mosquito populations.

Although thousands of putative long non-coding RNA (lncRNA) genes have been identified in the *A. aegypti* genome, these genes, once considered dark matter, have not yet been functionally validated as lncRNA genes. In this disclosure, it is described that lncRNAs encoded by genes in the sex-determining M locus region regulate *A. aegypti* sex-specific development. These identified lncRNAs are used to generate yeast interfering RNA larvicide strains corresponding to female-targeting larval lethal lncRNA genes or male-targeting larval lethal lncRNA genes. The female-targeting yeast interfering RNA larvicides may be used under mass-rearing conditions to produce large populations of male mosquitoes which can in turn be used for mosquito abatement methods. Further, as only adult female mosquitoes require blood and thus bite humans and transmit disease, the female-targeting larvicides may also be used to target female mosquitoes and reduce female mosquito populations. This provides an affordable, effective, and scalable female-targeting yeast interfering RNA larvicide technology that enhances the potential for mass-rearing male mosquitoes in remote and resource-limited regions throughout the world.

The iRNA may be sex-linked lethal and, for example, target lnc RNA genes at the M locus region or protein-encoding genes in the regions that are described herein to play a role is sex-specific growth and reproduction. Also, the iRNA may mediate silencing that can impact aspects of sexual dimorphism that could limit sexually dimorphic traits of vector importance. For example, reproduction can be impacted in males or females via the iRNA. Alternatively, for females, blood seeking behavior, blood meal acquisition, or oviposition can be impacted.

Methods of making and using engineered strains of *Saccharomyces cerevisiae* (baker's yeast) to produce shRNA corresponding to sex-linked lethal genes or genes that impact mosquito reproduction, behavior or growth (e.g. sexually dimorpohic traits such as blood seeking behavior, blood meal acquisition or oviposition, among others), are described herein to reduce specific female- or male mosquito populations. Use of this yeast interfering RNA expression and delivery system facilitates cost-effective production and delivery of RNA pesticides to mosquitoes. This technology, which can be adapted to resource-limited countries with constrained infrastructures, can be readily scaled to meet the needs of large mosquito release programs.

The present disclosure provides at least one iRNA able to target and suppress at least one gene required for sex-specific maturation and/or growth from larva to adult of at least one mosquito species (e.g., larva-lethal gene).

In some embodiments, the at least one iRNA is able to target and suppress at least one gene required for female mosquito survival at any life stage, i.e., larval and/or adult. In another embodiment, the at least one iRNA is able to target and suppress at least one gene required for male mosquito survival at any life stage, i.e., larval and/or adult.

In some embodiments, the iRNA-mediated silencing can impact aspects of sexual dimorphism that could limit sexually dimorphic traits of vector importance. In some embodiments, the at least one iRNA is able to target or suppress at least one gene or protein required for mosquito reproduction. In some embodiments, the at least one iRNA is able to target or suppress at least one gene or protein required for mosquito behavior or growth (e.g. sexually dimorpohic traits such as blood seeking behavior, blood meal acquisition or oviposition, among others).

For such sexually dimorphic genes, the iRNA may be fed to adults (i.e. in a sugar solution) to suppress the sexually dimorphic behavior. The iRNA may also be used to protect genetically engineered mosquitoes in which expression of the gene of interest is manipulated. For example, loss of function mutations can be induced in the gene of interest. Or the gene could be ectopically expressed in a transgenic mosquito. Such genetic manipulations could alter sexually dimorphic behaviors of vector importance.

The iRNA of the present disclosure may be a small interfering RNA (siRNA), a short hairpin RNA (shRNA), double stranded RNA (dsRNA), an RNA construct, or an antisense oligonucleotide. In some embodiments, the shRNA is encoded in a DNA construct or vector which allows for expression of the iRNA within a target cell.

The term "iRNA" refers to ribonucleic acid (RNA) molecules and constructs that are able to operate within the RNA interference (RNAi) pathway by interfering with transcriptional or post-transcriptional gene expression resulting in reduced or inhibited expression of a specific gene. The term "iRNA" refers herein to short interfering RNA (siRNA), short hairpin RNA (shRNA), double stranded RNA (dsRNA) molecules that operate within the RNAi pathway. The term is also intended to include antisense oligonucleotides capable of binding a target sequence and silencing gene expression.

In some instances, the iRNA is produced within a cell via a DNA construct that expresses said iRNA. The iRNA of the present disclosure are synthetic and can be expressed in a vector or host cell in which the iRNA is not normally expressed. For example, the siRNA may target an insect gene, e.g., a sex-linked mosquito gene and be expressed by an exogenous vector or expressed in a bacterial, plant, algal, or yeast cell that does not naturally contain the target gene or target sequence to which the siRNA binds. The iRNA may be modified in a manner that alters the iRNA properties in order to be exogenously expressed by the host cell, e.g., the siRNA or the complementary sequence used to express the iRNA may be modified at its ends or incorporated into an exogenous sequence in order to be able to be expressed in the host cell. In some embodiments, the iRNA is operably linked to an exogenous sequence that allows for its expression.

In some embodiments, the iRNA is an antisense oligonucleotide. Antisense oligonucleotides are short, synthetic, single-stranded oligodeoxy nucleotides capable of interacting with mRNA to prevent translation of a targeted gene. Their nucleotide sequence is complementary the specific mRNA target. They can be chemically modified to improve target engagement, improve efficacy, and reduce off-target effects.

In some embodiments of the present disclosure provide a DNA construct encoding the iRNA, wherein the DNA construct is able to express the iRNA. Suitable DNA constructs will depend on the type of cell in which the iRNA is to be expressed. In some embodiments, the DNA construct is a linear or a closed circular plasmid or expression vector. In some embodiments, the DNA constructs will be integrated into the host cell genome, for example, integrated in to a yeast or bacterial cell genome.

In some embodiment, the DNA construct is a suitable expression vector. Sequences that encode the iRNA of the present technology can be inserted into a vector under the control of a suitable promoter that functions in one or more microbial hosts to drive expression of a linked coding sequence or other DNA sequence. Suitable vectors are known in the art and selecting the appropriate vector will depend on the size of the nucleic acid to be inserted into the vector and the particular host cell to be transformed with the vector. Vectors may include, but are not limited to, one or more of the following: a signal sequence, an origin of replication, one or more selectable marker genes, terminators, enhancers and/or a constitutive or inducible promoter allowing expression of exogenous DNA. Vectors can also include viral vectors and the like.

siRNA, also referred to as small interfering RNA, short interfering RNA or silencing RNA, are short double-stranded RNA molecules of <30 base pairs in length, for example, about 19-30 base pairs in length that operate through the RNAi pathway. Each siRNA is unwound into two single-stranded RNAs (ssRNAs), one of which (i.e., the guide strand) is incorporated into the RNA-induced silencing complex (RISC) leading to post-transcriptional gene silencing. siRNAs can be generated in several ways. In some cases, long dsRNA is introduced to a cell, either by a virus, by endogenous RNA expression (i.e., microRNA), or as exogenously delivered dsRNA. The enzyme Dicer cleaves the long duplex RNAs into siRNAs. Another way to provide siRNA in cells is to express shRNA from plasmid vectors. Alternatively, chemically synthesized siRNA duplexes that mimic the structure of Dicer-processed products which are commonly used in gene silencing research, can also be employed. Chemically synthesized siRNAs simply bypass the Dicer cleavage step. In some preferred embodiments, the iRNA is about 25 bp in length.

shRNA (also referred to as small hairpin RNA) are artificial single-stranded RNAs having a secondary structure such that a portion of the single RNA strand forms a hairpin loop. shRNA are typically expressed in cells by delivering to the cells a DNA construct, e.g., through an expression vector that encodes the shRNA. Transcribed from the DNA construct under the control of RNA Pol-II or Pol-III promoters, the shRNA folds into a structure that resembles a siRNA duplex. shRNAs are then processed by Dicer into siRNAs.

dsRNA refers to long double-stranded RNA molecules that are cleaved by Dicer into short double-stranded fragments of about 20-25 nucleotide siRNAs.

RNA interference (RNAi) or Post-Transcriptional Gene Silencing (PTGS) refers to the biological process in which RNA molecules interfere or inhibit the expression of specific genes having nucleotide sequences complementary to the iRNA sequences (gene-specific suppression of gene expression). RNAi results in the degradation of mRNA after transcription, resulting in inhibited translation and no protein expression.

In some embodiments, the iRNA is produced by a host cell which can express the iRNA from a DNA construct or expression vector. Suitable cells, include, but are not limited to, a bacterial, algal or yeast cells engineered to produce or express the iRNA from the DNA construct. Other suitable host cells, e.g., microorganism cells or plant cells, are known in the art. In some embodiments, the host cell expresses at least two iRNA, alternatively at least three iRNA, alternatively at least four iRNA. In some embodiments, the host cell expresses from 1-8 iRNA.

In some embodiment, the host cell may be stably transformed to express at least one iRNA of interest. In further embodiments, the host cell may be stably transformed to express at least two iRNA, alternatively at least three iRNA, alternatively at least four iRNA, alternatively at least five iRNA. Suitable DNA constructs or vectors to express multiple iRNA from multiple sequences are known in the art, In some embodiments, the host cell may stably express from about 1-8 iRNA. In particular embodiments, the hose cell may stably express from about 1-5 iRNA.

Stable transformants may be produced by incorporating the sequence of the iRNA into the host cell genome. Methods of forming stable transformants of host cells are known in the art.

"Gene suppression" or "down-regulation of gene expression" or "inhibition or suppression of gene expression" are used interchangeably and refer to a measurable or observable reduction in gene expression or a complete abolition of detectable gene expression at the level of protein product ("gene silencing"), and/or mRNA product from the gene. In some embodiments, gene suppression results in gene silencing, referring to the ability of the iRNA to target mRNA for degradation, resulting in no translation and no protein expression. The ability of the iRNA to suppress or down-regulate at least one gene leads to the suppression or inhibition of the mosquito's growth or maturation or death of the mosquito larvae or adult mosquito. The down-regulation or inhibition may occur at the translational or post-translational stage of expression of the gene of interest by promoting transcript turnover, cleavage, or disruption of translation.

A gene refers to a polynucleotide sequence that comprises control and coding sequences necessary for the production of a polypeptide (protein). The polypeptide can be encoded by a full length coding sequence or by any portion of the coding sequence. A gene may be an uninterrupted coding sequence or may include one or more introns between splice junctions. As used herein, a gene may include variants of the gene, which include, but are not limited to, modifications such as mutations, insertions, deletions or substitutions of one or more nucleotides. The target gene is the gene targeted for down-regulation or suppression by the iRNA of the present disclosure. In certain embodiments, the target gene is a sex-linked gene required for the survival or maturation of a specific sex mosquito.

The reduction, inhibition or suppression of expression of the target gene results in the inability of the larvae to mature into an adult arthropod insect, e.g., mosquito. The target gene required for maturation and/or growth refers to a gene necessary for the survival, growth, or development of larvae into an adult and disruption thereof may ultimately result in larvae or pupae death. The gene may inhibit the ability of the larvae to develop into pupae, of pupae from developing into adults, or any intervening developmental step. In some instances, the inhibition or suppression of the target gene results in the inability of an adult insect to survive.

Down-regulation or inhibition of gene expression in cells of the mosquito can be confirmed by phenotypic analysis of the cell or the whole mosquito; for example, death of the mosquito larva, pupa or adult mosquito (which can be quantitated, for example, as a % mortality). Suitably, the iRNA or compositions provide a % mortality of at least about 50%, alternatively at least about 60%, alternatively at least about 70%, alternatively at least about 75%, alternatively at least about 80%, alternatively at least about 90%, alternatively at least about 95%, alternatively at least about 98%, alternatively about 100%, and any and all numerical values and ranges in between.

Other methods of confirming down-regulation of the gene expression are known in the art, and include, but are not limited to, measurement of mRNA or protein expression using molecular techniques such as RNA solution hybridization, nuclease protection, Northern hybridization, reverse transcription, gene expression monitoring with a microarray, antibody binding, enzyme-linked immunosorbent assay (ELISA), Western blotting, radioimmunoassay (RIA), other immunoassays, or fluorescence-activated cell analysis (FACS), and the like.

The term larvicide is used to describe a composition or iRNA which specifically down-regulates or suppresses a gene required for the maturation, development or survival of the larval stage of development of a specific sex of the mosquito. In other words, a larvicide kills larva or inhibits larva from maturing into the pupa and/or adult stage of development (i.e., can kill at the pupal stage), resulting in a reduction in the number of larva that develop into adults. In some instances, the larvicide may additionally be able to inhibit or reduce survival of adult mosquitoes resulting in adult mosquito death.

In some embodiments, the effectiveness of larvicide is characterized by the lethal concentrations (LC) for mortality and inhibition of adult emergence (IE). In some embodiments, the effectiveness of the insecticide is characterized by the lethal concentration or lethal dose (LD) for an adult insecticide.

The term juvenile mosquito, as referred to herein, refers to the stages of the mosquito life cycle before it becomes an adult but after hatching from an egg. Juvenile mosquito can refer to the larva or pupa stage.

Suitable target genes for use in the present invention include genes identified as sex-linked larval lethal genes in one or more species of mosquito, as described herein. Sex-linked larval lethal genes are genes that result in statistically significant lethality when compared to a control siRNA treatment and are specific to the sex to which they are linked, e.g., female-larval lethal or male-larval lethal genes. In some embodiments, the sex-linked larval lethal genes result in at least 50% mortality of larvae of the specific sex but does not result in appreciable lethality of the opposite sex. In some embodiments, the sex-linked larval lethal genes result in about 60% mortality, alternatively about 70% mortality, alternatively about 80% mortality, alternatively about 90% mortality, alternatively about 95% mortality, alternatively 100% mortality. Another suitable method to measure mortality is described in the WHO (2005) guidelines for larvicide testing.

Additional suitable genes for use in the methods of the present disclosure include genes identified as sex-linked adult lethal genes or genes linked to sex-specific for one or more species of mosquitoes. Adult lethal genes are genes that result in statistically significant lethality when compared to a control siRNA treatment for a specific sex of mosquito (e.g., female or male) but no appreciable lethality of the opposite sex. In some embodiments, the adult lethal genes result in about 60% mortality, alternatively about 70% mortality, alternatively about 80% mortality, alternatively about 90% mortality, alternatively about 95% mortality, alternatively 100% mortality. In some embodiments, the larval lethal gene is also an adult lethal gene.

In some embodiments, the iRNA inhibit gene expression and result in sex-specific larvae death or sex-specific inhibition of reproduction or maturation of at least two target mosquito species Target mosquito species include, by are not limited to, mosquitoes of the genera *Aedes, Anopheles, Culex, Ochlerotatus, Culiseta, Psorophora, Coquilletitidia*, and *Mansonia.*

Target mosquitoes that belong to the genus *Anopheles* include, but are not limited to, *An. aconitus, An. albimanus, An. albitarsis* s.l., *An. annularis, An. aquasalis, An. arabi-*

*ensis, An. atroparvus, An. coluzzii , An. arabiensis, An. balabacensis, An. barberi, An. barbitrosstris* s.l., *A. bellator, A. crucians, An. cruzii, An. culicifacies* s.l., *An. darlingi, An. dirus* s.l., *A. earlei, An. farauti* s.l., *An. flavirostris, An. fluviatilis* s.l., *An. freeborni, An. funestus, An. gambiae, An. gambiae* (Giles, 1902), *An. introlatus, An. koliensis, An. labranchiae, An. latens, An. lesteri, An. leucosphyrus/lateens, An. maculates, An. maculipennis, An. marajoara, An. messeae, An. minimus* s.l., *A. moucheti, An. nili, An. nuneztovari* s.l., *An. pseudopunctipennis, A. punctipennis, An. punctulatus* s.l., *An. quadrimaculatus* s.l., *An. sacharovi, An. sergentii, An. sinensis, An. stephensi, An. subpictus, An. sundaicus An. superpictus, An. Walker, An. epiroticus, An. maculates, melas, An. funestus An. quadriannulatus, and An. christyi*., and the like.

Target mosquitoes that belong to the genus Aedes include, but are not limited to, *A. aegypti, A. albopictus, A. australis, A. cinereus, A. polynesiensis, A. rusticus, A. vexans, A.abserratus, A.atlanticus, A.atropalpus, A.brelandi, A.campestris, A. canadensis, A. caritator, A.cataphylla, A.comunis, A.deserticola, A.dorsalis, A.dupreei, A.epacitus, A.excrucians, A.fitchii, A.falvescens, A.fulvus, A.grossbecki, A.hensilli, A.hersperonotius, A.hexodontus, A.implicatus, A.infirmatus, A.intrudens, A.melanimon, A.mitchellae, A.nigromaculis, A.provocans, A.solicitans, A.squamiger, A.sticticus, A.stimulans, A.taeniorrhynchus, A.triseriatus, A.trivittatus*, and the like.

Target mosquitoes that belong to the genus Culex include, but are not limited to, *Culex annulrostris, Culex annulus, Culex pipiens, Culex quinquefasciatus, Culex sitiens, Cules tritaeniorhynchus, Culex vishnui, Culex univittatus*, and the like.

In some embodiments, species able to transmit vector-borne illnesses, such as Zika virus, Dengue virus, malaria, etc. are preferentially targeted.

In certain embodiments, the at least one mosquito species includes *A. aegypti* (i.e., yellow fever mosquito). In another embodiment, the at least one mosquito species includes *An. gambiae* (i.e., African malaria mosquito). In another embodiment, the at least one mosquito species includes at least one species from the genus *Aedes* and at least one species from the genus *Anopheles*.

In certain embodiments, the sex-linked iRNA target sequences are conserved in multiple mosquito species but not conserved in non-targeted species.

In some embodiments, the iRNA includes a guide antisense strand having a nucleic acid sequence that is at least partially complementary or is perfectly complementary to the sex-linked iRNA target sequence.

In some embodiments, the iRNA includes a passenger sense strand having a nucleic add sequence that is complementary to the guide antisense strand.

In some embodiments, more than one sex-linked iRNA is provided, targeting one sex-linked target sequence.

In some embodiments, the at least one mosquito species is *A. aegypti*. The iRNA targets at least one sex-linked lethal gene of *A. aegypti*. Suitable sex-linked lethal genes of *A. aegypti*, include, but are not limited to, the genes listed in Tables 1 and 2, and combinations thereof. For example, suitable target genes include AAEL021446, AAEL022173, AAEL022531, AAEL023751, AAEL024907, AAEL027422, AAEL028165, AAEL025725, AAEL026346, AAEL022070, AAEL020580, AAEL024146, AAEL021059, AAEL020379, AAEL020813, AAEL022952, AAEL022321, AAEL024935, AAEL025316, AAEL026051, AAEL026137, AAEL026929, AAEL027085, AAEL027382, AAEL022649, AAEL011830, AAEL011832, AAEL026407, AAEL021597, AAEL022807, AAEL026655, AAEL024697, AAEL021470, AAEL027259, AAEL022756, AAEL024428, AAEL022640, AAEL025698, AAEL023836, AAEL022411, AAEL023838, AAEL027761, AAEL026768, AAEL026445, AAEL028113, AAEL021079, AAEL027827, AAEL017331, AAEL026925, AAEL022912; AAEL025669, AAEL022711, AAEL022861, AAEL024779, AAEL025301, AAEL015526, AAEL026283, AAEL021141, AAEL021969, AAEL020975, AAEL024704, GAPW01003631.1, AGAP000470, CPIJ011362, CPIJ011357, CPIJ011356, and a combination of any two or more thereof. Additional gene information can be found in Table 3.

in some embodiments, one or more iRNAs target a specific sequence within a sex-linked lethal gene; for example, the specific target sequences found in Tables 1 and 2, equivalent sequences in orthologs of the sex-linked lethal genes of tables 1 and 2, and combinations thereof.

Suitable target sequences within the sex-linked lethal genes identified herein include, but are not limited to, the specific target sequences listed in Tables 1 and 2 including, for example, for female-linked lethal genes, the sequence of any one of SEQ ID NOs: 2-45, and 47-51, or an equivalent sequence in an orthologous gene.

In other embodiments, one or more iRNAs target male mosquitoes, by targeting, for example, a target sequence of SEQ ID NO: 1, 46, or 52, or an equivalent sequence in an orthologous gene.

It is also predicted, and would be understood by the skilled person, that orthologs of the sex-linked target genes identified herein represent targets for down-regulation in the control of other insects and/or arachnid species. Thus, arthropod orthologs of the nucleic acid molecules of the present invention are also contemplated.

Protein or nucleotide sequences are likely to be homologous if they show a "significant" level of sequence similarity or identity. Truly homologous sequences are related by divergence from a common ancestor gene. Sequence homologs can be of two types: (i) where homologs exist in different species they are known as orthologs, e.g., the α-globin genes in mouse and human are orthologs, (ii) paralogs are homologous genes within a single species, e.g., the α- and β- globin genes in mouse are paralogs.

In one embodiment, an ortholog shares at least about 40%, 50% or 60% nucleotide-sequence identity with the nucleotide sequence of the genes identified in in Table 3. In certain embodiments, the ortholog will share at least about 70%, 75%, 80%, 85%, 90%, 95%, 96%, 97%, 98% or 99% sequence identity with the genes set forth in Table 3.

In some embodiments an iRNA disclosed and described herein can be used as an insecticide for an arthropod other than a mosquito. In some embodiments, the arthropod is an agricultural crop pest. Genes orthologous to those described herein can be identified and targeted in non-mosquito arthropods such as crop pests by methods known in the art. Many publicly available biological databases provide tools to identify and analyze orthologous gene sequences. For example, gene orthologs of AAEL011830 were identified in 19 mosquito species and 20 non-mosquito species using the VectorBase database. A gene tree (VectorBase) for AAEL011830 is presented in FIG. 7.

According to another embodiment, the disclosure encompasses target genes which are arthropod orthologs of a gene selected from AAEL021446, AAEL022173, AAEL022531, AAEL023751, AAEL024907, AAEL027422, AAEL028165, AAEL025725, AAEL026346, AAEL022070, AAEL020580, AAEL024146, AAEL021059, AAEL020379, AAEL020813, AAEL022952, AAEL022321, AAEL024935, AAEL025316, AAEL026051, AAEL026137, AAEL026929, AAEL027085, AAEL027382, AAEL022649, AAEL011830, AAEL011832, AAEL026407, AAEL021597, AAEL022807, AAEL026655, AAEL024697, AAEL021470, AAEL027259, AAEL022756, AAEL024428, AAEL022640, AAEL025698, AAEL021884, AAEL023836, AAEL022411, AAEL023838, AAEL027761, AAEL026768, AAEL026445, AAEL028113, AAEL021079, AAEL027827, AAEL017331, AAEL026925, AAEL022912; AAEL025669, AAEL022711, AAEL022861, AAEL024779, AAEL025301, AAEL015526, AAEL026283, AAEL021141, AAEL021969, AAEL020975, AAEL024704, GAPW01003631.1, AGAP000470, CPIJ011362, CPIJ011357, and CPIJ011356. In certain embodiments, an iRNA target sequence in one or more of these genes comprises, consists essentially of, or consists of a nucleotide sequence as represented in Tables 1 and 2 (e.g., SEQ ID NOs 1-52), or an equivalent sequence in a gene orthologous to a gene identified in Table 3. By way of example, an ortholog may comprise a nucleotide sequence as represented in any of SEQ ID NOs 1-52, or a fragment thereof.

In certain embodiments, the sequences and genes targeted are specific to a single sex, i.e., female or male mosquitoes. Down-regulation or inhibition of sex-linked target gene expression is "specific" when down-regulation or inhibition of the target gene occurs in the targeted sex only, without resulting in detrimental effects on other genes of the targeted organism or genes of other non-related organisms (e.g., humans, other mammals, etc.). The targeted sequences selected have little risk for targeting genes in humans. Methods of determining if iRNA sequences specifically target human genes are known in the art, and include, for example, assessing human risk empirically through toxicity testing on human cells in vitro and on animal models in vivo, and in silico methods to select only risk-reduced sequences for iRNA synthesis, as described in the Examples below.

To avoid introducing the replicating host cells or live microorganisms into the environment, host cells may be killed or inactivated (e.g., unable to grow and/or replicate) before being incorporated into the compositions of the present disclosure. Host cells are preferably killed or inactivated in a manner that maintains the ability of the host cell to act as a larvicide (i.e., the inactivation does not disrupt the iRNAs contained within said host cell). In some embodiments, the iRNA can be purified from the host cell before incorporating into the compositions. Suitable methods of killing or inactivating the host cell are known in the art, and include, but are not limited to, heat-inactivation, high pressure, plasma treatment at atmospheric pressure, sonication, low-amperage electric treatment, or dense phase carbon dioxide processing.

In some embodiments, a bacterial cell expressing at least one iRNA described herein is provided. Suitable bacterial cells are known in the art and include, but are not limited to, *E. coli, Bacillus thuringiensis israelensis*, and *Lactobacillus* spp., among others.

In some embodiments, a yeast cell expressing at least one iRNA as described herein is provided. Suitable strains of yeast are known in the art, and include, but are not limited to, *Saccharomyces cerevisiae* (baker's yeast), *Saccharomyces boulardii, Pichia pastoris*, among others. Yeast is an attractive food source for mosquito larvae, which makes it well-suited as a delivery system. Other advantages of yeast include a relatively low cost of production, the capacity to produce interfering RNA through yeast cultivation, and the ability to pack and ship dried yeast in shelf-stable forms. Concerns about introducing live organisms into treated sites can be alleviated by using heat-killed yeast that retain larvicidal potency.

In one embodiment, the yeast cell is *Saccharomyces cerevisiae. S. cerevisiae* is a model organism that is genetically tractable and inexpensive to culture and can be engineered to produce interfering RNA in the form of short hairpin RNA (shRNA), which can be easily amplified through yeast cultivation. Yeast is both a strong odorant attractant and a source of nutrition for laboratory-bred *A. aegypti* larvae. Moreover, dried yeast, a granulated form in which yeast is commercially sold, can be packaged and shipped, making it ideal for delivery to countries with extant *A. aegypti* populations and endemic virus transmission.

The present shRNA produced and delivered in *S. cerevisiae* can be utilized as a targeted and efficient mosquito larvicidal agent.

In some embodiments, the host cell expresses at least two iRNAs that target a single sex-linked gene, alternatively at least three iRNAs that target a single sex-linked gene, alternatively at least four iRNAs that target a single sex-linked gene. In another embodiment, the host cell expresses at least two iRNAs that target two different sex-linked genes, alternatively at least three iRNAs that target at least two different sex-linked genes, alternatively at least four iRNAs that target at least two different sex-linked genes, alternatively at least five different iRNAs that target at least two different sex-linked genes.

In one embodiment, a host cell, a yeast cell, expresses at least two iRNAs that target a single sex-linked gene. In one embodiment, a host cell expresses at least three iRNAs that target a single sex-linked gene. In one embodiment, a host cell expresses at least three iRNAs that target a single sex-linked gene. In one embodiment, a host cell expresses at least four iRNAs that target a single sex-linked gene.

In one embodiment, a host cell expresses at least two iRNA.s targeting at least two different genes required for sex-linked maturation from larva to adult of at least one insect, preferably a mosquito.

In some embodiments, the target sex-linked gene may also be required for adult insect survival.

In certain embodiments, more than one iRNA may either be expressed by a single DNA construct, or may be expressed by multiple DNA constructs, introduced into the host cell. In some embodiments, the DNA construct comprises multiple expression sites, each site able to drive the expression of a different nucleotide sequence. By this method, multiple iRNAs can be expressed in a single cell, where the multiple iRNAs can either target multiple sites on a single gene or target multiple genes within at least one mosquito species.

In a particular embodiment the iRNA(s) is(are) expressed in the yeast Saccharomyces cerevisiae.

The yeast may be heat-inactivated before contacting the larva. In some embodiments, it is preferred that the yeast is heat-inactivated to reduce or eliminate the ability of the yeast to grow once released into a treatment area.

In some embodiments, the yeast is provided as a ready-to use dry formulation.

In some embodiments, the female-lethal iRNAs described herein may be used to produce large populations of male mosquitoes. These male mosquitoes may be used for mosquito abatement programs, for example, use in sterile insect technique (SIT) and other genetic strategies designed to eliminate large populations of mosquitoes by large-scale release of sterile male mosquitoes. For example, the female-lethal iRNAs of the present disclosure may be used to obtain a large population of Wolbachia-infected sterile male *A. aegypti* mosquitoes for release en masse. The methods described herein provide an affordable means for sex-sorting (i.e., sexing) mass-reared animals that can be utilized in remote or resource-limited regions.

In some embodiments, provided herein are transgenic mosquitos that express one or more RNAi described herein. A transgene encoding the RNAi can be transformed into the mosquito genome under the control, for example, of a housekeeping gene promoter. In some embodiments, a female-lethal sex-linked RNAi is expressed by a transgenic mosquito, ultimately resulting a male-only population. In other embodiments, a male-lethal sex-linked RNAi is expressed by a transgenic mosquito, ultimately resulting in a female-only population. Methods for generating transgenic mosquitoes expressing a selected transgene are known in the art. In some embodiments, a DNA construct described herein is used to produce the transgenic mosquito.

The present disclosure also provides a mosquito insecticide composition for preventing and/or controlling mosquito infestations. The compositions may comprise at least one interfering RNA of the present disclosure or at least one host cell expressing at least one interfering RNA of the present disclosure and at least one suitable carrier, excipient, or diluent. In some embodiments, the at least one host cell is a yeast cell or a bacterial cell that expresses at least one iRNA of the present disclosure. In some embodiments, the mosquito insecticide is a female mosquito larvicide (i.e., an insecticide that specifically targets female mosquito larvae and not male mosquito larvae).

In some embodiments, the female mosquito larvicide does not kill or reduce the male mosquito population.

In one embodiment, the composition comprises at least one yeast cell comprising, containing, or expressing at least one sex-linked iRNA of the present disclosure. In some embodiments, the yeast cell is inactivated or killed but maintains its larvicidal properties. In certain embodiments, the yeast cell is heat-inactivated. In other embodiments, the yeast is inactivated by methods known in the art, for example, by high pressure, plasma treatment at atmospheric pressure, sonication, low-amperage electric treatment, or dense phase carbon dioxide processing.

In some embodiments, compositions include one or more iRNA of the present disclosure, for example, at least two iRNAs, alternatively at least three iRNAs, alternatively at least four iRNAs, alternatively at least five iRNAs, alternatively at least six iRNAs, alternatively at least seven iRNAs, alternatively at least eight iRNAs, etc. In some embodiments, the compositions include from 1-8 different iRNAs. In certain embodiments, the composition includes about 1-5 different iRNAs.

In some embodiments, the compositions include a host cell comprising, containing or expressing at least one iRNA described herein.

In some embodiments, the compositions comprise multiple iRNAs that target a single sex-linked gene required for female or male larval maturation or growth, and, in some embodiments, required for female or male adult insect survival. For example, the composition may comprise multiple female-lethal iRNAs. In some embodiments, the compositions comprise multiple iRNAs that target multiple sex-linked genes required for female or male mosquito larval maturation or growth, for example, at least two genes, at least three genes, at least four genes, etc.

Methods of delivery for iRNA of the present disclosure include, but are not limited to, e.g., larval soaking, nanoparticles (e.g., Chitosan nanoparticles), bacterial cells, yeast cells, algal cells, ovitraps, dried tablets, sugar feeding, and topical applications, among others. Other suitable methods of delivery are known in the art. Thus, compositions may include the necessary components to deliver the iRNA to the larva or adult mosquitoes. For example, compositions may comprise nanoparticles, bacterial cells, yeast cells, algal cells and the like that comprise, contain, or express the iRNA.

In some instances, the insecticide composition is placed in water. In other instances, the insecticide composition is placed in ovitraps. These are water-filled traps that are treated with the larvicides. They are designed to attract mosquitoes to lay their eggs in larvicide-treated water.

The terms "preventing" or "controlling" mosquito infestation include the reduction or inhibition of the maturation of mosquito larvae into adults and/or death or decreased survival of adult mosquitoes. The reduction or inhibition is measured by a reduction in the number of adult mosquitoes within an area, which can be readily determined using well-known methods.

Suitable carriers, excipients and diluents are known in the art and include, but are not limited to, water, saline, phosphate buffer saline, and the like. The carrier is formulated to the composition depending on the delivery method, for example, spray, powder, pellet, etc.

The compositions may be formulated into suitable forms for treatment of a mosquito infested area. For example, the composition may be in the form of a spray, powder, pellet, gel, capsule, food product, or the like. In some embodiments, the composition comprises inactive yeast cells expressing at least one sex-linked iRNA. In certain embodiments, the composition is a dried inactive yeast pellet, as described in Example 3, thus containing the interfering RNA in a tablet form. These tablets act as ready-to-use insecticidal lures. In other embodiments, the composition is a sugar bait solution containing the interfering RNA or yeast containing the interfering RNA, and/or microparticles. In some embodiments, the sugar bait solution includes chitosan or nanoparticles including the interfering RNA.

The disclosure further provides methods for controlling, reducing or treating a mosquito infestation comprising exposing at least one mosquito larvae to the at least one sex-linked interfering ribonucleic acid (iRNA) or a composition described herein in an effective amount to control, reduce or treat the mosquito infestation by reducing a specific female or male population of mosquitoes. As female mosquitoes usually transmit disease, certain embodiments target female-lethal genes by using female-linked iRNAs or compositions comprising such iRNAs. The mosquito infestation may be controlled, reduced or treated by inhibiting the larvae from maturing into adult mosquitoes by inhibiting at least one gene require for sex-linked larval maturation or by decreasing the survival of a specific sex of adult mosquitoes. Inhibition of maturation may result in the reduction in the number of adult mosquitoes found within a given area.

The disclosure further provides methods for controlling, reducing, or treating a female mosquito infestation comprising exposing at least one mosquito larvae or adult to the at least one interfering ribonucleic acid (RNA) having the sequence of any one of SEQ ID Nos: 2-45, 47-51 or a composition described herein including an iRNA having the sequence of any one of SEQ ID NOs: 2-45, 47-51 in an effective amount to control, reduce or treat the female mosquito infestation. The mosquito infestation may be controlled, reduced or treated by inhibiting the female larvae from maturing into adult female mosquitoes or by killing or decreasing survival of an adult female mosquito.

Mosquito infestations refers to a population of at least one species of mosquito within a given area. In some embodiments, the population comprises at least two mosquito species, alternatively at least three mosquito species, alternatively at least four mosquito species depending on location.

The present disclosure provides suitable insecticides comprising at least one iRNA which specifically targets and suppresses expression of one sex-linked target gene, e.g., a larva maturation gene or adult survival gene within an insect, preferably a mosquito.

The term insecticide is used to describe a composition or iRNA which is able to target and kill an insect at any stage of its life cycle. For example, the insecticide may target and kill the insect at the larval stage or as a mature adult insect. In some instances, the insecticide is a larvicide.

The mechanisms for delivering iRNA of the present invention allow for simultaneous delivery of multiple insecticides. This reduces the likelihood of developing insecticide resistant strains arising from point mutations in any one target sequence and also facilitates the development of broader-based insecticides targeting multiple mosquito species.

It should be apparent to those skilled in the art that many additional modifications beside those already described are possible without departing from the scope of the present disclosure.

The invention will be more fully understood upon consideration of the following non-limiting examples.

Example 1

This example demonstrates the development of a new class of sex-targeting insecticides for control of disease vector mosquitoes using short-length interfering RNA as mosquito specific larvicides. The present siRNA allow for the selective targeting of female or male mosquitoes to specifically reduce a desired population, or to provide a large population of male or female mosquitoes.

Generation of Sex-Specific Yeast Interfering RNA Larvicides:

The *A. aegypti* Liverpool-IB12 (LVP-M12) strain was reared as described by Clemons et al. (2011), PLoS one, 6(1):e16730. Custom siRNAs corresponding to target sequences in lncRNA genes linked to the M locus on chromosome one, as well as a control sequence with no known targets in *Aedes*, were obtained. Larval soaking experiments were performed (as described by Singh et al. (2013), J Insect Sci, 13:69) in duplicate, with 20 L1 larvae soaked at a concentration of 0.25 μg/μl for 4 hrs with control iRNA vs. iRNA targeting putative lncRNA genes. Following soaking, larvae were reared in accordance with the WHO guidelines for larvicide testing. The Fisher's exact test was utilized for evaluation of screen data.

Figure 3:
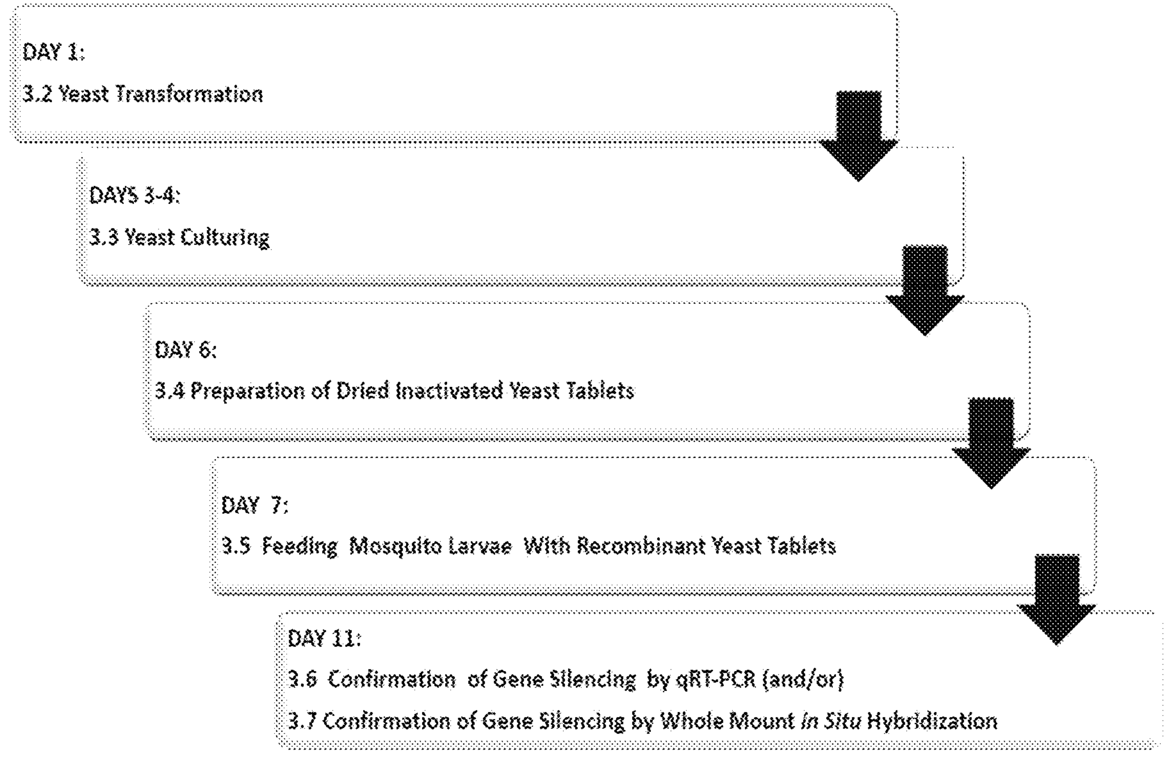
FIG. 3 depicts the experimental workflow for yeast insecticide. The sequence of experimental events over an ~11 day experimental timeline is presented, which initiate following preparation of the shRNA expression construct and conclude with analysis of silencing in fourth instar larvae.
Figure 4:
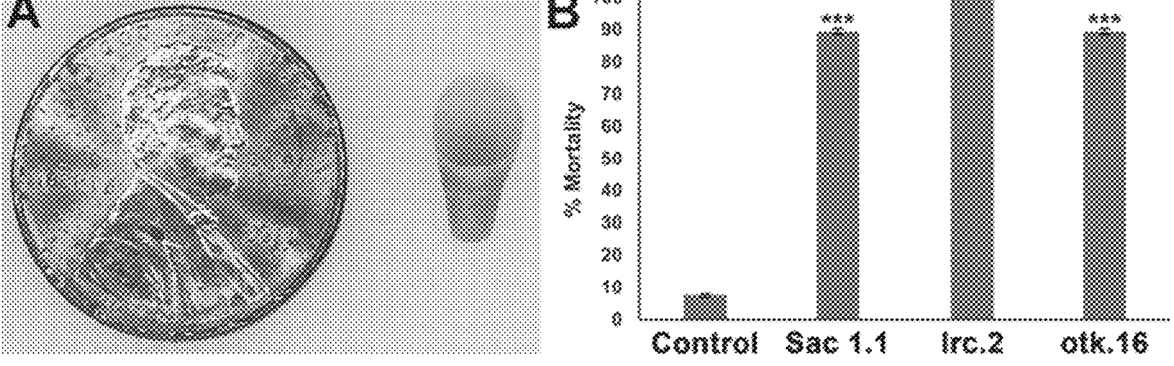
FIG. 4. Yeast interfering RNA tablets induce significant *A. gambiae* larval death. Dried inactivated yeast interfering RNA tablets (A; penny shown for scale) were prepared and fed to 20 *A. gambiae* larvae. Significant death was observed in larvae fed with yeast expressing shRNA hairpins corresponding to the Sacl, lrc, and otk genes as compared to larvae fed control yeast interfering RNA tablets. These data were compiled from three biological replicate experiments (n=240 larvae total/condition) and analyzed by ANOVA with Tukey's multiple comparison test. ***=p<0.001 as compared to control-fed larvae; error bars denote standard error of the mean (SEM). Reproduced through open access from Mysore et al. ((2017), Malar J., 16(1):461).
Figure 5:
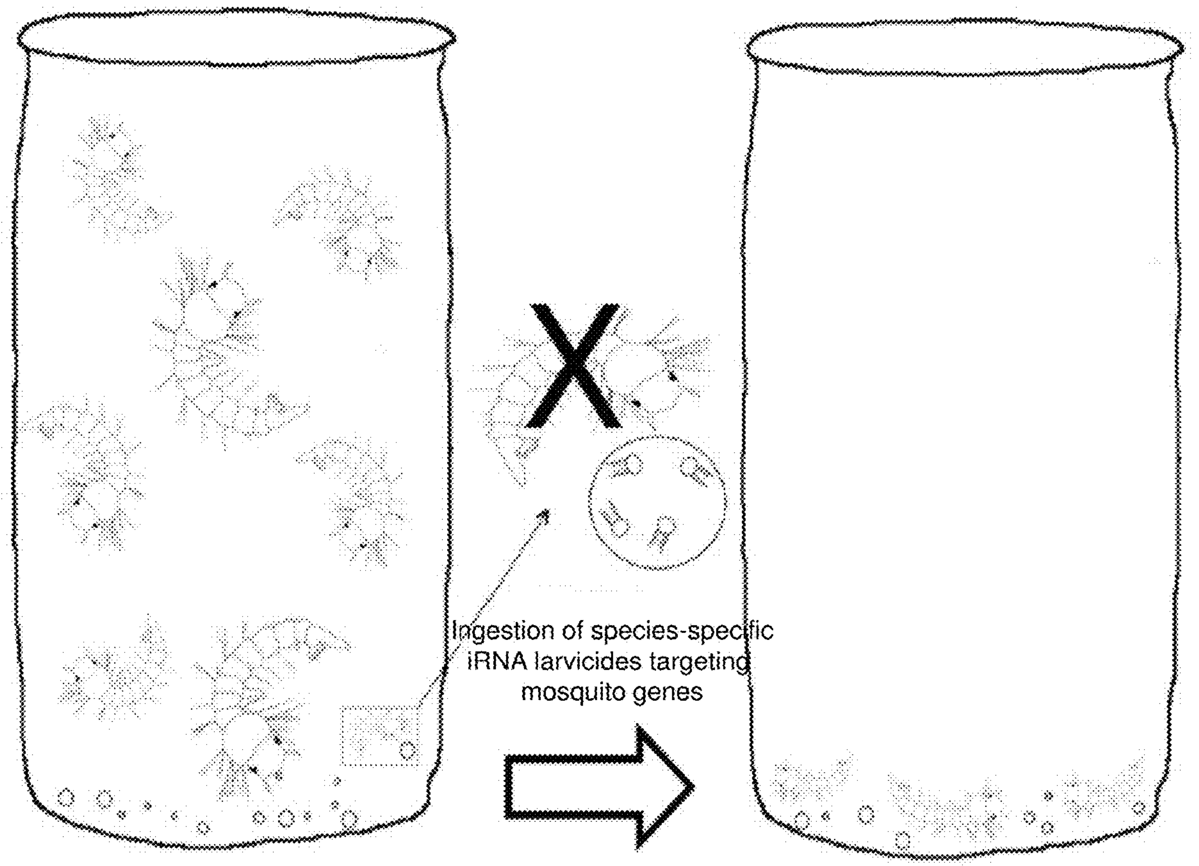
FIG. 5. Mosquito larval oral feeding assays. Larvae placed in a beaker consume yeast interfering RNA tablets. This procedure can be used to assay the impact of gene silencing on various larval phenotypes, including larval death.
Figure 6:
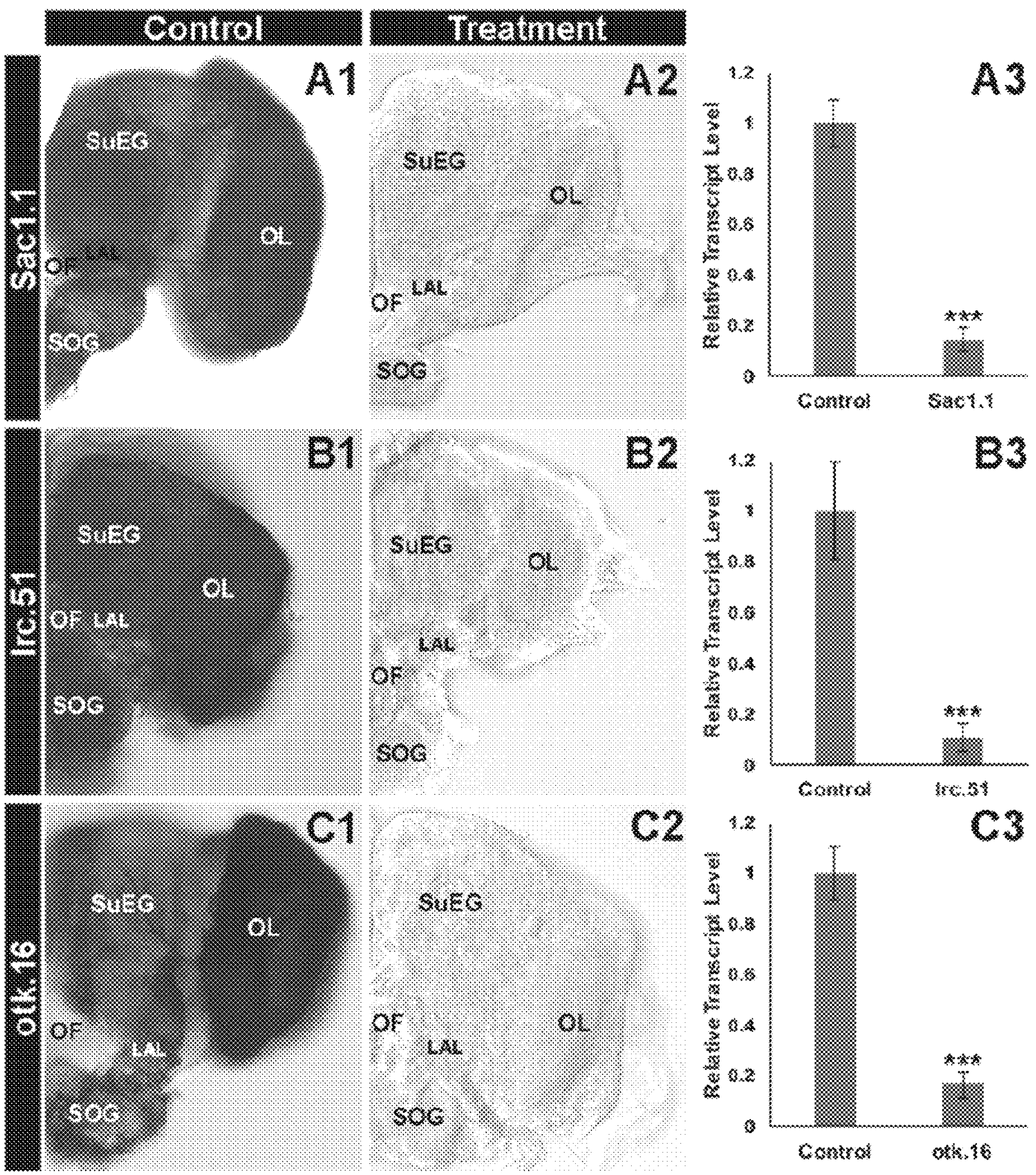
FIG. 6. Confirmed silencing of the Sacl, lrc, and otk genes in the *A. gambiae* larval brain by dried, inactivated yeast interfering RNA tablets. Significantly lower Sacl (A1-A3), lrc (B1-B3), and otk (C1-C3) transcript levels were detected through in situ hybridization in the L4 brains of larvae fed dried, inactivated yeast interfering RNA tablets corresponding to the Sacl (A1), lrc (B1), and otk (C1) genes vs. animals fed with control yeast interfering RNA tablets (A2, B2, C2). For each probe, results from three biological replicate experiments were compiled (n=85 total brains from larvae treated with the Sacl interfering RNA tablet, n=80 total brains from larvae treated with the lrc interfering RNA tablet, and n=80 brains from larvae treated with the otk interfering RNA tablets; n=40 brains from control-treated larvae/per experiment). Data were evaluated by the Student's t-test. All brains are oriented dorsal upward in this figure. LAL: Larval antennal lobe; OF: Olfactory foramen; OL: Optic lobe; SOG: Sub-oesophageal ganglion; SuEG: Supra-oesophageal ganglion. Reproduced through open access from Mysore et al. ((2017), Malar J., 16(1):461).

To investigate whether yeast interfering RNA larvicides can induce female- and male-specific larval lethality, we generated *S. cerevisiae* expressing various shRNAs (Tables 1 and 2; see FIG. 3). The strains were constructed using the protocol described in Hapairai et al. ((2017), Sci Rep, 7(1):13223) and Mysore et al. ((2017), Malar J., 16(1):461) (which are hereby incorporated by reference in their entireties), in which shRNA expression was placed under control of a constitutive promoter and expressed from a non-integrating plasmid. shRNA expression cassettes corresponding to siRNA sequences were designed using the Clonetech shRNA designer. Custom DNA oligonucleotides corresponding to these sequences were obtained and cloned into p426 GPD. This non-integrating bacteria-yeast shuttle vector bears a URA3 marker that permits constitutive expression of inserts cloned downstream of a GPD promoter. Following sequencing to confirm the inserts (using primers M13F (5'GTAAAACGACGGCCAGT3' (SEQ ID NO:53)) and M13R (5'CACACAGGAAACAGCTATGACCAT3' (SEQ ID NO: 54))) the plasmids were transformed into *S. cerevisiae* strain BY4742 (genotype MATα his3Δ1 leu2Δ0 lys2Δ0 ura3Δ0). Transformants were selected by growth on minimal media lacking uracil.

Inactivated yeast interfering RNA larvicide tablets were prepared and fed to *A. aegypti* larvae using the methodology described by Hapairai et al. (2017) (see FIG. 3). Following yeast selection as described above, dried inactivated yeast interfering RNA pellets are grown under standard conditions in synthetic media to an OD600 of 3.0. Dried inactivated yeast pellets from the iRNA or control strains were prepared. As discussed in Hapairai et al. (2017), larval bioassays, which conform to the WHO guidelines for larvicide testing are performed in the insectary (26.5° C., ~80% humidity, and under a 12 hr light/12 hr dark cycle with 1 hr crepuscular periods at the beginning and end of each light cycle). 20 newly hatched L1 larvae were placed in 500 ml plastic cups containing 50 ml of distilled water and a yeast pellet. Control and larvicidal yeast interfering RNA formulations were evaluated in parallel in at least three biological replicate experiments, each with at least three replicates per condition. Adult emergence rates and sexes were assessed, and data analyzed with ANOVA.

Testing of these lines has indicated that several of the larvicidal yeast iRNA can be used for effective sex-sorting of male or female mosquitoes (Tables 1 and 2).

Table 1 summarizes the data for 40 iRNAs targeting *Aedes aegypti* lncRNA target sequences. Larvae were either soaked with the indicated iRNA, or fed engineered heat-killed yeast including the indicated iRNA.

Table 2 summarizes the data for 12 iRNAs targeting target sequences in protein-encoding genes in the indicated species. Larvae were either soaked with the indicated iRNA, or fed engineered heat-killed yeast including the indicated iRNA.

siRNAs were identified that resulted in significant female-specific death, generating distorted sex ratios in adults (Tables 1 and 2). Although the percentages of expected female adult survivors were significantly reduced ($p<0.05$) in many instances following treatment or feeding, the siRNAs had no significant impact on male adult survival. Treatment or feeding with these siRNAs resulted in ratios of adult male:female mosquitos from 2 males: 1 female to 15 males: 0 females. The target genes corresponding to these siRNAs are known to be expressed in larvae. In some cases, expression of the genes is known to be sexually dimorphic. Sex-specific expression of the lncRNA genes corresponding to siRNAs 469, 486, and 487 has been observed in adults. In many instances, targeting the same sequences with yeast interfering RNA larvicides increased larval mortality when larvae were fed with the yeast larvicides throughout the larval developmental period relative to the soaking treatment (see, e.g., Table 1, siRNA/shRNA #469.2, 470, 474, 478, among others; Table 2, siRNA/shRNA #496, 497, 529, 523, 533, 534). In a few instances, targeting the same sequences with yeast iRNA larvicides decreased larval mortality or had no effect when larvae were fed the yeast larvicides throughout the larval developmental period relative to the soaking treatment (see, e.g., Table 1, siRNA/shRNA #506, 516, 517; Table 2, siRNA/shRNA #530, 531).

Interfering RNAs 469.1, 522, and 537 demonstrated male-specific lethality (Tables 1 and 2).

These results indicate that targeting both lncRNA and protein-encoding genes can generate altered male:female mosquito ratios, yielding mosquito populations consisting primarily of female or primarily male mosquitoes.

TABLE I

*Aedes aegypti* interfering RNA target sequences, corresponding lncRNA genes, and resulting altered male:female sex ratios observed following RNAi treatments

| siRNA/shRNA # | Target Sequence | Corresponding *Aedes aegypti* Genes | Males:Females after siRNA Soaking Treatment | Males:Females after Oral Feedings with Yeast |
|---|---|---|---|---|
| 469.1 | GAAGUAUUCUUCCAGCUAAUAUAAA (SEQ ID NO: 1) | AAEL021446, AAEL022173, AAEL022531, AAEL023751, AAEL024907, AAEL027422, AAEL028165, AAEL025725* | 1 to 2 | 1 to 4 |
| 469.2 | AUCAUAUACAUGUUGAAUUAUUGUU (SEQ ID NO: 2) | AAEL021446, AAEL022173, AAEL022531, AAEL023751, AAEL024907, AAEL027422, AAEL028165, AAEL025725* | 2 to 1 | 5 to 1 |
| 470 | GGUUUACUAAAAAUCACUUUCCUUG (SEQ ID NO: 3) | AAEL026346 | 2 to 1 | 5 to 1 |
| 474 | AGAAUCUUCUUACAAUCACUGCCUC (SEQ ID NO: 4) | AAEL020580, AAEL024146 | 2 to 1 | 3 to 1 |
| 478 | GACUAAUGUCUGGAAUUAGUAUAAA (SEQ ID NO: 5) | AAEL020379, AAEL020813, AAEL022952 | 3 to 1 | 9 to 1 |
| 486 | ACCAACUUAUAACAAAGAAAAGGUC (SEQ ID NO: 6) | AAEL022321, AAEL024935, AAEL025316, AAEL026051-RA, AAEL026137, AAEL026929, AAEL027085, AAEL027382 | 2 to 1 | |
| 487 | GUCACUAAGCUCUAUAAUCAAAAUA (SEQ ID NO: 7) | AAEL022649 | 2 to 1 | |
| 500 | GGACCAACUUUUACUUCAGAUAAGA (SEQ ID NO: 8) | AAEL011832 | 5 to 3 | |
| 504 | CAUCCAACCUUCAAGCGAAUCAGUG (SEQ ID NO: 9) | AAEL026407, AAEL021597, AAEL022807, AAEL026655 | 2 to 1 | |
| 505 | AUUGAGACUUACCAACUGAUCAGUU (SEQ ID NO: 10) | AAEL024697, AAEL021470, AAEL027259 | 2 to 1 | |
| 506 | CAAGUGAAAAUAAACAUCAAGAUUU (SEQ ID NO: 11) | AAEL022756, AAEL024428, AAEL022640 | 7 to 1 | 5 to 1 |
| 509 | GAUAAAGCAUUCAUUCCGCUACUUA (SEQ ID NO: 12) | AAEL025698, AAEL021884 | 2 to 1 | |
| 511 | GUUUUUAUUGUUUGCAUCAACAGUU (SEQ ID NO: 13) | AAEL023836 | 9 to 2 | 10 to 1 |
| 514 | AGCAGAAAGAUUGAAAUUAUUACCA (SEQ ID NO: 14) | AAEL022411, AAEL023838, AAEL027761 | 5 to 2 | 8 to 1 |
| 516 | AGCGUUGAAAAAUCUAUAAAAACCU (SEQ ID NO: 15) | AAEL026768, AAEL026445 | 8 to 1 | 6 to 1 |

TABLE I-continued

*Aedes aegypti* interfering RNA target sequences, corresponding lncRNA genes, and resulting altered male:female sex ratios observed following RNAi treatments

| siRNA/shRNA # | Target Sequence | Corresponding *Aedes aegypti* Genes | Males:Females after siRNA Soaking Treatment | Males:Females after Oral Feedings with Yeast |
|---|---|---|---|---|
| 517 | AGCGAUGGAAGAUUGUAAAAAUCGA (SEQ ID NO: 16) | AAEL026768, AAEL026445 | 5 to 1 | 3 to 1 |
| 518 | AGUCAGGGUUUAUUUCAUUGUUCGA (SEQ ID NO: 17) | AAEL021446, AAEL022173, AAEL023751, AAEL024907, AAEL027422, AAEL028165 | 5 to 2 | 5 to 1 |
| 519 | CAUGUUGAAUUAUUGUUUUGUUAAA (SEQ ID NO: 18) | AAEL022173, AAEL021446, AAEL023751, AAEL027422, AAEL028165, AAEL024907 | 5 to 3 | |
| 525 | UGGCAAAUUAUCCAAGAACAUCUAC (SEQ ID NO: 19) | AAEL028165 | 5 to 2 | |
| 526 | AAAUUAUCCAAGAACAUCUACAUCU (SEQ ID NO: 20) | AAEL028165 | 3 to 1 | |
| 527 | AAACGAGAAUUUGUGGAAAUAGUUG (SEQ ID NO: 21) | AAEL026346 | 2 to 1 | |
| 528 | AAACGAGAAUUUGUGGAAAUAGUUG (SEQ ID NO: 22) | AAEL026346 | 2 to 1 | |
| 538 | GGUCUCUUCUAUCAAGCAUAAGGUC (SEQ ID NO: 23) | AAEL028113* | 2 to 1 | |
| 539 | CUAUCAAGCAUAAGGUCUCUACAGU (SEQ ID NO: 24) | AAEL028113* | 2 to 1 | |
| 540 | AAAGUGCAUCAUGUGAUAAAAUCGA (SEQ ID NO: 25) | AAEL021079 | 2 to 1 | |
| 542 | AUUAUGAACAACAUGUUUAAAUAAA (SEQ ID NO: 26) | AAEL027827 | 6 to 1 | |
| 545 | UGCAAAGAAACGUUACUAUAUCUUG (SEQ ID NO: 27) | AAEL028113* | 4 to 1 | |
| 546 | GAAGCAUUCAAACAUGCUUACGGCA (SEQ ID NO: 28) | AAEL017331** | 12 to 0 | |
| 547 | CGGAGGUCAUUUCUUCAUCAAAGAA (SEQ ID NO: 29) | AAEL017331** | 6 to 1 | |
| 548 | CAUGAAUCAUUUGCCAAAUACCUCU (SEQ ID NO: 30) | AAEL026925** | 2 to 1 | |
| 549 | GAAUAAAUUGUUUUAGGAUCAAGAA (SEQ ID NO: 31) | AAEL022912-RA (non-translating CDS) | 4 to 1 | |
| 550 | CAGCAGUACUGAAUAAAUUGUUUUA (SEQ ID NO: 32) | AAEL022912-RA (non-translating CDS) | 15 to 0 | |
| 551 | GACCUGGAACAUGGGAAUAUCGAUA (SEQ ID NO: 33) | AAEL025669** | 5 to 1 | |
| 553 | GGCUAUGCAAACCAAUUCAAAAUCA (SEQ ID NO: 34) | AAEL022711 | 3 to 1 | |
| 554 | GUGGCAUUAAUGCAGCAAAUAAUCA (SEQ ID NO: 35) | AAEL022861, AAEL024779 | 2 to 1 | |
| 555 | CUGAAGCGUUUCCAACGAAACAAGU (SEQ ID NO: 36) | AAEL025301, AAEL015526** | 6 to 1 | |

TABLE I-continued

| *Aedes aegypti* interfering RNA target sequences, corresponding lncRNA genes, and resulting altered male:female sex ratios observed following RNAi treatments | | | | |
|---|---|---|---|---|
| siRNA/shRNA # | Target Sequence | Corresponding *Aedes aegypti* Genes | Males:Females after siRNA Soaking Treatment | Males:Females after Oral Feedings with Yeast |
| 556 | CAGUUUAUUCAUAAGUAAUCAUCUA (SEQ ID NO: 37) | AAEL026283, AAEL021141, AAEL021969 | 3 to 1 | |
| 557 | GGACAGUUUCCUACUAUCAAAACCG (SEQ ID NO: 38) | AAEL020975, AAEL024704 | 3 to 2 | |
| 558 | GUAAACAUGAGAAUUGAAAUUCAUA (SEQ ID NO: 39) | AAEL024704 | 4 to 1 | |
| 559 | AACCAGAAUCGGUAACCUAAAUUGU (SEQ ID NO: 40) | AAEL024704, AAEL020975 | 4 to 1 | |

Interfering RNAs, the target sequences/genes to which they correspond, and the altered *Aedes aegypti* male:female ratios resulting from treatments with siRNAs (through soaking) or shRNAs (through oral feedings with recombinant *S. cervesia*) are indicated.
*=encodes coding and non-coding transcripts.
**=encodes a protein rather than an lncRNA See Table 3 for additional gene information, including sequences.

TABLE 2

| Interfering RNA target sequences, corresponding genes, and resulting male:female sex ratios observed following RNAi treatments | | | | | |
|---|---|---|---|---|---|
| siRNA/shRNA # | Corresponding Target Sequence | Males:Females Genes | Males:Females Species | after siRNA Soaking Treatment | after Oral Feedings with Yeast |
| 496 | GAACAUGCUAUGAAAGAAUAUCCUG (SEQ ID NO: 41) | AAEL011830 | *Ae. aegypti* | 2 to 1 | 5 to 1 |
| 497 | AAAAUAUCGAUGGAGAUGAUCUGCA (SEQ ID NO: 42) | AAEL011830 | *Ae. aegypti* | 2 to 1 | 3 to 1 |
| 529 | GCAUCAAGCUUGAUGAUGAAAUUUA (SEQ ID NO: 43) | GAPW01003631.1, Aa-53178 mRNA sequence* | *Ae. albopictus* | 2 to 1 | 4 to 1 |
| 530 | AAACUUGGCAGAAGGCUAAAGCAAU (SEQ ID NO: 44) | GAPW01003631.1, Aa-53178 mRNA sequence | *Ae. albopictus* | 4 to 1 | 3 to 1 |
| 531 | AUAAAGGGAAUUUACGAUCAUGAAU (SEQ ID NO: 45) | GAPW01003631.1, Aa-53178 mRNA sequence | *Ae. albopictus* | 4 to 1 | 4 to 1 |
| 522 | AGCCACGUGGAUGCAUGAUAAUCGA (SEQ ID NO: 46) | AGAP000470** | *An. gambiae* | 1 to 2 | |
| 523 | CGUGGAUGCAUGAUAAUCGAAUAGU (SEQ ID NO: 47) | AGAP000470** | *An. gambiae* | 3 to 1 | 5 to 2 |
| 532 | AGCUUUCUGAAGAAGCCCAUCUCGA (SEQ ID NO: 48) | CPIJ011362 | *Culex quinquefasciatus* | 3 to 1 | |
| 533 | CAAUCCACAGCGUUGAGCUUUCUGA (SEQ ID NO: 49) | CPIJ011362 | *Culex quinquefasciatus* | 3 to 1 | 4 to 1 |
| 534 | AGAAUAUCGAUGGAGAUGAUCUGCA (SEQ ID NO: 50) | CPIJ011357 | *Culex quinquefasciatus* | 3 to 1 | 5 to 1 |

TABLE 2-continued

Interfering RNA target sequences, corresponding genes, and resulting male:female sex ratios observed following RNAi treatments

| siRNA/ shRNA # | Corresponding Target Sequence | Males:Females Genes | Males:Females Species | after siRNA Soaking Treatment | after Oral Feedings with Yeast |
|---|---|---|---|---|---|
| 535 | ACGAUUUGUUCAUUCAG AAUAUCGA (SEQ ID NO: 51) | CPIJ011357 | *Culex quinquefasciatus* | 2 to 1 | |
| 537 | AUCUUGAGGAUAGAAUG GCAAACGC (SEQ ID NO: 52) | CPIJ011356 | *Culex quinquefasciatus* | 1 to 2 | |

Interfering RNAs, the target sequences/genes to which they correspond in the indicated species, and the altered male:female ratios resulting from treatments with siRNAs (through soaking) or shRNAs (through oral feedings with recombinant *S. cerevisiae*) are indicated. Note that the genes in this table encode proteins rather than lncRNAs.

*Target is also conserved in *A. aegypti* ortholog.

**Target is also conserved in multiple *Anopheles* spp. orthologs See Table 3 for additional gene information, including sequences.

TABLE 3

Genes and Reference sequences

| Gene ID (Vectorbase.org) | Type | Ref Seq (from Vectorbase.org) | SEQ ID NO: |
|---|---|---|---|
| AAEL021446 | Genomic | | 55 |
| AAEL021446-RA | cDNA | XR_002501605.1 | 56 |
| AAEL021446-RB | cDNA | XR_002501602.1 | 57 |
| AAEL021446-RC | cDNA | XR_002501603.1 | 58 |
| AAEL022173 | Genomic | | 59 |
| AAEL022173-RA | cDNA | XR_002501584.1 | 60 |
| AAEL022173-RC | cDNA | XR_002501580.1 | 61 |
| AAEL022173-RB | cDNA | XR_002501582.1 | 62 |
| AAEL022531 | Genomic | | 63 |
| AAEL022531-RA | cDNA | XR_002502353.1 | 64 |
| AAEL023751 | Genomic | | 65 |
| AAEL023751-RA | cDNA | XR_002501542.1 | 66 |
| AAEL024907 | Genomic | | 67 |
| AAEL024907-RA | cDNA | XR_002501590.1 | 68 |
| AAEL027422 | Genomic | | 69 |
| AAEL027422-RA | cDNA | XR_002502112.1 | 70 |
| AAEL028165 | Genomic | | 71 |
| AAEL028165-RA | cDNA | XR_002501585.1 | 72 |
| AAEL025725* | Genomic | | 73 |
| AAEL025725-RA | cDNA | XR_002502086.1 | 74 |
| AAEL026346 | Genomic | | 75 |
| AAEL026346-RA | cDNA | XR_002498946.1 | 76 |
| AAEL022070 | Genomic | | 77 |
| AAEL022070-RA | cDNA | XR_002498945.1 | 78 |
| AAEL020580 | Genomic | | 79 |
| AAEL020580-RB | cDNA | XR_002501536.1 | 80 |
| AAEL020580-RA | Cdna | XR_002501537.1 | 81 |
| AAEL024146-RD | cDNA | XR_002499112.1 | 82 |
| AAEL024146 | Genomic | | 83 |
| AAEL024146-RA | cDNA | XR_002499114.1 | 84 |
| AAEL024146-RC | cDNA | XR_002499115.1 | 85 |
| AAEL024146-RB | cDNA | XR_002499115.1 | 86 |
| AAEL021059 | Genomic | | 87 |
| AAEL021059-RA* | cDNA | XR_002499763.1 | 88 |
| AAEL020379 | Genomic | | 89 |
| AAEL020379-RA | cDNA | XR_002501639.1 | 90 |
| AAEL020813 | Genomic | | 91 |
| AAEL020813-RA | cDNA | XR_002498943.1 | 92 |
| AAEL022952 | Genomic | | 93 |
| AAEL022952-RA | cDNA | XR_002498953.1 | 94 |
| AAEL022321 | Genomic | | 95 |
| AAEL022321-RA | cDNA | XR_002501549.1 | 96 |
| AAEL024935 | Genomic | | 97 |
| AAEL024935-RB | cDNA | XR_002501752.1 | 98 |
| AAEL024935-RA | cDNA | XR_002501752.1 | 99 |
| AAEL025316 | Genomic | | 100 |
| AAEL025316-RB | cDNA | XR_002501552.1 | 101 |
| AAEL025316-RA | cDNA | XR_002501553.1 | 102 |

TABLE 3-continued

Genes and Reference sequences

| Gene ID (Vectorbase.org) | Type | Ref Seq (from Vectorbase.org) | SEQ ID NO: |
|---|---|---|---|
| AAEL026051 | Genomic | | 103 |
| AAEL026051-RA | cDNA | XR_002503122.1 | 104 |
| AAEL026137 | Genomic | | 105 |
| AAEL026137-RA | cDNA | XR_002500683.1 | 106 |
| AAEL026929 | Genomic | | 107 |
| AAEL026929-RA | cDNA | XR_002503121.1 | 108 |
| AAEL027085 | Genomic | | 109 |
| AAEL027085-RA | cDNA | XR_002499739.1 | 110 |
| AAEL027382 | Genomic | | 111 |
| AAEL027382-RA | cDNA | XR_002500623.1 | 112 |
| AAEL022649 | Genomic | | 113 |
| AAEL022649-RA | cDNA | XR_002501554.1 | 114 |
| AAEL022649-RB | cDNA | XR_002501558.1 | 115 |
| AAEL011830** | Genomic | | 116 |
| AAEL011830-RD** | cDNA | XM_001655700.2 XP_001655750.2 | 117 |
| AAEL011830-RF** | cDNA | XM_011494673.2 XP_011492975.2 | 118 |
| AAEL011830-RC** | cDNA | XM_001655702.2 XP_001655752.2 | 119 |
| AAEL011830-RE** | cDNA | XM_001655705.2 XP_001655755.2 | 120 |
| AAEL011832** | Genomic | | 121 |
| AAEL011832-RA** | cDNA | XM_001655696.2 XP_001655746.1 | 122 |
| AAEL026407 | Genomic | | 123 |
| AAEL026407-RA | cDNA | XR_002501527.1 | 124 |
| AAEL021597 | Genomic | | 125 |
| AAEL021597-RA | cDNA | XR_002499160.1 | 126 |
| AAEL022807 | Genomic | | 127 |
| AAEL022807-RA | cDNA | XR_002499358.1 | 128 |
| AAEL026655 | Genomic | | 129 |
| AAEL026655-RA | cDNA | XR_002502213.1 | 130 |
| AAEL024697 | Genomic | | 131 |
| AAEL024697-RA | cDNA | XR_002501525.1 | 132 |
| AAEL021470 | Genomic | | 133 |
| AAEL021470-RA | cDNA | XR_002500565.1 | 134 |
| AAEL027259 | Genomic | | 135 |
| AAEL027259-RA | cDNA | XR_002500735.1 | 136 |
| AAEL022756 | Genomic | | 137 |
| AAEL022756-RA | cDNA | XR_002501530.1 | 138 |
| AAEL024428 | Genomic | | 139 |
| AAEL024428-RA | cDNA | XR_002502375.1 | 140 |
| AAEL022640 | Genomic | | 141 |
| AAEL022640-RA | cDNA | XR_002500704.1 | 142 |
| AAEL025698 | Genomic | | 143 |
| AAEL025698-RA | cDNA | XR_002501521.1 | 144 |
| AAEL023836 | Genomic | | 145 |

TABLE 3-continued

Genes and Reference sequences

| Gene ID (Vectorbase.org) | Type | Ref Seq (from Vectorbase.org) | SEQ ID NO: |
|---|---|---|---|
| AAEL023836-RA | cDNA | XR_002498951.1 | 146 |
| AAEL022411 | Genomic | | 147 |
| AAEL022411-RA | cDNA | XR_002501586.1 | 148 |
| AAEL023838 | Genomic | | 149 |
| AAEL023838-RA | cDNA | XR_002502445.1 | 150 |
| AAEL027761 | Genomic | | 151 |
| AAEL027761-RA | cDNA | XR_002498980.1 | 152 |
| AAEL026768 | Genomic | | 153 |
| AAEL026768-RA | cDNA | XR_002501599.1 | 154 |
| AAEL026445 | Genomic | | 155 |
| AAEL026445-RA | cDNA | XR_002501594.1 | 156 |
| AAEL028113** | Genomic | | 157 |
| AAEL028113-RA (Nontranslating CDS) | cDNA | XR_002501571.1 | 158 |
| AAEL028113-RB** | cDNA | XM_021851255.1 XP_021706947.1 | 159 |
| AAEL021079 | Genomic | | 160 |
| AAEL021079-RA | cDNA | XR_002501511.1 | 161 |
| AAEL027827 | Genomic | | 162 |
| AAEL027827-RA | cDNA | XR_002501690.1 | 163 |
| AAEL017331** | Genomic | | 164 |
| AAEL017331-RB** | cDNA | XM_021851045.1 XP_021706737.1 | 165 |
| AAEL017331-RC** | cDNA | XM_021851054.1 XP_021706746.1 | 166 |
| AAEL017331-RD** | cDNA | XM_021851035.1 XP_021706727.1 | 167 |
| AAEL026925** | Genomic | | 168 |
| AAEL026925-RA** | cDNA | XM_021838691.1 XP_021694383.1 | 169 |
| AAEL022912** | | | 170 |
| AAEL022912-RA (Nontranslating CDS) | | XR_002501548.1 | 171 |
| AAEL022912-RB** | | XM_021851185.1 XP_021706877.1 | 172 |
| AAEL025669 | Genomic | | 173 |
| AAEL025669-RA | cDNA | XM_021851169.1 XP_021706861.1 | 174 |
| AAEL022711 | Genomic | | 175 |
| AAEL022711-RA | cDNA | XR_002501520.1 | 176 |
| AAEL022861 | Genomic | | 177 |
| AAEL022861-RA | cDNA | XR_002501512.1 | 178 |
| AAEL024779 | Genomic | | 179 |
| AAEL024779-RA | cDNA | XR_002502003.1 | 180 |
| AAEL025301 | Genomic | | 181 |
| AAEL025301-RA | cDNA | XR_002498939.1 | 182 |
| AAEL015526** | Genomic | | 183 |
| AAEL015526-RA** | cDNA | XM_001647623.2 XP_001647673.1 | 184 |
| AAEL026283 | Genomic | | 185 |
| AAEL026283-RA | cDNA | XR_002501505.1 | 186 |
| AAEL021141 | Genomic | | 187 |
| AAEL021141-RA | cDNA | XR_002500416.1 | 188 |
| AAEL021969 | Genomic | | 189 |
| AAEL021969-RA | cDNA | XR_002498909.1 | 190 |
| AAEL020975 | Genomic | | 191 |
| AAEL020975-RA | cDNA | XR_002501508.1 | 192 |
| AAEL024704 | Genomic | | 193 |
| AAEL024704-RA | cDNA | XR_002501510.1 | 194 |
| GAPW01003631.1, Aa-53178 mRNA sequence* | mRNA | | 195 |
| AGAP000470** | Genomic | | 196 |
| AGAP000470-RA** | cDNA | XM_310624.5 XP_310624.5 | 197 |
| CPIJ011362 | Genomic | | 198 |
| CPIJ011362-RA | cDNA | XM_001861545.1 XP_001861580.1 | 199 |
| CPIJ011357 | Genomic | | 200 |
| CPIJ011357-RA | cDNA | XM_001861540.1 XP_001861575.1 | 201 |
| CPIJ011356 | Genomic | | 202 |
| CPIJ011356-RA | cDNA | XM_001861539.1 XP_001861574.1 | 203 |

Testing of these lines has indicated that the genes of Table 3 can be targeted or otherwise used for effective sex-sorting of male or female mosquitoes.

Example 2: siRNA Delivery Strategies

PCT Application No. US2017/041919 (Publication No: WO/2018/013801), which is hereby incorporated by reference in its entirety, describes several methods for interfering RNA delivery. These techniques, are summarized below.

Larval soaking: RNA interference was induced in *A. aegypti* mosquito larvae by soaking larvae in a solution of dsRNA for several hours (Singh et al. (2013)). We have had similar success with siRNA in *A. aegypti* and have found that the siRNA soaking strategy also works in anopheline mosquitoes. These laboratory experiments have been conducted using the Singh et al. (2013) protocol in conjunction with gene-specific 28-mer siRNAs at a concentration of 0.5 micrograms/microliter. siRNAs that kill up to 85% of larvae following a single four hour soaking treatment have been identified. These findings suggest that siRNA larvicides can effectively be added directly to larval breeding sites.

Chitosan/siRNA nanoparticles: We have previously been successful in delivering interfering RNA to mosquito larvae using non-toxic chitosan nanoparticles (see, e.g., Mysore et al. (2013), PLoS Neglected Tropical Diseases, 7(5):e2215 doi:10.1371/journal.pntd.0002215); Mysore et al. (2014), BMC Dev Biol, 14:9 doi:10.1186/1471-213X-14- 9; and Zhang et al. (2015), J Vis Exp, (97):doi:10.3791/52523). Chitosan/siRNA nanoparticles are formed by self-assembly of polycations with interfering RNA through the electrostatic forces between positive charges of the amino groups in chitosan and negative charges carried by the phosphate groups on the backbone of interfering RNA. Chitosan is believed to enhance the stability and/or cellular uptake of dsRNA. Chitosan/siRNA nanoparticles are mixed with larval food and then fed to larvae. This technique is relatively inexpensive, requires little equipment and labor, and facilitates high-throughput analyses. Our experiments have demonstrated that chitosan/siRNA targeting larval lethal genes results in up to 50% mosquito larval lethality. These nanoparticles along with other nanoparticles known in the art may be used to target the delivery of the iRNA of the present technology.

Bacterial delivery systems: *Bacillus thuringiensis* bacteria have been successfully used for mosquito larval control, making interfering RNA delivery through genetically-modified microbes another option. Such a microbial delivery mechanism is attractive since it would significantly reduce the cost of this intervention by eliminating the need to purchase siRNA or synthesize it in vitro. Whyard et al. ((2015), Parasit Vectors, 8:96 doi:10.1186/s13071-015-0716-6) fed mosquito larvae dsRNA-expressing non-pathogenic *E. coli* mixed with larval food as bait. They obtained significant levels of knockdown—even when using heat-killed bacteria. We used the Whyard et al. (2015) approach to deliver our siRNA larvicides. This strategy involves the use of nonpathogenic *E. coli* strain HT115-DE3, which is transformed with the dsRNA transcription plasmid pL4440 containing a fragment of interest or GFP (control). Expression plasmids and bacteria feeding lines are prepared and then fed to larvae as discussed by Whyard et al. (2015). Both live bacteria and heat-killed bacteria can be assessed in our laboratory experiments. Our data indicate that this microbial delivery system can provide an effective means of delivering interfering RNA larvicides. We have observed up to 100% larval death/failure to pupariate—even when the bacteria are heat-killed prior to treatment of mosquitoes. The plasmid-based expression system described above is appropriate for simulated field, semi-field, and small-scale field studies.

For large-scale field studies, dsRNA expression cassettes can be integrated into the bacterial genome, which eliminates risks of horizontal gene transfer or introduction of any antibiotic resistance marker genes carried on plasmids.

Yeast delivery system: Van Ekert et al. (2014) silenced *A. aegypti* larval genes by feeding them nonpathogenic *Pichia pastoris* yeast expressing a long hairpin RNA (lhRNA) sequence corresponding to the gene to be silenced. For proof of concept experiments, we are using the Van Ekert (2014) delivery protocol with the following modifications: i) we are using *Saccharomyces cerevisiae*, non-pathogenic baker's yeast commonly used in baking and beverage production, ii) we are using short hairpin RNAs (shRNAs), a short artificial RNA molecule with a hairpin turn that can be used to silence gene expression through RNAi. The short sequence of these shRNAs, which correspond to the sequences of our siRNA larvicides, is preferable to lhRNAs, which have a higher risk of off-species targeting than shorter shRNA molecules. iii) As with the bacterial studies, both live and heat-killed yeast are assessed. *Saccharomyces cerevisiae* is an appealing delivery system, as mosquito larvae are highly attracted to yeast and ingest it directly. Moreover, the yeast can be dried and packaged much in the same manner in which it is sold commercially, which would greatly facilitate the distribution of interfering RNA yeast larvicides. In one embodiment, the yeast is heat-killed and dried into a pellet formulation that is fed to larvae and has shown success in killing larvae.

Finally, as is the case for bacterial delivery systems, use of yeast is expected to significantly decrease the costs of siRNA production since shRNA expression is easily amplified through yeast cultivation. We have cloned inserts designed to produce shRNA corresponding to larval lethal genes into the pRS426 GPD bacteria/yeast shuttle vector (Mumberg et al., 1995). Yeast expressing these hairpins have been tested as described by Van Ekert et al. (2014) and according to the WHO (2005) protocol. Our preliminary data suggest that ingestion of yeast interfering RNA larvicides generates up to 100% larval death/failure to pupariate even when the yeast are heat-killed.

As with the bacterial studies, the yeast plasmid-based expression system described above is appropriate for simulated field, semi-field, and small-scale field studies. For large-scale field studies, advanced genome editing techniques such as CRISPR/Cas9 will facilitate stable and seamless genome integration of shRNA expression cassettes, which eliminates risks of horizontal gene transfer or introduction of any antibiotic resistance marker genes.

Stable Yeast Delivery System

The inventors have integrated the shRNA expression cassette into the *S. cerevisiae* genome to allow for stable expression of the siRNA. The expression of the shRNA was placed under the control of an inducible promoter. Stable transformants were generated by ligating downstream of the Gal1 promoter DNA that encodes shRNA and upstream of the cyc1 terminator.

The resulting Gal1 promoter-shRNA-cyc1 terminator expression cassettes were cloned into the multiple cloning sites of pRS404 and pRS406, yeast integrating plasmid shuttle vectors bearing TRP1 and URA3 markers, respectively. The resulting plasmids were used for genome integration of the shRNA expression cassettes at the trp1 and ura3 loci of the *S. cerevisiae* CEN.PK strain (genotype=MATa/α ura3-52/ura3-52 trp1-289/trp1-289 leu2-3_112/leu2-3_112 his3 Δ1/his3 Δ1 MAL2-8C/MAL2-8C SUC2/SUC2). Stable transformants were selected by growth on synthetic complete media lacking tryptophan or uracil. Integration events at both loci were confirmed via PCR and sequencing.

Generation of these stable transformants eliminates the use of plasmids with antibiotic resistance markers and the potential for horizontal transfer of shRNA expression cassettes.

Algal delivery system: Microorganisms, including microalgae, serve as a primary source of nutrition for mosquito larvae. A microalgal-based system for delivery of interfering RNA to mosquito larvae has been described. Silenced *Anopheles stephensi* larval genes were silenced by feeding them *Chlamydomonas reinhardtii* expressing a hairpin sequence corresponding to the gene to be silenced. We have separately confirmed that *A. aegypti* larvae will eat *Chlamydomonas* in a laboratory setting and believe that these microalgae can be used to deliver shRNA to *A. aegypti* larvae. For proof of concept experiments, using the GeneArt *Chlamydomonas* Engineering Kit (Invitrogen Life Technologies), inserts designed to produce shRNA corresponding to larval lethal genes are cloned into the pChlamy_3 shuttle vector. These constructs are used to transform algae. Algal interfering RNA larvicides are tested on mosquito larvae. This system is evaluated in simulated field, semifield, and in field experiments. As with the bacterial and yeast studies, the *Chlamydomonas* plasmid-based expression system described above is appropriate for simulated field, semi-field, and small-scale field studies. For large-scale field studies, hairpin expression constructs are integrated into the *Chlamydomonas reinhardtii* chloroplast genome. Use of algal species native to field sites in which the interfering RNA insecticides are used can also be used, preferably those normally ingested by mosquitoes. To this end, larval specimens are collected from the field to evaluate the algal species that they consume in the wild.

Field Studies

Field studies can be conducted as described in PCT Application No. US2017/041919 entitled "RNAi Insecticide Materials and Methods" which is hereby incorporated by reference in its entirety.

In a first example ("Example 1"), provided herein is an interfering ribonucleic acid (iRNA) corresponding to a target nucleotide sequence of at least one sex-linked arthropod gene required for maturation of at least one arthropod species, wherein binding of the target nucleotide sequence by the iRNA silences expression of the at least one sex-linked gene.

In another example ("Example 2"), further to Example 1, the at least one sex-linked gene is selected from the group consisting of AAEL021446, AAEL022173, AAEL022531, AAEL023751, AAEL024907, AAEL027422, AAEL028165, AAEL025725, AAEL026346, AAEL022070, AAEL020580, AAEL024146, AAEL021059, AAEL020379, AAEL020813, AAEL022952, AAEL022321, AAEL024935, AAEL025316, AAEL026051, AAEL026137, AAEL026929, AAEL027085, AAEL027382, AAEL022649, AAEL011830, AAEL011832, AAEL026407, AAEL021597, AAEL022807, AAEL026655, AAEL024697, AAEL021470, AAEL027259, AAEL022756, AAEL024428, AAEL022640, AAEL025698, AAEL021884, AAEL023836, AAEL022411, AAEL023838, AAEL027761, AAEL026768, AAEL026445, AAEL028113, AAEL021079, AAEL027827, AAEL017331, AAEL026925, AAEL022912; AAEL025669, AAEL022711, AAEL022861, AAEL024779, AAEL025301, AAEL015526, AAEL026283, AAEL021141, AAEL021969, AAEL020975, AAEL024704, GAPW01003631.1, AGAP000470, CPIJ011362, CPIJ011357, CPIJ011356, and orthologs thereof.

In another example ("Example 3"), further to Example 1 or Example 2, the target nucleotide sequence has a nucleotide sequence selected from the group consisting of SEQ ID NOs: 1-52, and combinations of any two or more of the foregoing.

In another example ("Example 4"), further to any one of Examples 1-3, the iRNA selectively affects females and the target nucleotide sequence has a nucleotide sequence selected from the group consisting of SEQ ID NO: 2-45, 47-51, and two or more of the foregoing.

In another example ("Example 5"), further to any one of Examples 1-3, the iRNA selectively affects males and the target nucleotide sequence has a nucleotide sequence selected from the group consisting of SEQ ID NO: 1, 46, 52, and two or more of the foregoing.

In another example ("Example 6"), further to any one of Examples 1-5, wherein the at least one arthropod species consists of at least one mosquito species.

In another example ("Example 7"), further to any of Examples 1-6, the at least one sex-linked gene is required for sex-linked maturation in at least two species of mosquito.

In another example ("Example 8"), further to any of Example 1-7, the at least one sex-linked gene is required for sex-linked adult mosquito survival or sex-specific behaviors.

In another example ("Example 9"), further to any of Examples 1-6, the at least one mosquito species is selected from the group consisting of *Aedes* spp., *Anopheles* spp., and *Culex* spp.

In another example ("Example 10"), further to any of Examples 1-9, the iRNA is a small interfering RNA (siRNA), a short hairpin RNA (shRNA), double stranded RNA (dsRNA), RNA construct, or anti sense oligonucleotide.

In another example ("Example 11"), further to any of Examples 1-10, the iRNA does not target any human gene.

In another example ("Example 12"), provided herein is a DNA construct encoding at least one iRNA of any one of Examples 1-11, wherein the DNA construct is capable of expressing the iRNA, In another example ("Example 13"), provided herein is a host cell comprising the DNA construct of Example 12.

In another example ("Example 14"), provided herein is a yeast cell engineered to produce at least one iRNA of any one of Examples 1-11.

In another example ("Example 15"), further to Example 12, the yeast cell expresses at least two iRNAs of any one of Examples 1-11.

In another example ("Example 16"), further to Example 12 or Example 13, the at least two iRNAs target (i) a single sex-linked gene required for maturation of females of the at least one arthropod species; or (ii) at least two different sex-linked genes required for maturation of females of the at least one arthropod species.

In another example ("Example 17"), further to any of Examples 14-16, the yeast cell is a Saccharomyces cerevisiae cell.

In another example ("Example 18"). provided herein is mosquito insecticide composition for preventing and/or controlling a mosquito infestation comprising: (i) at least one interfering ribonucleic acid (iRNA) according to any one of Examples 1-11, (ii) a bacterial cell expressing the iRNA according to any one of Examples 1-11, or (iii) the yeast cell according to any one of Examples 14-17; and at least one suitable carrier, excipient or diluent.

In another example ("Example 19"), further to Example 18, the mosquito insecticide composition comprises the yeast cell according to any one of Examples 14-17.

In another example ("Example 20"), further to Example 18 or Example 19, the yeast cell is heat-inactivated.

In another example ("Example 21"), further to any one of Examples 18-20, the composition selectively targets female mosquitoes and wherein the target nucleotide sequence has a nucleotide sequence selected from the group consisting of SEQ ID NO: 2-45, 47-51, and two or more of the foregoing.

In another example ("Example 22"), further to any one of Examples 18-20, the composition consists essentially of: a) the ANA; b) a DNA construct encoding the iRNA; c) a yeast cell engineered to produce the iRNA; or d) a bacterial cell expressing the iRNA; wherein the mosquito insecticide composition is able inhibit both larval maturation and adult survival.

In another example ("Example 23"), further to Example 22, the iRNA is a shRNA.

In another example ("Example 24"), further to Example 22, the iRNA targets a nucleotide sequence selected from the group consisting of SEQ ID NO: 1, 46, 52, and two or more of the foregoing.

In another example ("Example 25"), provided herein is a sugar bait comprising the mosquito insecticide composition of any one of Examples 22-24.

In another example ("Example 26"), provided herein is a dried, inactivated yeast composition comprising the mosquito insecticide composition of any one of Examples 22-24.

In another example ("Example 27"), provided herein is a chitosan or nanoparticle comprising the mosquito insecticide composition of any one of Examples 18-24.

In another example ("Example 28"), provided herein is a method for controlling, reducing or treating a mosquito infestation comprising exposing at least one mosquito larva or adult to the at least one interfering ribonucleic acid (iRNA) according to any one of Examples 1-11, or the mosquito insecticide composition of any one of Examples 18-24, in an effective amount to control, reduce or treat the mosquito infestation.

In another example ("Example 29"), further to Example 28, the mosquito infestation comprises female mosquitoes.

In another example ("Example 30"), further to Example 28 or Example 29, the mosquito infestation comprises mosquito of the species *A. aegypti*.

In another example ("Example 31"), further to any one of Example 28-30, the mosquito infestation is controlled, reduced or treated by inhibiting the larvae from maturing into adult mosquitoes by inhibiting at least one gene require for sex-specific larval maturation, adult reproduction or adult mosquito survival.

In another example ("Example 32"), further to any one of Example 28-31, the mosquito infestation is controlled, reduced or treated by killing or reducing survival of an adult female mosquito.

In another example ("Example 33"), further to any one of Example 28-32, the method comprises exposing the mosquito larvae or adult to at least two of the iRNAs.

In another example ("Example 34"), provided herein is a method for sex sorting a population of mosquito larva or adult mosquitoes comprising exposing at least one mosquito larva or adult to the at least one interfering ribonucleic acid (iRNA) according to any one of Examples 1-11, the mosquito insecticide composition of example 17, or the mosquito insecticide composition of example 22, in an effective amount to selectively kill at least a portion of the mosquito larva or adult of one sex.

In another example ("Example 35"), further to Example 34, the method comprises exposing the mosquito larvae or adult to at least two of the iRNAs.

While the disclosed subject matter is amenable to various modifications and alternative forms, specific embodiments are described herein in detail. The intention, however, is not to limit the disclosure to the particular embodiments described. On the contrary, the disclosure is intended to cover all modifications, equivalents, and alternatives falling within the scope of the disclosure as defined by the appended claims.

Similarly, although illustrative methods may be described herein, the description of the methods should not be interpreted as implying any requirement of, or particular order among or between, the various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step).

I claim:

1. A mosquito insecticide composition for preventing and/or controlling a mosquito infestation comprising:

(i) at least one interfering ribonucleic acid (iRNA);

(ii) a yeast cell expressing the iRNA; and (iii) at least one suitable carrier, excipient or diluent, wherein the interfering ribonucleic acid (IRNA) corresponding to a target nucleotide sequence of at least one sex-linked larval lethal arthropod gene required for maturation from larvae to adult of at least one arthropod species, wherein one of the sex-linked larval lethal arthropod genes is AAEL017331, and wherein binding of the target nucleotide sequence by the iRNA silences expression of the at least one sex-linked gene in female larvae, wherein the at least one arthropod species consists of at least one mosquito species.

2. The mosquito insecticide composition of claim 1, wherein the at least one mosquito species is selected from the group consisting of *Aedes* spp., *Anopheles* spp., and *Culex* spp.

3. The mosquito insecticide composition of claim 1, wherein the iRNA is a short hairpin RNA (shRNA).

4. The mosquito insecticide composition of claim 1, wherein the iRNA does not target any human gene.

5. The mosquito insecticide composition of claim 1, wherein the yeast cell is heat-inactivated.

6. The mosquito insecticide composition of claim 1, wherein the composition selectively targets female mosquitoes and wherein the target nucleotide sequence has a nucleotide sequence selected from the group consisting of SEQ ID NOs: 28 and 29, and combinations of the two.

7. The mosquito insecticide composition of claim 1, wherein the composition consists essentially of:

(a) the iRNA;

(b) a DNA construct encoding the iRNA; and (c) the yeast cell of claim 1 engineered to produce the iRNA;

wherein the mosquito insecticide composition is able inhibit both larval maturation and adult survival or the mosquito insecticide composition is able to inhibit sex-specific behavior.

8. The mosquito insecticide composition of claim 7, wherein the iRNA is a shRNA.

* * * * *